(12) United States Patent
Gebauer et al.

(10) Patent No.: US 7,629,294 B2
(45) Date of Patent: Dec. 8, 2009

(54) PYRAZOLOPYRIMIDINES

(75) Inventors: Olaf Gebauer, Köln (DE); Herbert Gayer, Monheim (DE); Ulrich Heinemann, Leichlingen (DE); Stefan Herrmann, Langenfeld (DE); Stefan Hillebrand, Neuss (DE); Hans-Ludwig Elbe, Wuppertal (DE); Ronald Ebbert, Monheim (DE); Ulrike Wachendorff-Neumann, Neuwied (DE); Peter Dahmen, Neuss (DE); Karl-Heinz Kuck, Langenfeld (DE)

(73) Assignee: Bayer CropScience LP, Monheim (DE)

( * ) Notice: Subject to any disclaimer, the term of this patent is extended or adjusted under 35 U.S.C. 154(b) by 336 days.

(21) Appl. No.: 11/063,191

(22) Filed: Feb. 22, 2005

(65) Prior Publication Data
US 2005/0187224 A1 Aug. 25, 2005

(30) Foreign Application Priority Data
Feb. 20, 2004 (DE) .................. 10 2004 008 807

(51) Int. Cl.
*C07D 487/04* (2006.01)
*A01N 43/56* (2006.01)
(52) U.S. Cl. .................. 504/241; 514/259.3; 544/281
(58) Field of Classification Search .................. 544/281; 514/259.3; 504/241
See application file for complete search history.

(56) References Cited

U.S. PATENT DOCUMENTS

| 3,515,715 | A | | 6/1970 | Straley et al. ............. 260/163 |
|---|---|---|---|---|
| 3,634,391 | A | | 1/1972 | Fisher et al. ............. 260/162 |
| 4,567,263 | A | * | 1/1986 | Eicken et al. ............. 544/263 |
| 4,617,303 | A | | 10/1986 | Eicken et al. ............. 514/258 |
| 5,922,732 | A | | 7/1999 | Urch et al. ............. 514/304 |
| 6,093,726 | A | | 7/2000 | Urch et al. ............. 514/299 |
| 6,099,593 | A | * | 8/2000 | Terranova et al. ............. 8/409 |
| 6,156,925 | A | | 12/2000 | Meyer et al. ............. 560/82 |
| 6,174,894 | B1 | | 1/2001 | Urch et al. ............. 514/299 |
| 6,177,442 | B1 | | 1/2001 | Urch et al. ............. 514/299 |
| 6,207,676 | B1 | | 3/2001 | Urch et al. ............. 514/304 |
| 6,291,474 | B1 | | 9/2001 | Brightwell et al. ............. 514/299 |
| 6,391,883 | B1 | | 5/2002 | Urch et al. ............. 514/255 |
| 6,573,275 | B1 | | 6/2003 | Urch et al. ............. 514/304 |
| 2002/0049318 | A1 | | 4/2002 | Pees et al. ............. 544/60 |
| 2002/0061913 | A1 | | 5/2002 | Urch et al. ............. 514/366 |
| 2006/0258685 | A1 | | 11/2006 | Wagner et al. | |

FOREIGN PATENT DOCUMENTS

| CA | 1288096 | 8/1991 |
|---|---|---|
| CA | 2 487 544 | 12/2003 |
| DE | 31 30 633 | 1/1981 |
| DE | 33 38 292 | 10/1983 |
| DE | 102 23 917 | 5/2002 |
| FR | 2 794 745 A1 | 12/2000 |
| GB | 2 132 607 A | 7/1984 |
| JP | 42003173 | * 2/1967 |
| JP | 42003174 | * 2/1967 |
| JP | 45030334 | * 10/1970 |
| WO | 02/48151 A1 | 6/2002 |
| WO | 03/009687 | 2/2003 |
| WO | 2004/106341 | 12/2004 |
| WO | 2005/000851 | 1/2005 |

OTHER PUBLICATIONS

Chem. Ber., 86, (month unavailable) 1956, pp. 996-1001, Emil Buchta und Günter Scheuere, Versuche zur Synthese von Steroiden, IX. Mitteil.: 2-[2-Methyl-cyclopentyl]-9-methyl-$\Delta^{4.10}$ bzw. $^{5.10}$-oktalon-(1).

Chem. Ber., 95, (month unavailable) 1962, pp. 2861-2870, Rudolf Gompper und Werner Töpfl, "Substituierte Dithiocarbonsäuren und Ketenmercaptale".

Tetrahedron, vol. 32, (month unavailable) 1976, pp. 1779-1787, S.M.S. Chauhan and H. Junjappa, "The Reaction of α-Keto and α-Cyanoketene-S,S-Acetals with Guanidine and Thiourea: A New General Synthesis of Alkoxy-Pyrimidines".

J. Med. Chem., vol. 11, Sep. 1968, pp. 1028-1031, E.C. Kornfeld et al, "This Synthesis and Pharmacology of 2-(2-Aminoethyl)imidazole (2-Isohistamine)".

J. Heterocyclic Chem., 24, Jan.-Feb. 1987, pp. 247-249, Teresa Ramos et al, "Reactivity of Aryl- and Heteroarylmalonates against ortho-Dinucleophiles. Triaryl(heteroaryl)methane Synthesis".

Heterocycles, vol. 27, No. 11, (month unavailable) 1988, pp. 2627-2633, Leonard M. Weinstock et al, "Diaryl-α-Heteroarylmalonates from Cerium (IV)—Promoted Reactions of Dialkyl Malonates with Heterocyclic Compounds".

Heterocycles, vol. 26, No. 12, (month unavailable) 1987, pp. 3259-3264, Shoetsu Konno et al, "Studies on as-Triazine Derivatives. VIII. Synthesis of 5-Substituted 1,2,4-Triazines".

(Continued)

*Primary Examiner*—Bruck Kifle
(74) *Attorney, Agent, or Firm*—Baker, Donelson, Bearman, Caldwell & Berkowitz PC; Raymond J. Harmuth

(57) ABSTRACT

The invention relates to prazolopyrimidines of the formula

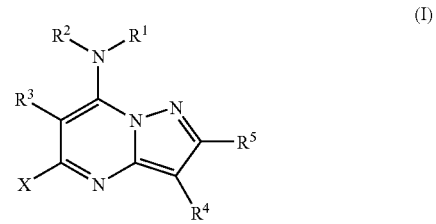

in which $R^1$, $R^2$, $R^3$, $R^4$, $R^5$, and X are as defined in the disclosure,
to a process for preparing these compounds, and to their use for controlling unwanted microorganisms.

9 Claims, No Drawings

OTHER PUBLICATIONS

Heterocycles, vol. 31, No. 5, (month unavailable) 1990, pp. 1115-1127, Hiroshi Yamanaka et al, "On the Reactivity of Halo-1,3-Azoles and Related Compounds Toward Aromatic $S_N2$ Substitution".

Bull. Chem.. Soc. Jpn., vol. 51, (2), Feb. 1978, pp. 665-666, Shigeo Tanimoto et al, "A Convenient Method for the Introduction of 1,3-Dithiolan-2-yl Group into Active Methylene Compounds".

J. Org. Chem. 51, (month unavailable) 1986, pp. 2351-2361, Donald Mackey et al, "Michael Adducts of Hal-blocked enedione as sources of 3-Substituted 2,5-Diketones and 2,5-Dialkylfurans".

Synth. Commun., vol. 20, (month unavailable) 1990, pp. 2965-2970, Mao-chin Liu et al, A One-Pot synthesis of 3-Nitro- and 3,5-Dinitro-2-Picolines.

J. Med. Chem., 39, (month unavailable) 1996, pp. 3019-3029, Youichiro Naito et al, "Synthesis and Pharmacological Activity of Triazole Derivatives Inhibiting Eosinophilia".

Novinson T et al: "Synthesis and antifungal properties of certain 7-alkylaminopyrazolo(1,5-a) pyrimidines" Journal of Medicinal Chemistry, American Chemical Society, US, Bd. 20, Nr. 2, 1977, Seiten 296-299, XP002970049.

* cited by examiner

PYRAZOLOPYRIMIDINES

RELATED APPLICATIONS

The present patent application claims the right of priority under 35 U.S.C. 119 of German Patent Application 102004008807.1, filed Feb. 20, 2004.

BACKGROUND OF THE INVENTION

The invention relates to pyrazolopyrimidines, to a process for their preparation and to their use for controlling unwanted microorganisms.

It is already known that certain pyrazolopyrimidines have fungicidal properties (see, for example WO-A 02/048 151, WO-A 04/000 844 or FR-A 2 794 745).

However, since the ecological and economical demands made on modern fungicides are increasing constantly, for example with respect to activity spectrum, toxicity, selectivity, application rate, formation of residues and favourable manufacture, and there can furthermore be problems, for example, with resistance, there is a constant need to develop novel fungicides which, at least in some areas, have advantages over those of the prior art.

SUMMARY OF THE INVENTION

This invention now provides novel pyrazolopyrimidines of the formula (I),

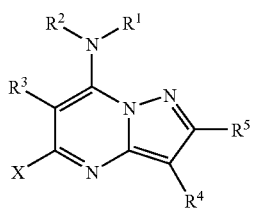

(I)

and agrochemically active salts thereof, in which $R^1$ is hydrogen, optionally substituted alkyl, optionally substituted alkenyl, optionally substituted alkynyl, optionally substituted cycloalkyl or optionally substituted heterocyclyl, hydroxyl, optionally substituted alkoxy, amine, optionally substituted alkylamine or optionally substituted dialkylamine;

$R^2$ is hydrogen or alkyl;

or $R^1$ and $R^2$ together with the nitrogen atom to which they are attached are an optionally substituted heterocyclic ring;

$R^3$ is optionally substituted aryl, optionally substituted heterocyclyl, optionally substituted alkyl, optionally substituted alkenyl, optionally substituted alkynyl, optionally substituted cycloalkyl, optionally substituted cycloalkenyl, optionally substituted aralkyl, halogen, an optionally substituted amino group, optionally substituted $(C_1-C_8)$-alkoxy, optionally substituted $(C_1-C_8)$-alkylthio, optionally substituted $(C_6-C_{10})$-aryloxy, optionally substituted $(C_6-C_{10})$-arylthio, optionally substituted heterocyclyloxy, optionally substituted $(C_6-C_{10})$-aryl-$(C_1-C_4)$-alkoxy, optionally substituted $(C_6-C_{10})$-aryl-$(C_1-C_4)$-alkylthio, optionally substituted heterocyclyl-$(C_1-C_4)$-alkoxy, or optionally substituted heterocyclyl-$(C_1-C_4)$-alkylthio, $C(S)OR^8$, $C(O)SR^8$ or $C(S)SR^8$;

$R^4$ is $CONR^6R^7$, $CONR^7-N(R^7)_2$, $CO-NR^7-OR^7$, $COOR^8$, $C(S)OR^7$, $C(O)SR^7$, $C(S)SR^7$, saturated partially or fully unsaturated or aromatic, optionally substituted 5- or 6-membered heterocyclyl, $SR^7$, $SOR^7$, $SO_2R^7$, $SO_3R^7$, $SON(R^7)_2$, $SO_2N(R^7)_2$, $P(O)(OR^7)_2$, $NR^7OR^7$, $-B(OR^7)_2$, $-(CR^7_2)_{0-6}-NR^7_2$ or $-(CR^7_2)_{0-6}-NR^7-NR^7_2$;

$R^5$ is H, halogen, optionally halogen-substituted alkyl or optionally halogen-substituted cycloalkyl, $O-(C_1-C_4)$-alkyl or $S(O)_{0-2}(C_1-C_4)$-alkyl;

X is halogen, cyano, hydroxyl, optionally substituted alkyl, optionally substituted alkoxy, optionally substituted phenyl, optionally substituted alkylthio, optionally substituted alkylsulphinyl or optionally substituted alkylsulphonyl;

$R^6$ is optionally substituted alkyl, optionally substituted alkenyl, optionally substituted alkynyl, optionally substituted cycloalkyl or optionally substituted cycloalkenyl, optionally substituted aryl and optionally substituted arylalkyl;

$R^7$ are identical or different and are H or $R^6$, or two radicals $R^7$ or one radical $R^7$ and one radical $R^6$ together form a cycle having 3 to 6 carbon atoms which is saturated or partially unsaturated and optionally contains 1 or 2 further nitrogen, sulphur or oxygen atoms, where oxygen atoms must not be adjacent to one another;

$R^8$ is H, a cation, for example an optionally alkyl- or aralkyl-substituted ammonium ion, substituted alkyl, optionally substituted alkenyl, optionally substituted alkynyl, optionally substituted cycloalkyl, optionally substituted cycloalkenyl or optionally substituted aralkyl.

DETAILED DESCRIPTION OF THE INVENTION

Pyrazolopyrimidines of the formula (I) are highly suitable for controlling unwanted microorganisms. Especially, they have strong fungicidal activity and can be used both in crop protection and in the protection of materials.

The compounds of the formula (I) can be present both in pure form and as mixtures of different possible isomeric forms, in particular of stereoisomers, such as E and Z, threo and erythro and also optical isomers, such as R and S isomers or atropisomers, and, if appropriate, also of tautomers. The invention encompasses both the pure isomers and their mixtures.

Depending on the nature of the substituents defined above, the compounds of the formula (I) have acidic or basic properties and are capable of forming salts, if appropriate also inner salts. If the compounds of the formula (I) carry hydroxyl groups, carboxyl groups or other groups which induce acidic properties, these compounds can be reacted with bases to form salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl radicals or aralkyl radicals, mono-, di- and trialkanolamines of $(C_1-C_4)$-alkanols, choline and chlorocholine. If the compounds of the formula (I) carry amino groups, alkylamino groups or other groups which induce basic properties, these compounds can be reacted with acids to give salts. Suitable acids are, for example, mineral acids, such as hydrochloric acid, sulphuric acid and phosphoric acid, organic acids, such as acetic acid or oxalic acid, and acetic salts, such as $NaHSO_4$ and $KHSO_4$. The salts obtainable in this manner also have fungicidal properties.

The formula (I) provides a general definition of the pyrazolopyrimidines according to the invention.

Preference is given to compounds of the formula (I) in which $R^4$ has one of the following meanings:

$a^1$: $CONR^6R^7$, $CONR7—N(R^7)_2$, $CONR^7—OR^7$, $COOR^8$, $CSOR^7$, $COSR^7$ or $CSSR^7$,
$a^2$: saturated, partially unsaturated or aromatic optionally substituted 5- or 6-membered heterocyclyl,
$a^3$: $SR^7$, $SOR^7$, $SO_2R^7$, $SO_3R^7$, $SON(R^7)_2$, or $SO_2N(R^7)_2$,
$a^4$: $P(O)—(OR^7)_2$,
$a^5$: $B(OR^7)_2$ or
$a^6$: $NR^7OR^7$.

Preference is also given to compounds of the formula (I) in which $R^4$ has one of the following meanings:
$a^1, a^1, a^2, a^3, a^4, a^5$
$a^2, a^1, a^2, a^3, a^4, a^6$
$a^3, a^1, a^2, a^3, a^5, a^6$
$a^4, a^1, a^2, a^3, a^4, a^5, a^6$
$a^5, a^1, a^3, a^4, a^5, a^6$
$a^6, a^2, a^3, a^4, a^5, a^6$ Preference is furthermore given to compounds of the formula (I) in which
$b^1$) $R^3$ represents optionally substituted aryl, or
$b^2$) $R^3$ represents optionally substituted heterocyclyl, or
$b^3$) $R^3$ represents optionally substituted alkyl, or
$b^4$) $R^3$ represents optionally substituted alkenyl, or
$b^5$) $R^3$ represents optionally substituted alkynyl, or
$b^6$) $R^3$ represents optionally substituted cycloalkyl, or
$b^7$) $R^3$ represents optionally substituted aralkyl, or
$b^8$) $R^3$ represents an optionally substituted amino group, or
$b^9$) $R^3$ represents optionally substituted $(C_1-C_8)$-alkylthio, or
$b^{10}$) $R^3$ represents optionally substituted $(C_1-C_8)$-alkoxy.

Preference is also given to compounds of the formula (I) in which $R^3$ has one of the following meanings:
$c^1$: $b^1, b^2, b^3, b^4, b^5, b^6, b^7, b^8, b^9$
$c^2$: $b^1, b^2, b^3, b^4, b^5, b^6, b^7, b^8, b^{10}$
$c^3$: $b^1, b^2, b^3, b^4, b^5, b^6, b^7, b^9, b^{10}$
$c^4$: $b^1, b^2, b^3, b^4, b^5, b^6, b^8, b^9, b^{10}$
$c^5$: $b^1, b^2, b^3, b^4, b^5, b^7, b^8, b^9, b^{10}$
$c^6$: $b^1, b^2, b^3, b^4, b^6, b^7, b^8, b^9, b^{10}$
$c^7$: $b^1, b^2, b^3, b^5, b^6, b^7, b^8, b^9, b^{10}$
$c^8$: $b^1, b^2, b^4, b^5, b^6, b^7, b^8, b^9, b^{10}$
$c^9$: $b^1, b^3, b^4, b^5, b^6, b^7, b^8, b^9, b^{10}$
$c^{10}$: $b^2, b^3, b^4, b^5, b^6, b^7, b^8, b^9, b^{10}$ Preference is furthermore given to those compounds of the formula (I) in which one or more groups have one of the preferred meanings given below, i.e., $R^1$ is hydrogen, alkyl having 1 to 10 carbon atoms which is unsubstituted or mono- to pentasubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or $R^1$ is alkenyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or $R^1$ is alkynyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or $R^1$ is cycloalkyl having 3 to 10 carbon atoms which is unsubstituted or mono- to trisubstituted by identical or different substituents from the group consisting of halogen and alkyl having 1 to 4 carbon atoms, or $R^1$ is saturated or unsaturated heterocyclyl having 3 to 10 ring members and 1 to 3 heteroatoms, such as nitrogen, oxygen and/or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms and/or mercapto;

$R^2$ is hydrogen or alkyl having 1 to 6 carbon atoms;

$R^1$ and $R^2$ together with the nitrogen atom to which they are attached are a saturated or unsaturated heterocyclic ring having 3 to 8 ring members, where the heterocycle optionally contains a further nitrogen, oxygen or sulphur atom as ring member and where the heterocycle may be unsubstituted or up to trisubstituted by fluorine, chlorine, bromine, alkyl having 1 to 4 carbon atoms, haloalkyl having 1 to 4 carbon atoms and 1 to 9 fluorine and/or chlorine atoms, hydroxyl, alkoxy having 1 to 4 carbon atoms, haloalkoxy having 1 to 4 carbon atoms and 1 to 9 fluorine and/or chlorine atoms, mercapto, thioalkyl having 1 to 4 carbon atoms and/or haloalkylthio having 1 to 4 carbon atoms and 1 to 9 fluorine and/or chlorine atoms;

$R^3$ is $C_1-C_{10}$-alkyl, $C_2-C_{10}$-alkenyl, $C_2-C_{10}$-alkynyl, $C_3-C_8$-cycloalkyl, phenyl-$C_1-C_{10}$-alkyl, where $R^3$ is unsubstituted or partially or fully halogenated and/or optionally carries one to three radicals from the group $R^X$, or $C_1-C_{10}$-haloalkyl which optionally carries one to three radicals from the group $R^X$, and $R^X$ is cyano, nitro, hydroxyl, $C_1-C_6$-alkyl, $C_1-C_6$-haloalkyl, $C_3-C_6$-cycloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, $C_1-C_6$-alkylamino, di-$C_1-C_6$-alkylamino, $C_2-C_6$-alkenyl, $C_2-C_6$-alkenyloxy, $C_2-C_6$-alkynyl, $C_3-C_6$-alkynyloxy and optionally halogenated oxy-$C_1-C_4$-alkyl-$C_1-C_4$-alkenoxy, oxy-$C_1-C_4$-alkenyl-$C_1-C_4$-alkoxy, oxy-$C_1-C_4$-alkyl-$C_1-C_4$-alkyloxy, or $R^3$ is phenyl which may be mono- to tetrasubstituted by identical or different substituents from the group consisting of halogen, cyano, nitro, amino, hydroxyl, formyl, carboxyl, carboxyalkyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6-carbon atoms in the individual alkyl moieties;

cycloalkyl having 3 to 8 carbon atoms;

1,3-propanediyl which is attached in the 2,3-position, 1,4-butanediyl, methylenedioxy (—O—$CH_2$—O—) or 1,2-ethylenedioxy (—O—$CH_2$—$CH_2$—O—), where these radicals may be mono- or polysubstituted by identical or different substituents from the group consisting of halogen, alkyl having 1 to 4 carbon atoms and haloalkyl having 1 to 4 carbon atoms and 1 to 9 identical or different halogen atoms;

or $R^3$ is saturated or fully or partially unsaturated or aromatic heterocyclyl having 3 to 8 ring members and 1 to 3 heteroatoms from the group consisting of nitrogen, oxygen and sulphur, where the heterocyclyl may be mono- or disubstituted by halogen, alkyl having 1 to 4 carbon atoms, alkoxy having 1 to 4 carbon atoms, alkylthio having 1 to 4 carbon atoms, haloalkoxy having 1 to 4 carbon atoms, haloalkylthio having 1 to 4 carbon atoms, hydroxyl, mercapto, cyano, nitro and/or cycloalkyl having 3 to 6 carbon atoms or/and carboxyalkyl;

$R^3$ is $C_1$-$C_8$-alkylamino, $C_2$-$C_8$-alkenylamino, $C_2$-$C_8$-alkynylamino, di-$C_1$-$C_8$-alkylamino, di-$C_2$-$C_8$-alkenylamino, di-$C_2$-$C_8$-alkynylamino, $C_2$-$C_8$-alkenyl-($C_2$-$C_8$)-alkynylamino, $C_2$-$C_6$-alkynyl-($C_1$-$C_8$)-alkylamino, $C_2$-$C_8$-alkenyl-($C_1$-$C_8$)-alkylamino, $C_6$-$C_{10}$-arylamino, $C_6$-$C_{10}$-aryl-($C_1$-$C_8$)-alkylamino, $C_6$-$C_{10}$-aryl-($C_1$-$C_4$)-alkyl-($C_1$-$C_8$)-alkylamino, heterocyclyl-($C_1$-$C_8$)-alkylamino or heterocyclyl-($C_1$-$C_4$)-alkyl-($C_1$-$C_8$)-alkylamino;

$R^4$ is $CONR^6R^7$, $CONR^7$—$N(R^7)_2$, $CO$—$NR^7$—$OR^7$, $COOR^8$, $CSOR^7$, $COSR^7$, $SR^7$, $SOR^7$, $SO_2R^7$, $SO_3R^7$, $SON(R^7)_2$, $SO_2N(R^7)_2$, $P(O)$—$(OR^7)_2$, $B(OR^7)_2$ or

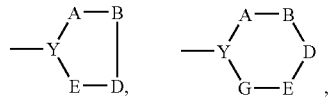

A, B, D, E, G are identical or different and are $CR^9$, $CR^9R^9$, N, $NR^9$, O or S, with the proviso that at least one such group is N, O or S and that oxygen atoms are not adjacent to one another;

Y is C, $CR^9$ or N;

$R^9$ is $R^7$, halogen, $NR^7_2$, OH, $SR^7$ or $OR^7$;

$R^5$ is H, halogen, ($C_1$-$C_4$)-alkyl which is unsubstituted or substituted by one or more halogen atoms, cyclopropyl which is unsubstituted or substituted by one or more halogen atoms, $SCH_3$, $SOCH_3$, $SO_2CH_3$ or $OCH_3$;

X is H, fluorine, chlorine, bromine, CN, hydroxyl, alkoxy having 1 to 4 carbon atoms or alkylthio having 1 to 4 carbon atoms;

$R^6$ is $C_1$-$C_{10}$-alkyl, $C_2$-$C_{10}$-alkenyl, $C_2$-$C_{11}$-alkynyl, $C_3$-$C_8$-cycloalkyl, $C_3$-$C_8$-cycloalkenyl, phenyl-$C_1$-$C_{10}$-alkyl, where $R^6$ is unsubstituted or partially or fully halogenated and/or optionally carries one to three radicals from the group $R^X$, or $C_1$-$C_{10}$-haloalkyl which optionally carries one to three radicals from the group $R^X$, and $R^X$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy and/or $CONR^6R^7$, $CONR^7OR^7$, $COOR^8$, carboxy-($C_1$-$C_4$)-alkyl;

$R^7$ is H or $R^6$, or two radicals $R^7$ or one radical $R^7$ and one radical $R^8$ together form a cycle having 3 to 6 carbon atoms which is saturated or partially unsaturated and optionally contains 1 or 2 further nitrogen, sulphur or oxygen atoms, where oxygen atoms may not be adjacent to one another;

$R^8$ is H, an alkali metal or alkaline earth metal, copper, $NH_4$, mono-($C_1$-$C_{10}$)-alkylammonium, di-($C_1$-$C_{10}$)-alkylammonium, tri-($C_1$-$C_{10}$)-alkylammonium, tetra-($C_1$-$C_{10}$)-alkylammonium, cholinium, $C_2$-$C_{10}$-alkenyl, $C_2$-$C_{10}$-alkynyl, $C_3$-$C_8$-cycloalkyl, $C_3$-$C_8$-cycloalkenyl, where $R^8$ is unsubstituted or partially or fully halogenated and/or optionally carries one to three radicals from the group $R^X$, or $C_1$-$C_{10}$-haloalkyl which optionally carries one to three radicals from the group $R^X$, or $C_1$-$C_{10}$-alkyl which is partially or fully halogenated and/or carries one to three radicals from the group $R^x$, and $R^X$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, $CONR^6R^7$, $CONR^7OR^7$, $COOR^8$, carboxy-$C_1$-$C_4$)-alkyl.

Particular preference is given to those pyrazolopyrimidines of the formula (I) in which one or more of the groups have one of the particularly preferred meanings listed below, i.e.

$R^1$ is hydrogen or a radical of the formula

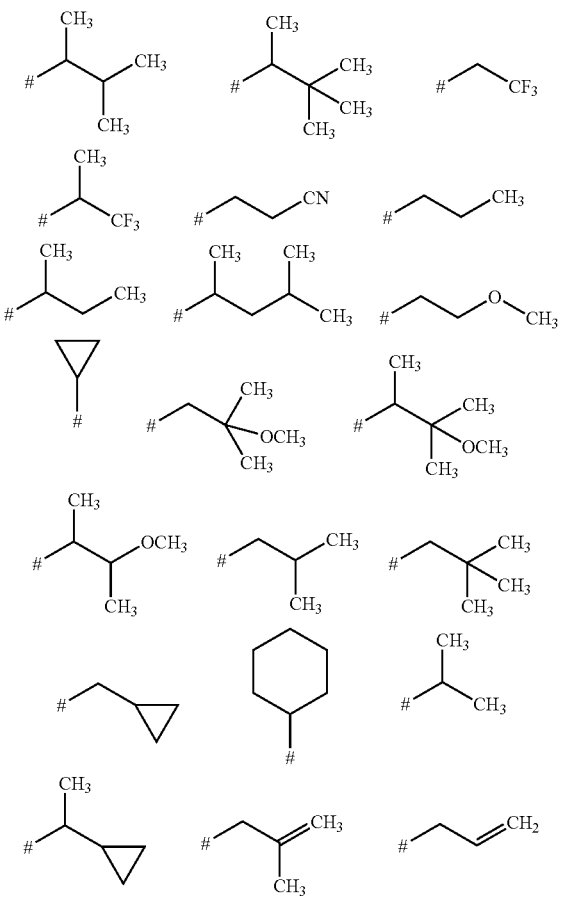

where # denotes the point of attachment (these radicals can be present both in optically pure form or as isomer mixtures);

$R^2$ is hydrogen, methyl, ethyl, propyl, or $R^1$ and $R^2$ together with the nitrogen atom to which they are attached are pyrrolidinyl, piperidinyl, morpholinyl, thiomorpholinyl, piperazinyl, 3,6-dihydro-1(2H)-pyridinyl or tetrahydro-1(2H)-pyridazinyl, where these radicals are unsubstituted or substituted by 1 to 3 fluorine atoms, 1 to 3 methyl groups and/or trifluoromethyl, or $R^1$ and $R^2$ together with the nitrogen atom to which they are attached are a radical of the formula

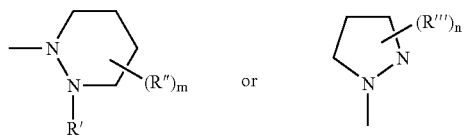

in which

R' represents hydrogen or methyl,

R'' represents methyl, ethyl, fluorine, chlorine or trifluoromethyl, m represents the number 0, 1, 2 or 3, where R'' represents identical or different radicals if m represents 2 or 3, R''' represents methyl, ethyl, fluorine, chlorine or trifluoromethyl and n represents the number 0, 1, 2 or 3, where R''' represents identical or different radicals if n represents 2 or 3;

$R^3$ is $(C_1-C_8)$-alkyl, $(C_1-C_8)$-cycloalkyl, where $R^3$ is unsubstituted or substituted by one or more fluorine or chlorine atoms, benzyl or $R^3$ is phenyl which may be mono- to trisubstituted by identical or different substituents from the group consisting of fluorine, chlorine, bromine, cyano, nitro, formyl, methyl, ethyl, n- or i-propyl, n-, i-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethynyloxy, trifluoroethynyloxy, chloroallyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl or cyclohexyl, or by 1,3-propanediyl which is attached in the 2,3-position, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents from the group consisting of fluorine, chlorine, methyl, ethyl, n-propyl, i-propyl, trifluoromethyl, carboxyl and carboxymethyl, $R^3$ is pyridyl which is attached in the 2- or 4-position and which may be mono- to tetrasubstituted by identical or different substituents from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl, or $R^3$ is pyrimidyl which is attached in the 2- or 4-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^3$ is thienyl which is attached in the 2- or 3-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^3$ is $C_1-C_8$-alkylamino or di-$C_1-C_8$-alkylamino, or $R^3$ is thiazolyl which is attached in the 2-, 4- or 5-position and which may be mono- or disubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^3$ is N-piperidinyl, N-tetrazolyl, N-pyrazolyl, N-imidazolyl, N-1,2,4-triazolyl, N-pyrrolyl or N-morpholinyl, each of which is unsubstituted or mono- or- if possible- polysubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl, $R^4$ is CONR$^6$R$^7$, CONR$^7$—N(R$^7$)$_2$, CO—NR$^7$—OR$^7$, COOR$^8$, CSOR$^7$, COSR$^7$, pyrrolyl, imidazolyl, pyrazolyl, 1,3,4-triazolyl, thiazolyl, 1,3,4-oxadiazolyl, 1,3,4-thiadiazolyl, oxazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1-C_4$-alkyl and halogen, SR$^7$, SOR$^7$, SO$_2$R$^7$, SO$_3$R$^7$, SON(R$^7$)$_2$, SO$_2$N(R$^7$)$_2$, P(O)—(OR$^7$)$_2$ or B(OR)$_2$;

$R^5$ is H, Cl, F, CH$_3$, —CH(CH$_3$)$_2$ or cyclopropyl; and

X is H, F, Cl, CN, $C_1-C_4$-alkyl which is unsubstituted or substituted by one or more fluorine or chlorine atoms;

$R^6$ is $(C_1-C_8)$-alkyl, $(C_3-C_6)$-alkenyl, $(C_1-C_8)$-cycloalkyl, benzyl, CONR$^6$R$^7$, CONR$^7$OR$^7$, COOR$^8$, carboxy-$(C_1-C_4)$-alkyl, cyano;

$R^7$ is H or $R^6$; or two radicals $R^7$ or one radical $R^6$ and one radical $R^7$ together form a cycle having 3 to 6 carbon atoms which is saturated or partially unsaturated and which optionally contains 1 or 2 further nitrogen, sulphur or oxygen atoms, where the oxygen atoms may not be adjacent to one another;

$R^8$ is H, Na, K, ½Ca, ½Mg, Cu, NH$_4$, NH(CH$_3$)$_3$, N(CH$_3$)$_4$, HN(C$_2$H$_5$)$_3$, N(C$_2$H$_5$)$_4$, H$_2$N(iC$_3$H$_7$)$_2$, $(C_1-C_4)$-alkyl which is optionally fully or partially substituted by F and/or Cl, CONR$^6$R$^7$, CONR$^7$OR$^7$, COOR$^8$, carboxy-$(C_1-C_4)$-alkyl($C_1-C_4$)-alkoxy-$(C_1-C_4)$-alkyl, allyl, propargyl, cyclopropyl, benzyl, $(CHR^Z—CHR^Z—O)_m—(C_1-C_4)$-alkyl, where $R^Z$=H, $CH_3$ and m=1 to 6.

Very particular preference is given to compounds of the formula (I) in which one or more of the groups have one of the very particularly preferred meanings listed below, i.e.

$R^1$ and $R^2$ have the particularly preferred meanings listed above;

$R^3$ is $(C_1-C_6)$-alkyl, $(C_3-C_6)$-alkenyl, $(C_3-C_6)$-alkynyl, $(C_3-C_8)$-cycloalkyl, where $R^3$ is unsubstituted or substituted by one or more fluorine or chlorine atoms and/or alkyl, or $R^3$ is 2,4-, 2,5- or 2,6-disubstituted phenyl or 2-substituted phenyl or 2,4,6- or 2,4,5-trisubstituted phenyl having substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^3$ is pyridyl which is attached in the 2- or 4-position and which may be mono- to tetrasubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^3$ is pyrimidyl which is attached in the 4-position and which may be mono- to trisubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl;

$R^3$ is thienyl which is attached in the 2- or 3-position and may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or $R^4$ is $CONR^6R^7$, $CONR^7—N(R^7)_2$, $CO—NR^7—OR^7$, $COOR^8$, 1H-pyrrolyl, 1H-imidazolyl, 1,3,4-oxadiazolyl, 1H-pyrazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1-C_4$-alkyl and halogen, $SR^7$, $SOR^7$, $SO_2R^7$, $SO_3R^7$, $SON(R^7)_2$, $SO_2N(R^7)_2$, or $P(O)—(OR^7)_2$;

$R^5$ is H, $—CH_3$, $—CH(CH_3)_2$, Cl or cyclopropyl; and

X is fluorine, chlorine, $(C_1-C_7)$-alkyl or $(C_1-C_3)$-haloalkyl;

$R^6$ is $(C_1-C_8)$-alkyl, $(C_3-C_6)$-alkenyl, $(C_1-C_8)$-cycloalkyl, benzyl, carboxy-$(C_1-C_4)$-alkyl, $CONR^6R^7$, $CONR^7OR^7$, $COOR^8$, cyano;

$R^7$ is H or $R^6$, or two radicals $R^7$ or one radical $R^6$ and one radical $R^7$ together form a cycle having 3 to 6 carbon atoms which is saturated or partially unsaturated and optionally contains 1 or 2 further nitrogen, sulphur or oxygen atoms, where oxygen atoms may not be adjacent to one another;

$R^8$ is H, Na, K, $NH_4$, $NH(Et)_3$, $H_2N(iPr)_2$, $H_2N(Bn_2)$, $H_3N(Bn)$, $(C_1-C_4)$-alkyl which is fully or partially substituted by F and/or Cl and/or carboxy-$(C_1-C_4)$-alkyl, $CONR^6R^7$, $CONR^7OR^7$, $COOR^8$, is $(C_1-C_4)$-alkoxy-$(C_1-C_4)$-alkyl, allyl, propargyl, cyclopropyl, benzyl, $(CHR^Z—CHR^Z—O)_m—(C_1-C_4)$-alkyl where $R^Z$=H, $CH_3$ and m=1 to 6.

The radical definitions mentioned above may be combined with one another as desired. Moreover, individual definitions may not apply.

Compounds of the formula (I) in which $R^4$ represents $CONR^6R^7$, $CONR^7—N(R_2)_2$, $CO—NR^7—OR^7$ or $COOR^8$ and X represents Cl can be prepared, for example, as shown in Scheme 1 starting with 3-aminopyrazole-4-carboxylic acid esters (II) which are known from the literature (see, for example, U.S. Pat. No. 3,515,715 and U.S. Pat. No. 3,634,391) and malonic acid esters (IIa) where $R^{11}$=$C_1-C_8$-alkyl or aryl:

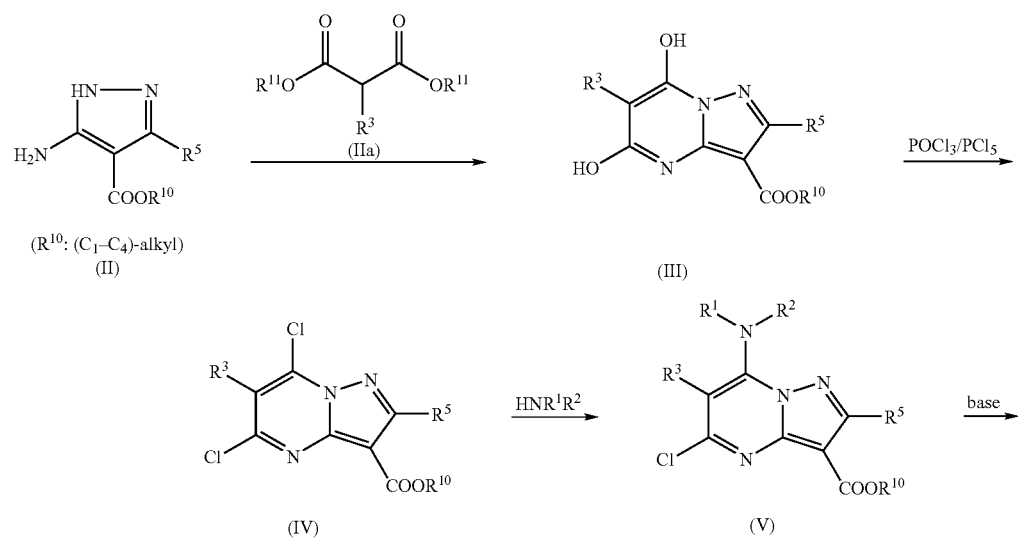

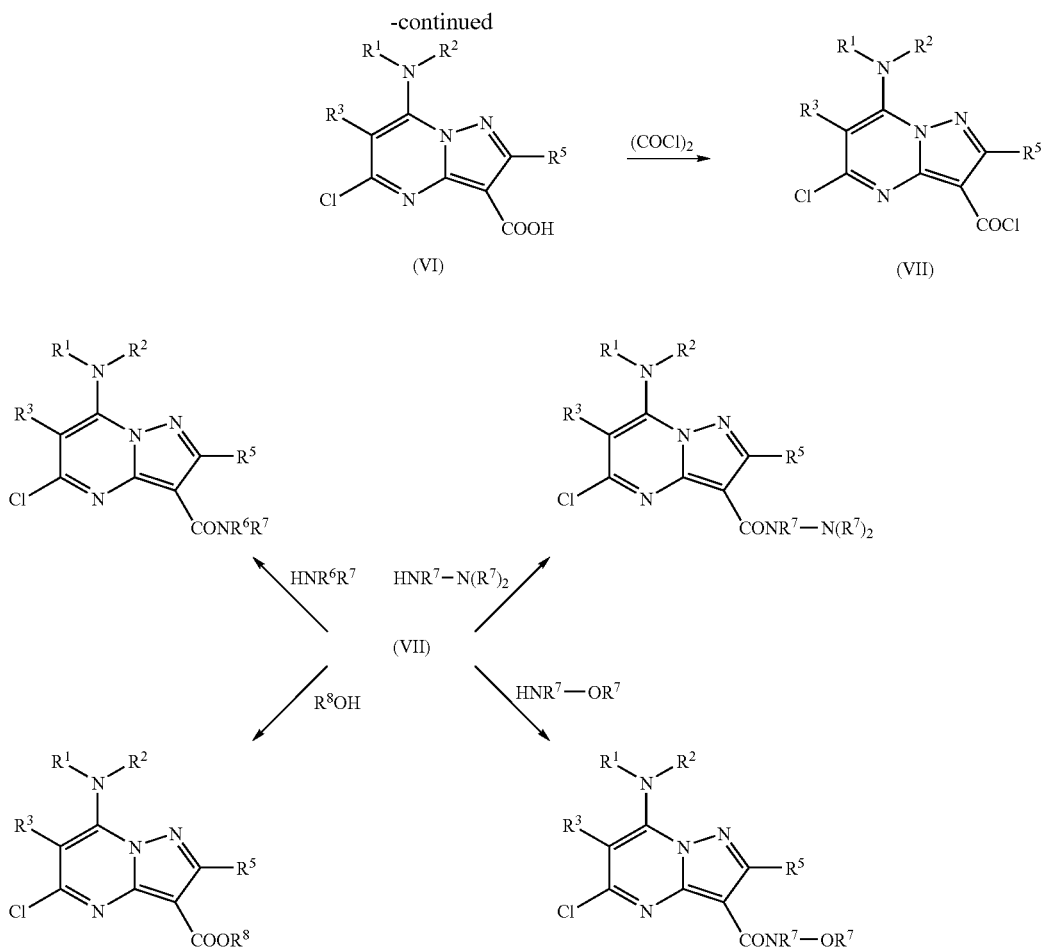

The intermediates of the formulae III, IV, V and VII are novel and also form part of the subject-matter of the invention.

The malonic acid ester (IIa) are known from the literature or can be prepared by processes known from literature (for example, $CR^3$=heterocyclyl), U.S. Pat. No. 6,156,925 ($R^3$=substituted phenyl), WO-A 03/009687 ($CR^3$=substituted alkyl), Chem. Ber. 1956, 89, 996 ($CR^3$=substituted cycloalkyl).

Malonic acid esters of the formula (IIa) where $R^3$=(2-chloro- or -methyl)-thiophen-3-yl can also be prepared according to Scheme 1a below.

Scheme 1a

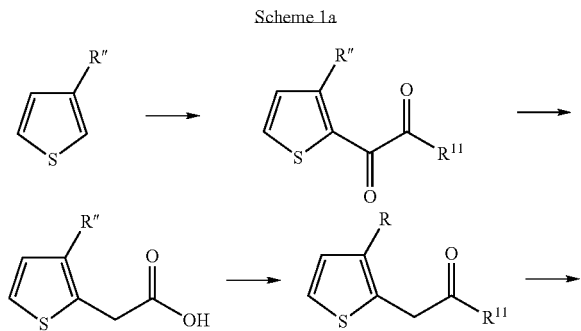

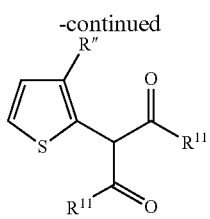

IIa

R″ = Me
R″ = Cl

Analogously to the last two steps of the synthesis sequence, dimethyl 2-(2-chlorothiophen-3-yl)malonate can also be prepared from (2-chlorothiophen-3-yl)acetic acid.

The step-wise conversion of the starting materials (II) into the amine (V) can be carried out, for example, analogously to the process of WO 04/000 844.

The amines, hydrazines, hydroxylamines or alcohols used for the further conversion of the acid chlorides (VII) are known. They are commercially available or can be prepared by known processes which are familiar to the person skilled in the art, as described, for example, in Houben-Weyl, methoden der Organischen Chemie [methods of Organic Chemistry].

Compounds of the formula (I) in which X represents a cyano group can be prepared, for example, starting with intermediates (V), as shown in Scheme 2.

Scheme 2
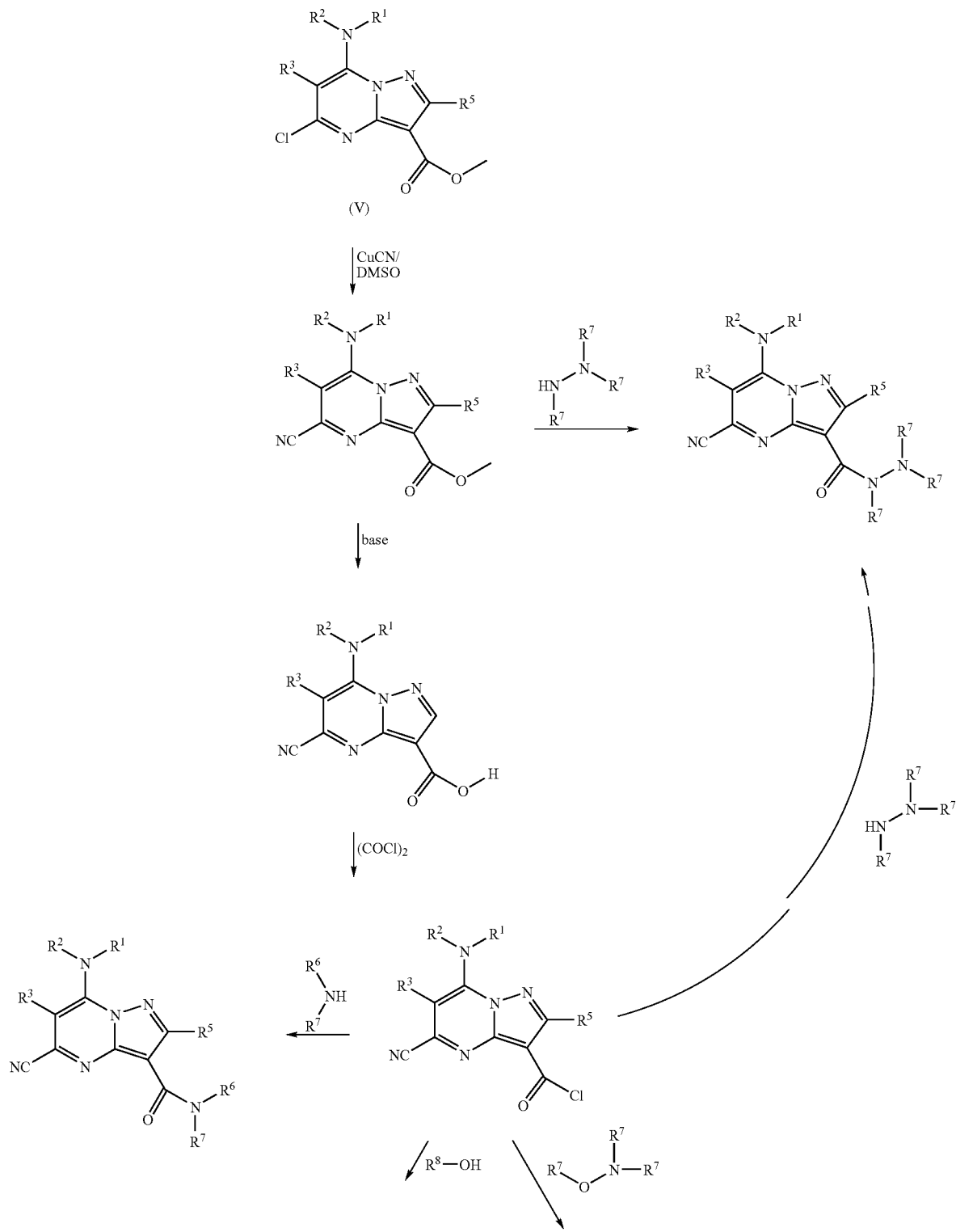

-continued
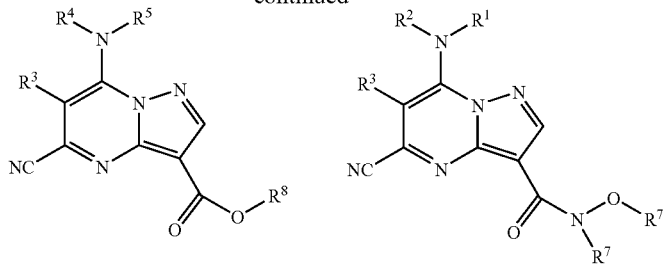
Compounds of the formula (I) in which X represents an optionally substituted alkyl or phenyl radical can be prepared from the esters (II), which are known from the literature, by reaction with β-keto esters, as shown in Scheme 3:
Scheme 3
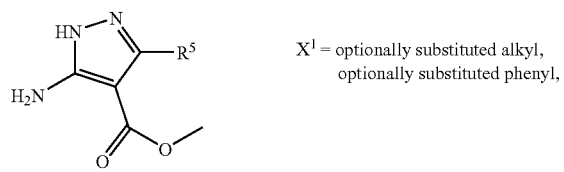
$X^1$ = optionally substituted alkyl, optionally substituted phenyl,
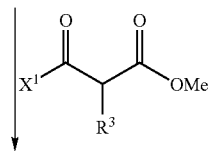
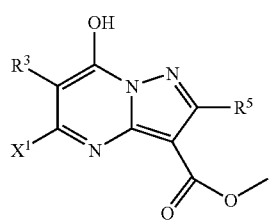
↓ POCl₃/PCl₅
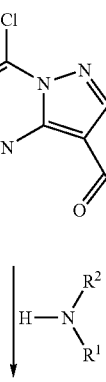

-continued
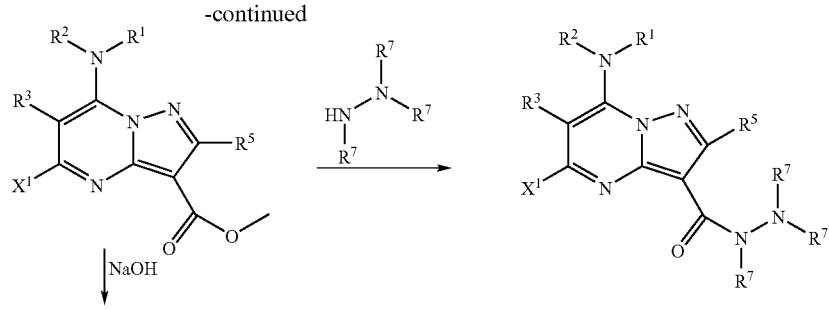
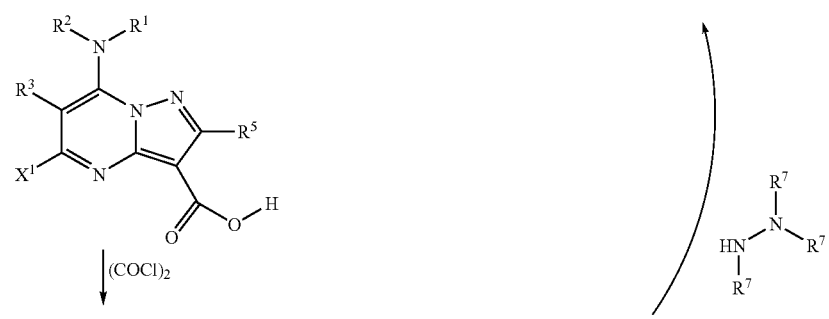
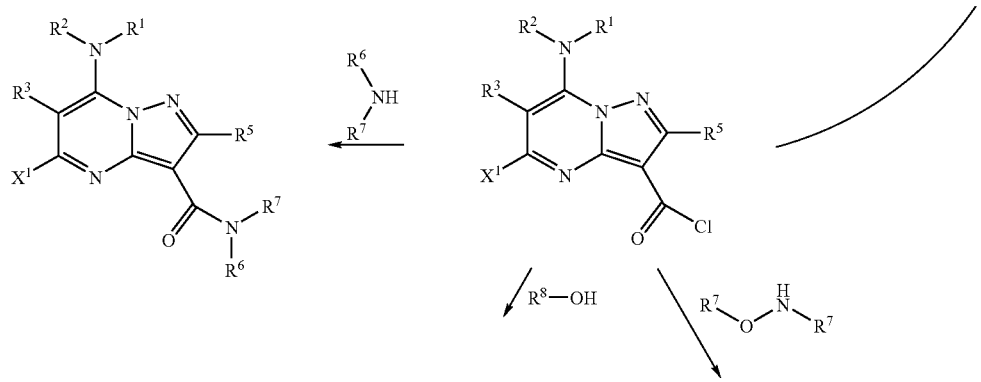
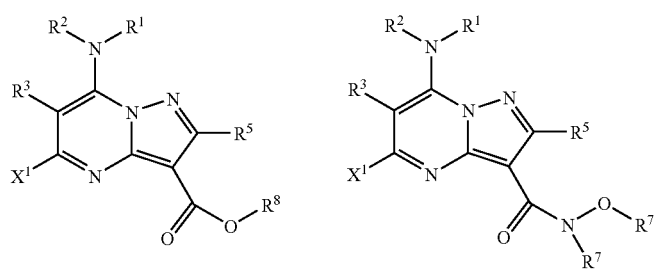
The synthesis of compounds of the formula (I) in which X represents a mercapto, sulphinyl or sulphonyl group is shown in Scheme 4 in an exemplary manner for compounds where $X=S(O)_{0-2}$—$CH_3$. Here, the cyanoalkenes can be prepared analogously to Compper et al., Chem. Ber. 1962, 95, 2861-70 or Chauhan et al., Tetrahedron 1976, 32, 1779-87.

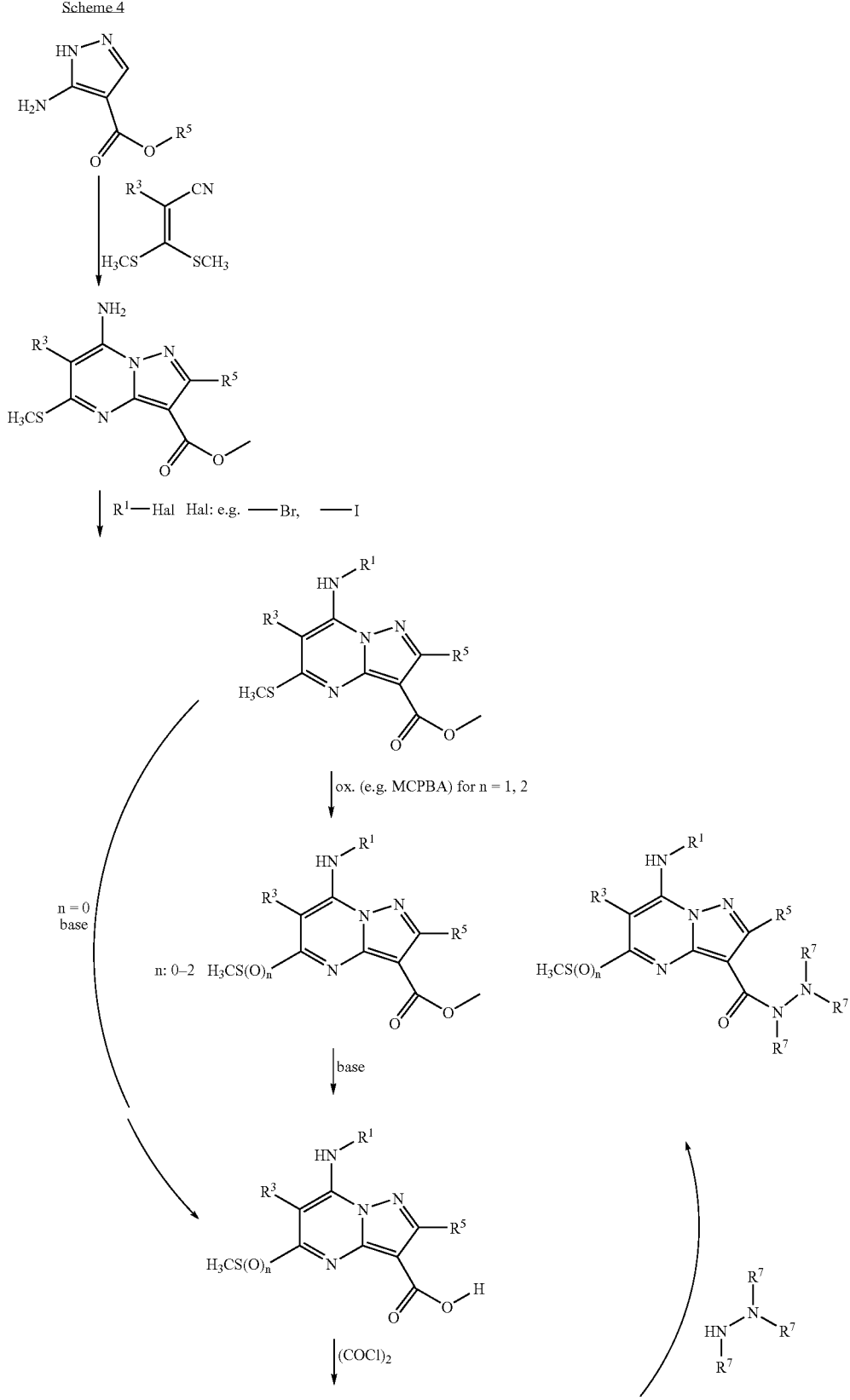

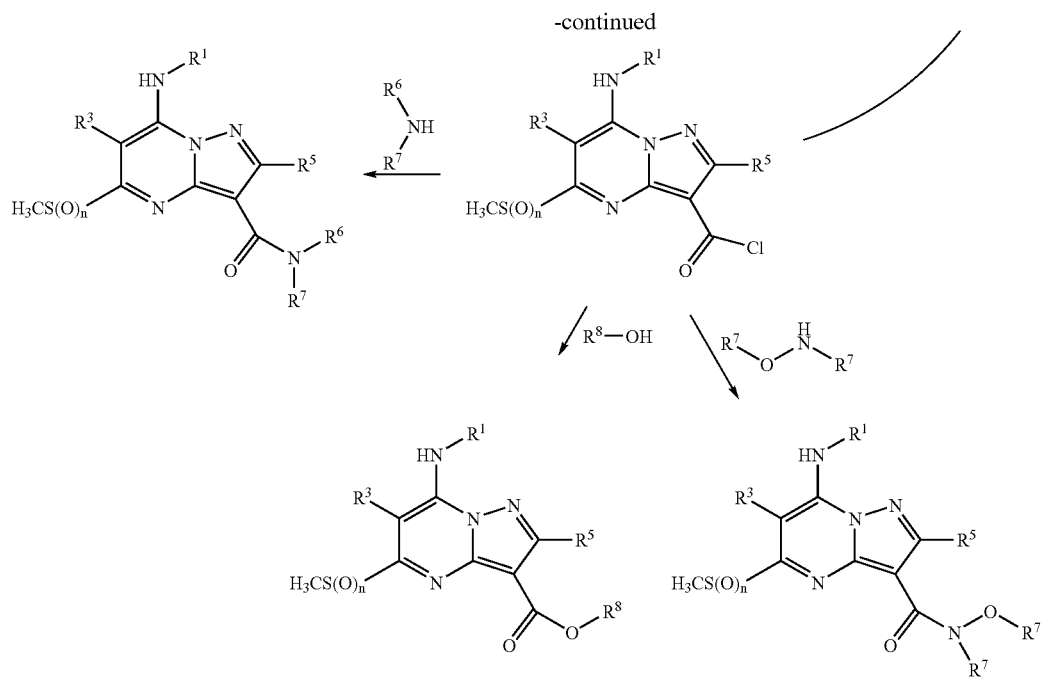

Compounds of the formula (I) in which R⁴ represents a sulphonic acid or sulphonamide radical and X represents Cl can be prepared, for example as shown in Scheme 5, where the synthesis of the starting materials can be carried out, for example, as described in WO-A 02/048151.

Scheme 5

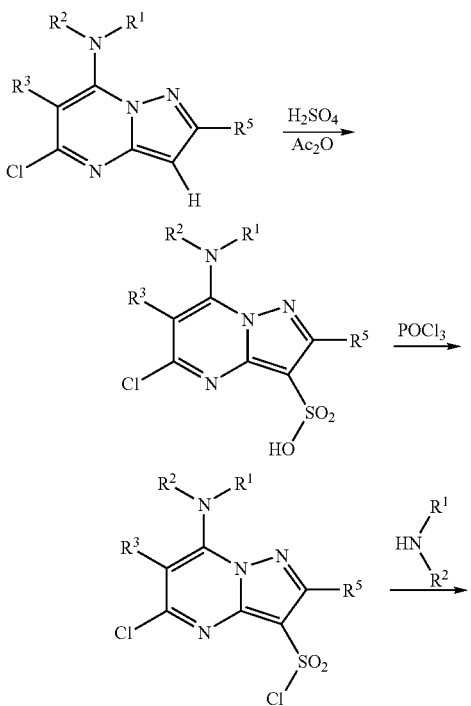

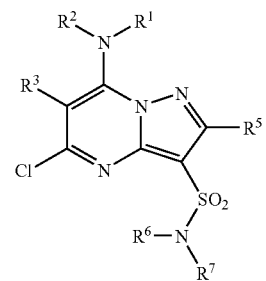

Compounds of the formula (I) in which R⁴ represents a mercapto, sulphinyl or sulphonyl radical and X represents Cl can be prepared, for example, as shown in Scheme 6 for R⁴=(S(O)$_{0-2}$—CH$_3$, where the starting materials can be synthesized, for example, as described in WO-A 02/048151.

Scheme 6

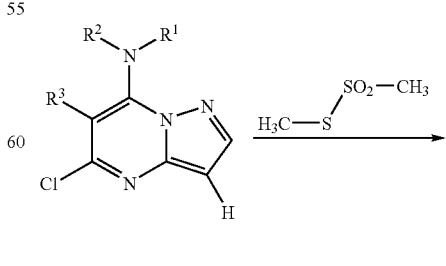

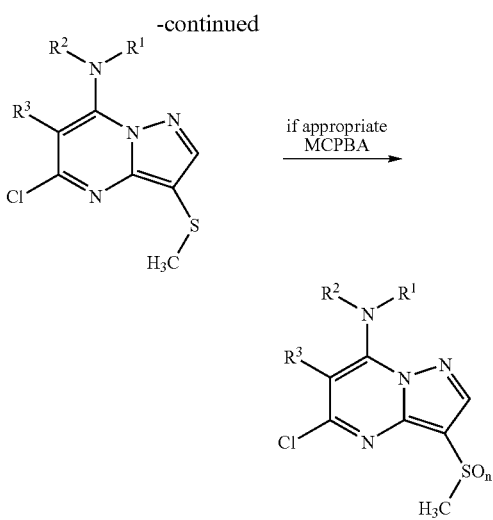

n = 1 or 2

Compounds of the formula (I) in $R^6$ represents an optionally substituted heterocyclyl group and X represents Cl can be prepared, for example, as shown in Scheme 7 for imidazole, where the starting material can be synthesized analogously to Kornfeld et al., J. Med. Chem. 1968, 11, 1028-31.

sium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributyl-amine, ethyldiisopropylamine, N,N-dimethylcyclohexylamine, dicyclohexylamine, ethyldicyclohexylamine, N,N-dimethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylaminopyridine, N-methylpiperidine, 1,4-diazabicyclo[2.2.2]octane (DABCO), 1,5-diazabicyclo[4.3.0]non-5-ene (DBN), or 1,8-diazabicyclo[5.4.0]undec-7-ene (DBU).

The processes according to the invention are preferably carried out using one or more diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and di-oxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide,

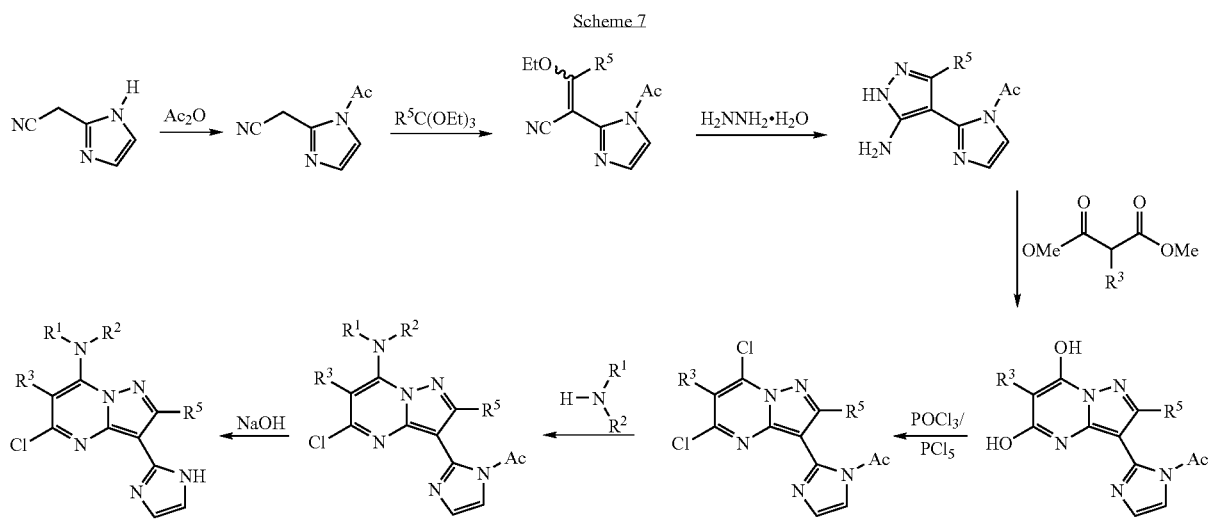

Scheme 7

The processes according to the invention for preparing the compounds of the formula (I) are preferably carried out using one or more reaction auxiliaries.

Suitable reaction auxiliaries are, if appropriate, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potasdimethylacetamide and N-methylpyrrolidone, and also dimethyl sulphoxide, tetramethylene sulphone and hexamethylphosphoric triamide.

The reaction temperatures in the processes according to the invention can be varied within a relatively wide range. In general, the processes are carried out at temperatures between 0° C. and 250° C., preferably at temperatures between 10° C. and 185° C.

The processes according to the invention are generally carried out under atmospheric pressure. However, it is also possible to operate under elevated or reduced pressure.

For carrying out the processes according to the invention, the starting materials required in each case are generally employed in approximately equimolar amounts. However, it is also possible to use a relatively large excess of one of the components employed in each case. Work-up in the processes according to the invention is in each case carried out by customary methods (cf. the Preparation Examples).

The compounds according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed with particularly good results for controlling cereal diseases, such as, for example, against Erysiphe species, and of diseases in viticulture and in the cultivation of fruit and vegetables, such as, for example, against Botrytis, Venturia, Sphaerotheca and Podosphaeva species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chloroinated aromatics or chloroinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benalaxyl-M, benodanil; benomyl; benthiavalicarb-isopropyl; benzamacril; benzamacril-isobutyl; bilanafos; binapacryl; biphenyl; bitertanol; blasticidin-S; boscalid; bromuconazole; bupirimate; buthiobate; butylamine; calcium polysulphide; capsimycin; captafol; captan; carbendazim; carboxin; carpropamid; carvone; chinomethionat; chlobenthiazone; chlorofenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph;

fluoromide; fluoxastrobin; fluquinconazole; flurprimidol; flusilazole; flusulphamide; flutolanil; flutriafol; folpet; fosetyl-A1; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloroaz; procymidone; propamocarb; propanosine-sodium; propiconazole; propineb; proquinazid; pro-thioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decane-3-amine; sodium tetrathiocarbonate;

and copper salts and preparations, such as Bordeaux mixture; copper hydroxide; copper naphthenate; copper oxychloride; copper sulphate; cufraneb; copper oxide; mancopper; oxinecopper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholinesterase (AChE) Inhibitors 1.1 carbamates (for example alanycarb, aldicarb, aldoxycarb, allyxycarb, aminocarb, azamethi-phos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 organophosphates (for example acephate, azamethiphos, azinphos (-methyl, -ethyl), bromophos-ethyl, bromfenvinfos (-methyl), butathiofos, cadusafos, carbophenothion, chloroethoxyfos, chlorofenvinphos, chloromephos, chloropyrifos (-methyl/-ethyl), coumaphos, cyanofenphos, cyanophos, chlorofenvinphos, demeton-s-methyl, demeton-s-methylsulphon, dialifos, diazinon, dichlofenthion, dichlorovos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemetonmethyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorovinphos, thiometon, triazophos, triclorfon, vamidothion)

2. Sodium Channel Modulators/Blockers of Voltage-dependent Sodium Channels 2.1 pyrethroids (for example acrinathrin, allethrin (d-cis-trans, d-trans), beta-cyfluthrin, bifenthrin, bioallethrin, bioallethrin-5-cyclopentyl-isomer, bioethanomethrin, biopermethrin, bioresmethrin, chlovaporthrin, cis-cypermethrin, cis-resmethrin, cis-permethrin, clocythrin, cycloprothrin, cyflu-thrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fen-valerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))

2.2 oxadiazines (for example indoxacarb)

3. Acetylcholine Receptor Agonists/Antagonists 3.1 chloronicotinyls/neonicotinoids (for example acetamiprid, clothianidin, dinotefuran, imidacloprid, nitenpyram, nithiazine, thiacloprid, thiamethoxam)

3.2 nicotine, bensultap, cartap

4. Acetylcholine Receptor Modulators 4.1 spinosyns (for example spinosad)

5. Antagonists of GABA-controlled Chloride Channels 5.1 cyclodiene organochlorines (for example camphechloro, chlordane, endosulfan, gamma-HCH, HCH, heptachloro, lindane, methoxychloro 5.2 fiproles (for example acetoprole, ethiprole, fipronil, vaniliprole)

6. Chloride Channel Activators 6.1 mectins (for example abamectin, avermectin, emamectin, emamectin-benzoate, ivermectin, milbemectin, milbemycin)

7. Juvenile-hormone Mimetics (for example diofenolan, epofenonane, fenoxycarb, hydroprene, kinoprene, methoprene, pyriproxifen, triprene)

8. Ecdyson Agonists/Disruptors 8.1 diacylhydrazines (for example chromafenozide, halofenozide, methoxyfenozide, tebufenozide)

9. Chitin Biosynthesis Inhibitors
   9.1 benzoylureas (for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron)
   9.2 buprofezin
   9.3 cyromazine 10. Inhibitors of Oxidative Phosphorylation, ATP Disruptors
    10.1 diafenthiuron
    10.2 organotins (for example azocyclotin, cyhexatin, fenbutatin-oxide)

11. Decouplers of Oxidative Phosphorylation Acting by Interrupting the H-proton Gradient
    11.1 pyrroles (for example chlorofenapyr)
    11.2 dinitrophenols (for example binapacryl, dinobuton, dinocap, DNOC)

12. Site-I Electron Transport Inhibitors
    12.1 METIs (for example fenazaquin, fenpyroximate, pyrimidifen, pyridaben, tebufenpyrad, tolfenpyrad)
    12.2 hydramethylnone
    12.3 dicofol 13. Site-II Electron Transport Inhibitors
    13.1 rotenone 14. Site-III Electron Transport Inhibitors
    14.1 acequinocyl, fluacrypyrim 15. Microbial disruptors of the insect gut membrane
    *Bacillus thuringiensis* strains 16. Inhibitors of Fat Synthesis
    16.1 tetronic acids (for example spirodiclofen, spiromesifen)
    16.2 tetramic acids [for example 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1)]

17. Carboxamides
    (for example flonicamid)

18. Octopaminergic Agonists
    (for example amitraz)

19. Inhibitors of Magnesium-stimulated ATPase
    (for example propargite)

20. Phthalamides
    (for example $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg. No.: 272451-65-7), flubendiamide)

21. Nereistoxin Analogues
    (for example thiocyclam hydrogen oxalate, thiosultap-sodium)

22. Biologicals, Hormones or Pheromones
    (for example azadirachtin, *Bacillus* spec., *Beauveria* spec., Codlemone, *Metarrhizium* spec., *Paecilomyces* spec., Thuringiensin, *Verticillium* spec.)

23. Active Compounds with Unknown or Unspecific Mechanisms of Action
    23.1 fumigants (for example aluminium phosphide, methyl bromide, sulphuryl fluoride)
    23.2 selective antifeedants (for example cryolite, flonicamid, pymetrozine)
    23.3 mite growth inhibitors (for example clofentezine, etoxazole, hexythiazox)
    23.4 amidoflumet, benclothiaz, benzoximate, bifenazate, bromopropylate, buprofezin, chinomethi-onat, chlorodimeform, chlorobenzilate, chloropicrin, clothiazoben, cycloprene, cyflumetofen, di-cyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo-isomer (CAS Reg. No. 185984-60-5) (cf. WO 96/37494, WO 98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum*, *Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5 000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The compounds of the formula (I) according to the invention are furthermore suitable for suppressing the growth of tumour cells in humans and mammals. This is based on an interaction of the compounds according to the invention with tubulin and microtubuli and by promoting microtubuli polymerization.

For this purpose, it is possible to administer an effective amount of one or more compounds of the formula (I) or pharmaceutically acceptable salts thereof.

The preparation and the use of the active compounds according to the invention is illustrated in the examples below.

EXAMPLES

Example I 5-chloro-6-(2-chloro-4-fluorophenyl)-7-(4-methylpiperidin-1-yl)-3-methylmercapto-pyrazolo [2,3-a] pyrimidine

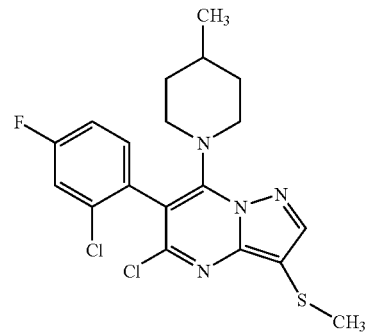

With stirring, 1.06 g of aluminium trichloride were initially added to 1 g of 5-chloro-6-(2-chloro-4-fluorophenyl)-7-(4-methylpiperidin-1-yl)pyrazolo[2,3-a]pyrimidine, the preparation of which is described, for example, in WO 02/048151, in 50 ml of dichloromethane, and 0.99 g of methyl methylthiosulphonate was then added dropwise. After 15 h of stirring at room temperature, the mixture was poured into ice-water and hydrochloric acid was added. The organic phase was separated off, and the aqueous phase was extracted two more times with in each case 15 ml of ethyl acetate. The combined organic phases were dried with sodium sulphate, and the solvent was removed under reduced pressure. The residue was chromatographed on silica gel using cyclohexane/ethyl acetate 4:1. This gave 0.65 g of an orange oil, $\log P_s = 5.73$.

Example II 5-chloro-6-(2-chloro-4-fluorophenyl)-7-(4-methylpiperidin-1-yl)-3-methylsulphonyl-pyrazolo[2,3-a]pyrimidine

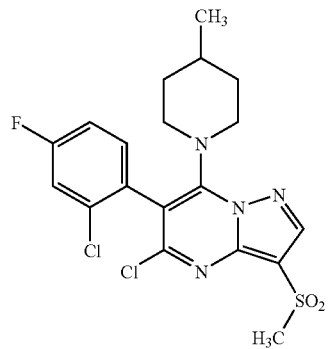

0.5 g of the compound obtained above was initially charged in 50 ml of dichloromethane. At room temperature, 0.58 g of 3-chloroperoxybenzoic acid was added, and the mixture was stirred at room temperature for another 24 h. The mixture was slightly concentrated using a rotary evaporator, and water and diethyl ether were then added and the mixture was made alkaline using aqueous ammonia. The mixture was extracted three times with diethyl ether, the combined organic phases were washed twice with aqueous ammonia and dried with sodium sulphate and the solvents were removed under reduced pressure. The residue was chromatographed on silica gel using cyclohexane/ethyl acetate 4:1. This gave 80 mg of a light-yellow solid, $\log P_s = 4.20$.

Example III 5-chloro-6-(2-chloro-4-fluorophenyl)-7-(4-methylpiperidin-1-yl)pyrazolo[2,3-a]pyrimidine-3-sulphonic acid

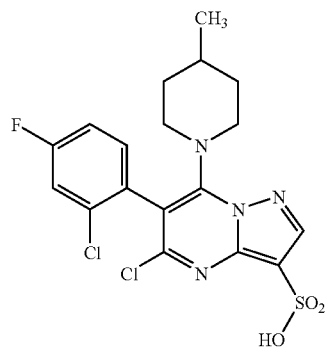

1 g of 5-chloro-6-(2-chloro-4-fluorophenyl)-7-(4-methylpiperidin-1-yl)pyrazalo[2,3-a]pyrimidine, the preparation of which is described, for example, in WO 02/048151, was initially charged in 20 ml of acetic anhydride, and 0.388 g of conc. sulphuric acid was added with ice-cooling. After 15 h of stirring at room temperature, the mixture was concentrated under reduced pressure and the residue was added to ice-water. The aqueous phase was extracted once with a little ethyl acetate, and the organic phase was discarded. The aqueous phase was filtered off with suction, and the residue was air-dried. This gave 80 mg of a pink solid, $\log P_s = 2.48$.

Example IV

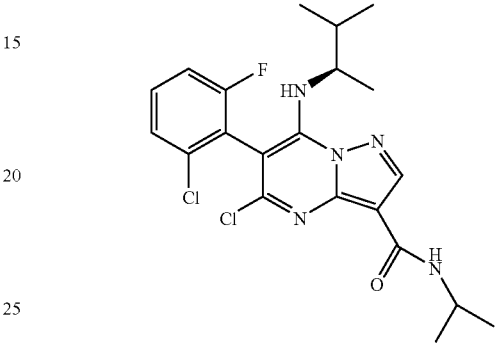

At room temperature, 0.185 g (1.46 mmol) of oxalyl chloride was added over a period of 5 minutes to 0.2 g (0.485 mmol) of 5-chloro-6-(2-chloro-6-fluorophenyl)-7-{[(1R)-1,2-dimethylpropyl]amino}pyrazolo[1,5-a]pyrimidine-3-carboxylic acid. The mixture was stirred for 30 minutes, until the evolution of gas had ceased. The reaction mixture was concentrated under reduced pressure and taken up in 5 ml of dichloromethane. At 25° C., the solution obtained in this manner was, over a period of 10 minutes, added dropwise to a mixture of 0.057 g (0.973 mmol) of isopropylamine and 5 ml of pyridine. The mixture was stirred at 25° C. for another 2 hours. 10 ml of dilute 1 N hydrochloric acid and 10 ml of dichloromethane was then added to the reaction mixture. The organic phase was dried over sodium sulphate and then concentrated under reduced pressure. The residue was chromatographed on silica gel using a mixture of cyclohexane: ethyl acetate=5:1. This gave 0.145 g of 5-chloro-6-(2-chloro-6-fluorophenyl)-7-{[(1R)-1,2-dimethylpropyl]amino}-N-isopropylpyrazolo[1,5-a]pyrimidine-3-carboxamide (logPs=4.72; content by HPLC: 93%).

Example V

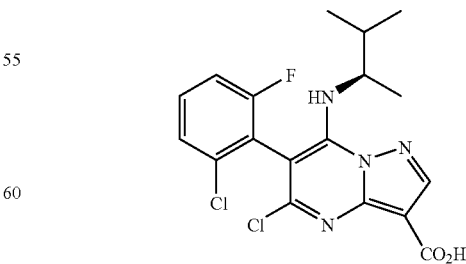

At room temperature, 2 g (4.7 mmol) of methyl 5-chloro-6-(2-chloro-6-fluorophenyl)-7-{[(1R)-1,2-dimethylpropyl]amino}pyrazolo[1,5-a]pyrimidine-3-carboxylate were mixed with a mixture of 50 ml of ethanol and 25 ml (25 mmol) of an aqueous 1 N solution of sodium hydroxide. The mixture was then stirred at 50° C. for 3 hours. The reaction mixture was concentrated under reduced pressure. 10 ml of dilute 1 N hydrochloric acid and 10 ml of dichloromethane were then added to the residue. The organic phase was dried over sodium sulphate and then concentrated under reduced pressure. This gave 1.7 g of 5-chloro-6-(2-chloro-6-fluorophenyl)-7-{[(1R)-1,2-dimethylpropyl]amino}pyrazolo[1,5-a]pyrimidine-3-carboxylic acid (logPs=3.24; content by HPLC: 92%).

Example VI a)

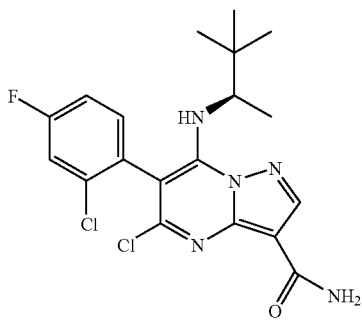

At 0° C., 0.50 g (1.23 mmol) of nitrile (described in WO-A 04/000 844) was stirred into 5 ml of conc. sulphuric acid and stirring at 0° C. was continued for 5 h, and the mixture was then stirred at RT for another 2 h. The mixture was stirred into ice and the resulting precipitate was filtered off with suction, washed thoroughly with water and dried.
Yield 0.48 g (80%), m.p. 190-2° C.
HPLC: logP=3.88 b)

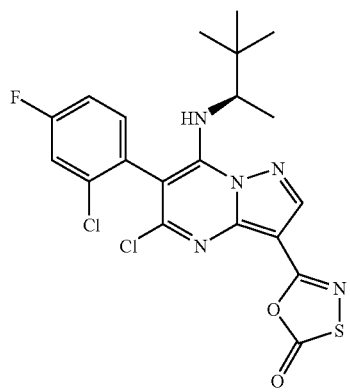

0.42 g (0.99 mmol) of amide in 25 ml of toluene was heated to 90° C., 0.21 g (1.58 mmol) of chlorocarbonylsulphenyl chloride was then added and the mixture was stirred at 90° C. for another 4 h. After the evolution of HCl had ended, the mixture was concentrated under reduced pressure and the residue was titrated thoroughly with petroleum ether and dried.
Yield 0.38 g (65%), m.p. 205-7° C. (decomp.)
HPLC: logP=5.38

Example VII

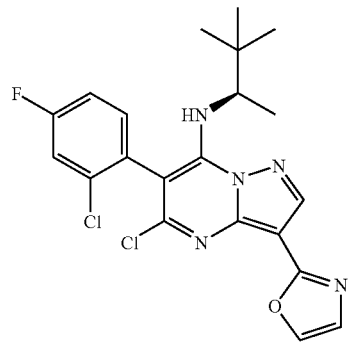

0.50 g (1.18 mmol) of the amide intermediate from Example VI a and 0.23 g (1.53 mmol) of chloroacetaldehyde diethyl acetal in 10 ml of ethanol were heated at the boil under reflux for 15 h. A further 0.23 g (1.53 mmol) of acetal was added, and the mixture was heated for another 15 h. The mixture was concentrated under reduced pressure, and the residue was purified on a silica gel cartridge (mobile phase: petroleum ether/MTBE 4:1).
Yield 0.14 g (19%)
HPLC: logP=4.72

Example VIII a)

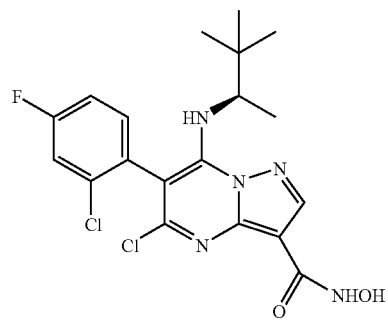

At RT, 0.5 g (1.13 mmol) of the appropriate acid chloride was dissolved in 15 ml of acetonitrile. 0.12 g (1.69 mmol) of hydroxylamine hydrochloride was added at RT, followed by 0.31 g (2.25 mmol) of potassium carbonate, also at RT. The mixture was stirred at RT for 1 hour, introduced into water, acidified and taken up in methylene chloride. The organic phase was washed with water, dried with sodium sulphate and concentrated under reduced pressure.
Yield 0.45 g (76%)
HPLC: logP=3.51 b)

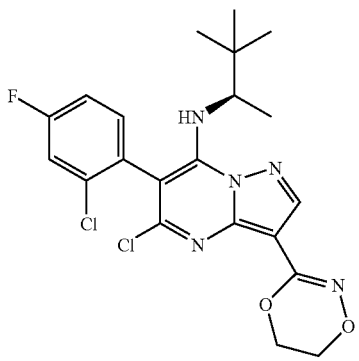

0.4 g (0.91 mmol) of hydroxamic acid was dissolved in 4 ml of methanol, and 0.30 g (1.36 mmol) of ethylene glycol bismesylate, followed by 0.13 g (0.91 mmol) of potassium carbonate dissolved in 1 ml of water, was added. The mixture was stirred at 60° C. for 30 min and then cooled to RT and introduced into a mixture of ice-water and dilute hydrochloric acid. The product was taken up in methylene chloride and the organic phase was extracted with water, dried with sodium sulphate and concentrated under reduced pressure. The oil that remained was chromatographed over a silica gel cartridge (mobile phase: petroleum ether/MTBE 4:1).

HPLC: logP=4.43

Examples IX and X a)

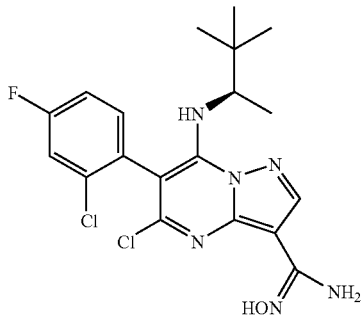

At RT, 0.4 g (0.99 mmol) of nitrile (described in WO-A 04/000 844) was dissolved in 25 ml of ethanol, and 0.10 g (1.48 mmol) of hydroxylammonium chloride and 0.8 g of Amberlyst A-21 were added. At RT, the mixture was shaken in a shaker overnight. To bring the reaction to completion, a further 0.04 g (0.59 mmol) of hydroxylammonium chloride and 0.2 g of Amberlyst A-21 were added, and the mixture was again shaken at RT overnight. After the Amberlyst A-21 had been filtered off with suction, the mother liquor was then concentrated under reduced pressure and the residue was purified on a silica gel cartridge (mobile phase: petroleum ether/MTBE 4:1).

Yield 0.24 g (55%), m.p. 233-6° C.

HPLC: logP=2.47 b)

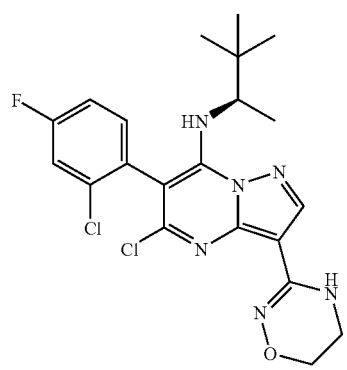

Ex. IX

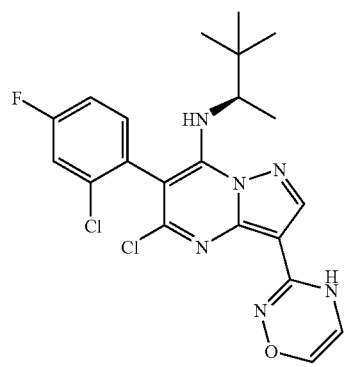

Ex. X
Atropisomers "A" and "B"

At RT, a suspension of 2.20 g (5.00 mmol) of amidoxime and 1.40 g (25.00 mmol) of powdered potassium hydroxide in 60 ml of acetonitrile was added to 1.09 g (5.00 mmol) of ethylene glycol bismesylate in 40 ml of acetonitrile, and the mixture was heated at the boil under reflux for 24 h. After cooling to RT, the mixture was poured into water, adjusted to pH 3 to 4 using dilute hydrochloric acid and extracted with ethyl acetate, and the organic phase was washed with water, dried with sodium sulphate and concentrated under reduced pressure. The residue was chromatographed on a silica gel cartridge (mobile phase: cyclohexane/ethyl acetate, gradient 9:1, 3:1, 1:1).

Fraction 1: Ex. X, yield 0.17 g (7%), (atropisomer "A")

HPLC: logP=4.87

Fraction 2: Ex. X, yield 0.18 g (8%), (atropisomer "B")

HPLC: logP=4.90

Fraction 3: Ex. IX, yield 0.03 g (1%)

HPLC: logP=3.23

Example XI a) analogously to Example IXa:

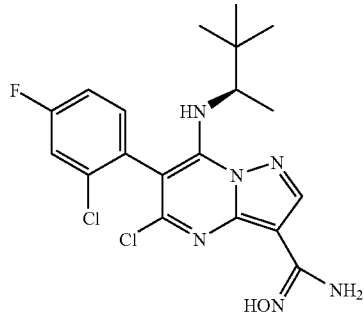

Yield 21.6 g (88%)
HPLC: logP=2.41 b) analogously to Example IX b:

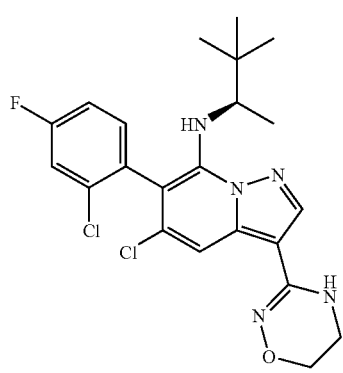

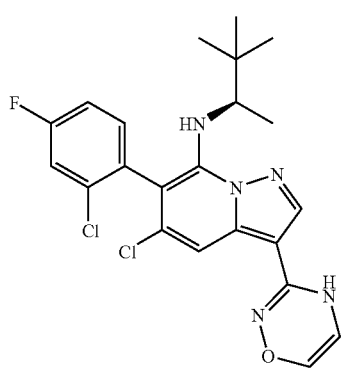

Atropisomers "A" and "B"

Yield 0.19 g (9%)
HPLC: logP=2.84

Example XII a)

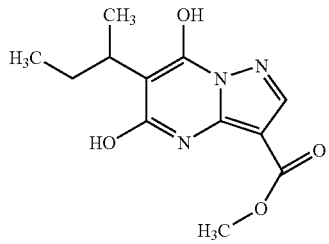

With stirring, a mixture of 10 g (0.046 mol) of diethyl sec-butylmalonate, 6.5 g (0.046 mol) of methyl 5-amino-1H-pyrazole-3-carboxylate and 9.4 g (0.051 mol) of tri-n-butylamine was heated at 180° C. for 6 hours. During this time, the ethanol released during the reaction was continuously distilled off. The reaction mixture was then concentred under reduced pressure. This gave 12.2 g (100% of theory) of methyl 5,7-dihydroxy-6-(sec-butyl)-pyrazolo[1,5-a]pyrimidine-3-carboxylate. The product was used for further syntheses without additional purification.

b)

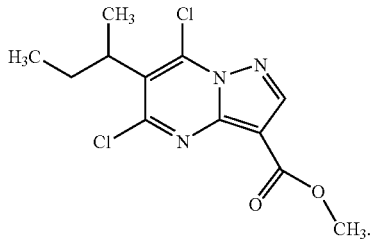

At room temperature, 5.5 g (0.026 mol) of phosphorus pentachloride were added with stirring to a mixture of 12.2 g (0.046 mol) of methyl 5,7-dihydroxy-6-(sec-butyl)-pyrazolo[1,5-a]pyrimidine-3-carboxylate and 63.1 g (0.412 mol) of phosphorus oxychloride. The reaction mixture was heated at 110° C. for 3 hours and then concentrated under reduced pressure. The residue that remained was dissolved in dichloromethane. The solution formed was initially washed with ice-water and then dried over sodium sulphate and concentrated under reduced pressure. The residue that remained was chromatographed on silica gel using petroleum ether:tert-butyl methyl ether=2:1. This gave 4.6 g (29.1% of theory) of methyl 5,7-dichloro-6-(sec-butyl)-pyrazolo[1,5-a]pyrimidine-3-carboxylate (content according to HPLC: 88%).

HPLC: logP=3.13 c)

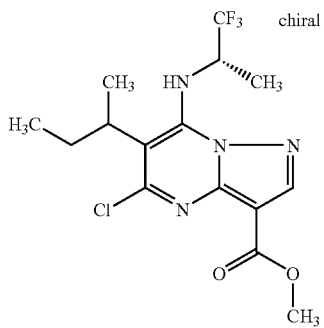

1.0 g (0.003 mol) of methyl 5,7-dichloro-6-(sec-butyl)-pyrazolo[1,5-a]pyrimidine-3-carboxylate and 0.92 g (0.003 mol) of potassium fluoroide in 10 ml of acetonitrile were stirred at 60° C. for 3 hours. 0.75 g (0.007 mol) of (S)-trifluoromethylisopropylamine were then added, and the mixture was stirred at 80° C. for 5 hours. The mixture was then allowed to cool to room temperature, acidified by addition of hydrochloric acid and extracted with dichloromethane. The combined organic phases were dried over sodium sulphate and then concentrated under reduced pressure. The residue that remained was chromatographed on silica gel using cyclohexane:ethyl acetate=8:2. This gave 0.4 g (31.3% of theory) of methyl 5-chloro-6-(sec-butyl)-7-[(S)-3-trifluoroisopropylamino]pyrazolo[1,5-a]pyrimidine-3-carboxylate.

HPLC: logP=3.76 d)

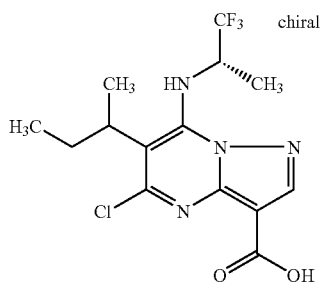

0.3 g (0.001 mol) of methyl 5-chloro-6-(sec-butyl)-7-[(S)-3-trifluoroisopropylamino]pyrazolo[1,5-a]pyrimidine-3-carboxylate was dissolved in 4.5 ml of dioxane. 0.63 g (0.0016 mol) of sodium hydroxide in 8 ml of an aqueous solution was added at room temperature, and the reaction mixture was then stirred for 100 hours. The mixture was then poured into water, acidified with hydrochloric acid and extracted with ethyl acetate. The organic phase was dried over sodium sulphate and concentrated under reduced pressure. The residue was chromatographed on silica gel using cyclohexane:ethyl acetate=8:2. This gave 0.15 g of 5-chloro-6-(sec-butyl)-7-[(S)-3-trifluoroisopropylamino]pyrazolo[1,5-a]pyrimidine-3-carboxylic acid.

HPLC: logP=2.88.

The following compounds were prepared analogously:

Example XIII a)

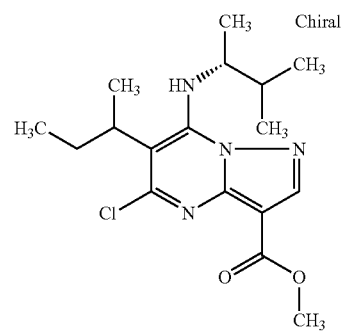

methyl 5-chloro-6-(sec-butyl)-7-[(R)-3-methyl-2-butylamino][1,5-a]pyrimidine-3-carboxylate HPLC: logP=4.49 b)

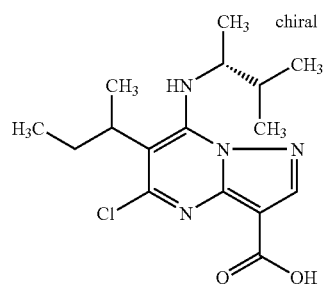

5-chloro-6-(sec-butyl)-7-[(S)-3-trifluoroisopropylamino]pyrazolo[1,5-a]pyrimidine-3-carboxylic acid HPLC: logP=3.52

Example XIV a)

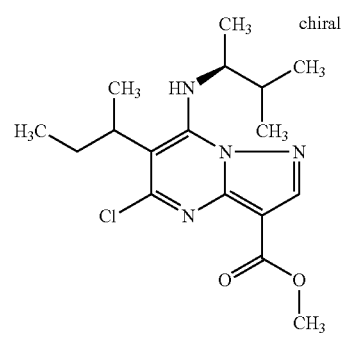

methyl 5-chloro-6-(sec-butyl)-7-[(S)-3-methyl-2-butylamino]pyrazolo[1,5-a]pyrimidine-3-carboxylate HPLC: logP=4.49 b)

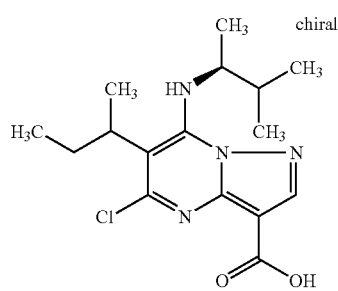

5-chloro-6-(sec-butyl)-7-[(S)-3-methyl-2-butylamino]pyrazolo[1,5-a]pyrimidine-3-carboxylic acid
HPLC: logP=3.52

Example XV a)

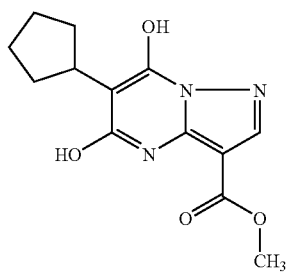

With stirring, a mixture of 14.15 g (0.071 mol) of dimethyl cyclopentylmalonate (WO2004/006926), 10 g (0.071 mol) of methyl 5-amino-1H-pyrazole-3-carboxylate and 14.4 g (0.078 mol) of tri-n-butylamine was heated at 180° C. for 6 hours. The methanol released during the reaction was continuously distilled off. The reaction mixture was then concentrated under reduced pressure. This gave 19.7 g (100% of theory) of methyl 5,7-dihydroxy-6-cyclopentylpyrazolo[1,5-a]pyrimidine-3-carboxylate. The product was used for further syntheses without additional purification.

b)

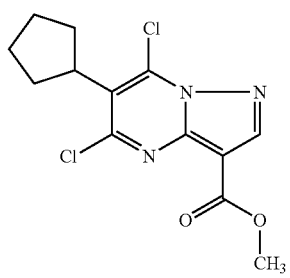

At room temperature, 8.4 g (0.04 mol) of phosphorus pentachloride were added with stirring to a mixture of 19.6 g (0.071 mol) of methyl 5,7-dihydroxy-6-cyclopentylpyrazolo[1,5-a]pyrimidine-3-carboxylate and 96.5 g (0.629 mol) of phosphorus oxychloride. The reaction mixture was heated at 110° C. for 3 hours and then concentrated under reduced pressure. The residue that remained was dissolved in dichloromethane. The solution formed was initially washed with ice-water and then dried over sodium sulphate and concentrated under reduced pressure. The residue that remained was chromatographed on silica gel using petroleum ether:tert-butyl methyl ether=2:1. This gave 4.5 g (20% of theory) of methyl 5,7-dichloro-6-cyclopentylpyrazolo[1,5-a]pyrimidine-3-carboxylate (content according to HPLC: 98%).

HPLC: logP=3.31 c)

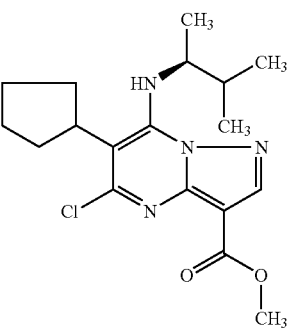

0.33 g (0.004 mol) of (R)-3-methyl-2-butylamine and 0.4 g (0.004 mol) of triethylamine were initially charged in dichloroethane. At 0° C., 1.0 g (0.003 mol) of methyl 5,7-dichloro-6-cyclopentylpyrazolo[1,5-a]pyrimidine-3-carboxylate was added. The mixture was then stirred at room temperature for 12 hours. The mixture was then acidified by addition of hydrochloric acid and extracted with diethyl ether. The organic phase was dried over sodium sulphate and then concentrated under reduced pressure. The residue was titrated with a mixture of diethyl ether and petroleum ether. This gave 0.1 g of 5-chloro-6-cyclopentyl-7-[(R)-3-methyl-2-butylamino]-pyrazolo[1,5-a]pyrimidine-3-carboxylic acid.

HPLC: logP=4.72

The following compounds were prepared analogously:

methyl 5-chloro-6-cyclopentyl-7-[(S)-3-methyl-2-butylamino]pyrazolo[1,5-a]pyrimidine-3-carboxylate HPLC: logP=4.72

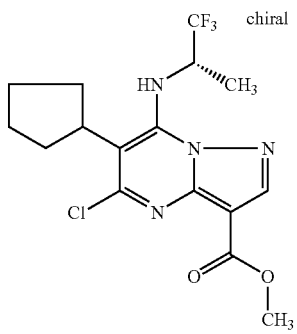

methyl 5-chloro-6-cyclopentyl-7-[(S)-3-trifluoroisopropylamino]pyrazolo[1,5-a]pyrimidine-3-carboxylate HPLC: logP=3.89 d)

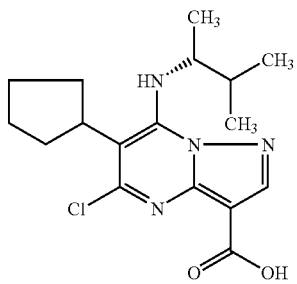

0.5 g (0.001 mol) of methyl 5-chloro-6-cyclopentyl-7-[(R)-3-methyl-2-butylamino]pyrazolo[1,5-a]pyrimidine-3-carboxlate was initially charged in 8 ml of dioxane. At room temperature, 0.63 g (0.016 mol) of potassium hydroxide in 8 ml of an aqueous solution was added, and the reaction mixture was then stirred for 1 hour. The mixture was then poured into water, acidified with hydrochloric acid and extracted with diethyl ether. The organic phase was dried over sodium sulphate and concentrated under reduced pressure. The residue was titrated with a mixture of diethyl ether and petroleum ether, filtered off with suction and dried. This gave 0.1 g of 5-chloro-6-cyclopentyl-7-[(R)-3-methyl-2-butylamino]pyrazolo[1,5-a]pyrimidine-3-carboxylic acid.

HPLC: logP=3.7

The following compounds were obtained analogously:

Example XVI

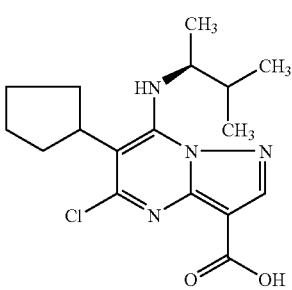

HPLC: logP=3.7

Example XVII

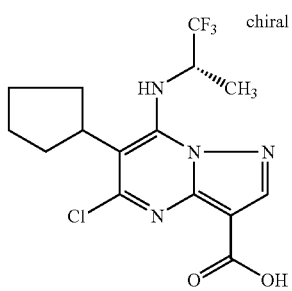

5-chloro-6-cyclopentyl-7-[(S)-3-trifluoroisopropylamino]pyrazolo[1,5-a]pyrimidine-3-carboxylic acid HPLC: logP=3.06

Example XVIII a)

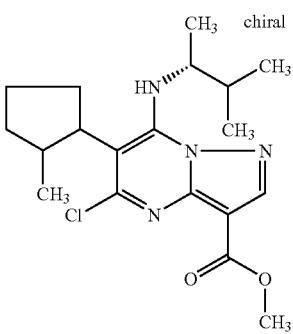

methyl 5-chloro-6-cyclopentyl-7-[(R)-3-methyl-2-butylamino]pyrazolo[1,5-a]pyrimidine-3-carboxylate HPLC: logP=4.99 b)

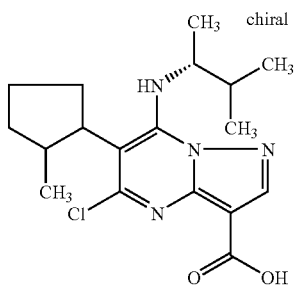

5-Chloro-6-cyclopentyl-7-[(R)-3-methyl-2-butylamino]pyrazolo[1,5-a]pyrimidine-3-carboxylic acid HPLC: logP=3.93

Example XIX a)

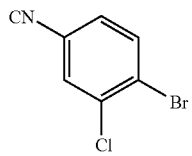

25 g (0.164 mol) of 3-amino-4-brombenzonitrile were initially charged in 230 ml of 48% strength hydrobromic acid. At from 0° C. to at most 5° C., 11.3 g (0.164 mol) of sodium nitrite, dissolved in water, were added dropwise. After the addition had ended, excess nitrous acid was destroyed by addition of urea. With stirring at 0° C., the solution was added dropwise to solution of 31.26 g (0.218 mol) of copper(I) bromide and 500 ml of 48% strength hydrobromic acid. The reaction mixture was then heated at 100° C. After the evolution of nitrogen had ceased, the mixture was cooled to room temperature and extracted with ethyl acetate. The organic phase was washed with aqueous sodium hydroxide solution, dried and concentrated. This gave 21.6 g of 3-chloro-4-brombenzonitrile.

HPLC: logP=2.82 b)

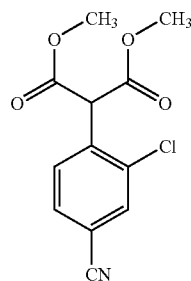

7.6 g (0.191 mol) of 60% strength sodium hydride in paraffin oil were initially charged in 300 ml of dioxane. At from 55° C. to 60° C., 22.9 g (0.173 mol) of diethyl malonate were added dropwise, and the mixture was stirred at 50° C. for 1-2 hours. 9.9 g (0.069 mol) of copper(1) bromide were added. At 80° C., 15 g (0.069 mol) of 3-chloro-4-bromobenzonitrile were then added dropwise, and the mixture was subsequently stirred at 100° C. for 14 hours. The reaction mixture was then cooled and acidified by dropwise addition of concentrated hydrochloric acid at from 15° C. to 20° C. Water was added, the mixture was extracted with dichloromethane, the organic phase was dried over sodium sulphate and the solvent was removed. The residue was distilled at 1 mbar, giving 17.5 g of dimethyl(2-chloro-4-cyanophenyl)malonate.

HPLC: logP=2.34 c)

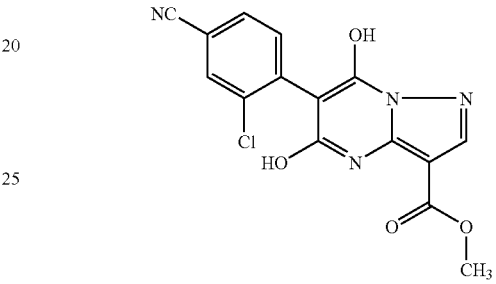

With stirring, a mixture of 10 g (0.037 mol) of dimethyl(2-chloro-4-cyanophenyl)malonate, 5.2 g (0.037 mol) of methyl 5-amino-1H-pyrazole-3-carboxylate and 7.6 g (0.041 mol) of tri-n-butyl-amine was heated at 180° C. for 6 hours. The methanol released during the reaction was continuously distilled off. The reaction mixture was then concentrated under reduced pressure. This gave 12.8 g (100% of theory) of methyl 5,7-dihydroxy-6-(2-chloro-4-cyanophenyl)pyrazolo[1,5-a]pyrimidine-3-carboxylate. The product was used for further syntheses without additional purification.

d)

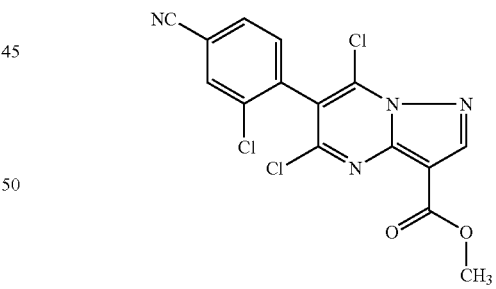

At room temperature, 4.4 g (0.021 mol) of phosphorus pentachloride were added with stirring to a mixture of 12.8 g (0.037 mol) of methyl 5,7-dihydroxy-6-(2-chloro-4-cyanophenyl)pyrazolo[1,5-a]pyrimidine-3-carboxylate and 50.5 g (0.329 mol) of phosphorus oxychloride. The reaction mixture was heated at 1 10° C. for 3 hours and then concentrated under reduced pressure. The residue that remained was dissolved in dichloromethane. The solution formed was initially washed with ice-water and then dried over sodium sulphate and concentrated under reduced pressure. The residue that remained was chromatographed on silica gel using petroleum ether:tert-butyl methyl ether=2:1. The product was then titrated with diethyl ether and filtered off with suction. This gave 2.2 g of methyl 5,7-dichloro-6-(2-chloro-4-cyanophenyl)pyrazolo[1,5-a]pyrimidine-3-carboxylate.

HPLC: logP=2.85 e)

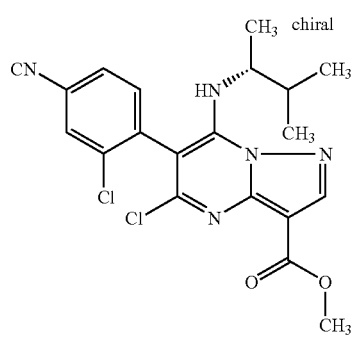

0.274 g (0.003 mol) of (R)-3-methyl-2-butylamine and 0.318 g (0.003 mol) of triethylamine were initially charged in dichloroethane. At 0° C., 1.0 g (0.003 mol) of methyl 5,7-dichloro-6-(2-chloro-4-cyanophenyl)pyrazolo[1,5-a]pyrimidine-3-carboxylate was added. The mixture was then stirred at room temperature for 12 hours. The mixture was then acidified by addition of hydrochloric acid and extracted with dichloromethane. The organic phase was dried over sodium sulphate and then concentrated under reduced pressure. The residue that remained was chromatographed on silica gel using tert-butyl methyl ether:petroleum ether=1:1. This gave 0.4 g of methyl 5-chloro-6-(2-chloro-4-cyanophenyl)-7-[(R)-3-methyl-2-butylamino]pyrazolo[1,5-a]pyrimidine-3-carboxylate as atropisomer A.

HPLC: logP=3.64

A further 0.4 g of methyl 5-chloro-6-(2-chloro-4-cyanophenyl)-7-[(R)-3-methyl-2-butylamino]pyrazolo[1,5-a]pyrimidine-3-carboxylate was obtained as atropisomer B.

HPLC: logP=3.74

The following compounds were obtained analogously:

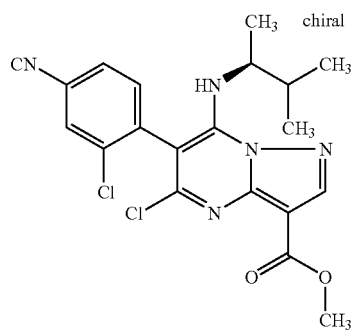

methyl 5-chloro-6-(2-chloro-4-cyanophenyl)-7-[(S)-3-methyl-2-butylamino]pyrazolo[1,5-a]pyrimidine-3-carboxylate, atropisomer A HPLC: logP=3.72 methyl 5-chloro-6-(2-chloro-4-cyanophenyl)-7-[(S)-3-methyl-2-butylamino]pyrazolo[1,5-a]pyrimidine-3-carboxylate, atropisomer B HPLC: logP=3.74

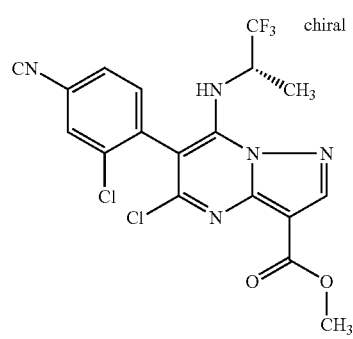

methyl 5-chloro-6-(2-chloro-4-cyanophenyl)-7-[(S)-trifluoroisopropylamino]pyrazolo-[1,5-a]pyrimidine-3-carboxylate HPLC: logP=3.32 atropisomer A
HPLC: logP=3.37 atropisomer B f)

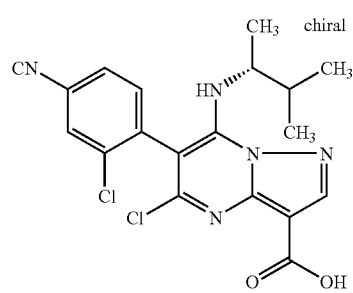

0.35 g (0.001 mol) of atropisomer A of methyl 5-chloro-6-(2-chloro-4-cyanophenyl)-7-[(R)-3-methyl-2-butylamino]pyrazolo[1,5-a]pyrimidine-3-carboxylate were dissolved in 4.6 ml of dioxane. 0.37 g (0.009 mol) of potassium hydroxide in 4.6 ml of aqueous solution was added at room temperature, and the reaction mixture was then stirred for 12 hours. The mixture was then poured into water and acidified with hydrochloric acid. 0.15 g of product was filtered off. The product was chromatographed on silica gel using ethyl acetate:cyclohexane:acetic acid=40:10:1, which gave the atropisomer A of 5-chloro-6-(2-chloro-4-cyanophenyl)-7-[(R)-3-methyl-2-butyl-amino]pyrazolo[1,5-a]pyrimidine-3-carboxylic acid.

HPLC: logP=2.90

Example XX

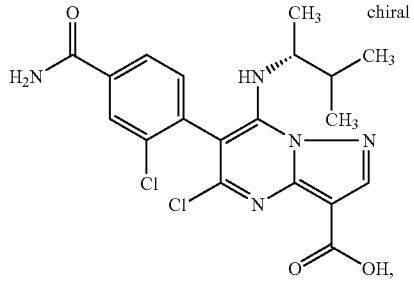

the Atropisomer A of 5-chloro-6-(2-chloro-4-aminocarbonylphenyl)-7-[(R)-3-methyl-2-butyl-amino]pyrazolo[1,5-a]pyrimidine-3-carboxylic acid HPLC: logP=1.96

The following compound was obtained analogously:

Atropisomer B of 5-chloro-6-(2-chloro-4-cyanophenyl)-7-[(R)-3-methyl-2-butylamino]-pyrazolo[1,5-a]pyrimidine-3-carboxylic acid HPLC: logP=2.92

Example XXI

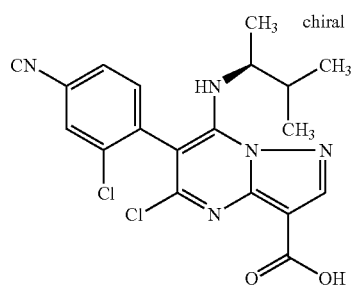

Atropisomer A of 5-chloro-6-(2-chloro-4-cyanophenyl)-7-[(S)-3-methyl-2-butylamino]-pyrazolo[1,5-a]pyrimidine-3-carboxylic acid HPLC: logP=2.90

Atropisomer B of 5-chloro-6-(2-chloro-4-cyanophenyl)-7-[(S)-3-methyl-2-butylamino]-pyrazolo[1,5-a]pyrimidine-3-carboxylic acid HPLC: logP=2.91

Example XXII

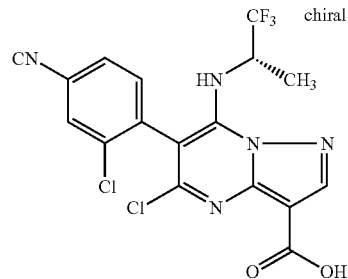

5-chloro-6-(2-chloro-4-cyanophenyl)-7-[(S)-trifluoroisopropylamino]pyrazolo[1,5-a]pyrimidine-3-carboxylic acid HPLC: logP=2.63 atropisomer B

Example XXIII a)

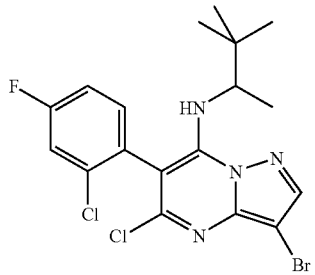

0.220 g (0.577 mol) of 5-chloro-6-(2-chloro-4-fluorophenyl)-N-(1,2,2-trimethylpropyl)-pyrazolo[1,5-a]pyrimidin-7-amine (which can be prepared according to processes from WO 2004 000844) was initially charged in 2 ml of DMF. At room temperature, a solution of 0.103 g (0.577 mmol) of N-bromosuccinimide was added dropwise with stirring, over a period of a few minutes. The mixture was stirred for another 30 minutes. The reaction mixture was then poured into water. The solid was subsequently filtered off with suction and dried. This gave 0.150 g (55% of theory) of 3-bromo-5-chloro-6-(2-chloro-4-fluorophenyl)-N-(1,2,2-trimethylpropyl)pyrazolo[1,5-a]pyrimidin-7-amine (content according to HPLC: 98%).

HPLC: logP=5.78 b)

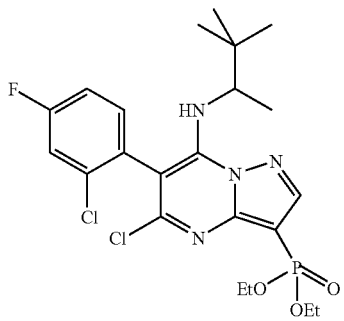

At −78° C., 0.200 g (0.435 mmol) of 3-bromo-5-chloro-6-(2-chloro-4-fluorophenyl)-N-(1,2,2-trimethylpropyl)pyrazolo[1,5-a]pyrimidin-7-amine was initially charged in 10 ml of tetrahydrofuran. At −78° C., 0.54 ml (0.869 mmol) of a 1.6 molar solution of n-butyllithium in hexane was slowly added dropwise. After 30 minutes, 0.082 g (0.478 mmol) of diethyl chlorophosphate, dissolved in 1 ml of THF, was added dropwise. After a further 30 minutes of stirring at −78° C., the mixture was poured into a mixture of 3 ml of 1 N HCl solution and 3 ml of dichloromethane. The phases were separated and the organic phase was then dried over sodium sulphate and subsequently concentrated under reduced pressure. The residue that remained was chromatographed on silica gel using cyclohexane:ethyl acetate=3:1, 1:1. This gave 0.050 g (20% of theory) of diethyl {5-chloro-6-(2-chloro-4-fluorophenyl)-7-[(1,2,2-trimethylpropyl)-amino]pyrazolo[1,5-a]pyrimidin-3-yl}phosphonate (content according to HPLC: 91%).

HPLC: logP=4.48

Example XXIV

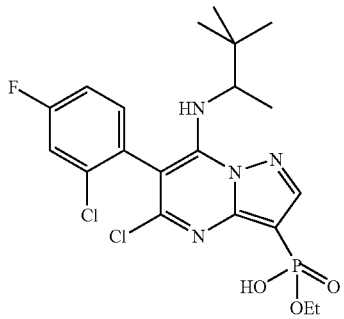

At 100° C., 0.430 g (0.831 mmol) of diethyl {5-chloro-6-(2-chloro-4-fluorophenyl)-7-[(1,2,2-trimethylpropyl)amino]pyrazolo[1,5-a]pyrimidin-3-yl}phosphonate was stirred for 3 hours in 2 ml of a concentrated solution of hydrochloric acid (36% strength in water). The mixture was then allowed to cool to room temperature and poured into a mixture of 5 ml of water and 5 ml of ethyl acetate. The combined organic phases were dried over sodium sulphate and then concentrated under reduced pressure. The residue that remained was chromatographed on silica gel using toluene:acetone=10:1, 1:1 and then dichloromethane:methanol=9:1. This gave 0.040 g (9% of theory) of ethyl hydrogen {5-chloro-6-(2-chloro-4-fluorophenyl)-7-[(1,2,2-trimethylpropyl)-amino]pyrazolo[1,5-a]pyrimidin-3-yl}phosphonate (content according to HPLC: 85%).

HPLC: logP=3.01

Example XXV a)

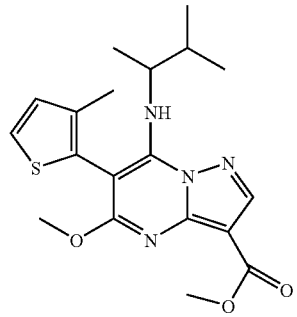

methyl 7-(1,2-dimethylpropylamino)-5-methoxy-6-(3-methylthiophen-2-yl)pyrazolo[1,5-a]-pyrimidine-3-carboxylate 0.17 g (3 mmol) of sodium methoxide was dissolved in 10 ml of methanol, and 0.79 g (2 mmol) of methyl 7-(1,2-dimethylpropylamino)-5-chloro-6-(3-methylthiophen-2-yl)pyrazolo[1,5-α]-pyrimidine-3-carboxylate was added. The mixture was stirred at 22° C. for 16 hours. 10 ml of water were then added, the methanol was distilled off and 10 ml of dichloromethane were added to the residue. The organic phase was separated off, dried over sodium sulphate and concentrated under reduced pressure. This gave 0.35 g of methyl 7-(1,2-dimethylpropylamino)-5-methoxy-6-(3-methylthiophen-2-yl)pyrazolo[1,5-α]pyrimidine-3-carboxylate (logPs=4.60; content according to HPLC: 96%).

b)

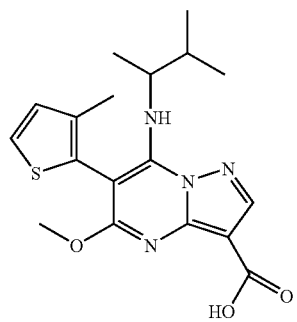

7-(1,2-dimethylpropylamino)-5-methoxy-6-(3-methylthiophen-2-yl)pyrazolo[1,5-α]pyrimidine-3-carboxylic acid At room temperature, 0.2 g (0.55 mmol) of methyl 7-(1,2-dimethylpropylamino)-5-methoxy-6-(3-methylthiophen-2-yl)pyrazolo[1,5-α]pyrimidine-3-carboxylate was mixed with a mixture of 5 ml of 1,4-dioxane and 2.5 ml (2.5 mmol) of a 1 N sodium hydroxide solution. The mixture was then stirred at 22° C. for 16 hours. 5 ml of water and 3 ml of 1 N hydrochloric acid were added to the reaction mixture. The precipitate formed was filtered off, washed with water and dried. This gave 0.2 g of 7-(1,2-dimethylpropylamino)-5-methoxy-6-(3-methylthiophen-2-yl)pyrazolo[1,5-α]-pyrimidine-3-carboxylic acid (logPs=3.65; content according to HPLC: 96%).

Example XXVI a)

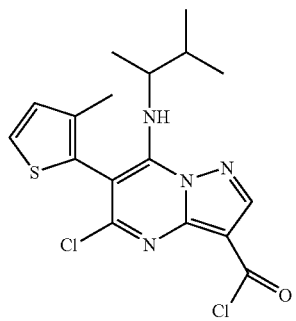

5-chloro-7-(1,2-dimethylpropylamino)-6-(3-methylthiophen-2-yl)pyrazolo[1,5-α]pyrimidine-3-carbonyl chloride At room temperature, 6.6 g (56 mmol) of thionyl chloride were added to 10.6 g (28 mmol) of 5-chloro-7-(1,2-dimethylpropylamino)-6-(3-methylthiophen-2-yl)pyrazolo[1,5-α] pyrimidine-3-carbxylic acid in 120 ml of toluene, and the mixture was stirred under reflux for 3 hours. The reaction mixture was then concentrated under reduced pressure. This gave 11.0 g of 5-chloro-7-(1,2-dimethylpropylamino)-6-(3-methylthiophen-2-yl)pyrazolo[1,5-α]pyrimidine-3-carbonyl chloride, which was reacted directly.

b)

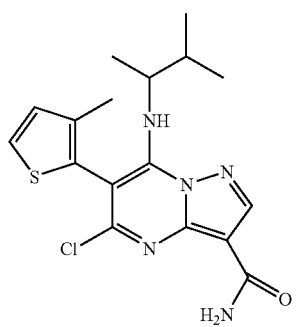

5-chloro-7-(1,2-dimethylpropylamino)-6-(3-methylthiophen-2-yl)pyrazolo[1,5-α]pyrimidine-3-carboxamide At room temperature, 15 ml of concentrated aqueous ammonia were added to 4.0 g (10 mmol) of 5-chloro-7-(1,2-dimethylpropylamino)-6-(3-methylthiophen-2-yl)pyrazolo[1,5-α]pyrimidine-3-carbonyl chloride in 30 ml of tetrahydrofuran. The mixture was stirred at 22° C. for 16 hours, and 50 ml of ethyl acetate were then added. The organic phase was separated off, dried over sodium sulphate and concentrated under reduced pressure. This gave 3.0 g of 5-chloro-7-(1,2-dimethyl-propylamino)-6-(3-methylthiophen-2-yl)pyrazolo[1,5-α]pyrimidine-3-carboxamide (logPs=3.5; content according to HPLC: 94%)

c)

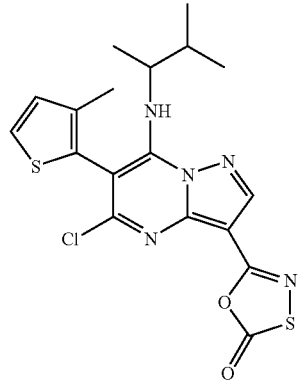

5-[5-Chloro-7-(1,2-dimethylpropylamino)-6-(3-methylthiophen-2-yl)pyrazolo[1,5-α]pyrimidin-3-yl]-[1,3,4]oxathiazol-2-one 1.5 g (4.0 mmol) of 5-chloro-7-(1,2-dimethylpropylamino)-6-(3-methylthiophen-2-yl)pyrazolo-[1,5-α]pyrimidine-3-carboxamide were dissolved in 60 ml of toluene, and 0.8 g (6.4 mmol) of chlorocarbonylsulphenyl chloride was added at 90° C. The mixture was stirred at 90° C. for 4 hours and then concentrated under reduced pressure. The residue that remained was chromatographed on silica gel using a mixture of cyclohexane:ethyl acetate=1:1. Two titrations with diisopropyl ether gave, after drying, 0.13 g of 5-[5-chloro-7-(1,2-dimethylpropylamino)-6-(3-methylthiophen-2-yl)-pyrazolo[1,5-α]pyrimidin-3-yl]-[1,3,4]oxathiazol-2-one as a crystalline solid (logPs=5.0; content according to HPLC: 94%).

Example XXVII

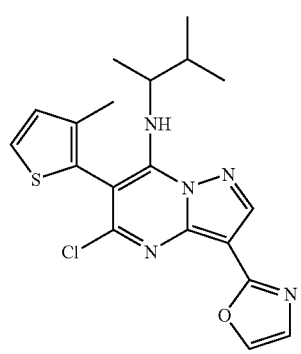

[5-Chloro-6-(3-methylthiophen-2-yl)-3-oxazol-2-ylpyrazolo[1,5-α]pyrimidin-7-yl](1,2-dimethyl-propyl)amine 0.95 g (2.5 mmol) of 5-chloro-7-(1,2-dimethylpropylamino)-6-(3-methylthiophen-2-yl)pyrazolo-[1,5-α]pyrimidine-3-carboxamide was dissolved in 25 ml of ethanol, and 1.0 g (6.5 mmol) of chloroacetaldehyde diethyl acetal was added. The mixture was stirred for 3 hours at 120° C. and 15 bar in a microwave oven (200 W). The reaction mixture was then concentrated under reduced pressure, and the residue that remained was chromatographed on silica gel using a mixture of cyclohexane:ethyl acetate=1:1. This gave 0.3 g of [5-chloro-6-(3-methylthiophen-2-yl)-3-oxazol-2-yl-pyrazolo[1,5-α]pyrimidin-7-yl](1,2-dimethylpropyl)amine (logPs=4.3; content according to HPLC: 98%)

Example XXVIII

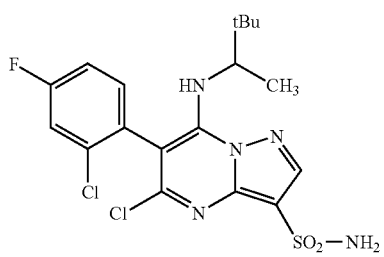

0.476 g of chlorosulphonic acid in 5 ml of dichloromethane was added to 0.847 g of 5-chloro-6-(2-chloro-4-fluorophenyl)-7-(1,2,2-trimethylpropylamino)pyrazolo[1,5-a]pyrimidine, the preparation of which is described, for example, in WO 02/048151, and the mixture was then stirred at room temperature for 16 h. 0.810 g of thionyl chloride was then added, and the mixture was heated under reflux for 24 hours. After cooling to 0° C., ammonia was introduced, stirring at room temperature was continued for 72 h and the mixture was filtered off with suction. The filtrate was concentrated and purified chromatographically on silica gel using cyclohexane/ethyl acetate 3:1.

logP$_s$: 3.65 If methylamine is introduced instead of ammonia, N-methyl-5-chloro-6-(2-chloro-4-fluorophenyl)-7-(1,2,2-trimethylpropylamino)pyrazolo[1,5-a]pyrimidine-3-sulphonamide, logP$_s$: 4.09, is obtained correspondingly

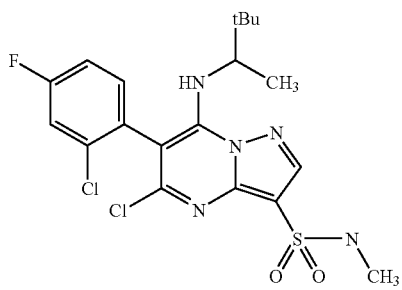

Example XXIX a) Thiosemicarbazone of 5-chloro-6-(2-chloro-4-fluorophenyl)-7-(1,2-dimethyl-propylamino)pyrazolo[1,5-a]pyrimidine-3-carbaldehyde

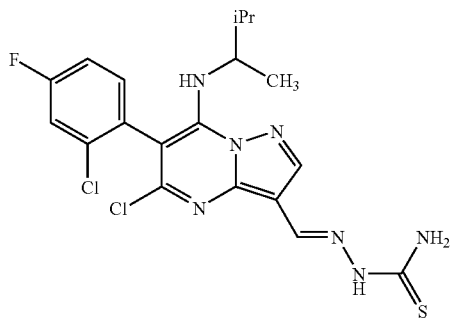

0.231 g of thiosemicarbazide, 18 ml of ethanol and a drop of acetic acid are added to 1 g of 5-chloro-6-(2-chloro-4-fluorophenyl)-7-(1,2-dimethylpropylamino)pyrazolo[1,5-a]pyrimidine-3-carbaldehyde, the preparation of which is described, for example, in LeA36087, and the mixture is stirred under reflux for 15 h. After cooling, the mixture is filtered. Yellow solid.

logP$_s$: 3.75 b) cyclization of the thiosemicarbazone

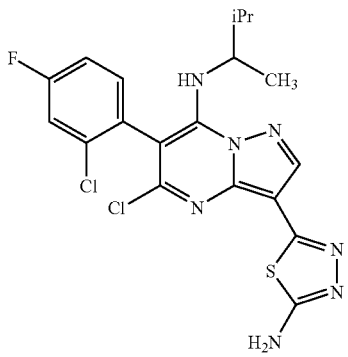

A solution of 1.625 g of iron(III) chloride in 10 ml of ethanol is added dropwise to a solution of 0.4 g of the thiosemicarbazone (prepared as above) in 50 ml of ethanol. The resulting solution is heated under reflux for 4 h. After cooling, water is added and the mixture is extracted 3 times with chloroform. The organic phases are separated off, dried and concentrated, giving a solid which is purified on silica gel using dichloromethane/ethyl acetate 5:1.

logP$_s$: 3.57

Example XXX

Aa) 3-aminopyrazole-4-carbohydrazide

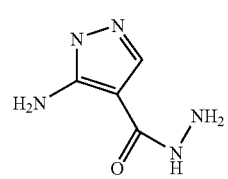

15 g of methyl 3-aminopyrazole-4-carboxylate (prepared, for example, according to J. Med. Chem. 1996, 39, 3019-3029) were introduced into 53.2 g of hydrazine hydrate, and the mixture was stirred under reflux for 24 h. The mixture was then evaporated to dryness, the residue was taken up in a little ice-water and the product was filtered off with suction. The crude product was reacted further without further purification.

Ab) N-(1-dimethylaminoethylidene)-5-amino-1H-pyrazole-4-carbohydrazide

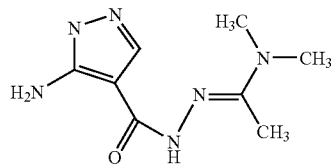

2.914 g of the above crude product were initially charged in 10 ml of acetonitrile and heated to reflux temperature. 3.3 g of dimethylacetamide dimethyl acetal (dissolved in a little acetonitrile) were then added dropwise, and the mixture was stirred under reflux for a further 20 h. After cooling, the mixture was concentrated to half of its original volume and cooled, and the product was filtered off with suction. The product was used further without further purification.

Ac) 4-(5-Methyl-[1,3,4]oxadiazol-2-yl)-2H-pyrazol-3-ylamine

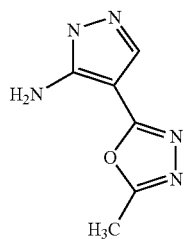

4.43 g of the product obtained as above were dissolved in 20 ml of ethanol, and 1.1 ml of acetic acid were added. After 3 h of stirring under reflux, the mixture was concentrated and the residue that remained was titrated with a little cold water, filtered off with suction and dried. The crude product obtained was used for the subsequent steps without further purification.

Ba) 3-Ethoxy-2-(5-methyl-1H-[1,2,4]triazol-3-yl)acrylonitrile

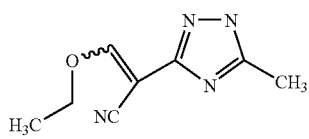

7 g of 3-methyl-1,2,4-triazol-5-ylacetonitrile and 8.494 g of triethyl orthoformate were stirred under reflux for 5.5 h and then concentrated under reduced pressure. The resulting crude product was immediately reacted further.

Bb) 4-(5-Methyl-1H-[1,2,4]triazol-3-yl)-2H-pyrazol-3-ylamine

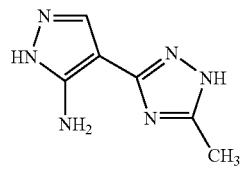

10 g of the crude product described above were initially charged in 40 ml of ethanol, and 2.128 g of hydrazine hydrate were added dropwise. After 15 h of stirring under reflux, the mixture was concentrated and the residue was titrated with a little ice-water, filtered off with suction and dried. The brown solid obtained was reacted further without further purification.

Ca) 3-Ethoxy-2-pyridin-2-ylacrylonitrile

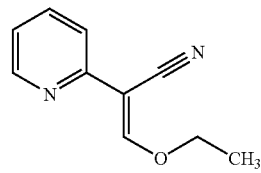

5 g of pyridin-2-ylacetonitrile, 6.27 g of triethyl orthoformate and 8.64 g of acetic anhydride were stirred under reflux for 5.5 h and then concentrated under reduced pressure. The crude product obtained was directly used further.

Cb) 4-Pyridin-2-yl-2H-pyrazol-3-ylamine

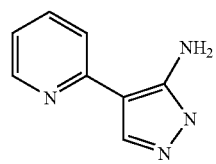

3.42 g of hydrazine hydrate were added to 11.9 g of the crude product obtained above, and the mixture was stirred under reflux for 15 h. The mixture was then concentrated under reduced pressure. The product obtained in this manner was then reacted further without further purification.

D) 6-(2-Chloro-4-fluorophenyl)-3-(5-methyl-[1,3,4]oxadiazol-2-yl)pyrazolo[1,5-a]pyrimidine-5,7-diol

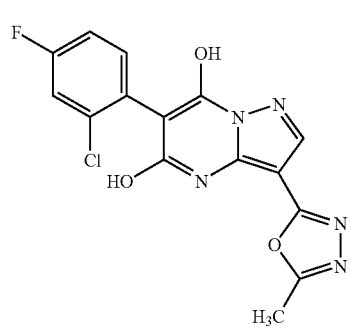

0.789 g of dimethyl 2-chloro-4-fluorophenylmalonate and 0.79 ml of tributyalmine were added to 0.5 g of the 4-(5-methyl-[1,3,4]oxadiazol-2-yl)-2H-pyrazol-3-ylamine obtained under Ac), and the mixture was stirred at 185° C. for 3 h. Concentration gave a glass-like substance.

logP$_s$: 0.67

The following compounds were obtained in the same manner: (Examples XXXI, XXXII)

from the product obtained under Bb): 6-(2-chloro-4-fluorophenyl)-3-(5-methyl-[1,3,4]triazol-2-yl)pyrazolo[1,5-a]pyrimidine-5,7-diol, logP$_s$=0.51

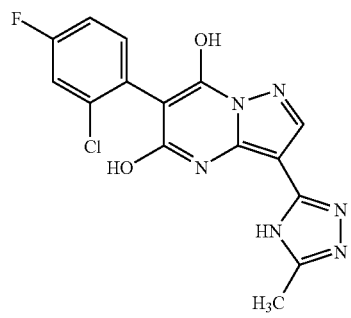

from the product obtained under Cb): 6-(2-chloro-4-fluorophenyl)-3-pyridin-2-ylpyrazolo[1,5-a]pyrimidine-5,7-diol, logP$_s$=0.91

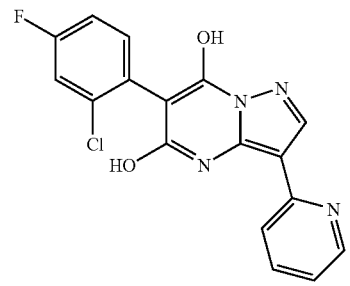

Example XXXIII

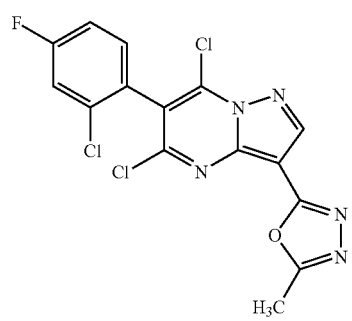

1.09 g of 6-(2-chloro-4-fluorophenyl)-3-(5-methyl-[1,3,4]oxadiazol-2-yl)pyrazolo[1,5-a]pyrimidine-5,7-diol were initially charged in 2.81 ml of phosphoryl chloride and stirred under reflux for 30 min and then cooled to 0° C., and 0.441 g of dimethylformamide was added carefully. Stirring was continued at room temperature for 15 h and then under reflux for another 2 h. After cooling, the mixture was poured onto ice and extracted three times with ethyl acetate. The organic phases were removed and concentrated. The crude product was converted without further purification into the end products.

The following compounds were obtained in the same manner:

Examples XXXIV, XXXV 5,7-Dichloro-6-(2-chloro-4-fluorophenyl)-3-(5-methyl-[1,3,4]triazol-2-yl)pyrazolo[1,5-a]pyrimidine

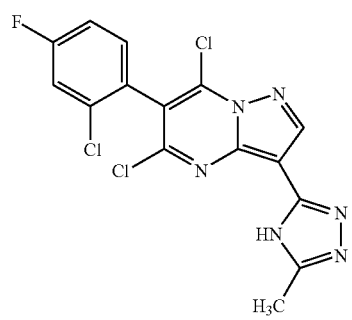

5,7-Dichloro-6-(2-chloro-4-fluorophenyl)-3-pyridin-2-ylpyrazolo[1,5-a]pyrimidine

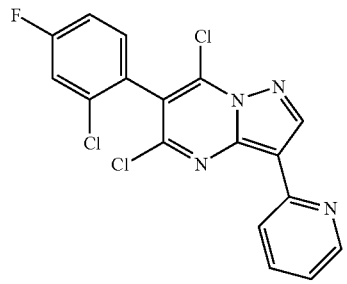

Example XXXVI

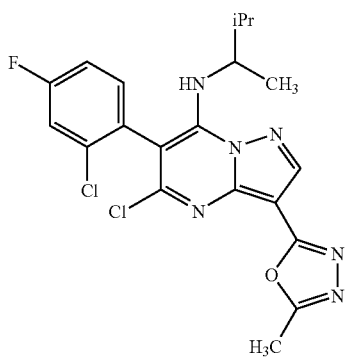

0.36 g of the 5,7-dichloro-6-(2-chloro-4-fluorophenyl)-3-(5-methyl-[1,3,4]oxadiazol-2-yl)pyrazolo[1,5-a]pyrimidine described above was initially charged in 40 ml of acetonitrile, and 110 mg of potassium carbonate and 6 mg of 18-crown-6 were added. The mixture was stirred at room temperature for 15 min, and 0.075 g of 3-methylbutyl-2-amine, dissolved in a little acetonitrile, was added over a period of 15 min. After 20 h of stirring at room temperature, 1 ml of water was added, stirring was continued for a further 1 h and the mixture was concentrated. The residue was titrated with cold water and filtered off with suction. Silica gel chromatography using ethyl acetate gave a beige solid.

logP$_s$: 3.94

The following compounds were obtained in the same manner:

Examples XXXVII, XXXVIII 5,7-Dichloro-6-(2-chloro-4-fluorophenyl)-3-(5-methyl-[1,3,4]triazol-2-yl)pyrazolo[1,5-a]-pyrimidine gave, after silica gel chromatography using ethyl acetate, [5-chloro-6-(2-chloro-4-fluorophenyl)-3-(5-methyl-[1,3,4]triazol-2-yl)pyrazolo[1,5-a]pyrimidin-7-yl](1,2-dimethylpropyl)-amine, logP$_s$: 2.91

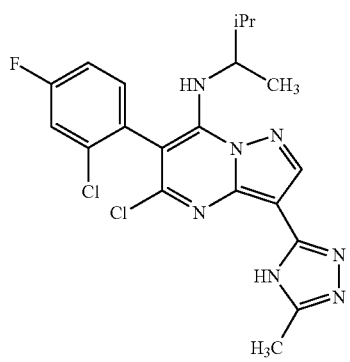

5,7-Dichloro-6-(2-chloro-4-fluorophenyl)-3-pyridin-2-ylpyrazolol[1,5-a]pyrimidine gave, after silica gel chromatography using cyclohexane/ethyl acetate 4:1, [5-chloro-6-(2-chloro-4-fluorophenyl)-3-pyridin-2-ylpyrazolo[1,5-a]pyrimidin-7-yl](1,2-dimethylpropyl)amine, logps: 3.54

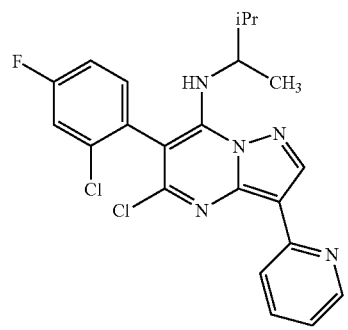

The compounds of the formula (I-a) listed in Table 1 below are/were obtained analogously to the methods described above.

TABLE 1

| Ex. No. | R¹ or —R¹+R²— | R² | R³ | X | R⁴ | log p |
|---|---|---|---|---|---|---|
| 1 | $CH(CH_3)-C(CH_3)_3$ | H | 2-Cl-6-F-phenyl | Cl | $CO-NH-CH_3$ | |
| 2 | $CH(CH_3)-C(CH_3)_3$ | H | 2-Cl-6-F-phenyl | Cl | $CON(CH_3)_2$ | |
| 3 | (R) $CH(CH_3)-C(CH_3)_3$ | H | 2-Cl-6-F-phenyl | Cl | CO—NH-i-propyl | 5.09 |
| 4 | (R) $CH(CH_3)-C(CH_3)_3$ | H | 2-Cl-6-F-phenyl | Cl | CO-morpholin-1-yl | 3.82 |
| 5 | (R) $CH(CH_3)-C(CH_3)_3$ | H | 2-Cl-6-F-phenyl | Cl | COOH | 3.54 |
| 6 | (R) $CH(CH_3)-C(CH_3)_3$ | H | 2-Cl-6-F-phenyl | Cl | COO-propen-3-yl | 5.14 |
| 7 | (R) $CH(CH_3)-C(CH_3)_3$ | H | 2-Cl-6-F-phenyl | Cl | COO-benzyl | 5.67 |
| 8 | (R) $CH(CH_3)-C(CH_3)_3$ | H | 2-Cl-6-F-phenyl | Cl | $COO-CH_2-CH_2-OCH_3$ | 4.44 |
| 9 | $CH(CH_3)-C(CH_3)_3$ | H | 2-Cl-6-F-phenyl | Cl | $SO_3H$ | |
| 10 | $CH(CH_3)-C(CH_3)_3$ | H | 2-Cl-6-F-phenyl | Cl | $SO_2CH_3$ | |
| 11 | $CH(CH_3)-C(CH_3)_3$ | H | 2,4,6-trifluorophenyl | Cl | $CO-NH-CH_3$ | |
| 12 | $CH(CH_3)-C(CH_3)_3$ | H | 2,4,6-trifluorophenyl | Cl | $CON(CH_3)_2$ | |
| 13 | $CH(CH_3)-C(CH_3)_3$ | H | 2,4,6-trifluorophenyl | Cl | CO—NH-i-propyl | |
| 14 | (R) $CH(CH_3)-C(CH_3)_3$ | H | 2,4,6-trifluorophenyl | Cl | CO-morpholin-1-yl | 3.78 |
| 15 | (R) $CH(CH_3)-C(CH_3)_3$ | H | 2,4,6-trifluorophenyl | Cl | COOH | 3.48 |
| 16 | $CH(CH_3)-C(CH_3)_3$ | H | 2,4,6-trifluorophenyl | Cl | COO-propen-3-yl | |
| 17 | $CH(CH_3)-C(CH_3)_3$ | H | 2,4,6-trifluorophenyl | Cl | COO-benzyl | |
| 18 | (R) $CH(CH_3)-C(CH_3)_3$ | H | 2,4,6-trifluorophenyl | Cl | $COO-CH_2-CH_2-OCH_3$ | 4.37 |
| 19 | $CH(CH_3)-C(CH_3)_3$ | H | 2,4,6-trifluorophenyl | Cl | $SO_3H$ | |
| 20 | $CH(CH_3)-C(CH_3)_3$ | H | 2,4,6-trifluorophenyl | Cl | $SO_2CH_3$ | |
| 21 | (R) $CH(CH_3)-C(CH_3)_3$ | H | 2-Cl-4-F-phenyl | Cl | $CO-NH-CH_3$ | 4.3 |
| 22 | $CH(CH_3)-C(CH_3)_3$ | H | 2-Cl-4-F-phenyl | Cl | $CON(CH_3)_2$ | |
| 23 | (R) $CH(CH_3)-C(CH_3)_3$ | H | 2-Cl-4-F-phenyl | Cl | CO—NH-i-propyl | 5.28 |
| 24 | (R) $CH(CH_3)-C(CH_3)_3$ | H | 2-Cl-4-F-phenyl | Cl | CO-morpholin-1-yl | 4.09 |
| 25 | (R) $CH(CH_3)-C(CH_3)_3$ | H | 2-Cl-4-F-phenyl | Cl | COOH | 3.77 |
| 26 | (R) $CH(CH_3)-C(CH_3)_3$ | H | 2-Cl-4-F-phenyl | Cl | COO-propen-3-yl | 5.28 |
| 27 | (R) $CH(CH_3)-C(CH_3)_3$ | H | 2-Cl-4-F-phenyl | Cl | COO-benzyl | 5.78 |
| 28 | (R) $CH(CH_3)-C(CH_3)_3$ | H | 2-Cl-4-F-phenyl | Cl | $COO-CH_2-CH_2-OCH_3$ | 4.64 |
| 29 | $CH(CH_3)-C(CH_3)_3$ | H | 2-Cl-4-F-phenyl | Cl | $SO_3H$ | |
| 30 | $CH(CH_3)-C(CH_3)_3$ | H | 2-Cl-4-F-phenyl | Cl | $SO_2CH_3$ | |
| 31 | (R) $CH(CH_3)-C(CH_3)_3$ | H | 2-Cl-phenyl | Cl | $CO-NH-CH_3$ | 4.26 |
| 32 | $CH(CH_3)-C(CH_3)_3$ | H | 2-Cl-phenyl | Cl | $CON(CH_3)_2$ | |
| 33 | $CH(CH_3)-C(CH_3)_3$ | H | 2-Cl-phenyl | Cl | CO—NH-i-propyl | |
| 34 | (R) $CH(CH_3)-C(CH_3)_3$ | H | 2-Cl-phenyl | Cl | CO-morpholin-1-yl | 3.94 |
| 35 | (R) $CH(CH_3)-C(CH_3)_3$ | H | 2-Cl-phenyl | Cl | COOH | 3.67 |
| 36 | (R) $CH(CH_3)-C(CH_3)_3$ | H | 2-Cl-phenyl | Cl | COO-propen-3-yl | 5.27 |
| 37 | $CH(CH_3)-C(CH_3)_3$ | H | 2-Cl-phenyl | Cl | COO-benzyl | |
| 38 | (R) $CH(CH_3)-C(CH_3)_3$ | H | 2-Cl-phenyl | Cl | $COO-CH_2-CH_2-OCH_3$ | 4.59 |
| 39 | $CH(CH_3)-C(CH_3)_3$ | H | 2-Cl-phenyl | Cl | $SO_3H$ | |
| 40 | $CH(CH_3)-C(CH_3)_3$ | H | 2-Cl-phenyl | Cl | $SO_2CH_3$ | |
| 41 | $CH(CH_3)-C(CH_3)_3$ | H | 5-Cl-pyrimidin-4-yl | Cl | $CO-NH-CH_3$ | |
| 42 | $CH(CH_3)-C(CH_3)_3$ | H | 5-Cl-pyrimidin-4-yl | Cl | $CON(CH_3)_2$ | |
| 43 | $CH(CH_3)-C(CH_3)_3$ | H | 5-Cl-pyrimidin-4-yl | Cl | CO—NH-i-propyl | |
| 44 | $CH(CH_3)-C(CH_3)_3$ | H | 5-Cl-pyrimidin-4-yl | Cl | CO-morpholin-1-yl | |
| 45 | (R) $CH(CH_3)-C(CH_3)_3$ | H | 5-Cl-pyrimidin-4-yl | Cl | COOH | 2.53 |
| 46 | $CH(CH_3)-C(CH_3)_3$ | H | 5-Cl-pyrimidin-4-yl | Cl | COO-propen-3-yl | |
| 47 | $CH(CH_3)-C(CH_3)_3$ | H | 5-Cl-pyrimidin-4-yl | Cl | COO-benzyl | |
| 48 | $CH(CH_3)-C(CH_3)_3$ | H | 5-Cl-pyrimidin-4-yl | Cl | $COO-CH_2-CH_2-OCH_3$ | |
| 49 | $CH(CH_3)-C(CH_3)_3$ | H | 5-Cl-pyrimidin-4-yl | Cl | $SO_3H$ | |
| 50 | $CH(CH_3)-C(CH_3)_3$ | H | 5-Cl-pyrimidin-4-yl | Cl | $SO_2CH_3$ | |
| 51 | (S) $CH(CH_3)(CF_3)$ | H | 2-Cl-6-F-phenyl | Cl | $CO-NH-CH_3$ | 3.22 |
| 52 | $CH(CH_3)(CF_3)$ | H | 2-Cl-6-F-phenyl | Cl | $CON(CH_3)_2$ | |
| 53 | $CH(CH_3)(CF_3)$ | H | 2-Cl-6-F-phenyl | Cl | CO—NH-i-propyl | |
| 54 | $CH(CH_3)(CF_3)$ | H | 2-Cl-6-F-phenyl | Cl | CO-morpholin-1-yl | |
| 55 | (S) $CH(CH_3)(CF_3)$ | H | 2-Cl-6-F-phenyl | Cl | COOH | 2.8 |
| 56 | (S) $CH(CH_3)(CF_3)$ | H | 2-Cl-6-F-phenyl | Cl | COO-propen-3-yl | 4.17 |
| 57 | $CH(CH_3)(CF_3)$ | H | 2-Cl-6-F-phenyl | Cl | COO-benzyl | |
| 58 | (S) $CH(CH_3)(CF_3)$ | H | 2-Cl-6-F-phenyl | Cl | $COO-CH_2-CH_2-OCH_3$ | 3.54 |
| 59 | $CH(CH_3)(CF_3)$ | H | 2-Cl-6-F-phenyl | Cl | $SO_3H$ | |
| 60 | $CH(CH_3)(CF_3)$ | H | 2-Cl-6-F-phenyl | Cl | $SO_2CH_3$ | |
| 61 | $CH(CH_3)(CF_3)$ | H | 2,4,6-trifluorophenyl | Cl | $CO-NH-CH_3$ | |
| 62 | $CH(CH_3)(CF_3)$ | H | 2,4,6-trifluorophenyl | Cl | $CON(CH_3)_2$ | |
| 63 | $CH(CH_3)(CF_3)$ | H | 2,4,6-trifluorophenyl | Cl | CO—NH-i-propyl | |
| 64 | (S) $CH(CH_3)(CF_3)$ | H | 2,4,6-trifluorophenyl | Cl | CO-morpholin-1-yl | 3.01 |
| 65 | (S) $CH(CH_3)(CF_3)$ | H | 2,4,6-trifluorophenyl | Cl | COOH | 2.74 |
| 66 | $CH(CH_3)(CF_3)$ | H | 2,4,6-trifluorophenyl | Cl | COO-propen-3-yl | |

TABLE 1-continued

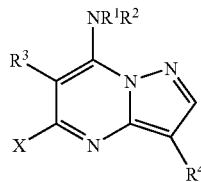

| Ex. No. | R¹ or —R¹+R²— | R² | R³ | X | R⁴ | log p |
|---|---|---|---|---|---|---|
| 67 | CH(CH₃)(CF₃) | H | 2,4,6-trifluorophenyl | Cl | COO-benzyl | |
| 68 | CH(CH₃)(CF₃) | H | 2,4,6-trifluorophenyl | Cl | COO—CH₂—CH₂—OCH₃ | |
| 69 | CH(CH₃)(CF₃) | H | 2,4,6-trifluorophenyl | Cl | SO₃H | |
| 70 | CH(CH₃)(CF₃) | H | 2,4,6-trifluorophenyl | Cl | SO₂CH₃ | |
| 71 | (S) CH(CH₃)(CF₃) | H | 2-Cl-4-F-phenyl | Cl | CO—NH—CH₃ | 3.33 |
| 72 | (S) CH(CH₃)(CF₃) | H | 2-Cl-4-F-phenyl | Cl | CON(CH₃)₂ | 3.96 |
| 73 | CH(CH₃)(CF₃) | H | 2-Cl-4-F-phenyl | Cl | CO—NH-i-propyl | |
| 74 | CH(CH₃)(CF₃) | H | 2-Cl-4-F-phenyl | Cl | CO-morpholin-1-yl | |
| 75 | (S) CH(CH₃)(CF₃) | H | 2-Cl-4-F-phenyl | Cl | COOH | 2.98 |
| 76 | CH(CH₃)(CF₃) | H | 2-Cl-4-F-phenyl | Cl | COO-propen-3-yl | 4.31 |
| 77 | CH(CH₃)(CF₃) | H | 2-Cl-4-F-phenyl | Cl | COO-benzyl | |
| 78 | (S) CH(CH₃)(CF₃) | H | 2-Cl-4-F-phenyl | Cl | COO—CH₂—CH₂—OCH₃ | 3.72 |
| 79 | CH(CH₃)(CF₃) | H | 2-Cl-4-F-phenyl | Cl | SO₃H | |
| 80 | CH(CH₃)(CF₃) | H | 2-Cl-4-F-phenyl | Cl | SO₂CH₃ | |
| 81 | (S) CH(CH₃)(CF₃) | H | 2-Cl-phenyl | Cl | CO—NH—CH₃ | 3.25 |
| 82 | CH(CH₃)(CF₃) | H | 2-Cl-phenyl | Cl | CON(CH₃)₂ | |
| 83 | CH(CH₃)(CF₃) | H | 2-Cl-phenyl | Cl | CO—NH-i-propyl | |
| 84 | CH(CH₃)(CF₃) | H | 2-Cl-phenyl | Cl | CO-morpholin-1-yl | |
| 85 | (S) CH(CH₃)(CF₃) | H | 2-Cl-phenyl | Cl | COOH | 2.86 |
| 86 | CH(CH₃)(CF₃) | H | 2-Cl-phenyl | Cl | COO-propen-3-yl | 4.21 |
| 87 | CH(CH₃)(CF₃) | H | 2-Cl-phenyl | Cl | COO-benzyl | |
| 88 | (S) CH(CH₃)(CF₃) | H | 2-Cl-phenyl | Cl | COO—CH₂—CH₂—OCH₃ | 3.59 |
| 89 | CH(CH₃)(CF₃) | H | 2-Cl-phenyl | Cl | SO₃H | |
| 90 | CH(CH₃)(CF₃) | H | 2-Cl-phenyl | Cl | SO₂CH₃ | |
| 91 | CH(CH₃)(CF₃) | H | 5-Cl-pyrimidin-4-yl | Cl | CO—NH—CH₃ | |
| 92 | CH(CH₃)(CF₃) | H | 5-Cl-pyrimidin-4-yl | Cl | CON(CH₃)₂ | |
| 93 | CH(CH₃)(CF₃) | H | 5-Cl-pyrimidin-4-yl | Cl | CO—NH-i-propyl | |
| 94 | CH(CH₃)(CF₃) | H | 5-Cl-pyrimidin-4-yl | Cl | CO-morpholin-1-yl | |
| 95 | CH(CH₃)(CF₃) | H | 5-Cl-pyrimidin-4-yl | Cl | COOH | |
| 96 | CH(CH₃)(CF₃) | H | 5-Cl-pyrimidin-4-yl | Cl | COO-propen-3-yl | |
| 97 | CH(CH₃)(CF₃) | H | 5-Cl-pyrimidin-4-yl | Cl | COO-benzyl | |
| 98 | CH(CH₃)(CF₃) | H | 5-Cl-pyrimidin-4-yl | Cl | COO—CH₂—CH₂—OCH₃ | |
| 99 | CH(CH₃)(CF₃) | H | 5-Cl-pyrimidin-4-yl | Cl | SO₃H | |
| 100 | CH(CH₃)(CF₃) | H | 5-Cl-pyrimidin-4-yl | Cl | SO₂CH₃ | |
| 101 | CH(CH₃)—CH(CH₃)₂ | H | 2-Cl-6-F-phenyl | Cl | CO—NH—CH₃ | |
| 102 | CH(CH₃)—CH(CH₃)₂ | H | 2-Cl-6-F-phenyl | Cl | CON(CH₃)₂ | |
| 103 | (R) CH(CH₃)—CH(CH₃)₂ | H | 2-Cl-6-F-phenyl | Cl | CO—NH-i-propyl | 4.72 |
| 104 | (R) CH(CH₃)—CH(CH₃)₂ | H | 2-Cl-6-F-phenyl | Cl | CO-morpholin-1-yl | 3.49 |
| 105 | (R) CH(CH₃)—CH(CH₃)₂ | H | 2-Cl-6-F-phenyl | Cl | COOH | 3.24 |
| 106 | (R) CH(CH₃)—CH(CH₃)₂ | H | 2-Cl-6-F-phenyl | Cl | COO-propen-3-yl | 4.75 |
| 107 | (R) CH(CH₃)—CH(CH₃)₂ | H | 2-Cl-6-F-phenyl | Cl | COO-benzyl | 5.3 |
| 108 | (R) CH(CH₃)—CH(CH₃)₂ | H | 2-Cl-6-F-phenyl | Cl | COO—CH₂—CH₂—OCH₃ | 4.07 |
| 109 | CH(CH₃)—CH(CH₃)₂ | H | 2-Cl-6-F-phenyl | Cl | SO₃H | |
| 110 | CH(CH₃)—CH(CH₃)₂ | H | 2-Cl-6-F-phenyl | Cl | SO₂CH₃ | |
| 111 | CH(CH₃)—CH(CH₃)₂ | H | 2,4,6-trifluorophenyl | Cl | CO—NH—CH₃ | |
| 112 | CH(CH₃)—CH(CH₃)₂ | H | 2,4,6-trifluorophenyl | Cl | CON(CH₃)₂ | |
| 113 | CH(CH₃)—CH(CH₃)₂ | H | 2,4,6-trifluorophenyl | Cl | CO—NH-i-propyl | |
| 114 | (R) CH(CH₃)—CH(CH₃)₂ | H | 2,4,6-trifluorophenyl | Cl | CO-morpholin-1-yl | 3.47 |
| 115 | (R) CH(CH₃)—CH(CH₃)₂ | H | 2,4,6-trifluorophenyl | Cl | COOH | 3.21 |
| 116 | CH(CH₃)—CH(CH₃)₂ | H | 2,4,6-trifluorophenyl | Cl | COO-propen-3-yl | |
| 117 | CH(CH₃)—CH(CH₃)₂ | H | 2,4,6-trifluorophenyl | Cl | COO-benzyl | |
| 118 | (R) CH(CH₃)—CH(CH₃)₂ | H | 2,4,6-trifluorophenyl | Cl | COO—CH₂—CH₂—OCH₃ | 4.08 |
| 119 | CH(CH₃)—CH(CH₃)₂ | H | 2,4,6-trifluorophenyl | Cl | SO₃H | |
| 120 | CH(CH₃)—CH(CH₃)₂ | H | 2,4,6-trifluorophenyl | Cl | SO₂CH₃ | |
| 121 | (R) CH(CH₃)—CH(CH₃)₂ | H | 2-Cl-4-F-phenyl | Cl | CO—NH—CH₃ | 3.95 |
| 122 | (R) CH(CH₃)—CH(CH₃)₂ | H | 2-Cl-4-F-phenyl | Cl | CON(CH₃)₂ | 3.77 |
| 123 | CH(CH₃)—CH(CH₃)₂ | H | 2-Cl-4-F-phenyl | Cl | CO—NH-i-propyl | |
| 124 | (R) CH(CH₃)—CH(CH₃)₂ | H | 2-Cl-4-F-phenyl | Cl | CO-morpholin-1-yl | 3.76 |
| 125 | (R) CH(CH₃)—CH(CH₃)₂ | H | 2-Cl-4-F-phenyl | Cl | COOH | 3.45 |
| 126 | (R) CH(CH₃)—CH(CH₃)₂ | H | 2-Cl-4-F-phenyl | Cl | COO-propen-3-yl | 4.92 |
| 127 | (R) CH(CH₃)—CH(CH₃)₂ | H | 2-Cl-4-F-phenyl | Cl | COO-benzyl | 5.44 |
| 128 | (R) CH(CH₃)—CH(CH₃)₂ | H | 2-Cl-4-F-phenyl | Cl | COO—CH₂—CH₂—OCH₃ | 4.27 |
| 129 | CH(CH₃)—CH(CH₃)₂ | H | 2-Cl-4-F-phenyl | Cl | SO₃H | 2.19 |
| 130 | CH(CH₃)—CH(CH₃)₂ | H | 2-Cl-4-F-phenyl | Cl | SO₂CH₃ | |
| 131 | (R) CH(CH₃)—CH(CH₃)₂ | H | 2-Cl-phenyl | Cl | CO—NH—CH₃ | 3.9 |
| 132 | CH(CH₃)—CH(CH₃)₂ | H | 2-Cl-phenyl | Cl | CON(CH₃)₂ | |

TABLE 1-continued

Structure: pyrazolo[1,5-a]pyrimidine core with $NR^1R^2$ at position 7, $R^3$ at position 6, X at position 5, $R^4$ at position 3.

| Ex. No. | $R^1$ or —$R^1$+$R^2$— | $R^2$ | $R^3$ | X | $R^4$ | log p |
|---|---|---|---|---|---|---|
| 133 | CH(CH$_3$)—CH(CH$_3$)$_2$ | H | 2-Cl-phenyl | Cl | CO—NH-i-propyl | |
| 134 | CH(CH$_3$)—CH(CH$_3$)$_2$ | H | 2-Cl-phenyl | Cl | CO-morpholin-1-yl | |
| 135 | (R) CH(CH$_3$)—CH(CH$_3$)$_2$ | H | 2-Cl-phenyl | Cl | COOH | 3.35 |
| 136 | (R) CH(CH$_3$)—CH(CH$_3$)$_2$ | H | 2-Cl-phenyl | Cl | COO-propen-3-yl | 4.89 |
| 137 | CH(CH$_3$)—CH(CH$_3$)$_2$ | H | 2-Cl-phenyl | Cl | COO-benzyl | |
| 138 | (R) CH(CH$_3$)—CH(CH$_3$)$_2$ | H | 2-Cl-phenyl | Cl | COO—CH$_2$—CH$_2$—OCH$_3$ | 4.21 |
| 139 | CH(CH$_3$)—CH(CH$_3$)$_2$ | H | 2-Cl-phenyl | Cl | SO$_3$H | |
| 140 | CH(CH$_3$)—CH(CH$_3$)$_2$ | H | 2-Cl-phenyl | Cl | SO$_2$CH$_3$ | |
| 141 | CH(CH$_3$)—CH(CH$_3$)$_2$ | H | 5-Cl-pyrimidin-4-yl | Cl | CO—NH—CH$_3$ | |
| 142 | CH(CH$_3$)—CH(CH$_3$)$_2$ | H | 5-Cl-pyrimidin-4-yl | Cl | CON(CH$_3$)$_2$ | |
| 143 | CH(CH$_3$)—CH(CH$_3$)$_2$ | H | 5-Cl-pyrimidin-4-yl | Cl | CO—NH-i-propyl | |
| 144 | CH(CH$_3$)—CH(CH$_3$)$_2$ | H | 5-Cl-pyrimidin-4-yl | Cl | CO-morpholin-1-yl | |
| 145 | CH(CH$_3$)—CH(CH$_3$)$_2$ | H | 5-Cl-pyrimidin-4-yl | Cl | COOH | |
| 146 | CH(CH$_3$)—CH(CH$_3$)$_2$ | H | 5-Cl-pyrimidin-4-yl | Cl | COO-propen-3-yl | |
| 147 | CH(CH$_3$)—CH(CH$_3$)$_2$ | H | 5-Cl-pyrimidin-4-yl | Cl | COO-benzyl | |
| 148 | CH(CH$_3$)—CH(CH$_3$)$_2$ | H | 5-Cl-pyrimidin-4-yl | Cl | COO—CH$_2$—CH$_2$—OCH$_3$ | |
| 149 | CH(CH$_3$)—CH(CH$_3$)$_2$ | H | 5-Cl-pyrimidin-4-yl | Cl | SO$_3$H | |
| 150 | CH(CH$_3$)—CH(CH$_3$)$_2$ | H | 5-Cl-pyrimidin-4-yl | Cl | SO$_2$CH$_3$ | |
| 151 | —CH$_2$—CH$_2$—CH(CH$_3$)—CH$_2$—CH$_2$— | | 2-Cl-6-F-phenyl | Cl | CO—NH—CH$_3$ | |
| 152 | —CH$_2$—CH$_2$—CH(CH$_3$)—CH$_2$—CH$_2$— | | 2-Cl-6-F-phenyl | Cl | CON(CH$_3$)$_2$ | |
| 153 | —CH$_2$—CH$_2$—CH(CH$_3$)—CH$_2$—CH$_2$— | | 2-Cl-6-F-phenyl | Cl | CO—NH-i-propyl | |
| 154 | —CH$_2$—CH$_2$—CH(CH$_3$)—CH$_2$—CH$_2$— | | 2-Cl-6-F-phenyl | Cl | CO-morpholin-1-yl | |
| 155 | —CH$_2$—CH$_2$—CH(CH$_3$)—CH$_2$—CH$_2$— | | 2-Cl-6-F-phenyl | Cl | COOH | 3.63 |
| 156 | —CH$_2$—CH$_2$—CH(CH$_3$)—CH$_2$—CH$_2$— | | 2-2-Cl-6-F-phenyl | Cl | COO-propen-3-yl | |
| 157 | —CH$_2$—CH$_2$—CH(CH$_3$)—CH$_2$—CH$_2$— | | 2-2-Cl-6-F-phenyl | Cl | COO-benzyl | |
| 158 | —CH$_2$—CH$_2$—CH(CH$_3$)—CH$_2$—CH$_2$— | | 2-Cl-6-F-phenyl | Cl | COO—CH$_2$—CH$_2$—OCH$_3$ | 4.55 |
| 159 | —CH$_2$—CH$_2$—CH(CH$_3$)—CH$_2$—CH$_2$— | | 2-Cl-6-F-phenyl | Cl | SO$_3$H | |
| 160 | —CH$_2$—CH$_2$—CH(CH$_3$)—CH$_2$—CH$_2$— | | 2-Cl-6-F-phenyl | Cl | SO$_2$CH$_3$ | |
| 161 | —CH$_2$—CH$_2$—CH(CH$_3$)—CH$_2$—CH$_2$— | | 2,4,6-trifluorophenyl | Cl | CO—NH—CH$_3$ | |
| 162 | —CH$_2$—CH$_2$—CH(CH$_3$)—CH$_2$—CH$_2$— | | 2,4,6-trifluorophenyl | Cl | CON(CH$_3$)$_2$ | |
| 163 | —CH$_2$—CH$_2$—CH(CH$_3$)—CH$_2$—CH$_2$— | | 2,4,6-trifluorophenyl | Cl | CO—NH-i-propyl | |
| 164 | —CH$_2$—CH$_2$—CH(CH$_3$)—CH$_2$—CH$_2$— | | 2,4,6-trifluorophenyl | Cl | CO-morpholin-1-yl | |
| 165 | —CH$_2$—CH$_2$—CH(CH$_3$)—CH$_2$—CH$_2$— | | 2,4,6-trifluorophenyl | Cl | COOH | 3.54 |
| 166 | —CH$_2$—CH$_2$—CH(CH$_3$)—CH$_2$—CH$_2$— | | 2,4,6-trifluorophenyl | Cl | COO-propen-3-yl | |
| 167 | —CH$_2$—CH$_2$—CH(CH$_3$)—CH$_2$—CH$_2$— | | 2,4,6-trifluorophenyl | Cl | COO-benzyl | |
| 168 | —CH$_2$—CH$_2$—CH(CH$_3$)—CH$_2$—CH$_2$— | | 2,4,6-trifluorophenyl | Cl | COO—CH$_2$—CH$_2$—OCH$_3$ | 4.43 |
| 169 | —CH$_2$—CH$_2$—CH(CH$_3$)—CH$_2$—CH$_2$— | | 2,4,6-trifluorophenyl | Cl | SO$_3$H | |
| 170 | —CH$_2$—CH$_2$—CH(CH$_3$)—CH$_2$—CH$_2$— | | 2,4,6-trifluorophenyl | Cl | SO$_2$CH$_3$ | |
| 171 | —CH$_2$—CH$_2$—CH(CH$_3$)—CH$_2$—CH$_2$— | | 2-Cl-4-F-phenyl | Cl | CO—NH—CH$_3$ | |
| 172 | —CH$_2$—CH$_2$—CH(CH$_3$)—CH$_2$—CH$_2$— | | 2-Cl-4-F-phenyl | Cl | CON(CH$_3$)$_2$ | |
| 173 | —CH$_2$—CH$_2$—CH(CH$_3$)—CH$_2$—CH$_2$— | | 2-Cl-4-F-phenyl | Cl | CO—NH-i-propyl | |
| 174 | —CH$_2$—CH$_2$—CH(CH$_3$)—CH$_2$—CH$_2$— | | 2-Cl-4-F-phenyl | Cl | CO-morpholin-1-yl | |
| 175 | —CH$_2$—CH$_2$—CH(CH$_3$)—CH$_2$—CH$_2$— | | 2-Cl-4-F-phenyl | Cl | COOH | 3.79 |
| 176 | —CH$_2$—CH$_2$—CH(CH$_3$)—CH$_2$—CH$_2$— | | 2-Cl-4-F-phenyl | Cl | COO-propen-3-yl | |
| 177 | —CH$_2$—CH$_2$—CH(CH$_3$)—CH$_2$—CH$_2$— | | 2-Cl-4-F-phenyl | Cl | COO-benzyl | |
| 178 | —CH$_2$—CH$_2$—CH(CH$_3$)—CH$_2$—CH$_2$— | | 2-Cl-4-F-phenyl | Cl | COO—CH$_2$—CH$_2$—OCH$_3$ | |
| 179 | —CH$_2$—CH$_2$—CH(CH$_3$)—CH$_2$—CH$_2$— | | 2-Cl-4-F-phenyl | Cl | SO$_3$H | 2.48 |
| 180 | —CH$_2$—CH$_2$—CH(CH$_3$)—CH$_2$—CH$_2$— | | 2-Cl-4-F-phenyl | Cl | SO$_2$CH$_3$ | |
| 181 | —CH$_2$—CH$_2$—CH(CH$_3$)—CH$_2$—CH$_2$— | | 2-Cl-phenyl | Cl | CO—NH—CH$_3$ | 4.1 |
| 182 | —CH$_2$—CH$_2$—CH(CH$_3$)—CH$_2$—CH$_2$— | | 2-Cl-phenyl | Cl | CON(CH$_3$)$_2$ | |
| 183 | —CH$_2$—CH$_2$—CH(CH$_3$)—CH$_2$—CH$_2$— | | 2-Cl-phenyl | Cl | CO—NH-i-propyl | |
| 184 | —CH$_2$—CH$_2$—CH(CH$_3$)—CH$_2$—CH$_2$— | | 2-Cl-phenyl | Cl | CO-morpholin-1-yl | |
| 185 | —CH$_2$—CH$_2$—CH(CH$_3$)—CH$_2$—CH$_2$— | | 2-Cl-phenyl | Cl | COOH | 3.69 |
| 186 | —CH$_2$—CH$_2$—CH(CH$_3$)—CH$_2$—CH$_2$— | | 2-Cl-phenyl | Cl | COO-propen-3-yl | 5.32 |
| 187 | —CH$_2$—CH$_2$—CH(CH$_3$)—CH$_2$—CH$_2$— | | 2-Cl-phenyl | Cl | COO-benzyl | |
| 188 | —CH$_2$—CH$_2$—CH(CH$_3$)—CH$_2$—CH$_2$— | | 2-Cl-phenyl | Cl | COO—CH$_2$—CH$_2$—OCH$_3$ | 4.61 |
| 189 | —CH$_2$—CH$_2$—CH(CH$_3$)—CH$_2$—CH$_2$— | | 2-Cl-phenyl | Cl | SO$_3$H | |
| 190 | —CH$_2$—CH$_2$—CH(CH$_3$)—CH$_2$—CH$_2$— | | 2-Cl-phenyl | Cl | SO$_2$CH$_3$ | |
| 191 | —CH$_2$—CH$_2$—CH(CH$_3$)—CH$_2$—CH$_2$— | | 5-Cl-pyrimidin-4-yl | Cl | CO—NH—CH$_3$ | |
| 192 | —CH$_2$—CH$_2$—CH(CH$_3$)—CH$_2$—CH$_2$— | | 5-Cl-pyrimidin-4-yl | Cl | CON(CH$_3$)$_2$ | |
| 193 | —CH$_2$—CH$_2$—CH(CH$_3$)—CH$_2$—CH$_2$— | | 5-Cl-pyrimidin-4-yl | Cl | CO—NH-i-propyl | |
| 194 | —CH$_2$—CH$_2$—CH(CH$_3$)—CH$_2$—CH$_2$— | | 5-Cl-pyrimidin-4-yl | Cl | CO-morpholin-1-yl | |
| 195 | —CH$_2$—CH$_2$—CH(CH$_3$)—CH$_2$—CH$_2$— | | 5-Cl-pyrimidin-4-yl | Cl | COOH | |
| 196 | —CH$_2$—CH$_2$—CH(CH$_3$)—CH$_2$—CH$_2$— | | 5-Cl-pyrimidin-4-yl | Cl | COO-propen-3-yl | |
| 197 | —CH$_2$—CH$_2$—CH(CH$_3$)—CH$_2$—CH$_2$— | | 5-Cl-pyrimidin-4-yl | Cl | COO-benzyl | |
| 198 | —CH$_2$—CH$_2$—CH(CH$_3$)—CH$_2$—CH$_2$— | | 5-Cl-pyrimidin-4-yl | Cl | COO—CH$_2$—CH$_2$—OCH$_3$ | |

TABLE 1-continued

| Ex. No. | R¹ or —R¹+R²— | R² | R³ | X | R⁴ | log p |
|---|---|---|---|---|---|---|
| 199 | —CH₂—CH₂—CH(CH₃)—CH₂—CH₂— | | 5-Cl-pyrimidin-4-yl | Cl | SO₃H | |
| 200 | —CH₂—CH₂—CH(CH₃)—CH₂—CH₂— | | 5-Cl-pyrimidin-4-yl | Cl | SO₂CH₃ | |
| 201 | 2-butyl | H | 2,4-dichloro,5-CH₃-phenyl | Cl | COOH | 4 |
| 202 | 2-butyl | H | 2,5-Cl-phenyl | Cl | COOH | 3.4 |
| 203 | 2-butyl | H | 2,5-Me-phenyl | Cl | COOH | 3.52 |
| 204 | 2-butyl | H | 2-Cl,4-methylphenyl | Cl | COO⁻K⁺ | |
| 205 | 2-butyl | H | 2-Cl,4-methylphenyl | Cl | COO⁻Na⁺ | |
| 206 | 2-butyl | H | 2-Cl,4-methylphenyl | Cl | COOH | 3.41 |
| 207 | 2-butyl | H | 2-Cl,5-Br-phenyl | Cl | COOH | 3.48 |
| 208 | 2-butyl | H | 2-Cl,5-F-phenyl | Cl | COOH | 3.06 |
| 209 | 2-butyl | H | 2-Cl,5-methoxy-phenyl | Cl | COOH | 3.1 |
| 210 | 2-butyl | H | 2-Cl-5-Me-phenyl | Cl | COOH | 3.38 |
| 211 | 2-butyl | H | 2-F,4-Cl-phenyl | Cl | COOH | 3.33 |
| 212 | 2-butyl | H | 2-F-phenyl | Cl | COOH | 2.82 |
| 213 | 2-butyl | H | 3,4-methylenedioxy-phenyl | Cl | COOH | 2.69 |
| 214 | C₂H₅ | H | 2,5-F-phenyl | Cl | COOH | 2.25 |
| 215 | (S) CH(CH₃)(CF₃) | H | 2,4-Cl-phenyl | Cl | COOH | 3.34 |
| 216 | (S) CH(CH₃)(CF₃) | H | 2,4-difluoro-,6-Cl-phenyl | Cl | CONCH₃OCH₃ | 3.3* |
| 217 | (S) CH(CH₃)(CF₃) | H | 2,4-difluoro-,6-Cl-phenyl | Cl | COOCH(CH₃)COOCH₃ | 4.08* |
| 218 | (S) CH(CH₃)(CF₃) | H | 2,4-difluoro-,6-Cl-phenyl | Cl | COOCH₂CH₂OCH₂CH₂OCH₃ | 3.68* |
| 219 | (S) CH(CH₃)(CF₃) | H | 2,4-difluoro-,6-Cl-phenyl | Cl | COO—CH₂—CH₂—OCH₃ | 3.76* |
| 220 | (S) CH(CH₃)(CF₃) | H | 2,4-difluoro-,6-Cl-phenyl | Cl | COOCH₂COOCH₃ | 3.73* |
| 221 | (S) CH(CH₃)(CF₃) | H | 2,4-difluoro-,6-Cl-phenyl | Cl | COOH | 2.95 |
| 222 | (S) CH(CH₃)(CF₃) | H | 2,5-F-phenyl | Cl | COOH | 2.69 |
| 223 | (S) CH(CH₃)(CF₃) | H | 2,5-Me-phenyl | Cl | COOH | 3.33 |
| 224 | (S) CH(CH₃)(CF₃) | H | 2-butyl | Cl | COOH | 2.88 |
| 225 | (S) CH(CH₃)(CF₃) | H | 2-Cl,4-methylphenyl | Cl | COO⁻Na⁺ | |
| 226 | (S) CH(CH₃)(CF₃) | H | 2-Cl,4-methylphenyl | Cl | COOH | 3.2 |
| 227 | (S) CH(CH₃)(CF₃) | H | 2-Cl,5-F-phenyl | Cl | COOH | 2.89 |
| 228 | (S) CH(CH₃)(CF₃) | H | 2-Cl-4-F-phenyl | Cl | COOC₂H₅ | 4.14 |
| 229 | (S) CH(CH₃)(CF₃) | H | 2-Cl-5-Me-phenyl | Cl | COOH | |
| 230 | (S) CH(CH₃)(CF₃) | H | 2-Cl-6-F-phenyl | Cl | COOC₂H₅ | 3.99 |
| 231 | (S) CH(CH₃)(CF₃) | H | 2-Cl-6-F-phenyl | Cl | COOCH₂CF₃ | 4.3 |
| 232 | (S) CH(CH₃)(CF₃) | H | 2-Cl-phenyl | Cl | COOC₂H₅ | 4.02 |
| 233 | (S) CH(CH₃)(CF₃) | H | 2-methyl-4-F-phenyl | Cl | COOH | 3.03 |
| 234 | (S) CH(CH₃)(CF₃) | H | 3-Me-thien-2-yl | Cl | COOH | 2.95 |
| 235 | (R) CH(CH₃)—C(CH₃)₃ | H | 2,4,6-trifluorophenyl | Cl | CONCH₃OCH₃ | 3.97* |
| 236 | (R) CH(CH₃)—C(CH₃)₃ | H | 2,4,6-trifluorophenyl | Cl | CONHCH(CH₃)COOCH₃ | 4.54** |
| 237 | (R) CH(CH₃)—C(CH₃)₃ | H | 2,4,6-trifluorophenyl | Cl | CONHCH₂COOCH₃ | 4.05** |
| 238 | (R) CH(CH₃)—C(CH₃)₃ | H | 2,4,6-trifluorophenyl | Cl | COO⁻K⁺ | |
| 239 | (R) CH(CH₃)—C(CH₃)₃ | H | 2,4,6-trifluorophenyl | Cl | COO⁻Na⁺ | |
| 240 | (R) CH(CH₃)—C(CH₃)₃ | H | 2,4,6-trifluorophenyl | Cl | COOCH(CH₃)COOCH₃ | 4.69* |
| 241 | (R) CH(CH₃)—C(CH₃)₃ | H | 2,4,6-trifluorophenyl | Cl | (R) COOCH(CH₃)CONHCH₃ | 4.25** |
| 242 | (R) CH(CH₃)—C(CH₃)₃ | H | 2,4,6-trifluorophenyl | Cl | COOCH₂CH₂OCH₂CH₂OCH₃ | 4.36* |
| 243 | (R) CH(CH₃)—C(CH₃)₃ | H | 2,4,6-trifluorophenyl | Cl | COOCH₂CONCH₃OCH₃ | 4.04** |
| 244 | (R) CH(CH₃)—C(CH₃)₃ | H | 2,4,6-trifluorophenyl | Cl | COOCH₂COOCH₃ | 4.31* |
| 245 | CH(CH₃)—C(CH₃)₃ | H | 2,4-Cl-phenyl | Cl | 2-pyridyl | 4.51 |
| 246 | CH(CH₃)—C(CH₃)₃ | H | 2,4-Cl-phenyl | Cl | 3-Me-1,2,4-triazol-5-yl | 3.92 |
| 247 | CH(CH₃)—C(CH₃)₃ | H | 2,4-Cl-phenyl | Cl | 5-Me-oxadiazol-2-yl | 4.78 |
| 248 | (R) CH(CH₃)—C(CH₃)₃ | H | 2,4-Cl-phenyl | Cl | CON(CH₃)₂ | 4.63** |
| 249 | (R) CH(CH₃)—C(CH₃)₃ | H | 2,4-Cl-phenyl | Cl | CONCH₃OCH₃ | 4.75** |
| 250 | (R) CH(CH₃)—C(CH₃)₃ | H | 2,4-Cl-phenyl | Cl | CONH(CH₂)₂OCH₃ | 5.05** |
| 251 | (R) CH(CH₃)—C(CH₃)₃ | H | 2,4-Cl-phenyl | Cl | CONHCH(CH₃)COOCH₃ | 5.22** |
| 252 | (R) CH(CH₃)—C(CH₃)₃ | H | 2,4-Cl-phenyl | Cl | CONHCH₂CN | 4.7** |
| 253 | (R) CH(CH₃)—C(CH₃)₃ | H | 2,4-Cl-phenyl | Cl | CONHCH₂COOCH₃ | 4.85** |
| 254 | (R) CH(CH₃)—C(CH₃)₃ | H | 2,4-Cl-phenyl | Cl | CO—NH—CH₃ | 4.51** |
| 255 | (R) CH(CH₃)—C(CH₃)₃ | H | 2,4-Cl-phenyl | Cl | COO⁻K⁺ | |
| 256 | (R) CH(CH₃)—C(CH₃)₃ | H | 2,4-Cl-phenyl | Cl | COO⁻Na⁺ | |
| 257 | (R) CH(CH₃)—C(CH₃)₃ | H | 2,4-Cl-phenyl | Cl | COO(CH₂)₂O(CH₂)₂O(CH₂)₂OCH₃ | 4.97** |
| 258 | (R) CH(CH₃)—C(CH₃)₃ | H | 2,4-Cl-phenyl | Cl | COO-2-carboxymethylphenyl | 5.83** |
| 259 | (R) CH(CH₃)—C(CH₃)₃ | H | 2,4-Cl-phenyl | Cl | COOCH(CH₃)COOCH₃ | 5.48** |
| 260 | (R) CH(CH₃)—C(CH₃)₃ | H | 2,4-Cl-phenyl | Cl | COOCH₂CH₂OCH₂CH₂OCH₃ | 5.04** |
| 261 | (R) CH(CH₃)—C(CH₃)₃ | H | 2,4-Cl-phenyl | Cl | COO—CH₂—CH₂—OCH₃ | 5.22* |
| 262 | (R) CH(CH₃)—C(CH₃)₃ | H | 2,4-Cl-phenyl | Cl | COOCH₂CONCH₃OCH₃ | 4.76** |
| 263 | (R) CH(CH₃)—C(CH₃)₃ | H | 2,4-Cl-phenyl | Cl | COOCH₂COOCH₃ | 5.1** |

TABLE 1-continued

[Structure: pyrazolo[1,5-a]pyrimidine core with NR¹R² at position 7, R³ at position 6, X at position 5, R⁴ at position 3]

| Ex. No. | R¹ or —R¹+R²— | R² | R³ | X | R⁴ | log p |
|---|---|---|---|---|---|---|
| 264 | (R) CH(CH$_3$)—C(CH$_3$)$_3$ | H | 2,4-Cl-phenyl | Cl | COOH | 4.26 |
| 265 | (R) CH(CH$_3$)—C(CH$_3$)$_3$ | H | 2,4-Cl-phenyl | Cl | COOphenyl | 6.12** |
| 266 | (R) CH(CH$_3$)—C(CH$_3$)$_3$ | H | 2,4-dichloro,5-CH$_3$-phenyl | Cl | COOH | 4.67 |
| 267 | (R) CH(CH$_3$)—C(CH$_3$)$_3$ | H | 2,4-difluoro-,6-Cl-phenyl | Cl | CONCH$_3$OCH$_3$ | 4.19* |
| 268 | (R) CH(CH$_3$)—C(CH$_3$)$_3$ | H | 2,4-difluoro-,6-Cl-phenyl | Cl | CONHCH(CH$_3$)COOCH$_3$ | 4.77** |
| 269 | (R) CH(CH$_3$)—C(CH$_3$)$_3$ | H | 2,4-difluoro-,6-Cl-phenyl | Cl | CONHCH$_2$COOCH$_3$ | 4.29** |
| 270 | (R) CH(CH$_3$)—C(CH$_3$)$_3$ | H | 2,4-difluoro-,6-Cl-phenyl | Cl | COOCH(CH$_3$)COOCH$_3$ | 4.95* |
| 271 | (R) CH(CH$_3$)—C(CH$_3$)$_3$ | H | 2,4-difluoro-,6-Cl-phenyl | Cl | (R) COOCH(CH$_3$)CONHCH$_3$ | 4.46** |
| 272 | (R) CH(CH$_3$)—C(CH$_3$)$_3$ | H | 2,4-difluoro-,6-Cl-phenyl | Cl | COOCH$_2$CH$_2$OCH$_2$CH$_2$OCH$_3$ | 4.6* |
| 273 | (R) CH(CH$_3$)—C(CH$_3$)$_3$ | H | 2,4-difluoro-,6-Cl-phenyl | Cl | COO—CH$_2$—CH$_2$—OCH$_3$ | 4.64* |
| 274 | (R) CH(CH$_3$)—C(CH$_3$)$_3$ | H | 2,4-difluoro-,6-Cl-phenyl | Cl | COOCH$_2$CONCH$_3$OCH$_3$ | 4.27** |
| 275 | (R) CH(CH$_3$)—C(CH$_3$)$_3$ | H | 2,4-difluoro-,6-Cl-phenyl | Cl | COOCH$_2$COOCH$_3$ | 4.61* |
| 276 | (R) CH(CH$_3$)—C(CH$_3$)$_3$ | H | 2,4-difluoro-,6-Cl-phenyl | Cl | COOH | 3.73 |
| 277 | (R) CH(CH$_3$)—C(CH$_3$)$_3$ | H | 2,4-F-phenyl | Cl | CONH(CH$_2$)$_2$OCH$_3$ | 4.2** |
| 278 | (R) CH(CH$_3$)—C(CH$_3$)$_3$ | H | 2,4-F-phenyl | Cl | CO—NH-morpholin-1-yl | 3.76** |
| 279 | (R) CH(CH$_3$)—C(CH$_3$)$_3$ | H | 2,4-F-phenyl | Cl | COO⁻Na⁺ | |
| 280 | (R) CH(CH$_3$)—C(CH$_3$)$_3$ | H | 2,4-F-phenyl | Cl | COO⁻K⁺ | |
| 281 | (R) CH(CH$_3$)—C(CH$_3$)$_3$ | H | 2,4-F-phenyl | Cl | COOH | 3.55 |
| 282 | (R) CH(CH$_3$)—C(CH$_3$)$_3$ | H | 2,5-Cl-phenyl | Cl | COOH | 4.06 |
| 283 | (R) CH(CH$_3$)—C(CH$_3$)$_3$ | H | 2,5-dimethylthien-3-yl | Cl | COO⁻Na⁺ | 4 |
| 284 | (R) CH(CH$_3$)—C(CH$_3$)$_3$ | H | 2,5-dimethylthien-3-yl | Cl | COOH | 4.15 |
| 285 | (R) CH(CH$_3$)—C(CH$_3$)$_3$ | H | 2,5-F-phenyl | Cl | CO-morpholin-1-yl | 3.69 |
| 286 | (R) CH(CH$_3$)—C(CH$_3$)$_3$ | H | 2,5-F-phenyl | Cl | CON(CH$_3$)$_2$ | 3.72 |
| 287 | (R) CH(CH$_3$)—C(CH$_3$)$_3$ | H | 2,5-F-phenyl | Cl | CONCH$_3$OCH$_3$ | 3.86 |
| 288 | (R) CH(CH$_3$)—C(CH$_3$)$_3$ | H | 2,5-F-phenyl | Cl | CONHC(CH$_3$)2—C≡CH | 4.99 |
| 289 | (R) CH(CH$_3$)—C(CH$_3$)$_3$ | H | 2,5-F-phenyl | Cl | CO—NH—CH$_3$ | 3.86 |
| 290 | (R) CH(CH$_3$)—C(CH$_3$)$_3$ | H | 2,5-F-phenyl | Cl | CONHCHMeCH$_2$OCH$_3$ | 4.48 |
| 291 | (R) OH(CH$_3$)—C(CH$_3$)$_3$ | H | 2,5-F-phenyl | Cl | COO⁻K⁺ | 3.36 |
| 292 | (R) CH(CH$_3$)—C(CH$_3$)$_3$ | H | 2,5-F-phenyl | Cl | COO⁻Na⁺ | 3.36 |
| 293 | (R) CH(CH$_3$)—C(CH$_3$)$_3$ | H | 2,5-F-phenyl | Cl | COO⁻NH$_4$ | 3.37 |
| 294 | (R) CH(CH$_3$)—C(CH$_3$)$_3$ | H | 2,5-F-phenyl | Cl | COO⁻NH2[CH(CH$_3$)$_2$]$_2$⁺ | |
| 295 | (R) CH(CH$_3$)—C(CH$_3$)$_3$ | H | 2,5-F-phenyl | Cl | COOCH$_2$CH$_2$OCH$_2$CH$_2$OCH$_3$ | 4.08 |
| 296 | (R) CH(CH$_3$)—C(CH$_3$)$_3$ | H | 2,5-F-phenyl | Cl | COO—CH$_2$—CH$_2$—OCH$_3$ | 4.24 |
| 297 | (R) CH(CH$_3$)—C(CH$_3$)$_3$ | H | 2,5-F-phenyl | Cl | COOH | 3.37 |
| 298 | (R) CH(CH$_3$)—C(CH$_3$)$_3$ | H | 2,5-F-phenyl | Cl | COO-propen-3-yl | 4.88 |
| 299 | (R) CH(CH$_3$)—C(CH$_3$)$_3$ | H | 2,5-Me-phenyl | Cl | CONHOH | 3.88 |
| 300 | (R) CH(CH$_3$)—C(CH$_3$)$_3$ | H | 2,5-Me-phenyl | Cl | COO⁻NH$_4$⁺ | 4.18 |
| 301 | (R) CH(CH$_3$)—C(CH$_3$)$_3$ | H | 2,5-Me-phenyl | Cl | COO⁻K⁺ | 4.18 |
| 302 | (R) CH(CH$_3$)—C(CH$_3$)$_3$ | H | 2,5-Me-phenyl | Cl | COO⁻Na⁺ | 4.18 |
| 303 | (R) CH(CH$_3$)—C(CH$_3$)$_3$ | H | 2,5-Me-phenyl | Cl | COOH | 4.18 |
| 304 | (R) CH(CH$_3$)—C(CH$_3$)$_3$ | H | 2,6-difluoro,4-Cl-phenyl | Cl | CONCH$_3$OCH$_3$ | 4.4* |
| 305 | (R) CH(CH$_3$)—C(CH$_3$)$_3$ | H | 2,6-difluoro,4-Cl-phenyl | Cl | CONHCH(CH$_3$)COOCH$_3$ | 5.01** |
| 306 | (R) CH(CH$_3$)—C(CH$_3$)$_3$ | H | 2,6-difluoro,4-Cl-phenyl | Cl | CONHCH$_2$COOCH$_3$ | 4.47** |
| 307 | (R) CH(CH$_3$)—C(CH$_3$)$_3$ | H | 2,6-difluoro,4-Cl-phenyl | Cl | COO⁻K⁺ | |
| 308 | (R) CH(CH$_3$)—C(CH$_3$)$_3$ | H | 2,6-difluoro,4-Cl-phenyl | Cl | COO⁻Na⁺ | |
| 309 | (R) CH(CH$_3$)—C(CH$_3$)$_3$ | H | 2,6-difluoro,4-Cl-phenyl | Cl | COOCH(CH$_3$)COOCH$_3$ | 5.19* |
| 310 | (R) CH(CH$_3$)—C(CH$_3$)$_3$ | H | 2,6-difluoro,4-Cl-phenyl | Cl | (R) COOCH(CH$_3$)CONHCH$_3$ | 4.69** |
| 311 | (R) CH(CH$_3$)—C(CH$_3$)$_3$ | H | 2,6-difluoro,4-Cl-phenyl | Cl | COOCH$_2$CH$_2$OCH$_2$CH$_2$OCH$_3$ | 4.73* |
| 312 | (R) CH(CH$_3$)—C(CH$_3$)$_3$ | H | 2,6-difluoro,4-Cl-phenyl | Cl | COO—CH$_2$—CH$_2$—OCH$_3$ | 4.88* |
| 313 | (R) CH(CH$_3$)—C(CH$_3$)$_3$ | H | 2,6-difluoro,4-Cl-phenyl | Cl | COOCH$_2$COOCH$_3$ | 4.79* |
| 314 | (R) CH(CH$_3$)—C(CH$_3$)$_3$ | H | 2,6-difluoro,4-phenyl | Cl | COOH | 3.95 |
| 315 | (R) CH(CH$_3$)—C(CH$_3$)$_3$ | H | 2,6-difluoro,4-methylphenyl | Cl | COOH | 3.75** |
| 316 | CH(CH$_3$)—C(CH$_3$)$_3$ | H | 2,6-F-phenyl | Cl | CON(CH$_3$)$_2$ | 3.66 |
| 317 | CH(CH$_3$)—C(CH$_3$)$_3$ | H | 2,6-F-phenyl | Cl | COO(CH$_2$)$_2$O(CH$_2$)$_2$O(CH$_2$)$_2$OCH$_3$ | 4.05 |
| 318 | CH(CH$_3$)—C(CH$_3$)$_3$ | H | 2,6-F-phenyl | Cl | COOCH(CH$_3$)COOCH$_3$ | 4.58 |
| 319 | CH(CH$_3$)—C(CH$_3$)$_3$ | H | 2,6-F-phenyl | Cl | COOCH$_2$CH$_2$CH$_3$ | 5.68 |
| 320 | CH(CH$_3$)—C(CH$_3$)$_3$ | H | 2,6-F-phenyl | Cl | COOCH$_2$CH$_2$OCH$_2$CH$_2$OCH$_3$ | 4.14 |
| 321 | CH(CH$_3$)—C(CH$_3$)$_3$ | H | 2,6-F-phenyl | Cl | COO—CH$_2$—CH$_2$—OCH$_3$ | 4.23 |
| 322 | CH(CH$_3$)—C(CH$_3$)$_3$ | H | 2,6-F-phenyl | Cl | COOCH$_2$COOCH$_3$ | 4.2 |
| 323 | CH(CH$_3$)—C(CH$_3$)$_3$ | H | 2,6-F-phenyl | Cl | COOH | 3.35 |
| 324 | (R) CH(CH$_3$)—C(CH$_3$)$_3$ | H | 2-Cl,4-MeO-phenyl | Cl | COO⁻Na⁺ | |
| 325 | (R) CH(CH$_3$)—C(CH$_3$)$_3$ | H | 2-Cl,4-MeO-phenyl | Cl | COOH | 3.57 |
| 326 | (R) CH(CH$_3$)—C(CH$_3$)$_3$ | H | 2-Cl,4-methylphenyl | Cl | CONH(CH$_2$)$_2$OCH$_3$ | 4.82** |
| 327 | (R) CH(CH$_3$)—C(CH$_3$)$_3$ | H | 2-Cl,4-methylphenyl | Cl | CO—NH-morpholin-1-yl | 4.41** |

TABLE 1-continued

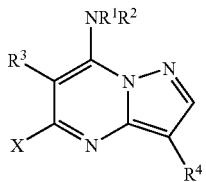

| Ex. No. | R¹ or —R¹+R²— | R² | R³ | X | R⁴ | log p |
|---|---|---|---|---|---|---|
| 328 | (R) CH(CH₃)—C(CH₃)₃ | H | 2-Cl,4-methylphenyl | Cl | COO⁻K⁺ | |
| 329 | (R) CH(CH₃)—C(CH₃)₃ | H | 2-Cl,4-methylphenyl | Cl | COO⁻Na⁺ | |
| 330 | (R) CH(CH₃)—C(CH₃)₃ | H | 2-Cl,4-methylphenyl | Cl | COOH | 4.04 |
| 331 | (S) CH(CH₃)—C(CH₃)₃ | H | 2-Cl,4-methylphenyl | Cl | COOH | 4.07 |
| 332 | (R) CH(CH₃)—C(CH₃)₃ | H | 2-Cl,5-Br-phenyl | Cl | COOH | 4.15 |
| 333 | (R) CH(CH₃)—C(CH₃)₃ | H | 2-Cl,5-F-phenyl | Cl | COO⁻K⁺ | |
| 334 | (R) CH(CH₃)—C(CH₃)₃ | H | 2-Cl,5-F-phenyl | Cl | COO⁻Na⁺ | |
| 335 | (R) CH(CH₃)—C(CH₃)₃ | H | 2-Cl,5-F-phenyl | Cl | COO⁻NH₄⁺ | |
| 336 | (R) CH(CH₃)—C(CH₃)₃ | H | 2-Cl,5-F-phenyl | Cl | COO⁻NH2[CH(CH₃)₂]2⁺ | |
| 337 | (R) CH(CH₃)—C(CH₃)₃ | H | 2-Cl,5-F-phenyl | Cl | COOH | 3.68 |
| 338 | (R) CH(CH₃)—C(CH₃)₃ | H | 2-Cl,5-methoxy-phenyl | Cl | COOH | 3.72 |
| 339 | (R) CH(CH₃)—C(CH₃)₃ | H | 2-Cl-4-F-phenyl | Cl | 1,3,4-oxathiazol-2-on-5-yl | 5.38 |
| 340 | CH(CH₃)—C(CH₃)₃ | H | 2-Cl-4-F-phenyl | Cl | 2-pyridyl | 4.02 |
| 341 | (R) CH(CH₃)—C(CH₃)₃ | H | 2-Cl-4-F-phenyl | Cl | 3-Me-1,2,4-triazol-5-yl | 3.48 |
| 342 | CH(CH₃)—C(CH₃)₃ | H | 2-Cl-4-F-phenyl | Cl | 5-amino-thiadiazol-2-yl | 3.91 |
| 343 | CH(CH₃)—C(CH₃)₃ | H | 2-Cl-4-F-phenyl | Cl | 5-Me-oxadiazol-2-yl | 4.24 |
| 344 | (R) CH(CH₃)—C(CH₃)₃ | H | 2-Cl-4-F-phenyl | OCH₂C CCNCH₂Cy3 | | 6.26 |
| 345 | (R) CH(CH₃)—C(CH₃)₃ | H | 2-Cl-4-F-phenyl | Cl | CONCH₃OCH₃ | 4.27 |
| 346 | (R) CH(CH₃)—C(CH₃)₃ | H | 2-Cl-4-F-phenyl | Cl | CONH(CH₂)₂OCH₃ | 4.45 |
| 347 | (R) CH(CH₃)—C(CH₃)₃ | H | 2-Cl-4-F-phenyl | Cl | CONH(CH₂)₂OCO(CH₃) | 4.39** |
| 348 | (R) CH(CH₃)—C(CH₃)₃ | H | 2-Cl-4-F-phenyl | Cl | CONHC(CH₃)₂—C≡CH | 5.44 |
| 349 | (R) CH(CH₃)—C(CH₃)₃ | H | 2-Cl-4-F-phenyl | Cl | CONHC(CH₃)₂CN | 5.02 |
| 350 | (R) CH(CH₃)—C(CH₃)₃ | H | 2-Cl-4-F-phenyl | Cl | CONH—CH(CH₃)CONHCH_S | 3.75 |
| 351 | (R) CH(CH₃)—C(CH₃)₃ | H | 2-Cl-4-F-phenyl | Cl | CONHCH(CH₃)COOCH₃ | 4.8 |
| 352 | (R) CH(CH₃)—C(CH₃)₃ | H | 2-Cl-4-F-phenyl | Cl | CONHCH₂CH₂OH | 3.53** |
| 353 | (R) CH(CH₃)—C(CH₃)₃ | H | 2-Cl-4-F-phenyl | Cl | CONHCH₂CN | 4.24 |
| 354 | (R) CH(CH₃)—C(CH₃)₃ | H | 2-Cl-4-F-phenyl | Cl | CONHCH₂COOCH₃ | 4.34 |
| 355 | (R) CH(CH₃)—C(CH₃)₃ | H | 2-Cl-4-F-phenyl | Cl | CONHCHMeCH₂OCH₃ | 4.9 |
| 356 | (R) CH(CH₃)—C(CH₃)₃ | H | 2-Cl-4-F-phenyl | Cl | CONHOH | 3.51** |
| 357 | (R) CH(CH₃)—C(CH₃)₃ | H | 2-Cl-4-F-phenyl | Cl | COO⁻K⁺ | |
| 358 | (R) CH(CH₃)—C(CH₃)₃ | H | 2-Cl-4-F-phenyl | Cl | COO(CH₂)₂O(CH₂)₂O(CH₂)₂OCH₃ | 4.53 |
| 359 | (R) CH(CH₃)—C(CH₃)₃ | H | 2-Cl-4-F-phenyl | Cl | COOC₂H₅ | 5.15 |
| 360 | CH(CH₃)—C(CH₃)₃ | H | 2-Cl-4-F-phenyl | Cl | COOC₂H₅ | 5.63 |
| 361 | (R) CH(CH₃)—C(CH₃)₃ | H | 2-Cl-4-F-phenyl | Cl | COOCH(CH₃)COOCH₃ | 5.01 |
| 362 | (R) CH(CH₃)—C(CH₃)₃ | H | 2-Cl-4-F-phenyl | Cl | (R) COOCH(CH₃)CONHCH₃ | 4.47 |
| 363 | (R) CH(CH₃)—C(CH₃)₃ | H | 2-Cl-4-F-phenyl | Cl | COOCH₂CH₂OCH₂CH₂OCH₃ | 4.57 |
| 364 | (R) CH(CH₃)—C(CH₃)₃ | H | 2-Cl-4-F-phenyl | Cl | COOCH₂CONCH₃OCH₃ | 4.28 |
| 365 | (R) CH(CH₃)—C(CH₃)₃ | H | 2-Cl-4-F-phenyl | Cl | COOCH₂COOCH₃ | 4.59 |
| 366 | (R) CH(CH₃)—C(CH₃)₃ | H | 2-Cl-4-F-phenyl | Cl | dioxazin-3-yl | 4.43 |
| 367 | (R) CH(CH₃)—C(CH₃)₃ | H | 2-Cl-4-F-phenyl | O-i-propyl | N(C≡N)CH(CH₃)₂ | 6.35 |
| 368 | (R) CH(CH₃)—C(CH₃)₃ | H | 2-Cl-4-F-phenyl | -n-butoxy | N(C≡N)CH₂CH₂CH₂CH₃ | 7.11 |
| 369 | (R) CH(CH₃)—C(CH₃)₃ | H | 2-Cl-4-F-phenyl | -O-n-propyl | N(C≡N)CH₂CH₂CH₃ | 6.46 |
| 370 | (R) CH(CH₃)—C(CH₃)₃ | H | 2-Cl-4-F-phenyl | —O—C₂H₅ | N(C≡N)Et | 5.71 |
| 371 | (R) CH(CH₃)—C(CH₃)₃ | H | 2-Cl-4-F-phenyl | Cl | —NH2 | |
| 372 | (R) CH(CH₃)—C(CH₃)₃ | H | 2-Cl-4-F-phenyl | Cl | oxadiazin-3-yl | 4.9 |
| 373 | (R) CH(CH₃)—C(CH₃)₃ | H | 2-Cl-4-F-phenyl | Cl | oxazol-2-yl | 4.72 |
| 374 | CH(CH₃)—C(CH₃)₃ | H | 2-Cl-4-F-phenyl | Cl | PO(OEt)₂ | 4.48** |
| 375 | CH(CH₃)—C(CH₃)₃ | H | 2-Cl-4-F-phenyl | Cl | PO(OH)OEt | 3.01** |
| 376 | CH(CH₃)—C(CH₃)₃ | H | 2-Cl-4-F-phenyl | Cl | SO₂NCH(CH₃)₂ | 4.73 |
| 377 | (R) CH(CH₃)—C(CH₃)₃ | H | 2-Cl-5-Me-phenyl | Cl | COOH | 4.05 |
| 378 | (R) CH(CH₃)—C(CH₃)₃ | H | 2-Cl-6-F-phenyl | Cl | CONCH₃OCH₃ | 4.02* |
| 379 | (R) CH(CH₃)—C(CH₃)₃ | H | 2-Cl-6-F-phenyl | Cl | CONHCH(CH₃)COOCH₃ | 4.59** |
| 380 | (R) CH(CH₃)—C(CH₃)₃ | H | 2-Cl-6-F-phenyl | Cl | CONHCH₂COOCH₃ | 4.11** |
| 381 | (R) CH(CH₃)—C(CH₃)₃ | H | 2-Cl-6-F-phenyl | Cl | COOC₂H₅ | 4.99 |
| 382 | (R) CH(CH₃)—C(CH₃)₃ | H | 2-Cl-6-F-phenyl | Cl | COOCH(CH₃)COOCH₃ | 4.87* |
| 383 | (R) CH(CH₃)—C(CH₃)₃ | H | 2-Cl-6-F-phenyl | Cl | (R) COOCH(CH₃)CONHCH₃ | 4.34** |
| 384 | (R) CH(CH₃)—C(CH₃)₃ | H | 2-Cl-6-F-phenyl | Cl | COOCH₂CH₂OCH₂CH₂OCH₃ | 4.41* |
| 385 | (R) CH(CH₃)—C(CH₃)₃ | H | 2-Cl-6-F-phenyl | Cl | COOCH₂COOCH₃ | 4.46* |
| 386 | (R) CH(CH₃)—C(CH₃)₃ | H | 2-Cl-6-F-phenyl | Cl | COO-i-propyl | 5.45 |
| 387 | (R) CH(CH₃)—C(CH₃)₃ | H | 2-Cl-phenyl | Cl | CONCH₃OCH₃ | 4.14* |
| 388 | (R) CH(CH₃)—C(CH₃)₃ | H | 2-Cl-phenyl | Cl | CONHCH(CH₃)COOCH₃ | 4.64** |
| 389 | (R) CH(CH₃)—C(CH₃)₃ | H | 2-Cl-phenyl | Cl | CONHCH₂COOCH₃ | 4.25** |
| 390 | (R) CH(CH₃)—C(CH₃)₃ | H | 2-Cl-phenyl | Cl | COOC₂H₅ | 5.11 |
| 391 | (R) CH(CH₃)—C(CH₃)₃ | H | 2-Cl-phenyl | Cl | COOCH(CH₃)COOCH₃ | 4.92* |

TABLE 1-continued

| Ex. No. | R¹ or —R¹+R²— | R² | R³ | X | R⁴ | log p |
|---|---|---|---|---|---|---|
| 392 | (R) CH(CH₃)—C(CH₃)₃ | H | 2-Cl-phenyl | Cl | COOCH₂CF₃ | 5.37 |
| 393 | (R) CH(CH₃)—C(CH₃)₃ | H | 2-Cl-phenyl | Cl | COOCH₂CH₂OCH₂CH₂OCH₃ | 4.51* |
| 394 | (R) CH(CH₃)—C(CH₃)₃ | H | 2-Cl-phenyl | Cl | COOCH₂COOCH₃ | 4.53* |
| 395 | (R) CH(CH₃)—C(CH₃)₃ | H | 2-F,4-Cl-phenyl | Cl | COO⁻K⁺ | |
| 396 | (R) CH(CH₃)—C(CH₃)₃ | H | 2-F,4-Cl-phenyl | Cl | COO⁻Na⁺ | |
| 397 | (R) CH(CH₃)—C(CH₃)₃ | H | 2-F,4-Cl-phenyl | Cl | COO⁻NH₄⁺ | |
| 398 | (R) CH(CH₃)—C(CH₃)₃ | H | 2-F,4-Cl-phenyl | Cl | COO⁻NH2[CH(CH₃)₂]₂⁺ | |
| 399 | (R) CH(CH₃)—C(CH₃)₃ | H | 2-F,4-Cl-phenyl | Cl | COOH | 3.93 |
| 400 | (R) CH(CH₃)—C(CH₃)₃ | H | 2-F-phenyl | Cl | COOH | 3.43 |
| 401 | CH(CH₃)—C(CH₃)₃ | H | 2-Me-phenyl | Cl | CONH(CH₂)₂OCH₃ | 4.5 |
| 402 | CH(CH₃)—C(CH₃)₃ | H | 2-Me-phenyl | Cl | COOCH(CH₃)COOCH₃ | 5.04 |
| 403 | CH(CH₃)—C(CH₃)₃ | H | 2-Me-phenyl | Cl | COOCH₂CH₂OCH₂CH₂OCH₃ | 4.59 |
| 404 | CH(CH₃)—C(CH₃)₃ | H | 2-Me-phenyl | Cl | COO—CH₂—CH₂—OCH₃ | 4.67 |
| 405 | CH(CH₃)—C(CH₃)₃ | H | 2-Me-phenyl | Cl | COOCH₂COOCH₃ | 4.64 |
| 406 | CH(CH₃)—C(CH₃)₃ | H | 2-Me-phenyl | Cl | COOH | 3.83 |
| 407 | (R) CH(CH₃)—C(CH₃)₃ | H | 3,4-methylenedioxy-phenyl | Cl | COOH | 3.22 |
| 408 | (R) CH(CH₃)—C(CH₃)₃ | H | 3-Cl-thien-2-yl | Cl | COO⁻Na⁺ | |
| 409 | (R) CH(CH₃)—C(CH₃)₃ | H | 3-Cl-thien-2-yl | Cl | COOH | 3.62 |
| 410 | (R) CH(CH₃)—C(CH₃)₃ | H | 3-Me-thien-2-yl | Cl | COOH | 3.68 |
| 411 | CH(CH₃)—C(CH₃)₃ | H | 4-chlorobenzyl | Cl | COOC₂H₅ | |
| 412 | (S) CH(CH₃)—C(CH₃)₃ | H | 4-chlorobenzyl | Cl | COOC₂H₅ | |
| 413 | (R) CH(CH₃)—C(CH₃)₃ | H | 4-chlorobenzyl | Cl | COOC₂H₅ | |
| 414 | CH(CH₃)—C(CH₃)₃ | H | 4-chlorobenzyl | Cl | COOH | |
| 415 | (S) CH(CH₃)—C(CH₃)₃ | H | 4-chlorobenzyl | Cl | COOH | |
| 416 | (R) CH(CH₃)—C(CH₃)₃ | H | 4-chlorobenzyl | Cl | COOH | |
| 417 | (R) CH(CH₃)—C(CH₃)₃ | H | 5-F-pyrimidin-4-yl | Cl | COOH | 2.35 |
| 418 | CH(CH₃)—C(CH₃)₃ | H | phenyl | Cl | 3-Me-1,2,4-triazol-5-yl | 3.25 |
| 419 | CH(CH₃)—C(CH₃)₃ | H | phenyl | Cl | 5-Me-oxadiazyl-2-yl | 4.03 |
| 420 | CH(CH₃)—C(CH₃)₃ | H | phenyl | Cl | COOH | 3.6 |
| 421 | (R) CH(CH₃)—CH(CH₃)₂ | H | 2,4,6-trifluorophenyl | Cl | CONCH₃OCH₃ | 3.67 |
| 422 | (R) CH(CH₃)—CH(CH₃)₂ | H | 2,4,6-trifluorophenyl | Cl | CONHCH(CH₃)COOCH₃ | 4.22** |
| 423 | (R) CH(CH₃)—CH(CH₃)₂ | H | 2,4,6-trifluorophenyl | Cl | CONHCH₂COOCH₃ | 3.76** |
| 424 | (R) CH(CH₃)—CH(CH₃)₂ | H | 2,4,6-trifluorophenyl | Cl | COO⁻K⁺ | |
| 425 | (R) CH(CH₃)—CH(CH₃)₂ | H | 2,4,6-trifluorophenyl | Cl | COO⁻Na⁺ | |
| 426 | (R) CH(CH₃)—CH(CH₃)₂ | H | 2,4,6-trifluorophenyl | Cl | COOCH(CH₃)COOCH₃ | 4.39 |
| 427 | (R) CH(CH₃)—CH(CH₃)₂ | H | 2,4,6-trifluorophenyl | Cl | (R) COOCH(CH₃)CONHCH₃ | 3.9** |
| 428 | (R) CH(CH₃)—CH(CH₃)₂ | H | 2,4,6-trifluorophenyl | Cl | COOCH₂CH₂OCH₂CH₂OCH₃ | 3.96 |
| 429 | (R) CH(CH₃)—CH(CH₃)₂ | H | 2,4,6-trifluorophenyl | Cl | COOCH₂CONCH₃OCH₃ | 3.73** |
| 430 | (R) CH(CH₃)—CH(CH₃)₂ | H | 2,4,6-trifluorophenyl | Cl | COOCH₂COOCH₃ | 4.05* |
| 431 | CH(CH₃)—CH(CH₃)₂ | H | 2,4-Cl-phenyl | Cl | 2-pyridyl | 4.02 |
| 432 | CH(CH₃)—CH(CH₃)₂ | H | 2,4-Cl-phenyl | Cl | 3-Me-1,2,4-triazol-5-yl | 3.6 |
| 433 | CH(CH₃)—CH(CH₃)₂ | H | 2,4-Cl-phenyl | Cl | 5-Me-oxadiazyl-2-yl | 4.42 |
| 434 | (R) CH(CH₃)—CH(CH₃)₂ | H | 2,4-Cl-phenyl | Cl | CON(CH₃)₂ | 4.3* |
| 435 | (R) CH(CH₃)—CH(CH₃)₂ | H | 2,4-Cl-phenyl | Cl | CONCH₃OCH₃ | 4.38* |
| 436 | (R) CH(CH₃)—CH(CH₃)₂ | H | 2,4-Cl-phenyl | Cl | CONH(CH₂)₂OCH₃ | 4.7** |
| 437 | (R) CH(CH₃)—CH(CH₃)₂ | H | 2,4-Cl-phenyl | Cl | CONHCH(CH₃)COOCH₃ | 5.15** |
| 438 | (R) CH(CH₃)—CH(CH₃)₂ | H | 2,4-Cl-phenyl | Cl | CONHCH₂CN | 4.38** |
| 439 | (R) CH(CH₃)—CH(CH₃)₂ | H | 2,4-Cl-phenyl | Cl | CONHCH₂COOCH₃ | 4.52** |
| 440 | (R) CH(CH₃)—CH(CH₃)₂ | H | 2,4-Cl-phenyl | Cl | CO—NH—CH₃ | 4.52** |
| 441 | (R) CH(CH₃)—CH(CH₃)₂ | H | 2,4-Cl-phenyl | Cl | COO⁻Na⁺ | |
| 442 | (R) CH(CH₃)—CH(CH₃)₂ | H | 2,4-Cl-phenyl | Cl | COO⁻NH2[CH(CH₃)₂]₂⁺ | |
| 443 | (R) CH(CH₃)—CH(CH₃)₂ | H | 2,4-Cl-phenyl | Cl | COO(CH₂)₂O(CH₂)₂O(CH₂)₂OCH₃ | 4.62** |
| 444 | CH(CH₃)—CH(CH₃)₂ | H | 2,4-Cl-phenyl | Cl | COOC₂H₅ | 5.71 |
| 445 | (R) CH(CH₃)—CH(CH₃)₂ | H | 2,4-Cl-phenyl | Cl | COOCH(CH₃)COOCH₃ | 5.15* |
| 446 | (R) CH(CH₃)—CH(CH₃)₂ | H | 2,4-Cl-phenyl | Cl | (R) COOCH(CH₃)CONHCH₃ | 4.62** |
| 447 | (R) CH(CH₃)—CH(CH₃)₂ | H | 2,4-Cl-phenyl | Cl | COOCH₂CH₂OCH₂CH₂OCH₃ | 4.89* |
| 448 | (R) CH(CH₃)—CH(CH₃)₂ | H | 2,4-Cl-phenyl | Cl | COO—CH₂—CH₂—OCH₃ | 4.78* |
| 449 | (R) CH(CH₃)—CH(CH₃)₂ | H | 2,4-Cl-phenyl | Cl | COOCH₂CONCH₃OCH₃ | 4.43* |
| 450 | (R) CH(CH₃)—CH(CH₃)₂ | H | 2,4-Cl-phenyl | Cl | COOCH₂COOCH₃ | 4.77* |
| 451 | (R) CH(CH₃)—CH(CH₃)₂ | H | 2,4-Cl-phenyl | Cl | COOH | 3.93 |
| 452 | (R) CH(CH₃)—CH(CH₃)₂ | H | 2,4-Cl-phenyl | Cl | COOphenyl | 5.75** |
| 453 | (R) CH(CH₃)—CH(CH₃)₂ | H | 2,4-dichloro,5-CH₃-phenyl | Cl | COOH | 4.32 |
| 454 | (R) CH(CH₃)—CH(CH₃)₂ | H | 2,4-difluoro-,6-Cl-phenyl | Cl | CONCH₃OCH₃ | 3.86* |
| 455 | (R) CH(CH₃)—CH(CH₃)₂ | H | 2,4-difluoro-,6-Cl-phenyl | Cl | CONHCH(CH₃)COOCH₃ | 4.48** |

TABLE 1-continued

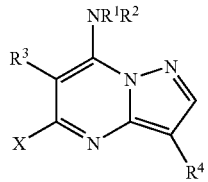

| Ex. No. | R¹ or —R¹+R²— | R² | R³ | X | R⁴ | log p |
|---|---|---|---|---|---|---|
| 456 | (R) CH(CH₃)—CH(CH₃)₂ | H | 2,4-difluoro-,6-Cl-phenyl | Cl | CONHCH₂COOCH₃ | 4.01** |
| 457 | (R) CH(CH₃)—CH(CH₃)₂ | H | 2,4-difluoro-,6-Cl-phenyl | Cl | COOCH(CH₃)COOCH₃ | 4.64* |
| 458 | (R) CH(CH₃)—CH(CH₃)₂ | H | 2,4-difluoro-,6-Cl-phenyl | Cl | (R) COOCH(CH₃)CONHCH₃ | 4.12** |
| 459 | (R) CH(CH₃)—CH(CH₃)₂ | H | 2,4-difluoro-,6-Cl-phenyl | Cl | COOCH₂CH₂OCH₂CH₂OCH₃ | 4.22* |
| 460 | (R) CH(CH₃)—CH(CH₃)₂ | H | 2,4-difluoro-,6-Cl-phenyl | Cl | COO—CH₂—CH₂—OCH₃ | 4.31* |
| 461 | (R) CH(CH₃)—CH(CH₃)₂ | H | 2,4-difluoro-,6-Cl-phenyl | Cl | COOCH₂CONCH₃OCH₃ | 3.96** |
| 462 | (R) CH(CH₃)—CH(CH₃)₂ | H | 2,4-difluoro-,6-Cl-phenyl | Cl | COOCH₂COOCH₃ | 4.26* |
| 463 | (R) CH(CH₃)—CH(CH₃)₂ | H | 2,4-difluoro-,6-Cl-phenyl | Cl | COOH | 3.46 |
| 464 | (R) CH(CH₃)—CH(CH₃)₂ | H | 2,4-F-phenyl | Cl | CON(CH₃)₂ | 3.55** |
| 465 | (R) CH(CH₃)—CH(CH₃)₂ | H | 2,4-F-phenyl | Cl | CONH(CH₂)₂OCH₃ | 3.85** |
| 466 | (R) CH(CH₃)—CH(CH₃)₂ | H | 2,4-F-phenyl | Cl | CONHCH(CH₃)CH₂OH | 3.41** |
| 467 | (R) CH(CH₃)—CH(CH₃)₂ | H | 2,4-F-phenyl | Cl | CONH—CH(CH₃)CONHCH_S | 3.29** |
| 468 | (R) CH(CH₃)—CH(CH₃)₂ | H | 2,4-F-phenyl | Cl | CONHCH(CH₃)COOCH₃ | 4.26** |
| 469 | (R) CH(CH₃)—CH(CH₃)₂ | H | 2,4-F-phenyl | Cl | CONHCH₂CN | 3.68** |
| 470 | (R) CH(CH₃)—CH(CH₃)₂ | H | 2,4-F-phenyl | Cl | CO—NH—CH₃ | 3.68** |
| 471 | (R) CH(CH₃)—CH(CH₃)₂ | H | 2,4-F-phenyl | Cl | CO—NH-morpholin-1-yl | 3.46** |
| 472 | (R) CH(CH₃)—CH(CH₃)₂ | H | 2,4-F-phenyl | Cl | COO⁻Na⁺ | |
| 473 | (R) CH(CH₃)—CH(CH₃)₂ | H | 2,4-F-phenyl | Cl | COO⁻K⁺ | |
| 474 | (R) CH(CH₃)—CH(CH₃)₂ | H | 2,4-F-phenyl | Cl | COO(CH₂)₂O-(4-carboxymethylphenyl) | 4.84** |
| 475 | (R) CH(CH₃)—CH(CH₃)₂ | H | 2,4-F-phenyl | Cl | COO(CH₂)₂O(CH₂)₂O(CH₂)₂OCH₃ | 3.89** |
| 476 | (R) CH(CH₃)—CH(CH₃)₂ | H | 2,4-F-phenyl | Cl | COO-2-carboxymethylphenyl | 4.74** |
| 477 | (R) CH(CH₃)—CH(CH₃)₂ | H | 2,4-F-phenyl | Cl | COOC₂H₅ | 4.47** |
| 478 | (R) CH(CH₃)—CH(CH₃)₂ | H | 2,4-F-phenyl | Cl | COOCH(CH₂OCH₃)₂ | 4.22** |
| 479 | (R) CH(CH₃)—CH(CH₃)₂ | H | 2,4-F-phenyl | Cl | COOCH(CH₃)COOCH₃ | 4.37 |
| 480 | (R) CH(CH₃)—CH(CH₃)₂ | H | 2,4-F-phenyl | Cl | (R) COOCH(CH₃)CONHCH₃ | 3.91** |
| 481 | (R) CH(CH₃)—CH(CH₃)₂ | H | 2,4-F-phenyl | Cl | COOCH₂—C≡CH | 4.23** |
| 482 | (R) CH(CH₃)—CH(CH₃)₂ | H | 2,4-F-phenyl | Cl | COOCH₂CF₃ | 4.79** |
| 483 | (R) CH(CH₃)—CH(CH₃)₂ | H | 2,4-F-phenyl | Cl | COO—CH₂—CH₂—OCH₃ | 4 |
| 484 | (R) CH(CH₃)—CH(CH₃)₂ | H | 2,4-F-phenyl | Cl | COOCH₂CONCH₃OCH₃ | 3.71** |
| 485 | (R) CH(CH₃)—CH(CH₃)₂ | H | 2,4-F-phenyl | Cl | COOCH₂COOCH₃ | 4** |
| 486 | (R) CH(CH₃)—CH(CH₃)₂ | H | 2,4-F-phenyl | Cl | COOH | 3.28 |
| 487 | (R) CH(CH₃)—CH(CH₃)₂ | H | 2,4-F-phenyl | Cl | COO-i-propyl | 4.89** |
| 488 | (R) CH(CH₃)—CH(CH₃)₂ | H | 2,4-F-phenyl | Cl | COOphenyl | 4.98** |
| 489 | (R) CH(CH₃)—CH(CH₃)₂ | H | 2,5-Cl-phenyl | Cl | COOH | 3.72 |
| 490 | (R) CH(CH₃)—CH(CH₃)₂ | H | 2,5-dimethylthien-3-yl | Cl | COO⁻Na⁺ | |
| 491 | (R) CH(CH₃)—CH(CH₃)₂ | H | 2,5-dimethylthien-3-yl | Cl | COO⁻K⁺ | |
| 492 | (R) CH(CH₃)—CH(CH₃)₂ | H | 2,5-dimethylthien-3-yl | Cl | COOH | 3.82 |
| 493 | (R) CH(CH₃)—CH(CH₃)₂ | H | 2,5-F-phenyl | Cl | CO-morpholin-1-yl | 3.39 |
| 494 | (R) CH(CH₃)—CH(CH₃)₂ | H | 2,5-F-phenyl | Cl | CON(CH₃)₂ | 3.43 |
| 495 | (R) CH(CH₃)—CH(CH₃)₂ | H | 2,5-F-phenyl | Cl | CONHCHMeCH₂OCH₃ | 4.19 |
| 496 | (R) CH(CH₃)—CH(CH₃)₂ | H | 2,5-F-phenyl | Cl | CONHOH | |
| 497 | (R) CH(CH₃)—CH(CH₃)₂ | H | 2,5-F-phenyl | Cl | COO⁻K⁺ | 3.06 |
| 498 | (R) CH(CH₃)—CH(CH₃)₂ | H | 2,5-F-phenyl | Cl | COO⁻Na⁺ | 3.06 |
| 499 | (R) CH(CH₃)—CH(CH₃)₂ | H | 2,5-F-phenyl | Cl | COO⁻NH4⁺ | 3.06 |
| 500 | (R) CH(CH₃)—CH(CH₃)₂ | H | 2,5-F-phenyl | Cl | COO⁻NH₂[CH(CH₃)₂]₂⁺ | |
| 501 | (R) CH(CH₃)—CH(CH₃)₂ | H | 2,5-F-phenyl | Cl | COOC₂H₅ | 4.37 |
| 502 | (R) CH(CH₃)—CH(CH₃)₂ | H | 2,5-F-phenyl | Cl | COOCH(CH₃)COOCH₃ | 4.29 |
| 503 | (R) CH(CH₃)—CH(CH₃)₂ | H | 2,5-F-phenyl | Cl | COOCH₂CH₂OCH₂CH₂OCH₃ | 3.84 |
| 504 | (R) CH(CH₃)—CH(CH₃)₂ | H | 2,5-F-phenyl | Cl | COO—CH₂—CH₂—OCH₃ | 3.91 |
| 505 | (R) CH(CH₃)—CH(CH₃)₂ | H | 2,5-F-phenyl | Cl | COOH | 3.06 |
| 506 | (R) CH(CH₃)—CH(CH₃)₂ | H | 2,5-F-phenyl | Cl | COO-propen-3-yl | 4.53 |
| 507 | (R) CH(CH₃)—CH(CH₃)₂ | H | 2,5-Me-phenyl | Cl | CONHOH | 3.55 |
| 508 | (R) CH(CH₃)—CH(CH₃)₂ | H | 2,5-Me-phenyl | Cl | COO⁻K⁺ | 3.85 |
| 509 | (R) CH(CH₃)—CH(CH₃)₂ | H | 2,5-Me-phenyl | Cl | COO⁻NH4⁺ | 3.85 |
| 510 | (R) CH(CH₃)—CH(CH₃)₂ | H | 2,5-Me-phenyl | Cl | COO⁻Na⁺ | 3.85 |
| 511 | (R) CH(CH₃)—CH(CH₃)₂ | H | 2,5-Me-phenyl | Cl | COOH | 3.85 |
| 512 | (R) CH(CH₃)—CH(CH₃)₂ | H | 2,6-difluoro,4-Cl-phenyl | Cl | CONCH₃OCH₃ | 4.1* |
| 513 | (R) CH(CH₃)—CH(CH₃)₂ | H | 2,6-difluoro,4-Cl-phenyl | Cl | CONHCH(CH₃)COOCH₃ | 4.68** |
| 514 | (R) CH(CH₃)—CH(CH₃)₂ | H | 2,6-difluoro,4-Cl-phenyl | Cl | CONHCH₂COOCH₃ | 4.17** |
| 515 | (R) CH(CH₃)—CH(CH₃)₂ | H | 2,6-difluoro,4-Cl-phenyl | Cl | COO⁻K⁺ | |
| 516 | (R) CH(CH₃)—CH(CH₃)₂ | H | 2,6-difluoro,4-Cl-phenyl | Cl | COO⁻Na⁺ | |
| 517 | (R) CH(CH₃)—CH(CH₃)₂ | H | 2,6-difluoro,4-Cl-phenyl | Cl | COOCH(CH₃)COOCH₃ | 4.77* |

TABLE 1-continued

| Ex. No. | R¹ or —R¹+R²— | R² | R³ | X | R⁴ | log p |
|---|---|---|---|---|---|---|
| 518 | (R) CH(CH₃)—CH(CH₃)₂ | H | 2,6-difluoro,4-Cl-phenyl | Cl | (R) COOCH(CH₃)CONHCH₃ | 4.34** |
| 519 | (R) CH(CH₃)—CH(CH₃)₂ | H | 2,6-difluoro,4-Cl-phenyl | Cl | COOCH₂CH₂OCH₂CH₂OCH₃ | 4.37* |
| 520 | (R) CH(CH₃)—CH(CH₃)₂ | H | 2,6-difluoro,4-Cl-phenyl | Cl | COO—CH₂—CH₂—OCH₃ | 4.44* |
| 521 | (R) CH(CH₃)—CH(CH₃)₂ | H | 2,6-difluoro,4-Cl-phenyl | Cl | COOCH₂CONCH₃OCH₃ | 4.1** |
| 522 | (R) CH(CH₃)—CH(CH₃)₂ | H | 2,6-difluoro,4-Cl-phenyl | Cl | COOCH₂COOCH₃ | 4.39* |
| 523 | (R) CH(CH₃)—CH(CH₃)₂ | H | 2,6-difluoro,4-Cl-phenyl | Cl | COOH | 3.61 |
| 524 | (R) CH(CH₃)—CH(CH₃)₂ | H | 2,6-difluoro,4-methylphenyl | Cl | COOH | 3.43** |
| 525 | CH(CH₃)—CH(CH₃)₂ | H | 2,6-F-phenyl | Cl | COOH | 3.08 |
| 526 | (R) CH(CH₃)—CH(CH₃)₂ | H | 2-butyl | Cl | COOH | 3.54 |
| 527 | (S) CH(CH₃)—CH(CH₃)₂ | H | 2-butyl | Cl | COOH | 3.52 |
| 528 | (R) CH(CH₃)—CH(CH₃)₂ | H | 2-Cl,4-MeO-phenyl | Cl | COO⁻Na⁺ | |
| 529 | (R) CH(CH₃)—CH(CH₃)₂ | H | 2-Cl,4-MeO-phenyl | Cl | COOH | 3.31 |
| 530 | (R) CH(CH₃)—CH(CH₃)₂ | H | 2-Cl,4-methylphenyl | Cl | COO⁻K⁺ | |
| 531 | (R) CH(CH₃)—CH(CH₃)₂ | H | 2-Cl,4-methylphenyl | Cl | COO⁻Na⁺ | |
| 532 | (R) CH(CH₃)—CH(CH₃)₂ | H | 2-Cl,4-methylphenyl | Cl | COOCH₂CH₂OCH₂CH₂OCH₃ | 4.51 |
| 533 | (R) CH(CH₃)—CH(CH₃)₂ | H | 2-Cl,4-methylphenyl | Cl | COO—CH₂—CH₂—OCH₃ | 4.59 |
| 534 | (R) CH(CH₃)—CH(CH₃)₂ | H | 2-Cl,4-methylphenyl | Cl | COOH | 3.72 |
| 535 | (R) CH(CH₃)—CH(CH₃)₂ | H | 2-Cl,5-Br-phenyl | Cl | COOH | 3.82 |
| 536 | (R) CH(CH₃)—CH(CH₃)₂ | H | 2-Cl,5-F-phenyl | Cl | COOH | 3.36 |
| 537 | (R) CH(CH₃)—CH(CH₃)₂ | H | 2-Cl,5-methoxy-phenyl | Cl | COOH | 3.4 |
| 538 | CH(CH₃)—CH(CH₃)₂ | H | 2-Cl-4-F-phenyl | Cl | 2-pyridyl | 3.54 |
| 539 | CH(CH₃)—CH(CH₃)₂ | H | 2-Cl-4-F-phenyl | Cl | 3-Me-1,2,4-triazol-5-yl | 3.23 |
| 540 | CH(CH₃)—CH(CH₃)₂ | H | 2-Cl-4-F-phenyl | Cl | 5-amino-thiadiazol-2-yl | 3.57 |
| 541 | CH(CH₃)—CH(CH₃)₂ | H | 2-Cl-4-F-phenyl | Cl | 5-Me-oxadiazyl-2-yl | 3.94 |
| 542 | (R) CH(CH₃)—CH(CH₃)₂ | H | 2-Cl-4-F-phenyl | OCH₂Cy3 | CCNCH₂Cy3 | 5.95 |
| 543 | (R) CH(CH₃)—CH(CH₃)₂ | H | 2-Cl-4-F-phenyl | Cl | CONCH₃OCH₃ | 3.95 |
| 544 | (R) CH(CH₃)—CH(CH₃)₂ | H | 2-Cl-4-F-phenyl | Cl | CONHCH(CH₃)COOCH₃ | 4.41** |
| 545 | (R) CH(CH₃)—CH(CH₃)₂ | H | 2-Cl-4-F-phenyl | Cl | CONHCH₂COOCH₃ | 4.05** |
| 546 | (R) CH(CH₃)—CH(CH₃)₂ | H | 2-Cl-4-F-phenyl | Cl | COOC₂H₅ | 4.75 |
| 547 | CH(CH₃)—CH(CH₃)₂ | H | 2-Cl-4-F-phenyl | Cl | COOC₂H₅ | 5.23 |
| 548 | (R) CH(CH₃)—CH(CH₃)₂ | H | 2-Cl-4-F-phenyl | Cl | COOCH(CH₃)COOCH₃ | 4.65 |
| 549 | (R) CH(CH₃)—CH(CH₃)₂ | H | 2-Cl-4-F-phenyl | Cl | (R) COOCH(CH₃)CONHCH₃ | 4.13** |
| 550 | (R) CH(CH₃)—CH(CH₃)₂ | H | 2-Cl-4-F-phenyl | Cl | COOCH₂CF₃ | 5.01 |
| 551 | (R) CH(CH₃)—CH(CH₃)₂ | H | 2-Cl-4-F-phenyl | Cl | COOCH₂CH₂OCH₂CH₂OCH₃ | 4.24 |
| 552 | (R) CH(CH₃)—CH(CH₃)₂ | H | 2-Cl-4-F-phenyl | Cl | COOCH₂CONCH₃OCH₃ | 3.99** |
| 553 | (R) CH(CH₃)—CH(CH₃)₂ | H | 2-Cl-4-F-phenyl | O-i-propyl | N(C≡N)CH(CH₃)₂ | 6.02 |
| 554 | (R) CH(CH₃)—CH(CH₃)₂ | H | 2-Cl-4-F-phenyl | -n-butoxy | N(C≡N)CH₂CH₂CH₃ | 6.83 |
| 555 | (R) CH(CH₃)—CH(CH₃)₂ | H | 2-Cl-4-F-phenyl | -O-n-propyl | N(C≡N)CH₂CH₃ | 6.12 |
| 556 | (R) CH(CH₃)—CH(CH₃)₂ | H | 2-Cl-4-F-phenyl | OCH₂Cybutyl | N(C≡N)CH₂Cybutyl | 7.16 |
| 557 | (R) CH(CH₃)—CH(CH₃)₂ | H | 2-Cl-4-F-phenyl | —O—C₂H₅ | N(C≡N)Et | 5.38 |
| 558 | CH(CH₃)—CH(CH₃)₂ | H | 2-Cl-4-F-phenyl | Cl | —NO2 | 4.28 |
| 559 | (R) CH(CH₃)—CH(CH₃)₂ | H | 2-Cl-5-Me-phenyl | Cl | COOH | 3.71 |
| 560 | (R) CH(CH₃)—CH(CH₃)₂ | H | 2-Cl-6-F-phenyl | Cl | CONCH₃OCH₃ | 3.66* |
| 561 | (R) CH(CH₃)—CH(CH₃)₂ | H | 2-Cl-6-F-phenyl | Cl | COOC₂H₅ | 4.58 |
| 562 | (R) CH(CH₃)—CH(CH₃)₂ | H | 2-Cl-6-F-phenyl | Cl | COOCH(CH₃)COOCH₃ | 4.46* |
| 563 | (R) CH(CH₃)—CH(CH₃)₂ | H | 2-Cl-6-F-phenyl | Cl | COOCH₂CH₂OCH₂CH₂OCH₃ | 4.03* |
| 564 | (R) CH(CH₃)—CH(CH₃)₂ | H | 2-Cl-6-F-phenyl | Cl | COOCH₂COOCH₃ | 4.08* |
| 565 | (R) CH(CH₃)—CH(CH₃)₂ | H | 2-Cl-6-F-phenyl | Cl | COO-i-propyl | 5.03 |
| 566 | (R) CH(CH₃)—CH(CH₃)₂ | H | 2-Cl-phenyl | Cl | CONCH₃OCH₃ | 3.77* |
| 567 | CH(CH₃)—CH(CH₃)₂ | H | 2-Cl-phenyl | Cl | CONH(CH₂)₂CH₃ | 4.78 |
| 568 | (R) CH(CH₃)—CH(CH₃)₂ | H | 2-Cl-phenyl | Cl | CONHCH(CH₃)COOCH₃ | 4.49** |
| 569 | (R) CH(CH₃)—CH(CH₃)₂ | H | 2-Cl-phenyl | Cl | CONHCH₂COOCH₃ | 3.92** |
| 570 | (R) CH(CH₃)—CH(CH₃)₂ | H | 2-Cl-phenyl | Cl | COOC₂H₅ | 4.71 |
| 571 | (R) CH(CH₃)—CH(CH₃)₂ | H | 2-Cl-phenyl | Cl | COOCH(CH₃)COOCH₃ | 4.56* |
| 572 | (R) CH(CH₃)—CH(CH₃)₂ | H | 2-Cl-phenyl | Cl | (R) COOCH(CH₃)CONHCH₃ | 4.17** |
| 573 | (R) CH(CH₃)—CH(CH₃)₂ | H | 2-Cl-phenyl | Cl | COOCH₂CF₃ | 5.01 |
| 574 | (R) CH(CH₃)—CH(CH₃)₂ | H | 2-Cl-phenyl | Cl | COOCH₂CH₂OCH₂CH₂OCH₃ | 4.13* |
| 575 | (R) CH(CH₃)—CH(CH₃)₂ | H | 2-Cl-phenyl | Cl | COOCH₂CONCH₃OCH₃ | 3.88** |
| 576 | (R) CH(CH₃)—CH(CH₃)₂ | H | 2-Cl-phenyl | Cl | COOCH₂COOCH₃ | 4.18* |
| 577 | CH(CH₃)—CH(CH₃)₂ | H | 2-Cl-phenyl | Cl | —NH2 | 2.54 |
| 578 | (R) CH(CH₃)—CH(CH₃)₂ | H | 2-F,4-Cl-phenyl | Cl | COOH | 3.64 |
| 579 | (R) CH(CH₃)—CH(CH₃)₂ | H | 2-F-phenyl | Cl | COO⁻Na⁺ | |

TABLE 1-continued

| Ex. No. | R¹ or —R¹⁺R²— | R² | R³ | X | R⁴ | log p |
|---|---|---|---|---|---|---|
| 580 | (R) CH(CH₃)—CH(CH₃)₂ | H | 2-F-phenyl | Cl | COOH | 3.13 |
| 581 | (R) CH(CH₃)—CH(CH₃)₂ | H | 2-Me-cyclopentyl | Cl | COOH | 3.93 |
| 582 | CH(CH₃)—CH(CH₃)₂ | H | 2-Me-phenyl | Cl | COOC₂H₅ | 3.8 |
| 583 | CH(CH₃)—CH(CH₃)₂ | H | 2-Me-phenyl | Cl | COO—CH₂—CH₂—OCH₃ | 4.32 |
| 584 | CH(CH₃)—CH(CH₃)₂ | H | 2-Me-phenyl | Cl | COOH | 3.53 |
| 585 | (R) CH(CH₃)—CH(CH₃)₂ | H | 2-methyl-4-F-phenyl | Cl | CONH-2-pyrimidinyl | 6.61 |
| 586 | (R) CH(CH₃)—CH(CH₃)₂ | H | 2-methyl-4-F-phenyl | Cl | CONHCH₂COOEt | 4.3 |
| 587 | (R) CH(CH₃)—CH(CH₃)₂ | H | 2-methyl-4-F-phenyl | Cl | COO⁻Na⁺ | 1.78 |
| 588 | (R) CH(CH₃)—CH(CH₃)₂ | H | 2-methyl-4-F-phenyl | Cl | COO⁻K⁺ | 1.78 |
| 589 | (R) CH(CH₃)—CH(CH₃)₂ | H | 2-methyl-4-F-phenyl | Cl | COO⁻NH(CH₂CH₃)₃⁺ | 1.77 |
| 590 | (R) CH(CH₃)—CH(CH₃)₂ | H | 2-methyl-4-F-phenyl | Cl | COO(CH₂)₂C(CH₃)₃ | 6.18 |
| 591 | (R) CH(CH₃)—CH(CH₃)₂ | H | 2-methyl-4-F-phenyl | Cl | COO(CH₂)₂—C≡CH | 4.6 |
| 592 | (R) CH(CH₃)—CH(CH₃)₂ | H | 2-methyl-4-F-phenyl | Cl | COO(CH₂)₂CF₃ | 4.95 |
| 593 | (R) CH(CH₃)—CH(CH₃)₂ | H | 2-methyl-4-F-phenyl | Cl | COO(CH₂)₂CH(CH₃)₂ | 5.91 |
| 594 | (R) CH(CH₃)—CH(CH₃)₂ | H | 2-methyl-4-F-phenyl | Cl | COO(CH₂)₂CH₂Br | 5.18 |
| 595 | (R) CH(CH₃)—CH(CH₃)₂ | H | 2-methyl-4-F-phenyl | Cl | COO(CH₂)₂CH₂Cl | 5.04 |
| 596 | (R) CH(CH₃)—CH(CH₃)₂ | H | 2-methyl-4-F-phenyl | Cl | COO(CH₂)₂CH₂F | 4.64 |
| 597 | (R) CH(CH₃)—CH(CH₃)₂ | H | 2-methyl-4-F-phenyl | Cl | COO(CH₂)₂CHCH₂ | 5.18 |
| 598 | (R) CH(CH₃)—CH(CH₃)₂ | H | 2-methyl-4-F-phenyl | Cl | COO(CH₂)₂OC(CH₃)₃ | 5.19 |
| 599 | (R) CH(CH₃)—CH(CH₃)₂ | H | 2-methyl-4-F-phenyl | Cl | COO(CH₂)₂OCH₂? | 4.57 |
| 600 | (R) CH(CH₃)—CH(CH₃)₂ | H | 2-methyl-4-F-phenyl | Cl | COO(CH₂)₃OCH₃ | 4.6 |
| 601 | (R) CH(CH₃)—CH(CH₃)₂ | H | 2-methyl-4-F-phenyl | Cl | COO(CH₂)4CH₃ | 5.96 |
| 602 | (R) CH(CH₃)—CH(CH₃)₂ | H | 2-methyl-4-F-phenyl | Cl | COO(CH₂)5CH₃ | 6.37 |
| 603 | (R) CH(CH₃)—CH(CH₃)₂ | H | 2-methyl-4-F-phenyl | Cl | COO(CH₂)9CH₃ | 7.36 |
| 604 | (R) CH(CH₃)—CH(CH₃)₂ | H | 2-methyl-4-F-phenyl | Cl | COO-2-carboxymethylphenyl | 4.94 |
| 605 | (R) CH(CH₃)—CH(CH₃)₂ | H | 2-methyl-4-F-phenyl | Cl | COO-4-iPrPh | 6.12 |
| 606 | (R) CH(CH₃)—CH(CH₃)₂ | H | 2-methyl-4-F-phenyl | Cl | COOC(CH₃)₂—C≡CH | 4.81 |
| 607 | (R) CH(CH₃)—CH(CH₃)₂ | H | 2-methyl-4-F-phenyl | Cl | COOC(CH₃)₂CH₂OCH₃ | 5.21 |
| 608 | (R) CH(CH₃)—CH(CH₃)₂ | H | 2-methyl-4-F-phenyl | Cl | COOC₂H₅ | 4.69 |
| 609 | (R) CH(CH₃)—CH(CH₃)₂ | H | 2-methyl-4-F-phenyl | Cl | COOCH(CH₃)C(CH₃)₃ | 6.24 |
| 610 | (R) CH(CH₃)—CH(CH₃)₂ | H | 2-methyl-4-F-phenyl | Cl | COOCH(CH₃)CF₃ | 5.35 |
| 611 | (R) CH(CH₃)—CH(CH₃)₂ | H | 2-methyl-4-F-phenyl | Cl | COOCH(CH₃)CH(CH₃)₂ | 5.91 |
| 612 | (R) CH(CH₃)—CH(CH₃)₂ | H | 2-methyl-4-F-phenyl | Cl | COOCH(CH₃)CH₂CH₃ | 5.53 |
| 613 | (R) CH(CH₃)—CH(CH₃)₂ | H | 2-methyl-4-F-phenyl | Cl | COOCH(CH₃)CH₂CHCH₂ | 5.56 |
| 614 | (R) CH(CH₃)—CH(CH₃)₂ | H | 2-methyl-4-F-phenyl | Cl | COOCH(CH₃)CH₂OCH₃ | 4.66 |
| 615 | (R) CH(CH₃)—CH(CH₃)₂ | H | 2-methyl-4-F-phenyl | Cl | COOCH(CH₃)cyclohexyl | 6.87 |
| 616 | (R) CH(CH₃)—CH(CH₃)₂ | H | 2-methyl-4-F-phenyl | Cl | COOCH(Et)-4-MePh | 6.53 |
| 617 | (R) CH(CH₃)—CH(CH₃)₂ | H | 2-methyl-4-F-phenyl | Cl | COOCH₂C(CH₃)₃ | 5.56 |
| 618 | (R) CH(CH₃)—CH(CH₃)₂ | H | 2-methyl-4-F-phenyl | Cl | COOCH₂—C≡CH | 5.17 |
| 619 | (R) CH(CH₃)—CH(CH₃)₂ | H | 2-methyl-4-F-phenyl | Cl | COOCH₂CF₃ | 4.98 |
| 620 | (R) CH(CH₃)—CH(CH₃)₂ | H | 2-methyl-4-F-phenyl | Cl | COOCH₂CH₂Br | 4.87 |
| 621 | (R) CH(CH₃)—CH(CH₃)₂ | H | 2-methyl-4-F-phenyl | Cl | COOCH₂CH₂CH₂CH₃ | 5.55 |
| 622 | (R) CH(CH₃)—CH(CH₃)₂ | H | 2-methyl-4-F-phenyl | Cl | COOCH₂CH₂CH₃ | 5.15 |
| 623 | (R) CH(CH₃)—CH(CH₃)₂ | H | 2-methyl-4-F-phenyl | Cl | COO—CH₂—CH₂—OCH₃ | 4.21 |
| 624 | (R) CH(CH₃)—CH(CH₃)₂ | H | 2-methyl-4-F-phenyl | Cl | COOCH₂CHCHCH₃ | 4.42 |
| 625 | (R) CH(CH₃)—CH(CH₃)₂ | H | 2-methyl-4-F-phenyl | Cl | COOCH₂Cl | 4.72 |
| 626 | (R) CH(CH₃)—CH(CH₃)₂ | H | 2-methyl-4-F-phenyl | Cl | COOCH₂F | 4.32 |
| 627 | (R) CH(CH₃)—CH(CH₃)₂ | H | 2-methyl-4-F-phenyl | Cl | COOCH(CH₃)CH═CH₂ | 5.25 |
| 628 | (R) CH(CH₃)—CH(CH₃)₂ | H | 2-methyl-4-F-phenyl | Cl | COOCyhexyl | 6.05 |
| 629 | (R) CH(CH₃)—CH(CH₃)₂ | H | 2-methyl-4-F-phenyl | Cl | COOH | 3.45 |
| 630 | (S) CH(CH₃)—CH(CH₃)₂ | H | 2-methyl-4-F-phenyl | Cl | COOH | 3.45 |
| 631 | (R) CH(CH₃)—CH(CH₃)₂ | H | 2-methyl-4-F-phenyl | Cl | COO-i-propyl | 5.11 |
| 632 | (R) CH(CH₃)—CH(CH₃)₂ | H | 2-methyl-4-F-phenyl | Cl | COOphenyl | 5.2 |
| 633 | CH(CH₃)—CH(CH₃)₂ | H | 2-methyl-5-(4-Cl)-phenyl | Cl | COOH | 4.92 |
| 634 | (R) CH(CH₃)—CH(CH₃)₂ | H | 3,4-methylendioxy-phenyl | Cl | COOH | 2.96 |
| 635 | (R) CH(CH₃)—CH(CH₃)₂ | H | 3-Cl-thien-2-yl | Cl | COO⁻Na⁺ | |
| 636 | (R) CH(CH₃)—CH(CH₃)₂ | H | 3-Cl-thien-2-yl | Cl | COOH | 3.3 |
| 637 | (R) CH(CH₃)—CH(CH₃)₂ | H | 3-Me-thien-2-yl | Cl | 1,3,4-oxathiazol-2-on-5-yl | 4.98 |
| 638 | (R) CH(CH₃)—CH(CH₃)₂ | H | 3-Me-thien-2-yl | Cl | CON(CH₃)COCHNH2CH₃ | 3.41** |
| 639 | (R) CH(CH₃)—CH(CH₃)₂ | H | 3-Me-thien-2-yl | Cl | CONH(CH₂)₂OCH₃ | 4.1** |
| 640 | (R) CH(CH₃)—CH(CH₃)₂ | H | 3-Me-thien-2-yl | Cl | CONH2 | 3.49 |
| 641 | (R) CH(CH₃)—CH(CH₃)₂ | H | 3-Me-thien-2-yl | Cl | CONHCH(CH₃)COOCH₃ | 4.46** |
| 642 | (R) CH(CH₃)—CH(CH₃)₂ | H | 3-Me-thien-2-yl | Cl | CO—NH-morpholin-1-yl | 3.63** |
| 643 | (R) CH(CH₃)—CH(CH₃)₂ | H | 3-Me-thien-2-yl | Cl | COO⁻K⁺ | |
| 644 | (R) CH(CH₃)—CH(CH₃)₂ | H | 3-Me-thien-2-yl | Cl | COO⁻Na⁺ | |
| 645 | (R) CH(CH₃)—CH(CH₃)₂ | H | 3-Me-thien-2-yl | —O—CH₃ | COO⁻Na⁺ | |

TABLE 1-continued

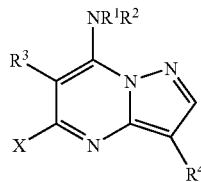

| Ex. No. | R$^1$ or —R$^1$+R$^2$— | R$^2$ | R$^3$ | X | R$^4$ | log p |
|---|---|---|---|---|---|---|
| 646 | (R) CH(CH$_3$)—CH(CH$_3$)$_2$ | H | 3-Me-thien-2-yl | Cl | COOCH(CH$_3$)COOCH$_3$ | 4.6 |
| 647 | (R) CH(CH$_3$)—CH(CH$_3$)$_2$ | H | 3-Me-thien-2-yl | Cl | COOCH$_2$CH$_2$OCH$_2$CH$_2$OCH$_3$ | 4.11 |
| 648 | (R) CH(CH$_3$)—CH(CH$_3$)$_2$ | H | 3-Me-thien-2-yl | Cl | COO—CH$_2$—CH$_2$—OCH$_3$ | 4.17 |
| 649 | (R) CH(CH$_3$)—CH(CH$_3$)$_2$ | H | 3-Me-thien-2-yl | —O—CH$_3$ | COOH | 3.65 |
| 650 | (R) CH(CH$_3$)—CH(CH$_3$)$_2$ | H | 3-Me-thien-2-yl | Cl | oxazol-2-yl | 4.27 |
| 651 | (R) CH(CH$_3$)—CH(CH$_3$)$_2$ | H | 5-F-pyrimidin-4-yl | Cl | COOH | 2.06 |
| 652 | (R) CH(CH$_3$)—CH(CH$_3$)$_2$ | H | cyclopentyl | Cl | COOH | 3.7 |
| 653 | (S) CH(CH$_3$)—CH(CH$_3$)$_2$ | H | cyclopentyl | Cl | COOH | 3.7 |
| 654 | CH(CH$_3$)—CH(CH$_3$)$_2$ | H | phenyl | Cl | 2-pyridyl | 3.03 |
| 655 | CH(CH$_3$)—CH(CH$_3$)$_2$ | H | phenyl | Cl | 3-Me-1,2,4-triazol-5-yl | 2.91 |
| 656 | CH(CH$_3$)—CH(CH$_3$)$_2$ | H | phenyl | Cl | 5-Me-oxadiazol-2-yl | 3.7 |
| 657 | CH(CH$_3$)—CH(CH$_3$)$_2$ | H | phenyl | Cl | COOC$_2$H$_5$ | 4.98 |
| 658 | CH(CH$_3$)—CH(CH$_3$)$_2$ | H | phenyl | Cl | COOCH(CH$_3$)COOEt | 4.76 |
| 659 | CH(CH$_3$)—CH(CH$_3$)$_2$ | H | phenyl | Cl | COO—CH$_2$—CH$_2$—OCH$_3$ | 6.61 |
| 660 | CH(CH$_3$)—CH(CH$_3$)$_2$ | H | phenyl | Cl | COOH | 3.29 |
| 661 | CH(CH$_3$)—CH$_2$—CH(CH$_3$)$_2$ | H | 2-Cl,4-methylphenyl | Cl | COOH | 4.12 |
| 662 | CH(CH$_3$)—CH$_2$—CH(CH$_3$)$_2$ | H | 3-Me-thien-2-yl | Cl | COOH | 3.75 |
| 663 | CH$_2$—C(CH$_3$)$_3$ | H | 2,4,6-trifluorophenyl | Cl | CONCH$_3$OCH$_3$ | 3.8* |
| 664 | CH$_2$—C(CH$_3$)$_3$ | H | 2,4,6-trifluorophenyl | Cl | COO$^-$K$^+$ | |
| 665 | CH$_2$—C(CH$_3$)$_3$ | H | 2,4,6-trifluorophenyl | Cl | COO$^-$Na$^+$ | |
| 666 | CH$_2$—C(CH$_3$)$_3$ | H | 2,4,6-trifluorophenyl | Cl | COOCH(CH$_3$)COOCH$_3$ | 4.45* |
| 667 | CH$_2$—C(CH$_3$)$_3$ | H | 2,4,6-trifluorophenyl | Cl | COOCH$_2$CH$_2$OCH$_2$CH$_2$OCH$_3$ | 4.04* |
| 668 | CH$_2$—C(CH$_3$)$_3$ | H | 2,4,6-trifluorophenyl | Cl | COO—CH$_2$—CH$_2$—OCH$_3$ | 4.12* |
| 669 | CH$_2$—C(CH$_3$)$_3$ | H | 2,4,6-trifluorophenyl | Cl | COOCH$_2$COOCH$_3$ | 4.44* |
| 670 | CH$_2$—C(CH$_3$)$_3$ | H | 2,4,6-trifluorophenyl | Cl | COOH | 3.31 |
| 671 | CH$_2$—C(CH$_3$)$_3$ | H | 2,4-Cl-phenyl | Cl | CONCH$_3$OCH$_3$ | 4.51* |
| 672 | CH$_2$—C(CH$_3$)$_3$ | H | 2,4-Cl-phenyl | Cl | COO$^-$K | |
| 673 | CH$_2$—C(CH$_3$)$_3$ | H | 2,4-Cl-phenyl | Cl | COO$^-$Na$^+$ | |
| 674 | CH$_2$—C(CH$_3$)$_3$ | H | 2,4-Cl-phenyl | Cl | COOCH(CH$_3$)COOCH$_3$ | 5.27* |
| 675 | CH$_2$—C(CH$_3$)$_3$ | H | 2,4-Cl-phenyl | Cl | COOCH$_2$CH$_2$OCH$_2$CH$_2$OCH$_3$ | 4.82* |
| 676 | CH$_2$—C(CH$_3$)$_3$ | H | 2,4-Cl-phenyl | Cl | COO—CH$_2$—CH$_2$—OCH$_3$ | 4.9* |
| 677 | CH$_2$—C(CH$_3$)$_3$ | H | 2,4-Cl-phenyl | Cl | COOCH$_2$COOCH$_3$ | 4.88* |
| 678 | CH$_2$—C(CH$_3$)$_3$ | H | 2,4-Cl-phenyl | Cl | COOH | 4.05 |
| 679 | CH$_2$—C(CH$_3$)$_3$ | H | 2,4-F-phenyl | Cl | COO$^-$K$^+$ | |
| 680 | CH$_2$—C(CH$_3$)$_3$ | H | 2,4-F-phenyl | Cl | COO$^-$Na$^+$ | |
| 681 | CH$_2$—C(CH$_3$)$_3$ | H | 2,4-F-phenyl | Cl | COOH | 3.33 |
| 682 | CH$_2$—C(CH$_3$)$_3$ | H | 2,5-Me-phenyl | Cl | COOH | 3.9 |
| 683 | CH$_2$—C(CH$_3$)$_3$ | H | 2,6-difluoro,4-Cl-phenyl | Cl | CONCH$_3$OCH$_3$ | 4.21* |
| 684 | CH$_2$—C(CH$_3$)$_3$ | H | 2,6-difluoro,4-Cl-phenyl | Cl | COO$^-$K$^+$ | |
| 685 | CH$_2$—C(CH$_3$)$_3$ | H | 2,6-difluoro,4-Cl-phenyl | Cl | COO$^-$Na$^+$ | |
| 686 | CH$_2$—C(CH$_3$)$_3$ | H | 2,6-difluoro,4-Cl-phenyl | Cl | COOCH(CH$_3$)COOCH$_3$ | 4.85* |
| 687 | CH$_2$—C(CH$_3$)$_3$ | H | 2,6-difluoro,4-Cl-phenyl | Cl | COOCH$_2$CH$_2$OCH$_2$CH$_2$OCH$_3$ | 4.45* |
| 688 | CH$_2$—C(CH$_3$)$_3$ | H | 2,6-difluoro,4-Cl-phenyl | Cl | COO—CH$_2$—CH$_2$—OCH$_3$ | 4.96* |
| 689 | CH$_2$—C(CH$_3$)$_3$ | H | 2,6-difluoro,4-Cl-phenyl | Cl | COOCH$_2$COOCH$_3$ | 4.46* |
| 690 | CH$_2$—C(CH$_3$)$_3$ | H | 2,6-difluoro,4-Cl-phenyl | Cl | COOH | 3.71 |
| 691 | CH$_2$—C(CH$_3$)$_3$ | H | 2-Cl,4-methylphenyl | Cl | COO$^-$Na | |
| 692 | CH$_2$—C(CH$_3$)$_3$ | H | 2-Cl,4-methylphenyl | Cl | COOH | 3.84 |
| 693 | CH$_2$—C(CH$_3$)$_3$ | H | 2-Cl,5-F-phenyl | Cl | COOH | 3.53 |
| 694 | CH$_2$—C(CH$_3$)$_3$ | H | 2-Cl-4-F-phenyl | Cl | CONCH$_3$OCH$_3$ | 4.03* |
| 695 | CH$_2$—C(CH$_3$)$_3$ | H | 2-Cl-4-F-phenyl | Cl | COO$^-$K$^+$ | |
| 696 | CH$_2$—C(CH$_3$)$_3$ | H | 2-Cl-4-F-phenyl | Cl | COO$^-$Na$^+$ | |
| 697 | CH$_2$—C(CH$_3$)$_3$ | H | 2-Cl-4-F-phenyl | Cl | COOCH(CH$_3$)COOCH$_3$ | 4.77* |
| 698 | CH$_2$—C(CH$_3$)$_3$ | H | 2-Cl-4-F-phenyl | Cl | COOCH$_2$CH$_2$OCH$_2$CH$_2$OCH$_3$ | 4.41* |
| 699 | CH$_2$—C(CH$_3$)$_3$ | H | 2-Cl-4-F-phenyl | Cl | COO—CH$_2$—CH$_2$—OCH$_3$ | 4.46* |
| 700 | CH$_2$—C(CH$_3$)$_3$ | H | 2-Cl-4-F-phenyl | Cl | COOCH$_2$COOCH$_3$ | 4.42* |
| 701 | CH$_2$—C(CH$_3$)$_3$ | H | 2-Cl-4-F-phenyl | Cl | COOH | 3.61 |
| 702 | CH$_2$—C(CH$_3$)$_3$ | H | 2-Cl-5-Me-phenyl | Cl | COOH | 3.8 |
| 703 | CH$_2$—C(CH$_3$)$_3$ | H | 2-Cl-6-F-phenyl | Cl | CONCH$_3$OCH$_3$ | 3.9* |
| 704 | CH$_2$—C(CH$_3$)$_3$ | H | 2-Cl-6-F-phenyl | Cl | COOCH(CH$_3$)COOCH$_3$ | 4.59* |
| 705 | CH$_2$—C(CH$_3$)$_3$ | H | 2-Cl-6-F-phenyl | Cl | COOCH$_2$CH$_2$OCH$_2$CH$_2$OCH$_3$ | 4.16* |
| 706 | CH$_2$—C(CH$_3$)$_3$ | H | 2-Cl-6-F-phenyl | Cl | COO—CH$_2$—CH$_2$—OCH$_3$ | 4.25* |
| 707 | CH$_2$—C(CH$_3$)$_3$ | H | 2-Cl-6-F-phenyl | Cl | COOCH$_2$COOCH$_3$ | 4.2* |
| 708 | CH$_2$—C(CH$_3$)$_3$ | H | 2-Cl-6-F-phenyl | Cl | COOH | 3.39 |
| 709 | CH$_2$—C(CH$_3$)$_3$ | H | 2-Cl-phenyl | Cl | CONCH$_3$OCH$_3$ | 3.89* |
| 710 | CH$_2$—C(CH$_3$)$_3$ | H | 2-Cl-phenyl | Cl | COOCH(CH$_3$)COOCH$_3$ | 4.69* |
| 711 | CH$_2$—C(CH$_3$)$_3$ | H | 2-Cl-phenyl | Cl | COOCH$_2$CH$_2$OCH$_2$CH$_2$OCH$_3$ | 4.25* |

TABLE 1-continued

| Ex. No. | R¹ or —R¹⁺R²— | R² | R³ | X | R⁴ | log p |
|---|---|---|---|---|---|---|
| 712 | CH₂—C(CH₃)₃ | H | 2-Cl-phenyl | Cl | COO—CH₂—CH₂—OCH₃ | 4.37* |
| 713 | CH₂—C(CH₃)₃ | H | 2-Cl-phenyl | Cl | COOCH₂COOCH₃ | 4.24* |
| 714 | CH₂—C(CH₃)₃ | H | 2-Cl-phenyl | Cl | COOH | 3.5 |
| 715 | CH₂—C(CH₃)₃ | H | 2-F,4-Cl-phenyl | Cl | COOH | 3.69 |
| 716 | CH₂—C(CH₃)₃ | H | 3-Me-thien-2-yl | Cl | COOH | 3.47 |
| 717 | CH₂—CH₂—CH(CH₃)₂ | H | 2,4-F-phenyl | Cl | COO⁻K⁺ | |
| 718 | CH₂—CH₂—CH(CH₃)₂ | H | 2,4-F-phenyl | Cl | COO⁻Na⁺ | |
| 719 | CH₂—CH₂—CH(CH₃)₂ | H | 2,4-F-phenyl | Cl | COOH | 3.29 |
| 720 | CH₂—CH₂—CH(CH₃)₂ | H | 2-Cl,4-methylphenyl | Cl | COO⁻Na⁺ | |
| 721 | CH₂—CH₂—CH(CH₃)₂ | H | 2-Cl,4-methylphenyl | Cl | COO⁻K⁺ | |
| 722 | CH₂—CH₂—CH(CH₃)₂ | H | 2-Cl,4-methylphenyl | Cl | COOH | 3.81 |
| 723 | CH₂—CH₂—CH(CH₃)₂ | H | 3-Me-thien-2-yl | Cl | COOH | 3.47 |
| 724 | —CH₂—CH₂—CH(CH₃)—CH₂—CH₂— | | 2,4,6-trifluorophenyl | Cl | CONCH₃OCH₃ | 3.99* |
| 725 | —CH₂—CH₂—CH(CH₃)—CH₂—CH₂— | | 2,4,6-trifluorophenyl | Cl | COOCH(CH₃)COOCH₃ | 4.76* |
| 726 | —CH₂—CH₂—CH(CH₃)—CH₂—CH₂— | | 2,4,6-trifluorophenyl | Cl | COOCH₂CH₂OCH₂CH₂OCH₃ | 4.36* |
| 727 | —CH₂—CH₂—CH(CH₃)—CH₂—CH₂— | | 2,4,6-trifluorophenyl | Cl | COOCH₂COOCH₃ | 4.41* |
| 728 | —CH₂—CH₂—CH(CH₃)—CH₂—CH₂— | | 2,4-Cl-phenyl | Cl | 2-pyridyl | 4.34 |
| 729 | —CH₂—CH₂—CH(CH₃)—CH₂—CH₂— | | 2,4-Cl-phenyl | Cl | 3-Me-1,2,4-triazol-5-yl | 3.91 |
| 730 | —CH₂—CH₂—CH(CH₃)—CH₂—CH₂— | | 2,4-Cl-phenyl | Cl | 5-Me-oxadiazol-2-yl | 4.82 |
| 731 | —CH₂—CH₂—CH(CH₃)—CH₂—CH₂— | | 2,4-Cl-phenyl | Cl | COOC₂H₅ | 6.31 |
| 732 | —CH₂—CH₂—CH(CH₃)—CH₂—CH₂— | | 2,4-difluoro-,6-Cl-phenyl | Cl | CONCH₃OCH₃ | 4.26* |
| 733 | —CH₂—CH₂—CH(CH₃)—CH₂—CH₂— | | 2,4-difluoro-,6-Cl-phenyl | Cl | COOCH(CH₃)COOCH₃ | 5.04* |
| 734 | —CH₂—CH₂—CH(CH₃)—CH₂—CH₂— | | 2,4-difluoro-,6-Cl-phenyl | Cl | COOCH₂CH₂OCH₂CH₂OCH₃ | 4.63* |
| 735 | —CH₂—CH₂—CH(CH₃)—CH₂—CH₂— | | 2,4-difluoro-,6-Cl-phenyl | Cl | COO—CH₂—CH₂—OCH₃ | 4.73* |
| 736 | —CH₂—CH₂—CH(CH₃)—CH₂—CH₂— | | 2,4-difluoro-,6-Cl-phenyl | Cl | COOCH₂COOCH₃ | 4.64* |
| 737 | —CH₂—CH₂—CH(CH₃)—CH₂—CH₂— | | 2,4-difluoro-,6-Cl-phenyl | Cl | COOH | 3.77 |
| 738 | —CH₂—CH₂—CH(CH₃)—CH₂—CH₂— | | 2,4-F-phenyl | Cl | COO⁻Na⁺ | |
| 739 | —CH₂—CH₂—CH(CH₃)—CH₂—CH₂— | | 2,4-F-phenyl | Cl | COOH | 3.56 |
| 740 | —CH₂—CH₂—CH(CH₃)—CH₂—CH₂— | | 2,5-dimethylthien-3-yl | Cl | COOH | 4.15 |
| 741 | —CH₂—CH₂—CH(CH₃)—CH₂—CH₂— | | 2,5-F-phenyl | Cl | COOH | 3.48 |
| 742 | —CH₂—CH₂—CH(CH₃)—CH₂—CH₂— | | 2,5-Me-phenyl | Cl | COOH | 4.1 |
| 743 | —CH₂—CH₂—CH(CH₃)—CH₂—CH₂— | | 2,6-F-phenyl | Cl | COOCH(CH₃)COOCH₃ | 4.63 |
| 744 | —CH₂—CH₂—CH(CH₃)—CH₂—CH₂— | | 2,6-F-phenyl | Cl | COO—CH₂—CH₂—OCH₃ | 4.27 |
| 745 | —CH₂—CH₂—CH(CH₃)—CH₂—CH₂— | | 2,6-F-phenyl | Cl | COOCH₂COOCH₃ | 4.24 |
| 746 | —CH₂—CH₂—CH(CH₃)—CH₂—CH₂— | | 2,6-F-phenyl | Cl | COOH | 3.39 |
| 747 | —CH₂—CH₂—CH(CH₃)—CH₂—CH₂— | | 2-Cl,4-MeO-phenyl | Cl | COO⁻K⁺ | |
| 748 | —CH₂—CH₂—CH(CH₃)—CH₂—CH₂— | | 2-Cl,4-MeO-phenyl | Cl | COO⁻Na⁺ | |
| 749 | —CH₂—CH₂—CH(CH₃)—CH₂—CH₂— | | 2-Cl,4-MeO-phenyl | Cl | COOH | 3.6 |
| 750 | —CH₂—CH₂—CH(CH₃)—CH₂—CH₂— | | 2-Cl,4-methylphenyl | Cl | COO⁻Na⁺ | |
| 751 | —CH₂—CH₂—CH(CH₃)—CH₂—CH₂— | | 2-Cl,4-methylphenyl | Cl | COOH | 4.12 |
| 752 | —CH₂—CH₂—CH(CH₃)—CH₂—CH₂— | | 2-Cl,4-methylphenyl | —OH | COOH | |
| 753 | —CH₂—CH₂—CH(CH₃)—CH₂—CH₂— | | 2-Cl,5-F-phenyl | Cl | COOH | 3.71 |
| 754 | —CH₂—CH₂—CH(CH₃)—CH₂—CH₂— | | 2-Cl-4-F-phenyl | Cl | 2-pyridyl | 3.8 |
| 755 | —CH₂—CH₂—CH(CH₃)—CH₂—CH₂— | | 2-Cl-4-F-phenyl | Cl | 3-Me-1,2,4-triazol-5-yl | 3.49 |
| 756 | —CH₂—CH₂—CH(CH₃)—CH₂—CH₂— | | 2-Cl-4-F-phenyl | Cl | 5-amino-thiadiazol-2-yl | |
| 757 | —CH₂—CH₂—CH(CH₃)—CH₂—CH₂— | | 2-Cl-4-F-phenyl | Cl | 5-Me-oxadiazyl-2-yl | 4.35 |
| 758 | —CH₂—CH₂—CH(CH₃)—CH₂—CH₂— | | 2-Cl-4-F-phenyl | Cl | COOC₂H₅ | 5.78 |
| 759 | —CH₂—CH₂—CH(CH₃)—CH₂—CH₂— | | 2-Cl-4-F-phenyl | Cl | —NO2 | 4.69 |
| 760 | —CH₂—CH₂—CH(CH₃)—CH₂—CH₂— | | 2-Cl-4-F-phenyl | Cl | SO₂OCH₂CH₂OCH₂CH₂OMe | 4.56 |
| 761 | —CH₂—CH₂—CH(CH₃)—CH₂—CH₂— | | 2-Cl-4-F-phenyl | Cl | SO₂OEt | 4.86 |
| 762 | —CH₂—CH₂—CH(CH₃)—CH₂—CH₂— | | 2-Cl-4-F-phenyl | Cl | SO₂OiPr | 5.09 |
| 763 | —CH₂—CH₂—CH(CH₃)—CH₂—CH₂— | | 2-Cl-4-F-phenyl | Cl | SO₃⁻NH₄⁺ | 2.26 |
| 764 | —CH₂—CH₂—CH(CH₃)—CH₂—CH₂— | | 2-Cl-5-Me-phenyl | Cl | COOH | 4.06 |
| 765 | —CH₂—CH₂—CH(CH₃)—CH₂—CH₂— | | 2-Cl-6-F-phenyl | Cl | CONCH₃OCH₃ | 4.08* |
| 766 | —CH₂—CH₂—CH(CH₃)—CH₂—CH₂— | | 2-Cl-6-F-phenyl | Cl | COOCH(CH₃)COOCH₃ | 4.89* |
| 767 | —CH₂—CH₂—CH(CH₃)—CH₂—CH₂— | | 2-Cl-6-F-phenyl | Cl | COOCH₂CH₂OCH₂CH₂OCH₃ | 4.45* |
| 768 | —CH₂—CH₂—CH(CH₃)—CH₂—CH₂— | | 2-Cl-6-F-phenyl | Cl | COOCH₂COOCH₃ | 4.48* |
| 769 | —CH₂—CH₂—CH(CH₃)—CH₂—CH₂— | | 2-Cl-phenyl | Cl | COOC₂H₅ | 5.15 |
| 770 | —CH₂—CH₂—CH(CH₃)—CH₂—CH₂— | | 2-F-phenyl | Cl | COOH | 3.45 |
| 771 | —CH₂—CH₂—CH(CH₃)—CH₂—CH₂— | | 2-Me-phenyl | Cl | CONH(CH₂)₂OCH₃ | 4.33 |
| 772 | —CH₂—CH₂—CH(CH₃)—CH₂—CH₂— | | 2-Me-phenyl | Cl | COOCH(CH₃)COOCH₃ | 4.98 |
| 773 | —CH₂—CH₂—CH(CH₃)—CH₂—CH₂— | | 2-Me-phenyl | Cl | COO—CH₂—CH₂—OCH₃ | 4.6 |
| 774 | —CH₂—CH₂—CH(CH₃)—CH₂—CH₂— | | 2-Me-phenyl | Cl | COOH | 3.76 |
| 775 | —CH₂—CH₂—CH(CH₃)—CH₂—CH₂— | | 3-Me-thien-2-yl | Cl | COOH | 3.62 |
| 776 | —CH₂—CH₂—CH(CH₃)—CH₂—CH₂— | | phenyl | Cl | 3-Me-1,2,4-triazol-5-yl | 3.15 |
| 777 | —CH₂—CH₂—CH(CH₃)—CH₂—CH₂— | | phenyl | Cl | 5-Me-oxadiazol-2-yl | 4.01 |

TABLE 1-continued

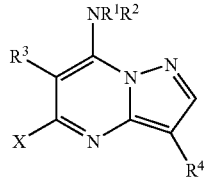

| Ex. No. | R¹ or —R¹⁺R²— | R² | R³ | X | R⁴ | log p |
|---|---|---|---|---|---|---|
| 778 | —CH₂—CH₂—CH(CH₃)—CH₂—CH₂— | | phenyl | Cl | COOC₂H₅ | 5.45 |
| 779 | —CH₂—CH₂—CH(CH₃)—CH₂—CH₂— | | phenyl | Cl | COOH | 3.56 |
| 780 | —CH₂—CH₂—CH₂—CH(CH₃)— | | 2,4-Cl-phenyl | Cl | 2-pyridyl | 3.57 |
| 781 | —CH₂—CH₂—CH₂—CH(CH₃)— | | 2,4-Cl-phenyl | Cl | 5-Me-oxadiazol-2-yl | 4.2 |
| 782 | —CH₂—CH₂—CH₂—CH(CH₃)— | | 2,6-F-phenyl | Cl | COOH | 2.91 |
| 783 | —CH₂—CH₂—CH₂—CH(CH₃)— | | 2-Cl,4-methylphenyl | Cl | COO⁻K⁺ | |
| 784 | —CH₂—CH₂—CH₂—CH(CH₃)— | | 2-Cl,4-methylphenyl | Cl | COO⁻Na⁺ | |
| 785 | —CH₂—CH₂—CH₂—CH(CH₃)— | | 2-Cl,4-methylphenyl | Cl | COOH | 3.59 |
| 786 | —CH₂—CH₂—CH₂—CH(CH₃)— | | 2-Cl,5-Br-phenyl | Cl | COOH | 3.59 |
| 787 | —CH₂—CH₂—CH₂—CH(CH₃)— | | 2-Cl,5-methoxy-phenyl | Cl | COOH | 3.21 |
| 788 | —CH₂—CH₂—CH₂—CH(CH₃)— | | 2-Cl-4-F-phenyl | Cl | 2-pyridyl | 3.15 |
| 789 | —CH₂—CH₂—CH₂—CH(CH₃)— | | 2-Cl-4-F-phenyl | Cl | 3-Me-1,2,4-triazol-5-yl | 2.9 |
| 790 | —CH₂—CH₂—CH₂—CH(CH₃)— | | 2-Cl-4-F-phenyl | Cl | 5-Me-oxadiazol-2-yl | 3.77 |
| 791 | —CH₂—CH₂—CH₂—CH(CH₃)— | | 2-Cl-4-F-phenyl | Cl | COOC₂H₅ | 5.08 |
| 792 | —CH₂—CH₂—CH₂—CH(CH₃)— | | 2-Cl-4-F-phenyl | Cl | SO₃H | 2.01 |
| 793 | —CH₂—CH₂—CH₂—CH(CH₃)— | | 2-F-phenyl | Cl | COOH | 2.93 |
| 794 | —CH₂—CH₂—CH₂—CH(CH₃)— | | 2-Me-phenyl | Cl | COOH | 3.2 |
| 795 | —CH₂—CH₂—CH₂—CH(CH₃)— | | phenyl | Cl | 5-Me-oxadiazol-2-yl | 3.42 |
| 796 | —CH₂—CH₂—CH₂—CH(CH₃)— | | phenyl | Cl | COOC₂H₅ | 4.7 |
| 797 | —CH₂—CH₂—O—CH₂—CH₂— | | 2-Cl,5-NO2-phenyl | Cl | —NO2 | 2.91 |
| 798 | CH₃ | H | 2,5-F-phenyl | Cl | COOH | 2.05 |
| 799 | CH₃ | H | 2-methyl-4-F-phenyl | Cl | COOH | 2.22 |
| 800 | cyclopentyl | H | 2-Cl,4-methylphenyl | Cl | COO⁻Na⁺ | |
| 801 | cyclopentyl | H | 2-Cl,4-methylphenyl | Cl | COOH | 3.59 |
| 802 | cyclopentyl | H | 2-F-phenyl | Cl | COOH | 2.98 |
| 803 | cyclopropylmethyl | H | 2,4-F-phenyl | Cl | COOH | 2.77 |
| 804 | cyclopropylmethyl | H | 2-Cl,4-methylphenyl | Cl | COOH | 3.18 |
| 805 | cyclopropylmethyl | H | 3-Me-thien-2-yl | Cl | COOH | 2.83 |
| 806 | H | H | 2-Cl-4-F-phenyl | Cl | SO₂NH2 | 1.89 |
| 807 | i-butyl | H | 2,4,6-trifluorophenyl | Cl | CONCH₃OCH₃ | 3.31* |
| 808 | i-butyl | H | 2,4,6-trifluorophenyl | Cl | COO⁻K⁺ | |
| 809 | i-butyl | H | 2,4,6-trifluorophenyl | Cl | COO⁻Na⁺ | |
| 810 | i-butyl | H | 2,4,6-trifluorophenyl | Cl | COOCH(CH₃)COOCH₃ | 4.1* |
| 811 | i-butyl | H | 2,4,6-trifluorophenyl | Cl | COOCH₂CH₂OCH₂CH₂OCH₃ | 3.64* |
| 812 | i-butyl | H | 2,4,6-trifluorophenyl | Cl | COO—CH₂—CH₂—OCH₃ | 3.7* |
| 813 | i-butyl | H | 2,4,6-trifluorophenyl | Cl | COOCH₂COOCH₃ | 3.69* |
| 814 | i-butyl | H | 2,4,6-trifluorophenyl | Cl | COOH | 2.97 |
| 815 | i-butyl | H | 2,4-Cl-phenyl | Cl | CONCH₃OCH₃ | 4.04* |
| 816 | i-butyl | H | 2,4-Cl-phenyl | Cl | COO⁻K⁺ | |
| 817 | i-butyl | H | 2,4-Cl-phenyl | Cl | COO⁻Na⁺ | |
| 818 | i-butyl | H | 2,4-Cl-phenyl | Cl | COOCH(CH₃)COOCH₃ | 4.77* |
| 819 | i-butyl | H | 2,4-Cl-phenyl | Cl | COOCH₂CH₂OCH₂CH₂OCH₃ | 4.37* |
| 820 | i-butyl | H | 2,4-Cl-phenyl | Cl | COO—CH₂—CH₂—OCH₃ | 4.47* |
| 821 | i-butyl | H | 2,4-Cl-phenyl | Cl | COOCH₂COOCH₃ | 4.45* |
| 822 | i-butyl | H | 2,4-Cl-phenyl | Cl | COOH | 3.65 |
| 823 | i-butyl | H | 2,4-F-phenyl | Cl | COOH | 2.97 |
| 824 | i-butyl | H | 2,6-difluoro,4-Cl-phenyl | Cl | CONCH₃OCH₃ | 3.78* |
| 825 | i-butyl | H | 2,6-difluoro,4-Cl-phenyl | Cl | COO⁻K⁺ | |
| 826 | i-butyl | H | 2,6-difluoro,4-Cl-phenyl | Cl | COO⁻Na⁺ | |
| 827 | i-butyl | H | 2,6-difluoro,4-Cl-phenyl | Cl | COOCH(CH₃)COOCH₃ | 4.43* |
| 828 | i-butyl | H | 2,6-difluoro,4-Cl-phenyl | Cl | COOCH₂CH₂OCH₂CH₂OCH₃ | 4.03* |
| 829 | i-butyl | H | 2,6-difluoro,4-Cl-phenyl | Cl | COO—CH₂—CH₂—OCH₃ | 4.1* |
| 830 | i-butyl | H | 2,6-difluoro,4-Cl-phenyl | Cl | COOCH₂COOCH₃ | 4.44* |
| 831 | i-butyl | H | 2,6-difluoro,4-Cl-phenyl | Cl | COCH | 3.35 |
| 832 | i-butyl | H | 2-Cl,4-methylphenyl | Cl | COO⁻Na⁺ | |
| 833 | i-butyl | H | 2-Cl,4-methylphenyl | Cl | COOH | 3.44 |
| 834 | i-butyl | H | 2-Cl-4-F-phenyl | Cl | CONCH₃OCH₃ | 3.59* |
| 835 | i-butyl | H | 2-Cl-4-F-phenyl | Cl | COO⁻K⁺ | |
| 836 | i-butyl | H | 2-Cl-4-F-phenyl | Cl | COO⁻Na⁺ | |
| 837 | i-butyl | H | 2-Cl-4-F-phenyl | Cl | COOCH(CH₃)COOCH₃ | 4.33* |
| 838 | i-butyl | H | 2-Cl-4-F-phenyl | Cl | COOCH₂CH₂OCH₂CH₂OCH₃ | 3.9* |
| 839 | i-butyl | H | 2-Cl-4-F-phenyl | Cl | COO—CH₂—CH₂—OCH₃ | 3.97* |
| 840 | i-butyl | H | 2-Cl-4-F-phenyl | Cl | COOCH₂COOCH₃ | 3.95* |
| 841 | i-butyl | H | 2-Cl-4-F-phenyl | Cl | COOH | 3.24 |
| 842 | i-butyl | H | 2-Cl-6-F-phenyl | Cl | COOH | 3.01 |
| 843 | i-butyl | H | 2-Cl-phenyl | Cl | CONCH₃OCH₃ | 3.43* |

TABLE 1-continued

Structure: pyrazolo[1,5-a]pyrimidine with NR¹R² at 7-position, R³ at 6, X at 5, R⁴ at 3.

| Ex. No. | R¹ or —R¹+R²— | R² | R³ | X | R⁴ | log p |
|---|---|---|---|---|---|---|
| 844 | i-butyl | H | 2-Cl-phenyl | Cl | COOCH(CH₃)COOCH₃ | 4.22* |
| 845 | i-butyl | H | 2-Cl-phenyl | Cl | COOCH₂CH₂OCH₂CH₂OCH₃ | 3.79* |
| 846 | i-butyl | H | 2-Cl-phenyl | Cl | COO—CH₂—CH₂—OCH₃ | 3.85* |
| 847 | i-butyl | H | 2-Cl-phenyl | Cl | COOCH₂COOCH₃ | 3.84* |
| 848 | i-butyl | H | 2-Cl-phenyl | Cl | COOH | 3.1 |
| 849 | i-butyl | H | 3-Me-thien-2-yl | Cl | COO⁻Na⁺ | |
| 850 | i-butyl | H | 3-Me-thien-2-yl | Cl | COOH | 3.09 |
| 851 | i-propyl | H | 2,4,6-Me-phenyl | Cl | COOH | 3.39 |
| 852 | i-propyl | H | 2,4,6-trifluorophenyl | Cl | CONCH₃OCH₃ | 3.03* |
| 853 | i-propyl | H | 2,4,6-trifluorophenyl | Cl | COO⁻K⁺ | |
| 854 | i-propyl | H | 2,4,6-trifluorophenyl | Cl | COO⁻Na⁺ | |
| 855 | i-propyl | H | 2,4,6-trifluorophenyl | Cl | COOCH(CH₃)COOCH₃ | 3.81* |
| 856 | i-propyl | H | 2,4,6-trifluorophenyl | Cl | COOCH₂CH₂OCH₂CH₂OCH₃ | 3.36* |
| 857 | i-propyl | H | 2,4,6-trifluorophenyl | Cl | COOCH₂COOCH₃ | 3.37* |
| 858 | i-propyl | H | 2,4,6-trifluorophenyl | Cl | COOH | 2.69 |
| 859 | i-propyl | H | 2,4-Cl-phenyl | Cl | CONCH₃OCH₃ | 3.68* |
| 860 | i-propyl | H | 2,4-Cl-phenyl | Cl | COO⁻K⁺ | |
| 861 | i-propyl | H | 2,4-Cl-phenyl | Cl | COO⁻Na⁺ | |
| 862 | i-propyl | H | 2,4-Cl-phenyl | Cl | COOCH(CH₃)COOCH₃ | 4.42* |
| 863 | i-propyl | H | 2,4-Cl-phenyl | Cl | COOCH₂CH₂OCH₂CH₂OCH₃ | 3.99* |
| 864 | i-propyl | H | 2,4-Cl-phenyl | Cl | COO—CH₂—CH₂—OCH₃ | 4.05* |
| 865 | i-propyl | H | 2,4-Cl-phenyl | Cl | COOCH₂COOCH₃ | 4.04* |
| 866 | i-propyl | H | 2,4-Cl-phenyl | Cl | COOH | 3.3 |
| 867 | i-propyl | H | 2,4-dichloro,5-CH₃-phenyl | Cl | COOH | 3.64 |
| 868 | i-propyl | H | 2,5-Me-phenyl | Cl | COOH | 3.18 |
| 869 | i-propyl | H | 2,6-difluoro,4-Cl-phenyl | Cl | CONCH₃OCH₃ | 3.36* |
| 870 | i-propyl | H | 2,6-difluoro,4-Cl-phenyl | Cl | COOCH(CH₃)COOCH₃ | 4.13* |
| 871 | i-propyl | H | 2,6-difluoro,4-Cl-phenyl | Cl | COOCH₂CH₂OCH₂CH₂OCH₃ | 3.71* |
| 872 | i-propyl | H | 2,6-difluoro,4-Cl-phenyl | Cl | COO—CH₂—CH₂—OCH₃ | 3.78* |
| 873 | i-propyl | H | 2,6-difluoro,4-Cl-phenyl | Cl | COOCH₂COOCH₃ | 3.77* |
| 874 | i-propyl | H | 2-Cl,4-methylphenyl | Cl | COOH | 3.1 |
| 875 | i-propyl | H | 2-Cl,5-Br-phenyl | Cl | COOH | 3.17 |
| 876 | i-propyl | H | 2-Cl,5-F-phenyl | Cl | COOH | 2.78 |
| 877 | i-propyl | H | 2-Cl-4-F-phenyl | Cl | CONCH₃OCH₃ | 3.31* |
| 878 | i-propyl | H | 2-Cl-4-F-phenyl | Cl | COOCH(CH₃)COOCH₃ | 3.98* |
| 879 | i-propyl | H | 2-Cl-4-F-phenyl | Cl | COOCH₂CH₂OCH₂CH₂OCH₃ | 3.56* |
| 880 | i-propyl | H | 2-Cl-4-F-phenyl | Cl | COO—CH₂—CH₂—OCH₃ | 3.61* |
| 881 | i-propyl | H | 2-Cl-4-F-phenyl | Cl | COOCH₂COOCH₃ | 3.62* |
| 882 | i-propyl | H | 2-Cl-4-F-phenyl | Cl | COOH | 2.91 |
| 883 | i-propyl | H | 2-Cl-4-F-phenyl | Cl | SO₂NCH(CH₃)₂ | 3.75 |
| 884 | i-propyl | H | 2-Cl-5-Me-phenyl | Cl | COOH | 3.09 |
| 885 | i-propyl | H | 2-Cl-6-F-phenyl | Cl | COOH | 2.7 |
| 886 | i-propyl | H | 2-Cl-phenyl | Cl | CONCH₃OCH₃ | 3.07* |
| 887 | i-propyl | H | 2-Cl-phenyl | Cl | COOCH(CH₃)COOCH₃ | 3.85* |
| 888 | i-propyl | H | 2-Cl-phenyl | Cl | COOCH₂CH₂OCH₂CH₂OCH₃ | 3.41* |
| 889 | i-propyl | H | 2-Cl-phenyl | Cl | COO—CH₂—CH₂—OCH₃ | 3.46* |
| 890 | i-propyl | H | 2-Cl-phenyl | Cl | COOCH₂COOCH₃ | 3.49* |
| 891 | i-propyl | H | 2-Cl-phenyl | Cl | COOH | 2.77 |
| 892 | i-propyl | H | 2-F,4-Cl-phenyl | Cl | COOH | 3.29 |
| 893 | i-propyl | H | 3-Me-thien-2-yl | Cl | COOH | 2.74 |
| 894 | sec-butyl | H | 2,5-Cl-phenyl | Cl | COO⁻Na⁺ | 3.41 |
| 895 | sec-butyl | H | 2,5-Cl-phenyl | Cl | COOH | 3.41 |
| 896 | sec-butyl | H | 2-Cl,5-Br-phenyl | Cl | COOH | 3.48 |
| 897 | sec-butyl | H | 2-Cl,5-F-phenyl | Cl | COO⁻Na⁺ | 3.07 |
| 898 | sec-butyl | H | 2-Cl,5-F-phenyl | Cl | COOH | 3.07 |
| 899 | sec-butyl | H | 2-Cl-5-Me-phenyl | Cl | COO⁻Na⁺ | 3.38 |
| 900 | sec-butyl | H | 2-Cl-5-Me-phenyl | Cl | COOH | 3.38 |
| 901 | sec-butyl | H | 2-F,4-Cl-phenyl | Cl | COO⁻Na⁺ | 3.34 |
| 902 | sec-butyl | H | 2-F,4-Cl-phenyl | Cl | COOH | 3.34 |
| 903 | CH(CH₃)—C(CH₃)₃ | H | 2-Cl-6-F-phenyl | CH₃ | CO—NH—CH₃ | |
| 904 | CH(CH₃)—C(CH₃)₃ | H | 2-Cl-6-F-phenyl | CH₃ | CON(CH₃)₂ | |
| 905 | CH(CH₃)—C(CH₃)₃ | H | 2-Cl-6-F-phenyl | CH₃ | CO—NH-i-propyl | |
| 906 | CH(CH₃)—C(CH₃)₃ | H | 2-Cl-6-F-phenyl | CH₃ | CO-morpholin-1-yl | |
| 907 | CH(CH₃)—C(CH₃)₃ | H | 2-Cl-6-F-phenyl | CH₃ | COOH | |
| 908 | CH(CH₃)—C(CH₃)₃ | H | 2-Cl-6-F-phenyl | CH₃ | COO-propen-3-yl | |
| 909 | CH(CH₃)—C(CH₃)₃ | H | 2-Cl-6-F-phenyl | CH₃ | COO-benzyl | |

TABLE 1-continued

| Ex. No. | R¹ or —R¹+R²— | R² | R³ | X | R⁴ | log p |
|---|---|---|---|---|---|---|
| 910 | CH(CH₃)—C(CH₃)₃ | H | 2-Cl-6-F-phenyl | CH₃ | COO—CH₂—CH₂—OCH₃ | |
| 911 | CH(CH₃)—C(CH₃)₃ | H | 2-Cl-6-F-phenyl | CH₃ | SO₃H | |
| 912 | CH(CH₃)—C(CH₃)₃ | H | 2-Cl-6-F-phenyl | CH₃ | SO₂CH₃ | |
| 913 | CH(CH₃)—C(CH₃)₃ | H | 2,4,6-trifluorophenyl | CH₃ | CO—NH—CH₃ | |
| 914 | CH(CH₃)—C(CH₃)₃ | H | 2,4,6-trifluorophenyl | CH₃ | CON(CH₃)₂ | |
| 915 | CH(CH₃)—C(CH₃)₃ | H | 2,4,6-trifluorophenyl | CH₃ | CO—NH-i-propyl | |
| 916 | CH(CH₃)—C(CH₃)₃ | H | 2,4,6-trifluorophenyl | CH₃ | CO-morpholin-1-yl | |
| 917 | CH(CH₃)—C(CH₃)₃ | H | 2,4,6-trifluorophenyl | CH₃ | COOH | |
| 918 | CH(CH₃)—C(CH₃)₃ | H | 2,4,6-trifluorophenyl | CH₃ | COO-propen-3-yl | |
| 919 | CH(CH₃)—C(CH₃)₃ | H | 2,4,6-trifluorophenyl | CH₃ | COO-benzyl | |
| 920 | CH(CH₃)—C(CH₃)₃ | H | 2,4,6-trifluorophenyl | CH₃ | COO—CH₂—CH₂—OCH₃ | |
| 921 | CH(CH₃)—C(CH₃)₃ | H | 2,4,6-trifluorophenyl | CH₃ | SO₃H | |
| 922 | CH(CH₃)—C(CH₃)₃ | H | 2,4,6-trifluorophenyl | CH₃ | SO₂CH₃ | |
| 923 | CH(CH₃)—C(CH₃)₃ | H | 2-Cl-4-F-phenyl | CH₃ | CO—NH—CH₃ | |
| 924 | CH(CH₃)—C(CH₃)₃ | H | 2-Cl-4-F-phenyl | CH₃ | CON(CH₃)₂ | |
| 925 | CH(CH₃)—C(CH₃)₃ | H | 2-Cl-4-F-phenyl | CH₃ | CO—NH-i-propyl | |
| 926 | CH(CH₃)—C(CH₃)₃ | H | 2-Cl-4-F-phenyl | CH₃ | CO-morpholin-1-yl | |
| 927 | CH(CH₃)—C(CH₃)₃ | H | 2-Cl-4-F-phenyl | CH₃ | COOH | |
| 928 | CH(CH₃)—C(CH₃)₃ | H | 2-Cl-4-F-phenyl | CH₃ | COO-propen-3-yl | |
| 929 | CH(CH₃)—C(CH₃)₃ | H | 2-Cl-4-F-phenyl | CH₃ | COO-benzyl | |
| 930 | CH(CH₃)—C(CH₃)₃ | H | 2-Cl-4-F-phenyl | CH₃ | COO—CH₂—CH₂—OCH₃ | |
| 931 | CH(CH₃)—C(CH₃)₃ | H | 2-Cl-4-F-phenyl | CH₃ | SO₃H | |
| 932 | CH(CH₃)—C(CH₃)₃ | H | 2-Cl-4-F-phenyl | CH₃ | SO₂CH₃ | |
| 933 | CH(CH₃)—C(CH₃)₃ | H | 2-Cl-phenyl | CH₃ | CO—NH—CH₃ | |
| 934 | CH(CH₃)—C(CH₃)₃ | H | 2-Cl-phenyl | CH₃ | CON(CH₃)₂ | |
| 935 | CH(CH₃)—C(CH₃)₃ | H | 2-Cl-phenyl | CH₃ | CO—NH-i-propyl | |
| 936 | CH(CH₃)—C(CH₃)₃ | H | 2-Cl-phenyl | CH₃ | CO-morpholin-1-yl | |
| 937 | CH(CH₃)—C(CH₃)₃ | H | 2-Cl-phenyl | CH₃ | COOH | |
| 938 | CH(CH₃)—C(CH₃)₃ | H | 2-Cl-phenyl | CH₃ | COO-propen-3-yl | |
| 939 | CH(CH₃)—C(CH₃)₃ | H | 2-Cl-phenyl | CH₃ | COO-benzyl | |
| 940 | CH(CH₃)—C(CH₃)₃ | H | 2-Cl-phenyl | CH₃ | COO—CH₂—CH₂—OCH₃ | |
| 941 | CH(CH₃)—C(CH₃)₃ | H | 2-Oi-phenyl | CH₃ | SO₃H | |
| 942 | CH(CH₃)—C(CH₃)₃ | H | 2-Cl-phenyl | CH₃ | SO₂CH₃ | |
| 943 | CH(CH₃)—C(CH₃)₃ | H | 5-Cl-pyrimidin-4-yl | CH₃ | CO—-NH—CH₃ | |
| 944 | CH(CH₃)—C(CH₃)₃ | H | 5-Cl-pyrimidin-4-yl | CH₃ | CON(CH₃)₂ | |
| 945 | CH(CH₃)—C(CH₃)₃ | H | 5-Cl-pyrimidin-4-yl | CH₃ | CO—NH-i-propyl | |
| 946 | CH(CH₃)—C(CH₃)₃ | H | 5-Cl-pyrimidin-4-yl | CH₃ | CO-morpholin-1-yl | |
| 947 | CH(CH₃)—C(CH₃)₃ | H | 5-Cl-pyrimidin-4-yl | CH₃ | COOH | |
| 948 | CH(CH₃)—C(CH₃)₃ | H. | 5-Cl-pyrimidin-4-yl | CH₃ | COO-propen-3-yl | |
| 949 | CH(CH₃)—C(CH₃)₃ | H | 5-Cl-pyrimidin-4-yl | CH₃ | COO-benzyl | |
| 950 | CH(CH₃)—C(CH₃)₃ | H | 5-Cl-pyrimidin-4-yl | CH₃ | COO—CH₂—CH₂—OCH₃ | |
| 951 | CH(CH₃)—C(CH₃)₃ | H | 5-Cl-pyrimidin-4-yl | CH₃ | SO₃H | |
| 952 | CH(CH₃)—C(CH₃)₃ | H | 5-Cl-pyrimidin-4-yl | CH₃ | SO₂CH₃ | |
| 953 | CH(CH₃)(CF₃) | H | 2-Cl-6-F-phenyl | CH₃ | CO—NH—CH₃ | |
| 954 | CH(CH₃)(CF₃) | H | 2-Cl-6-F-phenyl | CH₃ | CON(CH₃)₂ | |
| 955 | CH(CH₃)(CF₃) | H | 2-Cl-6-F-phenyl | CH₃ | CO—NH-i-propyl | |
| 956 | CH(CH₃)(CF₃) | H | 2-Cl-6-F-phenyl | CH₃ | CO-morpholin-1-yl | |
| 957 | CH(CH₃)(CF₃) | H | 2-Cl-6-F-phenyl | CH₃ | COOH | |
| 958 | CH(CH₃)(CF₃) | H | 2-Cl-6-F-phenyl | CH₃ | COO-propen-3-yl | |
| 959 | CH(CH₃)(CF₃) | H | 2-Cl-6-F-phenyl | CH₃ | COO-benzyl | |
| 960 | CH(CH₃)(CF₃) | H | 2-Cl-6-F-phenyl | CH₃ | COO—CH₂—CH₂—OCH₃ | |
| 961 | CH(CH₃)(CF₃) | H | 2-Cl-6-F-phenyl | CH₃ | SO₃H | |
| 962 | CH(CH₃)(CF₃) | H | 2-Cl-6-F-phenyl | CH₃ | SO₂CH₃ | |
| 963 | CH(CH₃)(CF₃) | H | 2,4,6-trifluorophenyl | CH₃ | CO—NH—CH₃ | |
| 964 | CH(CH₃)(CF₃) | H | 2,4,6-trifluorophenyl | CH₃ | CON(CH₃)₂ | |
| 965 | CH(CH₃)(CF₃) | H | 2,4,6-trifluorophenyl | CH₃ | CO—NH-i-propyl | |
| 966 | CH(CH₃)(CF₃) | H | 2,4,6-trifluorophenyl | CH₃ | CO-morpholin-1-yl | |
| 967 | CH(CH₃)(CF₃) | H | 2,4,6-trifluorophenyl | CH₃ | COOH | |
| 968 | CH(CH₃)(CF₃) | H | 2,4,6-trifluorophenyl | CH₃ | COO-propen-3-yl | |
| 969 | CH(CH₃)(CF₃) | H | 2,4,6-trifluorophenyl | CH₃ | COO-benzyl | |
| 970 | CH(CH₃)(CF₃) | H | 2,4,6-trifluorophenyl | CH₃ | COO—CH₂—CH₂—OCH₃ | |
| 971 | CH(CH₃)(CF₃) | H | 2,4,6-trifluorophenyl | CH₃ | SO₃H | |
| 972 | CH(CH₃)(0F3) | H | 2,4,6-trifluorophenyl | CH₃ | SO₂CH₃ | |
| 973 | CH(CH₃)(CF₃) | H | 2-Cl-4-F-phenyl | CH₃ | CO—NH—CH₃ | |
| 974 | CH(CH₃)(CF₃) | H | 2-Cl-4-F-phenyl | CH₃ | CON(CH₃)₂ | |
| 975 | CH(CH₃)(CF₃) | H | 2-Cl-4-F-phenyl | CH₃ | CO—NH-i-propyl | |

TABLE 1-continued

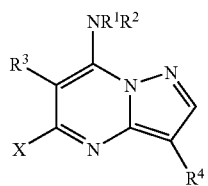

| Ex. No. | $R^1$ or —$R^{1+}R^2$— | $R^2$ | $R^3$ | X | $R^4$ | log p |
|---|---|---|---|---|---|---|
| 976 | CH(CH$_3$)(CF$_3$) | H | 2-Cl-4-F-phenyl | CH$_3$ | CO-morpholin-1-yl | |
| 977 | CH(CH$_3$)(CF$_3$) | H | 2-Cl-4-F-phenyl | CH$_3$ | COOH | |
| 978 | CH(CH$_3$)(CF$_3$) | H | 2-Cl-4-F-phenyl | CH$_3$ | COO-propen-3-yl | |
| 979 | CH(CH$_3$)(CF$_3$) | H | 2-Cl-4-F-phenyl | CH$_3$ | COO-benzyl | |
| 980 | CH(CH$_3$)(CF$_3$) | H | 2-Cl-4-F-phenyl | CH$_3$ | COO—CH$_2$—CH$_2$—OCH$_3$ | |
| 981 | CH(CH$_3$)(CF$_3$) | H | 2-Cl-4-F-phenyl | CH$_3$ | SO$_3$H | |
| 982 | CH(CH$_3$)(CF$_3$) | H | 2-Cl-4-F-phenyl | CH$_3$ | SO$_2$CH$_3$ | |
| 983 | CH(CH$_3$)(CF$_3$) | H | 2-Cl-phenyl | CH$_3$ | CO—NH—CH$_3$ | |
| 984 | CH(CH$_3$)(CF$_3$) | H | 2-Cl-phenyl | CH$_3$ | CON(CH$_3$)$_2$ | |
| 985 | CH(CH$_3$)(CF$_3$) | H | 2-Cl-phenyl | CH$_3$ | CO—NH-i-propyl | |
| 986 | CH(CH$_3$)(CF$_3$) | H | 2-Cl-phenyl | CH$_3$ | CO-morpholin-1-yl | |
| 987 | CH(CH$_3$)(CF$_3$) | H | 2-Cl-phenyl | CH$_3$ | COOH | |
| 988 | CH(CH$_3$)(CF$_3$) | H | 2-Cl-phenyl | CH$_3$ | COO-propen-3-yl | |
| 989 | CH(CH$_3$)(CF$_3$) | H | 2-Cl-phenyl | CH$_3$ | COO-benzyl | |
| 990 | CH(CH$_3$)(CF$_3$) | H | 2-Cl-phenyl | CH$_3$ | COO—CH$_2$—CH$_2$—OCH$_3$ | |
| 991 | CH(CH$_3$)(CF$_3$) | H | 2-Cl-phenyl | CH$_3$ | SO$_3$H | |
| 992 | CH(CH$_3$)(CF$_3$) | H | 2-Cl-phenyl | CH$_3$ | SO$_2$CH$_3$ | |
| 993 | CH(CH$_3$)(CF$_3$) | H | 5-Cl-pyrimidin-4-yl | CH$_3$ | CO—NH—CH$_3$ | |
| 994 | CH(CH$_3$)(CF$_3$) | H | 5-Cl-pyrimidin-4-yl | CH$_3$ | CON(CH$_3$)$_2$ | |
| 995 | CH(CH$_3$)(CF$_3$) | H | 5-Cl-pyrimidin-4-yl | CH$_3$ | CO—NH-i-propyl | |
| 996 | CH(CH$_3$)(CF$_3$) | H | 5-Cl-pyrimidin-4-yl | CH$_3$ | CO-morpholin-1-yl | |
| 997 | CH(CH$_3$)(CF$_3$) | H | 5-Cl-pyrimidin-4-yl | CH$_3$ | COOH | |
| 998 | CH(CH$_3$)(CF$_3$) | H | 5-Cl-pyrimidin-4-yl | CH$_3$ | COO-propen-3-yl | |
| 999 | CH(CH$_3$)(CF$_3$) | H | 5-Cl-pyrimidin-4-yl | CH$_3$ | COO-benzyl | |
| 1000 | CH(CH$_3$)(CF$_3$) | H | 5-Cl-pyrimidin-4-yl | CH$_3$ | COO—CH$_2$—CH$_2$—OCH$_3$ | |
| 1001 | CH(CH$_3$)(CF$_3$) | H | 5-Cl-pyrimidin-4-yl | CH$_3$ | SO$_3$H | |
| 1002 | CH(CH$_3$)(CF$_3$) | H | 5-Cl-pyrimidin-4-yl | CH$_3$ | SO$_2$CH$_3$ | |
| 1003 | CH(CH$_3$)—CH(CH$_3$)$_2$ | H | 2-Cl-6-F-phenyl | CH$_3$ | CO—NH—CH$_3$ | |
| 1004 | CH(CH$_3$)—CH(CH$_3$)$_2$ | H | 2-Cl-6-F-phenyl | CH$_3$ | CON(CH$_3$)$_2$ | |
| 1005 | CH(CH$_3$)—CH(CH$_3$)$_2$ | H | 2-Cl-6-F-phenyl | CH$_3$ | CO—NH-i-propyl | |
| 1006 | CH(CH$_3$)—CH(CH$_3$)$_2$ | H | 2-Cl-6-F-phenyl | CH$_3$ | CO-morpholin-1-yl | |
| 1007 | CH(CH$_3$)—CH(CH$_3$)$_2$ | H | 2-Cl-6-F-phenyl | CH$_3$ | COOH | |
| 1008 | CH(CH$_3$)—CH(CH$_3$)$_2$ | H | 2-Cl-6-F-phenyl | CH$_3$ | COO-propen-3-yl | |
| 1009 | CH(CH$_3$)—CH(CH$_3$)$_2$ | H | 2-Cl-6-F-phenyl | CH$_3$ | COO-benzyl | |
| 1010 | CH(CH$_3$)—CH(CH$_3$)$_2$ | H | 2-Cl-6-F-phenyl | CH$_3$ | COO—CH$_2$—CH$_2$—OCH$_3$ | |
| 1011 | CH(CH$_3$)—CH(CH$_3$)$_2$ | H | 2-Cl-6-F-phenyl | CH$_3$ | SO$_3$H | |
| 1012 | CH(CH$_3$)—CH(CH$_3$)$_2$ | H | 2-Cl-6-F-phenyl | CH$_3$ | SO$_2$CH$_3$ | |
| 1013 | CH(CH$_3$)—CH(CH$_3$)$_2$ | H | 2,4,6-trifluorophenyl | CH$_3$ | CO—NH—CH$_3$ | |
| 1014 | CH(CH$_3$)—CH(CH$_3$)$_2$ | H | 2,4,6-trifluorophenyl | CH$_3$ | CON(CH$_3$)$_2$ | |
| 1015 | CH(CH$_3$)—CH(CH$_3$)$_2$ | H | 2,4,6-trifluorophenyl | CH$_3$ | CO—NH-i-propyl | |
| 1016 | CH(CH$_3$)—CH(CH$_3$)$_2$ | H | 2,4,6-trifluorophenyl | CH$_3$ | CO-morpholin-1-yl | |
| 1017 | CH(CH$_3$)—CH(CH$_3$)$_2$ | H | 2,4,6-trifluorophenyl | CH$_3$ | COOH | |
| 1018 | CH(CH$_3$)—CH(CH$_3$)$_2$ | H | 2,4,6-trifluorophenyl | CH$_3$ | COO-propen-3-yl | |
| 1019 | CH(CH$_3$)—CH(CH$_3$)$_2$ | H | 2,4,6-trifluorophenyl | CH$_3$ | COO-benzyl | |
| 1020 | CH(CH$_3$)—CH(CH$_3$)$_2$ | H | 2,4,6-trifluorophenyl | CH$_3$ | COO—CH$_2$—CH$_2$—OCH$_3$ | |
| 1021 | CH(CH$_3$)—CH(CH$_3$)$_2$ | H | 2,4,6-trifluorophenyl | CH$_3$ | SO$_3$H | |
| 1022 | CH(CH$_3$)—CH(CH$_3$)$_2$ | H | 2,4,6-trifluorophenyl | CH$_3$ | SO$_2$CH$_3$ | |
| 1023 | CH(CH$_3$)—CH(CH$_3$)$_2$ | H | 2-Cl-4-F-phenyl | CH$_3$ | CO—NH—CH$_3$ | |
| 1024 | CH(CH$_3$)—CH(CH$_3$)$_2$ | H | 2-Cl-4-F-phenyl | CH$_3$ | CON(CH$_3$)$_2$ | |
| 1025 | CH(CH$_3$)—CH(CH$_3$)$_2$ | H | 2-Cl-4-F-phenyl | CH$_3$ | CO—NH-i-propyl | |
| 1026 | CH(CH$_3$)—CH(CH$_3$)$_2$ | H | 2-Cl-4-F-phenyl | CH$_3$ | CO-morpholin-1-yl | |
| 1027 | CH(CH$_3$)—CH(CH$_3$)$_2$ | H | 2-Cl-4-F-phenyl | CH$_3$ | COOH | |
| 1028 | CH(CH$_3$)—CH(CH$_3$)$_2$ | H | 2-Cl-4-F-phenyl | CH$_3$ | COO-propen-3-yl | |
| 1029 | CH(CH$_3$)—CH(CH$_3$)$_2$ | H | 2-Cl-4-F-phenyl | CH$_3$ | COO-benzyl | |
| 1030 | CH(CH$_3$)—CH(CH$_3$)$_2$ | H | 2-Cl-4-F-phenyl | CH$_3$ | COO—CH$_2$—CH$_2$—OCH$_3$ | |
| 1031 | CH(CH$_3$)—CH(CH$_3$)$_2$ | H | 2-Cl-4-F-phenyl | CH$_3$ | SO$_3$H | |
| 1032 | CH(CH$_3$)—CH(CH$_3$)$_2$ | H | 2-Cl-4-F-phenyl | CH$_3$ | SO$_2$CH$_3$ | |
| 1033 | CH(CH$_3$)—CH(CH$_3$)$_2$ | H | 2-Cl-phenyl | CH$_3$ | CO—NH—CH$_3$ | |
| 1034 | CH(CH$_3$)—CH(CH$_3$)$_2$ | H | 2-Cl-phenyl | CH$_3$ | CON(CH$_3$)$_2$ | |
| 1035 | CH(CH$_3$)—CH(CH$_3$)$_2$ | H | 2-Cl-phenyl | CH$_3$ | CO—NH-i-propyl | |
| 1036 | CH(CH$_3$)—CH(CH$_3$)$_2$ | H | 2-Cl-phenyl | CH$_3$ | CO-morpholin-1-yl | |
| 1037 | CH(CH$_3$)—CH(CH$_3$)$_2$ | H | 2-Cl-phenyl | CH$_3$ | COOH | |
| 1038 | CH(CH$_3$)—CH(CH$_3$)$_2$ | H | 2-Cl-phenyl | CH$_3$ | COO-propen-3-yl | |
| 1039 | CH(CH$_3$)—CH(CH$_3$)$_2$ | H | 2-Cl-phenyl | CH$_3$ | COO-benzyl | |
| 1040 | CH(CH$_3$)—CH(CH$_3$)$_2$ | H | 2-Cl-phenyl | CH$_3$ | COO—CH$_2$—CH$_2$—OCH$_3$ | |
| 1041 | CH(CH$_3$)—CH(CH$_3$)$_2$ | H | 2-Cl-phenyl | CH$_3$ | SO$_3$H | |

TABLE 1-continued

Structure: pyrazolo[1,5-a]pyrimidine core with NR¹R² at position 7, R³ at position 6, X at position 5, R⁴ at position 3.

| Ex. No. | R¹ or —R¹+R²— | R² | R³ | X | R⁴ | log p |
|---|---|---|---|---|---|---|
| 1042 | CH(CH₃)—CH(CH₃)₂ | H | 2-Cl-phenyl | CH₃ | SO₂CH₃ | |
| 1043 | CH(CH₃)—CH(CH₃)₂ | H | 5-Cl-pyrimidin-4-yl | CH₃ | CO—NH—CH₃ | |
| 1044 | CH(CH₃)—CH(CH₃)₂ | H | 5-Cl-pyrimidin-4-yl | CH₃ | CON(CH₃)₂ | |
| 1045 | CH(CH₃)—CH(CH₃)₂ | H | 5-Cl-pyrimidin-4-yl | CH₃ | CO—NH-i-propyl | |
| 1046 | CH(CH₃)—CH(CH₃)₂ | H | 5-Cl-pyrimidin-4-yl | CH₃ | CO-morpholin-1-yl | |
| 1047 | CH(CH₃)—CH(CH₃)₂ | H | 5-Cl-pyrimidin-4-yl | CH₃ | COOH | |
| 1048 | CH(CH₃)—CH(CH₃)₂ | H | 5-Cl-pyrimidin-4-yl | CH₃ | COO-propen-3-yl | |
| 1049 | CH(CH₃)—CH(CH₃)₂ | H | 5-Cl-pyrimidin-4-yl | CH₃ | COO-benzyl | |
| 1050 | CH(CH₃)—CH(CH₃)₂ | H | 5-Cl-pyrimidin-4-yl | CH₃ | COO—CH₂—CH₂—OCH₃ | |
| 1051 | CH(CH₃)—CH(CH₃)₂ | H | 5-Cl-pyrimidin-4-yl | CH₃ | SO₃H | |
| 1052 | CH(CH₃)—CH(CH₃)₂ | H | 5-Cl-pyrimidin-4-yl | CH₃ | SO₂CH₃ | |
| 1053 | —CH₂—CH₂—CH(CH₃)—CH₂—CH₃— | | 2-Cl-6-F-phenyl | CH₃ | CO—NH—CH₃ | |
| 1054 | —CH₂—CH₂—CH(CH₃)—CH₂—CH₂— | | 2-Cl-6-F-phenyl | CH₃ | CON(CH₃)₂ | |
| 1055 | —CH₂—CH₂—CH(CH₃)—CH₂—CH₂— | | 2-Cl-6-F-phenyl | CH₃ | CO—NH-i-propyl | |
| 1056 | —CH₂—CH₂—CH(CH₃)—CH₂—CH₂— | | 2-Cl-6-F-phenyl | CH₃ | CO-morpholin-1-yl | |
| 1057 | —CH₂—CH₂—CH(CH₃)—CH₂—CH₂— | | 2-Cl-6-F-phenyl | CH₃ | COOH | |
| 1058 | —CH₂—CH₂—CH(CH₃)—CH₂—CH₂— | | 2-Cl-6-F-phenyl | CH₃ | COO-propen-3-yl | |
| 1059 | —CH₂—CH₂—CH(CH₃)—CH₂—CH₂— | | 2-Cl-6-F-phenyl | CH₃ | COO-benzyl | |
| 1060 | —CH₂—CH₂—CH(CH₃)—CH₂—CH₂— | | 2-Cl-6-F-phenyl | CH₃ | COO—CH₂—CH₂—OCH₃ | |
| 1061 | —CH₂—CH₂—CH(CH₃)—CH₂—CH₂— | | 2-Cl-6-F-phenyl | CH₃ | SO₃H | |
| 1062 | —CH₂—CH₂—CH(CH₃)—CH₂—CH₂— | | 2-Cl-6-F-phenyl | CH₃ | SO₂CH₃ | |
| 1063 | —CH₂—CH₂—CH(CH₃)—CH₂—CH₂— | | 2,4,6-trifluorophenyl | CH₃ | CO—NH—CH₃ | |
| 1064 | —CH₂—CH₂—CH(CH₃)—CH₂—CH₂— | | 2,4,6-trifluorophenyl | CH₃ | CON(CH₃)₂ | |
| 1065 | —CH₂—CH₂—CH(CH₃)—CH₂—CH₂— | | 2,4,6-trifluorophenyl | CH₃ | CO—NH-i-propyl | |
| 1066 | —CH₂—CH₂—CH(CH₃)—CH₂—CH₂— | | 2,4,6-trifluorophenyl | CH₃ | CO-morpholin-1-yl | |
| 1067 | —CH₂—CH₂—CH(CH₃)—CH₂—CH₂— | | 2,4,6-trifluorophenyl | CH₃ | COOH | |
| 1068 | —CH₂—CH₂—CH(CH₃)—CH₂—CH₂— | | 2,4,6-trifluorophenyl | CH₃ | COO-propen-3-yl | |
| 1069 | —CH₂—CH₂—CH(CH₃)—CH₂—CH₂— | | 2,4,6-trifluorophenyl | CH₃ | COO-benzyl | |
| 1070 | —CH₂—CH₂—CH(CH₃)—CH₂—CH₂— | | 2,4,6-trifluorophenyl | CH₃ | COO—CH₂—CH₂—OCH₃ | |
| 1071 | —CH₂—CH₂—CH(CH₃)—CH₂—CH₂— | | 2,4,6-trifluorophenyl | CH₃ | SO₃H | |
| 1072 | —CH₂—CH₂—CH(CH₃)—CH₂—CH₂— | | 2,4,6-trifluorophenyl | CH₃ | SO₂CH₃ | |
| 1073 | —CH₂—CH₂—CH(CH₃)—CH₂—CH₂— | | 2-Cl-4-F-phenyl | CH₃ | CO—NH—CH₃ | |
| 1074 | —CH₂—CH₂—CH(CH₃)—CH₂—CH₂— | | 2-Cl-4-F-phenyl | CH₃ | CON(CH₃)₂ | |
| 1075 | —CH₂—CH₂—CH(CH₃)—CH₂—CH₂— | | 2-Cl-4-F-phenyl | CH₃ | CO—NH-i-propyl | |
| 1076 | —CH₂—CH₂—CH(CH₃)—CH₂—CH₂— | | 2-Cl-4-F-phenyl | CH₃ | CO-morpholin-1-yl | |
| 1077 | —CH₂—CH₂—CH(CH₃)—CH₂—CH₂— | | 2-Cl-4-F-phenyl | CH₃ | COOH | |
| 1078 | —CH₂—CH₂—CH(CH₃)—CH₂—CH₂— | | 2-Cl-4-F-phenyl | CH₃ | COO-propen-3-yl | |
| 1079 | —CH₂—CH₂—CH(CH₃)—CH₂—CH₂— | | 2-Cl-4-F-phenyl | CH₃ | COO-benzyl | |
| 1080 | —CH₂—CH₂—CH(CH₃)—CH₂—CH₂— | | 2-Cl-4-F-phenyl | CH₃ | COO—CH₂—CH₂—OCH₃ | |
| 1081 | —CH₂—CH₂—CH(CH₃)—CH₂—CH₂— | | 2-Cl-4-F-phenyl | CH₃ | SO₃H | |
| 1082 | —CH₂—CH₂—CH(CH₃)—CH₂—CH₂— | | 2-Cl-4-F-phenyl | CH₃ | SO₂CH₃ | |
| 1083 | —CH₂—CH₂—CH(CH₃)—CH₂—CH₂— | | 2-Cl-phenyl | CH₃ | CO—NH—CH₃ | |
| 1084 | —CH₂—CH₂—CH(CH₃)—CH₂—CH₂— | | 2-Cl-phenyl | CH₃ | CON(CH₃)₂ | |
| 1085 | —CH₂—CH₂—CH(CH₃)—CH₂—CH₂— | | 2-Cl-phenyl | CH₃ | CO—NH-i-propyl | |
| 1086 | —CH₂—CH₂—CH(CH₃)—CH₂—CH₂— | | 2-Cl-phenyl | CH₃ | CO-morpholin-1-yl | |
| 1087 | —CH₂—CH₂—CH(CH₃)—CH₂—CH₂— | | 2-Cl-phenyl | CH₃ | COOH | |
| 1088 | —CH₂—CH₂—CH(CH₃)—CH₂—CH₂— | | 2-Cl-phenyl | CH₃ | COO-propen-3-yl | |
| 1089 | —CH₂—CH₂—CH(CH₃)—CH₂—CH₂— | | 2-Cl-phenyl | CH₃ | COO-benzyl | |
| 1090 | —CH₂—CH₂—CH(CH₃)—CH₂—CH₂— | | 2-Cl-phenyl | CH₃ | COO—CH₂—CH₂—OCH₃ | |
| 1091 | —CH₂—CH₂—CH(CH₃)—CH₂—CH₂— | | 2-Cl-phenyl | CH₃ | SO₃H | |
| 1092 | —CH₂—CH₂—CH(CH₃)—CH₂—CH₂— | | 2-Cl-phenyl | CH₃ | SO₂CH₃ | |
| 1093 | —CH₂—CH₂—CH(CH₃)—CH₂—CH₂— | | 5-Cl-pyrimidin-4-yl | CH₃ | CO—NH—CH₃ | |
| 1094 | —CH₂—CH₂—CH(CH₃)—CH₂—CH₂— | | 5-Cl-pyrimidin-4-yl | CH₃ | CON(CH₃)₂ | |
| 1095 | —CH₂—CH₂—CH(CH₃)—CH₂—CH₂— | | 5-Cl-pyrimidin-4-yl | CH₃ | CO—NH-i-propyl | |
| 1096 | —CH₂—CH₂—CH(CH₃)—CH₂—CH₂— | | 5-Cl-pyrimidin-4-yl | CH₃ | CO-morpholin-1-yl | |
| 1097 | —CH₂—CH₂—CH(CH₃)—CH₂—CH₂— | | 5-Cl-pyrimidin-4-yl | CH₃ | COOH | |
| 1098 | —CH₂—CH₂—CH(CH₃)—CH₂—CH₂— | | 5-Cl-pyrimidin-4-yl | CH₃ | COO-propen-3-yl | |
| 1099 | —CH₂—CH₂—CH(CH₃)—CH₂—CH₂— | | 5-Cl-pyrimidin-4-yl | CH₃ | COO-benzyl | |
| 1100 | —CH₂—CH₂—CH(CH₃)—CH₂—CH₂— | | 5-Cl-pyrimidin-4-yl | CH₃ | COO—CH₂—CH₂—OCH₃ | |
| 1101 | —CH₂—CH₂—CH(CH₃)—CH₂—CH₂— | | 5-Cl-pyrimidin-4-yl | CH₃ | SO₃H | |
| 1102 | —CH₂—CH₂—CH(CH₃)—CH₂—CH₂— | | 5-Cl-pyrimidin-4-yl | CH₃ | SO₂CH₃ | |
| 1103 | CH(CH₃)—C(CH₃)₃ | H | 2-Cl-6-F-phenyl | SCH₃ | CO—NH—CH₃ | |
| 1104 | CH(CH₃)—C(CH₃)₃ | H | 2-Cl-6-F-phenyl | SCH₃ | CON(CH₃)₂ | |
| 1105 | CH(CH₃)—C(CH₃)₃ | H | 2-Cl-6-F-phenyl | SCH₃ | CO—NH-i-propyl | |
| 1106 | CH(CH₃)—C(CH₃)₃ | H | 2-Cl-6-F-phenyl | SCH₃ | CO-morpholin-1-yl | |
| 1107 | CH(CH₃)—C(CH₃)₃ | H | 2-Cl-6-F-phenyl | SCH₃ | COOH | |

TABLE 1-continued

| Ex. No. | R¹ or —R¹+R²— | R² | R³ | X | R⁴ | log p |
|---|---|---|---|---|---|---|
| 1108 | CH(CH$_3$)—C(CH$_3$)$_3$ | H | 2-Cl-6-F-phenyl | SCH$_3$ | COO-propen-3-yl | |
| 1109 | CH(CH$_3$)—C(CH$_3$)$_3$ | H | 2-Cl-6-F-phenyl | SCH$_3$ | COO-benzyl | |
| 1110 | CH(CH$_3$)—C(CH$_3$)$_3$ | H | 2-Cl-6-F-phenyl | SCH$_3$ | COO—CH$_2$—CH$_2$—OCH$_3$ | |
| 1111 | CH(CH$_3$)—C(CH$_3$)$_3$ | H | 2-Cl-6-F-phenyl | SCH$_3$ | SO$_3$H | |
| 1112 | CH(CH$_3$)—C(CH$_3$)$_3$ | H | 2-Cl-6-F-phenyl | SCH$_3$ | SO$_2$CH$_3$ | |
| 1113 | CH(CH$_3$)—C(CH$_3$)$_3$ | H | 2,4,6-trifluorophenyl | SCH$_3$ | CO—NH—CH$_3$ | |
| 1114 | CH(CH$_3$)—C(CH$_3$)$_3$ | H | 2,4,6-trifluorophenyl | SCH$_3$ | CON(CH$_3$)$_2$ | |
| 1115 | CH(CH$_3$)—C(CH$_3$)$_3$ | H | 2,4,6-trifluorophenyl | SCH$_3$ | CO—NH-i-propyl | |
| 1116 | CH(CH$_3$)—C(CH$_3$)$_3$ | H | 2,4,6-trifluorophenyl | SCH$_3$ | CO-morpholin-1-yl | |
| 1117 | CH(CH$_3$)—C(CH$_3$)$_3$ | H | 2,4,6-trifluorophenyl | SCH$_3$ | COOH | |
| 1118 | CH(CH$_3$)—C(CH$_3$)$_3$ | H | 2,4,6-trifluorophenyl | SCH$_3$ | COO-propen-3-yl | |
| 1119 | CH(CH$_3$)—C(CH$_3$)$_3$ | H | 2,4,6-trifluorophenyl | SCH$_3$ | COO-benzyl | |
| 1120 | CH(CH$_3$)—C(CH$_3$)$_3$ | H | 2,4,6-trifluorophenyl | SCH$_3$ | COO—CH$_2$—CH$_2$—OCH$_3$ | |
| 1121 | CH(CH$_3$)—C(CH$_3$)$_3$ | H | 2,4,6-trifluorophenyl | SCH$_3$ | SO$_3$H | |
| 1122 | CH(CH$_3$)—C(CH$_3$)$_3$ | H | 2,4,6-trifluorophenyl | SCH$_3$ | SO$_2$CH$_3$ | |
| 1123 | CH(CH$_3$)—C(CH$_3$)$_3$ | H | 2-Cl-4-F-phenyl | SCH$_3$ | CO—NH—CH$_3$ | |
| 1124 | CH(CH$_3$)—C(CH$_3$)$_3$ | H | 2-Cl-4-F-phenyl | SCH$_3$ | CON(CH$_3$)$_2$ | |
| 1125 | CH(CH$_3$)—C(CH$_3$)$_3$ | H | 2-Cl-4-F-phenyl | SCH$_3$ | CO—NH-i-propyl | |
| 1126 | CH(CH$_3$)—C(CH$_3$)$_3$ | H | 2-Cl-4-F-phenyl | SCH$_3$ | CO-morpholin-1-yl | |
| 1127 | CH(CH$_3$)—C(CH$_3$)$_3$ | H | 2-Cl-4-F-phenyl | SCH$_3$ | COOH | |
| 1128 | CH(CH$_3$)—C(CH$_3$)$_3$ | H | 2-Cl-4-F-phenyl | SCH$_3$ | COO-propen-3-yl | |
| 1129 | CH(CH$_3$)—C(CH$_3$)$_3$ | H | 2-Cl-4-F-phenyl | SCH$_3$ | COO-benzyl | |
| 1130 | CH(CH$_3$)—C(CH$_3$)$_3$ | H | 2-Cl-4-F-phenyl | SCH$_3$ | COO—CH$_2$—CH$_2$—OCH$_3$ | |
| 1131 | CH(CH$_3$)—C(CH$_3$)$_3$ | H | 2-Cl-4-F-phenyl | SCH$_3$ | SO$_3$H | |
| 1132 | CH(CH$_3$)—C(CH$_3$)$_3$ | H | 2-Cl-4-F-phenyl | SCH$_3$ | SO$_2$CH$_3$ | |
| 1133 | CH(CH$_3$)—C(CH$_3$)$_3$ | H | 2-Cl-phenyl | SCH$_3$ | CO—NH—CH$_3$ | |
| 1134 | CH(CH$_3$)—C(CH$_3$)$_3$ | H | 2-Cl-phenyl | SCH$_3$ | CON(CH$_3$)$_2$ | |
| 1135 | CH(CH$_3$)—C(CH$_3$)$_3$ | H | 2-Cl-phenyl | SCH$_3$ | CO—NH-i-propyl | |
| 1136 | CH(CH$_3$)—C(CH$_3$)$_3$ | H | 2-Cl-phenyl | SCH$_3$ | CO-morpholin-1-yl | |
| 1137 | CH(CH$_3$)—C(CH$_3$)$_3$ | H | 2-Cl-phenyl | SCH$_3$ | COOH | |
| 1138 | CH(CH$_3$)—C(CH$_3$)$_3$ | H | 2-Cl-phenyl | SCH$_3$ | COO-propen-3-yl | |
| 1139 | CH(CH$_3$)—C(CH$_3$)$_3$ | H | 2-Cl-phenyl | SCH$_3$ | COO-benzyl | |
| 1140 | CH(CH$_3$)—C(CH$_3$)$_3$ | H | 2-Cl-phenyl | SCH$_3$ | COO—CH$_2$—CH$_2$—OCH$_3$ | |
| 1141 | CH(CH$_3$)—C(CH$_3$)$_3$ | H | 2-Cl-phenyl | SCH$_3$ | SO$_3$H | |
| 1142 | CH(CH$_3$)—C(CH$_3$)$_3$ | H | 2-Cl-phenyl | SCH$_3$ | SO$_2$CH$_3$ | |
| 1143 | CH(CH$_3$)—C(CH$_3$)$_3$ | H | 5-Cl-pyrimidin-4-yl | SCH$_3$ | CO—NH—CH$_3$ | |
| 1144 | CH(CH$_3$)—C(CH$_3$)$_3$ | H | 5-Cl-pyrimidin-4-yl | SCH$_3$ | CON(CH$_3$)$_2$ | |
| 1145 | CH(CH$_3$)—C(CH$_3$)$_3$ | H | 5-Cl-pyrimidin-4-yl | SCH$_3$ | CO—NH-i-propyl | |
| 1146 | CH(CH$_3$)—C(CH$_3$)$_3$ | H | 5-Cl-pyrimidin-4-yl | SCH$_3$ | CO-morpholin-1-yl | |
| 1147 | CH(CH$_3$)—C(CH$_3$)$_3$ | H | 5-Cl-pyrimidin-4-yl | SCH$_3$ | COOH | |
| 1148 | CH(CH$_3$)—C(CH$_3$)$_3$ | H | 5-Cl-pyrimidin-4-yl | SCH$_3$ | COO-propen-3-yl | |
| 1149 | CH(CH$_3$)—C(CH$_3$)$_3$ | H | 5-Cl-pyrimidin-4-yl | SCH$_3$ | COO-benzyl | |
| 1150 | CH(CH$_3$)—C(CH$_3$)$_3$ | H | 5-Cl-pyrimidin-4-yl | SCH$_3$ | COO—CH$_2$—CH$_2$—OCH$_3$ | |
| 1151 | CH(CH$_3$)—C(CH$_3$)$_3$ | H | 5-Cl-pyrimidin-4-yl | SCH$_3$ | SO$_3$H | |
| 1152 | CH(CH$_3$)—C(CH$_3$)$_3$ | H | 5-Cl-pyrimidin-4-yl | SCH$_3$ | SO$_2$CH$_3$ | |
| 1153 | CH(CH$_3$)(CF$_3$) | H | 2-Cl-6-F-phenyl | SCH$_3$ | CO—NH—CH$_3$ | |
| 1154 | CH(CH$_3$)(CF$_3$) | H | 2-Cl-6-F-phenyl | SCH$_3$ | CON(CH$_3$)$_2$ | |
| 1155 | CH(CH$_3$)(CF$_3$) | H | 2-Cl-6-F-phenyl | SCH$_3$ | CO—NH-i-propyl | |
| 1156 | CH(CH$_3$)(CF$_3$) | H | 2-Cl-6-F-phenyl | SCH$_3$ | CO-morpholin-1-yl | |
| 1157 | CH(CH$_3$)(CF$_3$) | H | 2-Cl-6-F-phenyl | SCH$_3$ | COOH | |
| 1158 | CH(CH$_3$)(CF$_3$) | H | 2-Cl-6-F-phenyl | SCH$_3$ | COO-propen-3-yl | |
| 1159 | CH(CH$_3$)(CF$_3$) | H | 2-Cl-6-F-phenyl | SCH$_3$ | COO-benzyl | |
| 1160 | CH(CH$_3$)(CF$_3$) | H | 2-Cl-6-F-phenyl | SCH$_3$ | COO—CH$_2$—CH$_2$—OCH$_3$ | |
| 1161 | CH(CH$_3$)(CF$_3$) | H | 2-Cl-6-F-phenyl | SCH$_3$ | SO$_3$H | |
| 1162 | CH(CH$_3$)(CF$_3$) | H | 2-Cl-6-F-phenyl | SCH$_3$ | SO$_2$CH$_3$ | |
| 1163 | CH(CH$_3$)(CF$_3$) | H | 2,4,6-trifluorophenyl | SCH$_3$ | CO—NH—CH$_3$ | |
| 1164 | CH(CH$_3$)(CF$_3$) | H | 2,4,6-trifluorophenyl | SCH$_3$ | CON(CH$_3$)$_2$ | |
| 1165 | CH(CH$_3$)(CF$_3$) | H | 2,4,6-trifluorophenyl | SCH$_3$ | CO—NH-i-propyl | |
| 1166 | CH(CH$_3$)(CF$_3$) | H | 2,4,6-trifluorophenyl | SCH$_3$ | CO-morpholin-1-yl | |
| 1167 | CH(CH$_3$)(CF$_3$) | H | 2,4,6-trifluorophenyl | SCH$_3$ | COCH | |
| 1168 | CH(CH$_3$)(CF$_3$) | H | 2,4,6-trifluorophenyl | SCH$_3$ | COO-propen-3-yl | |
| 1169 | CH(CH$_3$)(CF$_3$) | H | 2,4,6-trifluorophenyl | SCH$_3$ | COO-benzyl | |
| 1170 | CH(CH$_3$)(CF$_3$) | H | 2,46-trifluorophenyl | SCH$_3$ | COO—CH$_2$—CH$_2$—OCH$_3$ | |
| 1171 | CH(CH$_3$)(CF$_3$) | H | 2,4,6-trifluorophenyl | SCH$_3$ | SO$_3$H | |
| 1172 | CH(CH$_3$)(CF$_3$) | H | 2,4,6-trifluorophenyl | SCH$_3$ | SO$_2$CH$_3$ | |
| 1173 | CH(CH$_3$)(CF$_3$) | H | 2-Cl-4-F-phenyl | SCH$_3$ | CO—NH—CH$_3$ | |

TABLE 1-continued

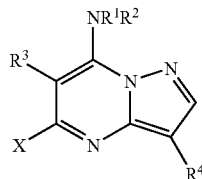

| Ex. No. | R¹ or —R¹⁺R²— | R² | R³ | X | R⁴ | log p |
|---|---|---|---|---|---|---|
| 1174 | CH(CH₃)(CF₃) | H | 2-Cl-4-F-phenyl | SCH₃ | CON(CH₃)₂ | |
| 1175 | CH(CH₃)(CF₃) | H | 2-Cl-4-F-phenyl | SCH₃ | CO—NH-i-propyl | |
| 1176 | CH(CH₃)(CF₃) | H | 2-Cl-4-F-phenyl | SCH₃ | CO-morpholin-1-yl | |
| 1177 | CH(CH₃)(CF₃) | H | 2-Cl-4-F-phenyl | SCH₃ | COOH | |
| 1178 | CH(CH₃)(CF₃) | H | 2-Cl-4-F-phenyl | SCH₃ | COO-propen-3-yl | |
| 1179 | CH(CH₃)(CF₃) | H | 2-Cl-4-F-phenyl | SCH₃ | COO-benzyl | |
| 1180 | CH(CH₃)(CF₃) | H | 2-Cl-4-F-phenyl | SCH₃ | COO—CH₂—CH₂—OCH₃ | |
| 1181 | CH(CH₃)(CF₃) | H | 2-Cl-4-F-phenyl | SCH₃ | SO₃H | |
| 1182 | CH(CH₃)(CF₃) | H | 2-Cl-4-F-phenyl | SCH₃ | SO₂CH₃ | |
| 1183 | CH(CH₃)(CF₃) | H | 2-Cl-phenyl | SCH₃ | CO—NH—CH₃ | |
| 1184 | CH(CH₃)(CF₃) | H | 2-Cl-phenyl | SCH₃ | CON(CH₃)₂ | |
| 1185 | CH(CH₃)(CF₃) | H | 2-Cl-phenyl | SCH₃ | CO—NH-i-propyl | |
| 1186 | CH(CH₃)(CF₃) | H | 2-Cl-phenyl | SCH₃ | CO-morpholin-1-yl | |
| 1187 | CH(CH₃)(CF₃) | H | 2-Cl-phenyl | SCH₃ | COOH | |
| 1188 | CH(CH₃)(CF₃) | H | 2-Cl-phenyl | SCH₃ | COO-propen-3-yl | |
| 1189 | CH(CH₃)(CF₃) | H | 2-Cl-phenyl | SCH₃ | COO-benzyl | |
| 1190 | CH(CH₃)(CF₃) | H | 2-Cl-phenyl | SCH₃ | COO—CH₂—CH₂—OCH₃ | |
| 1191 | CH(CH₃)(CF₃) | H | 2-Cl-phenyl | SCH₃ | SO₃H | |
| 1192 | CH(CH₃)(CF₃) | H | 2-Cl-phenyl | SCH₃ | SO₂CH₃ | |
| 1193 | CH(CH₃)(CF₃) | H | 5-Cl-pyrimidin-4-yl | SCH₃ | CO—NH—CH₃ | |
| 1194 | CH(CH₃)(CF₃) | H | 5-Cl-pyrimidin-4-yl | SCH₃ | CON(CH₃)₂ | |
| 1195 | CH(CH₃)(CF₃) | H | 5-Cl-pyrimidin-4-yl | SCH₃ | CO—NH-i-propyl | |
| 1196 | CH(CH₃)(CF₃) | H | 5-Cl-pyrimidin-4-yl | SCH₃ | CO-morpholin-1-yl | |
| 1197 | CH(CH₃)(CF₃) | H | 5-Cl-pyrimidin-4-yl | SCH₃ | COOH | |
| 1198 | CH(CH₃)(CF₃) | H | 5-Cl-pyrimidin-4-yl | SCH₃ | COO-propen-3-yl | |
| 1199 | CH(CH₃)(CF₃) | H | 5-Cl-pyrimidin-4-yl | SCH₃ | COO-benzyl | |
| 1200 | CH(CH₃)(CF₃) | H | 5-Cl-pyrimidin-4-yl | SCH₃ | COO—CH₂—CH₂—OCH₃ | |
| 1201 | CH(CH₃)(CF₃) | H | 5-Cl-pyrimidin-4-yl | SCH₃ | SO₃H | |
| 1202 | CH(CH₃)(CF₃) | H | 5-Cl-pyrimidin-4-yl | SCH₃ | SO₂CH₃ | |
| 1203 | CH(CH₃)—CH(CH₃)₂ | H | 2-Cl-6-F-phenyl | SCH₃ | CO—NH—CH₃ | |
| 1204 | CH(CH₃)—CH(CH₃)₂ | H | 2-Cl-6-F-phenyl | SCH₃ | CON(CH₃)₂ | |
| 1205 | CH(CH₃)—CH(CH₃)₂ | H | 2-Cl-6-F-phenyl | SCH₃ | CO—NH-i-propyl | |
| 1206 | CH(CH₃)—CH(CH₃)₂ | H | 2-Cl-6-F-phenyl | SCH₃ | CO-morpholin-1-yl | |
| 1207 | CH(CH₃)—CH(CH₃)₂ | H | 2-Cl-6-F-phenyl | SCH₃ | COOH | |
| 1208 | CH(CH₃)—CH(CH₃)₂ | H | 2-Cl-6-F-phenyl | SCH₃ | COO-propen-3-yl | |
| 1209 | CH(CH₃)—CH(CH₃)₂ | H | 2-Cl-6-F-phenyl | SCH₃ | COO-benzyl | |
| 1210 | CH(CH₃)—CH(CH₃)₂ | H | 2-Cl-6-F-phenyl | SCH₃ | COO—CH₂—CH₂—OCH₃ | |
| 1211 | CH(CH₃)—CH(CH₃)₂ | H | 2-Cl-6-F-phenyl | SCH₃ | SO₃H | |
| 1212 | CH(CH₃)—CH(CH₃)₂ | H | 2-Cl-6-F-phenyl | SCH₃ | SO₂CH₃ | |
| 1213 | CH(CH₃)—CH(CH₃)₂ | H | 2,4,6-trifluorophenyl | SCH₃ | CO—NH—CH₃ | |
| 1214 | CH(CH₃)—CH(CH₃)₂ | H | 2,4,6-trifluorophenyl | SCH₃ | CON(CH₃)₂ | |
| 1215 | CH(CH₃)—CH(CH₃)₂ | H | 2,4,6-trifluorophenyl | SCH₃ | CO—NH-i-propyl | |
| 1216 | CH(CH₃)—CH(CH₃)₂ | H | 2,4,6-trifluorophenyl | SCH₃ | CO-morpholin-1-yl | |
| 1217 | CH(CH₃)—CH(CH₃)₂ | H | 2,4,6-trifluorophenyl | SCH₃ | COOH | |
| 1218 | CH(CH₃)—CH(CH₃)₂ | H | 2,4,6-trifluorophenyl | SCH₃ | COO-propen-3-yl | |
| 1219 | CH(CH₃)—CH(CH₃)₂ | H | 2,4,6-trifluorophenyl | SCH₃ | COO-benzyl | |
| 1220 | CH(CH₃)—CH(CH₃)₂ | H | 2,4,6-trifluorophenyl | SCH₃ | COO—CH₂—CH₂—OCH₃ | |
| 1221 | CH(CH₃)—CH(CH₃)₂ | H | 2,4,6-trifluorophenyl | SCH₃ | SO₃H | |
| 1222 | CH(CH₃)—CH(CH₃)₂ | H | 2,4,6-trifluorophenyl | SCH₃ | SO₂CH₃ | |
| 1223 | CH(CH₃)—CH(CH₃)₂ | H | 2-Cl-4-F-phenyl | SCH₃ | CO—NH—CH₃ | |
| 1224 | CH(CH₃)—CH(CH₃)₂ | H | 2-Cl-4-F-phenyl | SCH₃ | CON(CH₃)₂ | |
| 1225 | CH(CH₃)—CH(CH₃)₂ | H | 2-Cl-4-F-phenyl | SCH₃ | CO—NH-i-propyl | |
| 1226 | CH(CH₃)—CH(CH₃)₂ | H | 2-Cl-4-F-phenyl | SCH₃ | CO-morpholin-1-yl | |
| 1227 | CH(CH₃)—CH(CH₃)₂ | H | 2-Cl-4-F-phenyl | SCH₃ | COOH | |
| 1228 | CH(CH₃)—CH(CH₃)₂ | H | 2-Cl-4-F-phenyl | SCH₃ | COO-propen-3-yl | |
| 1229 | CH(CH₃)—CH(CH₃)₂ | H | 2-Cl-4-F-phenyl | SCH₃ | COO-benzyl | |
| 1230 | CH(CH₃)—CH(CH₃)₂ | H | 2-Cl-4-F-phenyl | SCH₃ | COO—CH₂—CH₂—OCH₃ | |
| 1231 | CH(CH₃)—CH(CH₃)₂ | H | 2-Cl-4-F-phenyl | SCH₃ | SO₃H | |
| 1232 | CH(CH₃)—CH(CH₃)₂ | H | 2-Cl-4-F-phenyl | SCH₃ | SO₂CH₃ | |
| 1233 | CH(CH₃)—CH(CH₃)₂ | H | 2-Cl-phenyl | SCH₃ | CO—NH—CH₃ | |
| 1234 | CH(CH₃)—CH(CH₃)₂ | H | 2-Cl-phenyl | SCH₃ | CON(CH₃)₂ | |
| 1235 | CH(CH₃)—CH(CH₃)₂ | H | 2-Cl-phenyl | SCH₃ | CO—NH-i-propyl | |
| 1236 | CH(CH₃)—CH(CH₃)₂ | H | 2-Cl-phenyl | SCH₃ | CO-morpholin-1-yl | |
| 1237 | CH(CH₃)—CH(CH₃)₂ | H | 2-Cl-phenyl | SCH₃ | COOH | |
| 1238 | CH(CH₃)—CH(CH₃)₂ | H | 2-Cl-phenyl | SCH₃ | COO-propen-3-yl | |
| 1239 | CH(CH₃)—CH(CH₃)₂ | H | 2-Cl-phenyl | SCH₃ | COO-benzyl | |

TABLE 1-continued

| Ex. No. | R¹ or —R¹+R²— | R² | R³ | X | R⁴ | log p |
|---|---|---|---|---|---|---|
| 1240 | CH(CH₃)—CH(CH₃)₂ | H | 2-Cl-phenyl | SCH₃ | COO—CH₂—CH₂—OCH₃ | |
| 1241 | CH(CH₃)—CH(CH₃)₂ | H | 2-Cl-phenyl | SCH₃ | SO₃H | |
| 1242 | CH(CH₃)—CH(CH₃)₂ | H | 2-Cl-phenyl | SCH₃ | SO₂CH₃ | |
| 1243 | CH(CH₃)—CH(CH₃)₂ | H | 5-Cl-pyrimidin-4-yl | SCH₃ | CO—NH—CH₃ | |
| 1244 | CH(CH₃)—CH(CH₃)₂ | H | 5-Cl-pyrimidin-4-yl | SCH₃ | CON(CH₃)₂ | |
| 1245 | CH(CH₃)—CH(CH₃)₂ | H | 5-Cl-pyrimidin-4-yl | SCH₃ | CO—NH-i-propyl | |
| 1246 | CH(CH₃)—CH(CH₃)₂ | H | 5-Cl-pyrimidin-4-yl | SCH₃ | CO-morpholin-1-yl | |
| 1247 | CH(CH₃)—CH(CH₃)₂ | H | 5-Cl-pyrimidin-4-yl | SCH₃ | COOH | |
| 1248 | CH(CH₃)—CH(CH₃)₂ | H | 5-Cl-pyrimidin-4-yl | SCH₃ | COO-propen-3-yl | |
| 1249 | CH(CH₃)—CH(CH₃)₂ | H | 5-Cl-pyrimidin-4-yl | SCH₃ | COO-benzyl | |
| 1250 | CH(CH₃)—CH(CH₃)₂ | H | 5-Cl-pyrimidin-4-yl | SCH₃ | COO—CH₂—CH₂—OCH₃ | |
| 1251 | CH(CH₃)—CH(CH₃)₂ | H | 5-Cl-pyrimidin-4-yl | SCH₃ | SO₃H | |
| 1252 | CH(CH₃)—CH(CH₃)₂ | H | 5-Cl-pyrimidin-4-yl | SCH₃ | SO₂CH₃ | |
| 1253 | —CH₂—CH₂—CH(CH₃)—CH₂—CH₂— | | 2-Cl-6-F-phenyl | SCH₃ | CO—NH—CH₃ | |
| 1254 | —CH₂—CH₂—CH(CH₃)—CH₂—CH₂— | | 2-Cl-6-F-phenyl | SCH₃ | CON(CH₃)₂ | |
| 1255 | —CH₂—CH₂—CH(CH₃)—CH₂—CH₂— | | 2-Cl-6-F-phenyl | SCH₃ | CO—NH-i-propyl | |
| 1256 | —CH₂—CH₂—CH(CH₃)—CH₂—CH₂— | | 2-Cl-6-F-phenyl | SCH₃ | CO-morpholin-1-yl | |
| 1257 | —CH₂—CH₂—CH(CH₃)—CH₂—CH₂— | | 2-Cl-6-F-phenyl | SCH₃ | COOH | |
| 1258 | —CH₂—CH₂—CH(CH₃)—CH₂—CH₂— | | 2-Cl-6-F-phenyl | SCH₃ | COO-propen-3-yl | |
| 1259 | —CH₂—CH₂—CH(CH₃)—CH₂—CH₂— | | 2-Cl-6-F-phenyl | SCH₃ | COO-benzyl | |
| 1260 | —CH₂—CH₂—CH(CH₃)—CH₂—CH₂— | | 2-Cl-6-F-phenyl | SCH₃ | COO—CH₂—CH₂—OCH₃ | |
| 1261 | —CH₂—CH₂—CH(CH₃)—CH₂—CH₂— | | 2-Cl-6-F-phenyl | SCH₃ | SO₃H | |
| 1262 | —CH₂—CH₂—CH(CH₃)—CH₂—CH₂— | | 2-Cl-6-F-phenyl | SCH₃ | SO₂CH₃ | |
| 1263 | —CH₂—CH₂—CH(CH₃)—CH₂—CH₂— | | 2,4,6-trifluorophenyl | SCH₃ | CO—NH—CH₃ | |
| 1264 | —CH₂—CH₂—CH(CH₃)—CH₂—CH₂— | | 2,4,6-trifluorophenyl | SCH₃ | CON(CH₃)₂ | |
| 1265 | —CH₂—CH₂—CH(CH₃)—CH₂—CH₂— | | 2,4,6-trifluorophenyl | SCH₃ | CO—NH-i-propyl | |
| 1266 | —CH₂—CH₂—CH(CH₃)—CH₂—CH₂— | | 2,4,6-trifluorophenyl | SCH₃ | CO-morpholin-1-yl | |
| 1267 | —CH₂—CH₂—CH(CH₃)—CH₂—CH₂— | | 2,4,6-trifluorophenyl | SCH₃ | COOH | |
| 1268 | —CH₂—CH₂—CH(CH₃)—CH₂—CH₂— | | 2,4,6-trifluorophenyl | SCH₃ | COO-propen-3-yl | |
| 1269 | —CH₂—CH₂—CH(CH₃)—CH₂—CH₂— | | 2,4,6-trifluorophenyl | SCH₃ | COO-benzyl | |
| 1270 | —CH₂—CH₂—CH(CH₃)—CH₂—CH₂— | | 2,4,6-trifluorophenyl | SCH₃ | COO—CH₂—CH₂—OCH₃ | |
| 1271 | —CH₂—CH₂—CH(CH₃)—CH₂—CH₂— | | 2,4,6-trifluorophenyl | SCH₃ | SO₃H | |
| 1272 | —CH₂—CH₂—CH(CH₃)—CH₂—CH₂— | | 2,4,6-trifluorophenyl | SCH₃ | SO₂CH₃ | |
| 1273 | —CH₂—CH₂—CH(CH₃)—CH₂—CH₂— | | 2-Cl-4-F-phenyl | SCH₃ | CO—NH—CH₃ | |
| 1274 | —CH₂—CH₂—CH(CH₃)—CH₂—CH₂— | | 2-Cl-4-F-phenyl | SCH₃ | CON(CH₃)₂ | |
| 1275 | —CH₂—CH₂—CH(CH₃)—CH₂—CH₂— | | 2-Cl-4-F-phenyl | SCH₃ | CO—NH-i-propyl | |
| 1276 | —CH₂—CH₂—CH(CH₃)—CH₂—CH₂— | | 2-Cl-4-F-phenyl | SCH₃ | CO-morpholin-1-yl | |
| 1277 | —CH₂—CH₂—CH(CH₃)—CH₂—CH₂— | | 2-Cl-4-F-phenyl | SCH₃ | COOH | |
| 1278 | —CH₂—CH₂—CH(CH₃)—CH₂—CH₂— | | 2-Cl-4-F-phenyl | SCH₃ | COO-propen-3-yl | |
| 1279 | —CH₂—CH₂—CH(CH₃)—CH₂—CH₂— | | 2-Cl-4-F-phenyl | SCH₃ | COO-benzyl | |
| 1280 | —CH₂—CH₂—CH(CH₃)—CH₂—CH₂— | | 2-Cl-4-F-phenyl | SCH₃ | COO—CH₂—CH₂—OCH₃ | |
| 1281 | —CH₂—CH₂—CH(CH₃)—CH₂—CH₂— | | 2-Cl-4-F-phenyl | SCH₃ | SO₃H | |
| 1282 | —CH₂—CH₂—CH(CH₃)—CH₂—CH₂— | | 2-Cl-4-F-phenyl | SCH₃ | SO₂CH₃ | |
| 1283 | —CH₂—CH₂—CH(CH₃)—CH₂—CH₂— | | 2-Cl-phenyl | SCH₃ | CO—NH—CH₃ | |
| 1284 | —CH₂—CH₂—CH(CH₃)—CH₂—CH₂— | | 2-Cl-phenyl | SCH₃ | CON(CH₃)₂ | |
| 1285 | —CH₂—CH₂—CH(CH₃)—CH₂—CH₂— | | 2-Cl-phenyl | SCH₃ | CO—NH-i-propyl | |
| 1286 | —CH₂—CH₂—CH(CH₃)—CH₂—CH₂— | | 2-Cl-phenyl | SCH₃ | CO-morpholin-1-yl | |
| 1287 | —CH₂—CH₂—CH(CH₃)—CH₂—CH₂— | | 2-Cl-phenyl | SCH₃ | COOH | |
| 1288 | —CH₂—CH₂—CH(CH₃)—CH₂—CH₂— | | 2-Cl-phenyl | SCH₃ | COO-propen-3-yl | |
| 1289 | —CH₂—CH₂—CH(CH₃)—CH₂—CH₂— | | 2-Cl-phenyl | SCH₃ | COO-benzyl | |
| 1290 | —CH₂—CH₂—CH(CH₃)—CH₂—CH₂— | | 2-Cl-phenyl | SCH₃ | COO—CH₂—CH₂—OCH₃ | |
| 1291 | —CH₂—CH₂—CH(CH₃)—CH₂—CH₂— | | 2-Cl-phenyl | SCH₃ | SO₃H | |
| 1292 | —CH₂—CH₂—CH(CH₃)—CH₂—CH₂— | | 2-Cl-phenyl | SCH₃ | SO₂CH₃ | |
| 1293 | —CH₂—CH₂—CH(CH₃)—CH₂—CH₂— | | 5-Cl-pyrimidin-4-yl | SCH₃ | CO—NH—CH₃ | |
| 1294 | —CH₂—CH₂—CH(CH₃)—CH₂—CH₂— | | 5-Cl-pyrimidin-4-yl | SCH₃ | CON(CH₃)₂ | |
| 1295 | —CH₂—CH₂—CH(CH₃)—CH₂—CH₂— | | 5-Cl-pyrimidin-4-yl | SCH₃ | CO—NH-i-propyl | |
| 1296 | —CH₂—CH₂—CH(CH₃)—CH₂—CH₂— | | 5-Cl-pyrimidin-4-yl | SCH₃ | CO-morpholin-1-yl | |
| 1297 | —CH₂—CH₂—CH(CH₃)—CH₂—CH₂— | | 5-Cl-pyrimidin-4-yl | SCH₃ | COOH | |
| 1298 | —CH₂—CH₂—CH(CH₃)—CH₂—CH₂— | | 5-Cl-pyrimidin-4-yl | SCH₃ | COO-propen-3-yl | |
| 1299 | —CH₂—CH₂—CH(CH₃)—CH₂—CH₂— | | 5-Cl-pyrimidin-4-yl | SCH₃ | COO-benzyl | |
| 1300 | —CH₂—CH₂—CH(CH₃)—CH₂—CH₂— | | 5-Cl-pyrimidin-4-yl | SCH₃ | COO—CH₂—CH₂—OCH₃ | |
| 1301 | —CH₂—CH₂—CH(CH₃)—CH₂—CH₂— | | 5-Cl-pyrimidin-4-yl | SCH₃ | SO₃H | |
| 1302 | —CH₂—CH₂—CH(CH₃)—CH₂—CH₂— | | 5-Cl-pyrimidin-4-yl | SCH₃ | SO₂CH₃ | |
| 1303 | —CH₂—CH₂—CH(CH₃)—CH₂—CH₂— | | 2-Cl-4-F-phenyl | Cl | SO₂NH2 | 3.66 |
| 1304 | —CH₂—CH₂—CH(CH₃)—CH₂—CH₂— | | 2-Cl-4-F-phenyl | Cl | SCH₃ | 5.73 |
| 1305 | —CH₂—CH₂—CH(CH₃)—CH₂—CH₂— | | 2-Cl-4-F-phenyl | CH₃ | SO₂NHCH₃ | |

TABLE 1-continued

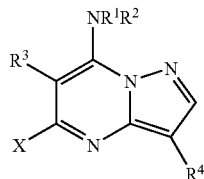

| Ex. No. | R¹ or —R¹+R²— | R² | R³ | X | R⁴ | log p |
|---|---|---|---|---|---|---|
| 1306 | —CH₂—CH₂—CH(CH₃)—CH₂—CH₂— | | 2-Cl-4-F-phenyl | CH₃ | SO₂NH2 | |
| 1307 | —CH₂—CH₂—CH(CH₃)—CH₂—CH₂— | | 2-Cl-4-F-phenyl | CH₃ | SCH₃ | |
| 1308 | —CH₂—CH₂—CH(CH₃)—CH₂—CH₂— | | 2-Cl-4-F-phenyl | Cl | SO₂NHCH₃ | |
| 1309 | CH(CH₃)—CH(CH₃)₂ | H | 2-Cl-6-F-phenyl | Cl | SO₂NH2 | |
| 1310 | CH(CH₃)—CH(CH₃)₂ | H | 2-Cl-6-F-phenyl | Cl | SCH₃ | |
| 1311 | CH(CH₃)—CH(CH₃)₂ | H | 2-Cl-6-F-phenyl | Cl | SO₂NHCH₃ | |
| 1312 | CH(CH₃)—C(CH₃)₃ | H | 2-Cl-6-F-phenyl | Cl | SO₂NH2 | |
| 1313 | CH(CH₃)—C(CH₃)₃ | H | 2-Cl-6-F-phenyl | Cl | SCH₃ | |
| 1314 | CH(CH₃)—C(CH₃)₃ | H | 2-Cl-6-F-phenyl | Cl | SO₂NHCH₃ | |
| 1315 | CH(CH₃)(CF₃) | H | 2-Cl-6-F-phenyl | Cl | SO₂NH2 | |
| 1316 | CH(CH₃)(CF₃) | H | 2-Cl-6-F-phenyl | Cl | SCH₃ | |
| 1317 | CH(CH₃)(CF₃) | H | 2-Cl-6-F-phenyl | Cl | SO₂NHCH₃ | |
| 1318 | CH(CH₃)—CH(CH₃)₂ | H | 2-Cl-6-F-phenyl | SCH₃ | SO₂NH2 | |
| 1319 | CH(CH₃)—CH(CH₃)₂ | H | 2-Cl-6-F-phenyl | SCH₃ | SCH₃ | |
| 1320 | CH(CH₃)—CH(CH₃)₂ | H | 2-Cl-6-F-phenyl | SCH₃ | SO₂NHCH₃ | |
| 1321 | CH(CH₃)—C(CH₃)₃ | H | 2-Cl-6-F-phenyl | SCH₃ | SO₂NH2 | |
| 1322 | CH(CH₃)—C(CH₃)₃ | H | 2-Cl-6-F-phenyl | SCH₃ | SCH₃ | |
| 1323 | CH(CH₃)—C(CH₃)₃ | H | 2-Cl-6-F-phenyl | SCH₃ | SO₂NHCH₃ | |
| 1324 | CH(CH₃)(CF₃) | H | 2-Cl-6-F-phenyl | SCH₃ | SO₂NH2 | |
| 1325 | CH(CH₃)(CF₃) | H | 2-Cl-6-F-phenyl | SCH₃ | SCH₃ | |
| 1326 | CH(CH₃)(CF₃) | H | 2-Cl-6-F-phenyl | SCH₃ | SO₂NHCH₃ | |
| 1327 | CH(CH₃)—CH(CH₃)₂ | H | 2,4,6-trifluorophenyl | Cl | SO₂NH2 | |
| 1328 | CH(CH₃)—CH(CH₃)₂ | H | 2,4,6-trifluorophenyl | Cl | SCH₃ | |
| 1329 | CH(CH₃)—CH(CH₃)₂ | H | 2,4,6-trifluorophenyl | Cl | SO₂NHCH₃ | |
| 1330 | CH(CH₃)—C(CH₃)₃ | H | 2,4,6-trifluorophenyl | Cl | SO₂NH2 | |
| 1331 | CH(CH₃)—C(CH₃)₃ | H | 2,4,6-trifluorophenyl | Cl | SCH₃ | |
| 1332 | CH(CH₃)—C(CH₃)₃ | H | 2,4,6-trifluorophenyl | Cl | SO₂NHCH₃ | |
| 1333 | CH(CH₃)(CF₃) | H | 2,4,6-trifluorophenyl | Cl | SO₂NH2 | |
| 1334 | CH(CH₃)(CF₃) | H | 2,4,6-trifluorophenyl | Cl | SCH₃ | |
| 1335 | CH(CH₃)(CF₃) | H | 2,4,6-trifluorophenyl | Cl | SO₂NHCH₃ | |
| 1336 | CH(CH₃)—CH(CH₃)₂ | H | 2,4,6-trifluorophenyl | CH₃ | SO₂NH2 | |
| 1337 | CH(CH₃)—CH(CH₃)₂ | H | 2,4,6-trifluorophenyl | CH₃ | SCH₃ | |
| 1338 | CH(CH₃)—CH(CH₃)₂ | H | 2,4,6-trifluorophenyl | CH₃ | SO₂NHCH₃ | |
| 1339 | CH(CH₃)—C(CH₃)₃ | H | 2,4,6-trifluorophenyl | CH₃ | SO₂NH2 | |
| 1340 | CH(CH₃)—C(CH₃)₃ | H | 2,4,6-trifluorophenyl | CH₃ | SCH₃ | |
| 1341 | CH(CH₃)—C(CH₃)₃ | H | 2,4,6-trifluorophenyl | CH₃ | SO₂NHCH₃ | |
| 1342 | CH(CH₃)(CF₃) | H | 2,4,6-trifluorophenyl | CH₃ | SO₂NH2 | |
| 1343 | CH(CH₃)(CF₃) | H | 2,4,6-trifluorophenyl | CH₃ | SCH₃ | |
| 1344 | CH(CH₃)(CF₃) | H | 2,4,6-trifluorophenyl | CH₃ | SO₂NHCH₃ | |
| 1345 | CH(CH₃)—CH(CH₃)₂ | H | 2-Cl-phenyl | Cl | SO₂NH2 | |
| 1346 | CH(CH₃)—CH(CH₃)₂ | H | 2-Cl-phenyl | Cl | SCH₃ | |
| 1347 | CH(CH₃)—CH(CH₃)₂ | H | 2-Cl-phenyl | Cl | SO₂NHCH₃ | |
| 1348 | CH(CH₃)—C(CH₃)₃ | H | 2-Cl-phenyl | Cl | SO₂NH2 | |
| 1349 | CH(CH₃)—C(CH₃)₃ | H | 2-Cl-phenyl | Cl | SCH₃ | |
| 1350 | CH(CH₃)—C(CH₃)₃ | H | 2-Cl-phenyl | Cl | SO₂NHCH₃ | |
| 1351 | CH(CH₃)(CF₃) | H | 2-Cl-phenyl | Cl | SO₂NH2 | |
| 1352 | CH(CH₃)(CF₃) | H | 2-Cl-phenyl | Cl | SCH₃ | |
| 1353 | CH(CH₃)(CF₃) | H | 2-Cl-phenyl | Cl | SO₂NHCH₃ | |
| 1354 | CH(CH₃)—CH(CH₃)₂ | H | 2-Cl-phenyl | CH₃ | SO₂NH2 | |
| 1355 | CH(CH₃)—CH(CH₃)₂ | H | 2-Cl-phenyl | CH₃ | SCH₃ | |
| 1356 | CH(CH₃)—CH(CH₃)₂ | H | 2-Cl-phenyl | CH₃ | SO₂NHCH₃ | |
| 1357 | CH(CH₃)—C(CH₃)₃ | H | 2-Cl-phenyl | CH₃ | SO₂NH2 | |
| 1358 | CH(CH₃)—C(CH₃)₃ | H | 2-Cl-phenyl | CH₃ | SCH₃ | |
| 1359 | CH(CH₃)—C(CH₃)₃ | H | 2-Cl-phenyl | CH₃ | SO₂NHCH₃ | |
| 1360 | CH(CH₃)(CF₃) | H | 2-Cl-phenyl | CH₃ | SO₂NH2 | |
| 1361 | CH(CH₃)(CF₃) | H | 2-Cl-phenyl | CH₃ | SCH₃ | |
| 1362 | CH(CH₃)(CF₃) | H | 2-Cl-phenyl | CH₃ | SO₂NHCH₃ | |
| 1363 | CH(CH₃)—CH(CH₃)₂ | H | 2-Cl-4-F-phenyl | Cl | SO₂NH2 | 3.39 |
| 1364 | CH(CH₃)—CH(CH₃)₂ | H | 2-Cl-4-F-phenyl | Cl | SCH₃ | |
| 1365 | CH(CH₃)—CH(CH₃)₂ | H | 2-Cl-4-F-phenyl | Cl | SO₂NHCH₃ | |
| 1366 | CH(CH₃)—C(CH₃)₃ | H | 2-Cl-4-F-phenyl | Cl | SO₂NH2 | 3.63 |
| 1367 | CH(CH₃)—C(CH₃)₃ | H | 2-Cl-4-F-phenyl | Cl | SCH₃ | |
| 1368 | CH(CH₃)—C(CH₃)₃ | H | 2-Cl-4-F-phenyl | Cl | SO₂NHCH₃ | 4.09 |
| 1369 | CH(CH₃)(CF₃) | H | 2-Cl-4-F-phenyl | Cl | SO₂NH2 | |
| 1370 | CH(CH₃)(CF₃) | H | 2-Cl-4-F-phenyl | Cl | SCH₃ | |
| 1371 | CH(CH₃)(CF₃) | H | 2-Cl-4-F-phenyl | Cl | SO₂NHCH₃ | |

TABLE 1-continued

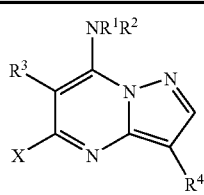

| Ex. No. | R¹ or —R¹⁺R²— | R² | R³ | X | R⁴ | log p |
|---|---|---|---|---|---|---|
| 1372 | CH(CH₃)—CH(CH₃)₂ | H | 2-Cl-4-F-phenyl | CH₃ | SO₂NH2 | |
| 1373 | CH(CH₃)—CH(CH₃)₂ | H | 2-Cl-4-F-phenyl | CH₃ | SCH₃ | |
| 1374 | CH(CH₃)—CH(CH₃)₂ | H | 2-Cl-4-F-phenyl | CH₃ | SO₂NHCH₃ | |
| 1375 | CH(CH₃)—C(CH₃)₃ | H | 2-Cl-4-F-phenyl | CH₃ | SO₂NH2 | |
| 1376 | CH(CH₃)—C(CH₃)₃ | H | 2-Cl-4-F-phenyl | CH₃ | SCH₃ | |
| 1377 | CH(CH₃)—C(CH₃)₃ | H | 2-Cl-4-F-phenyl | CH₃ | SO₂NHCH₃ | |
| 1378 | CH(CH₃)(CF₃) | H | 2-Cl-4-F-phenyl | CH₃ | SO₂NH2 | |
| 1379 | CH(CH₃)(CF₃) | H | 2-Cl-4-F-phenyl | CH₃ | SCH₃ | |
| 1380 | CH(CH₃)(CF₃) | H | 2-Cl-4-F-phenyl | CH₃ | SO₂NHCH₃ | |
| 1381 | CH(CH₃)—CH(CH₃)₂ | H | 5-Cl-pyrimidin-4-yl | Cl | SO₂NH2 | |
| 1382 | CH(CH₃)—CH(CH₃)₂ | H | 5-Cl-pyrimidin-4-yl | Cl | SCH₃ | |
| 1383 | CH(CH₃)—CH(CH₃)₂ | H | 5-Cl-pyrimidin-4-yl | Cl | SO₂NHCH₃ | |
| 1384 | CH(CH₃)—C(CH₃)₃ | H | 5-Cl-pyrimidin-4-yl | Cl | SO₂NH2 | |
| 1385 | CH(CH₃)—C(CH₃)₃ | H | 5-Cl-pyrimidin-4-yl | Cl | SCH₃ | |
| 1386 | CH(CH₃)—C(CH₃)₃ | H | 5-Cl-pyrimidin-4-yl | Cl | SO₂NHCH₃ | |
| 1387 | CH(CH₃)(CF₃) | H | 5-Cl-pyrimidin-4-yl | Cl | SO₂NH2 | |
| 1388 | CH(CH₃)(CF₃) | H | 5-Cl-pyrimidin-4-yl | Cl | SCH₃ | |
| 1389 | CH(CH₃)(CF₃) | H | 5-Cl-pyrimidin-4-yl | Cl | SO₂NHCH₃ | |
| 1390 | CH(CH₃)—CH(CH₃)₂ | H | 5-Cl-pyrimidin-4-yl | CH₃ | SO₂NH2 | |
| 1391 | CH(CH₃)—CH(CH₃)₂ | H | 5-Cl-pyrimidin-4-yl | CH₃ | SCH₃ | |
| 1392 | CH(CH₃)—CH(CH₃)₂ | H | 5-Cl-pyrimidin-4-yl | CH₃ | SO₂NHCH₃ | |
| 1393 | CH(CH₃)—C(CH₃)₃ | H | 5-Cl-pyrimidin-4-yl | CH₃ | SO₂NH2 | |
| 1394 | CH(CH₃)—C(CH₃)₃ | H | 5-Cl-pyrimidin-4-yl | CH₃ | SCH₃ | |
| 1395 | CH(CH₃)—C(CH₃)₃ | H | 5-Cl-pyrimidin-4-yl | CH₃ | SO₂NHCH₃ | |
| 1396 | CH(CH₃)(CF₃) | H | 5-Cl-pyrimidin-4-yl | CH₃ | SO₂NH2 | |
| 1397 | CH(CH₃)(CF₃) | H | 5-Cl-pyrimidin-4-yl | CH₃ | SCH₃ | |
| 1398 | CH(CH₃)(CF₃) | H | 5-Cl-pyrimidin-4-yl | CH₃ | SO₂NHCH₃ | |
| 1399 | CH(CH₃)—C(CH₃)₃ | H | 2-Cl-4-F-phenyl | Cl | SO₂NH₂ | 3.66 |
| 1400 | CH(CH₃)—CH(CH₃)₂ | H | 2-Cl-4-F-phenyl | Cl | SO₂NH₂ | 3.39 |
| 1401 | CH(CH₃)—C(CH₃)₃ | H | 2-Cl-4-F-phenyl | Cl | SO₂NHCH₃ | 4.09 |
| 1402 | CH(CH₃)—C(CH₃)₃ | H | 2-Cl-4-F-phenyl | NHCH₃ | SO₂NHCH₃ | 3.86 |

The logP values were determined in accordance with EEC Directive 79/831 Annex V.A8 by HPLC (gradient method, acetonitrile/0.1% aqueous phosphoric acid).
**These logP values were determined in accordance with EEC Directive 79/831 Annex V.A8 by HPLC (gradient method, acetonitrile/0.1% aqueous formic acid).

Table 2 shows the melting points of selected compounds of the formula (I):

| Ex. No. | R1 or -R1 + R2- | R2 | R3 | X | R4 | m.p. |
|---|---|---|---|---|---|---|
| 204 | 2-butyl | H | 2-Cl,4-methylphenyl | Cl | COO⁻K⁺ | 189-193 dec |
| 205 | 2-butyl | H | 2-Cl,4-methylphenyl | Cl | COO⁻Na⁺ | >280 |
| 279 | (R) CH(CH₃)—C(CH₃)₃ | H | 2,4-F-phenyl | Cl | COO⁻Na⁺ | 266-271° C. |
| 280 | (R) CH(CH₃)—C(CH₃)₃ | H | 2,4-F-phenyl | Cl | COO⁻K⁺ | 245-247° C. |
| 283 | (R) CH(CH₃)—C(CH₃)₃ | H | 2,5-dimethylthien-3-yl | Cl | COO⁻Na⁺ | 269-270 dec |
| 324 | (R) CH(CH₃)—C(CH₃)₃ | H | 2-Cl,4-MeO-phenyl | Cl | COO⁻Na⁺ | 250-255° C. |
| 328 | (R) CH(CH₃)—C(CH₃)₃ | H | 2-Cl,4-methylphenyl | Cl | COO⁻K⁺ | 220-222 |

-continued

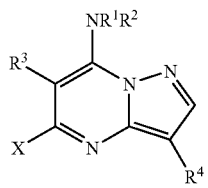

| Ex. No. | R1 or -R1 + R2- | R2 | R3 | X | R4 | m.p. |
|---|---|---|---|---|---|---|
| 329 | (R) CH(CH₃)—C(CH₃)₃ | H | 2-Cl,4-methylphenyl | Cl | COO⁻Na⁺ | 238-241 dec |
| 414 | CH(CH₃)—C(CH₃)₃ | H | 4-chlorobenzyl | Cl | COOH | 208-209 |
| 415 | (S) CH(CH₃)—C(CH₃)₃ | H | 4-chlorobenzyl | Cl | COOH | 100-107 |
| 416 | (R) CH(CH₃)—C(CH₃)₃ | H | 4-chlorobenzyl | Cl | COOH | 183-186 |
| 472 | (R) CH(CH₃)—CH(CH₃)₂ | H | 2,4-F-phenyl | Cl | COO⁻Na⁺ | 268-272° C. |
| 473 | (R) CH(CH₃)—CH(CH₃)₂ | H | 2,4-F-phenyl | Cl | COO⁻K⁺ | 247-251° C. |
| 490 | (R) CH(CH₃)—CH(CH₃)₂ | H | 2,5-dimethylthien-3-yl | Cl | COO⁻Na⁺ | 280-281 |
| 491 | (R) CH(CH₃)—CH(CH₃)₂ | H | 2,5-dimethylthien-3-yl | Cl | COO⁻K⁺ | 207-211 dec |
| 528 | (R) CH(CH₃)—CH(CH₃)₂ | H | 2-Cl,4-MeO-phenyl | Cl | COO⁻Na⁺ | 290-300° C. |
| 530 | (R) CH(CH₃)—CH(CH₃)₂ | H | 2-Cl,4-methylphenyl | Cl | COO⁻K⁺ | 204-205 dec. |
| 531 | (R) CH(CH₃)—CH(CH₃)₂ | H | 2-Cl,4-methylphenyl | Cl | COO⁻Na⁺ | 194-196 |
| 635 | (R) CH(CH₃)—CH(CH₃)₂ | H | 3-Cl-thien-2-yl | Cl | COO⁻Na⁺ | 285-287 dec. |
| 644 | (R) CH(CH₃)—CH(CH₃)₂ | H | 3-Me-thien-2-yl | Cl | COO⁻Na⁺ | 270-273 dec. |
| 645 | (R) CH(CH₃)—CH(CH₃)₂ | H | 3-Me-thien-2-yl | —O—CH₃ | COO⁻Na⁺ | 258-259 dec. |
| 679 | CH₂—C(CH₃)₃ | H | 2,4-F-phenyl | Cl | COO⁻K⁺ | ~245° C. |
| 680 | CH₂—C(CH₃)₃ | H | 2,4-F-phenyl | Cl | COO⁻Na⁺ | 245.8° C |
| 691 | CH₂—C(CH₃)₃ | H | 2-Cl,4-methylphenyl | Cl | COO⁻Na⁺ | 214-217 dec |
| 717 | CH₂—CH₂—CH(CH₃)₂ | H | 2,4-F-phenyl | Cl | COO⁻K⁺ | 220-225° C. |
| 718 | CH₂—CH₂—CH(CH₃)₂ | H | 2,4-F-phenyl | Cl | COO⁻Na⁺ | 252.6° C. |
| 720 | CH₂—CH₂—CH(CH₃)₂ | H | 2-Cl,4-methylphenyl | Cl | COO⁻Na⁺ | 220-225 dec. |
| 738 | —CH₂—CH₂—CH(CH₃)—CH₂—CH₂— | | 2,4-F-phenyl | Cl | COO⁻Na⁺ | 285-290° C. |
| 747 | —CH₂—CH₂—CH(CH₃)—CH₂—CH₂— | | 2-Cl,4-MeO-phenyl | Cl | COO⁻K⁺ | ~250° C. |
| 748 | —CH₂—CH₂—CH(CH₃)—CH₂—CH₂— | | 2-Cl,4-MeO-phenyl | Cl | COO⁻Na⁺ | 215.3° C. |
| 752 | —CH₂—CH₂—CH(CH₃)—CH₂—CH₂— | | 2-Cl,4-methylphenyl | —OH | COOH | 218-221 |
| 783 | —CH₂—CH₂—CH₂—CH(CH₃)— | | 2-Cl,4-methylphenyl | Cl | COO⁻K⁺ | 236-239 |
| 784 | —CH₂—CH₂—CH₂—CH(CH₃)— | | 2-Cl,4-methylphenyl | Cl | COO⁻N⁺ | 265-266 |
| 800 | cyclopentyl | H | 2-Cl,4-methylphenyl | Cl | COO⁻Na⁺ | 248-251 |
| 832 | i-butyl | H | 2-Cl,4-methylphenyl | Cl | COO⁻Na⁺ | 248-252 dec |

Preparation of the Starting Materials:

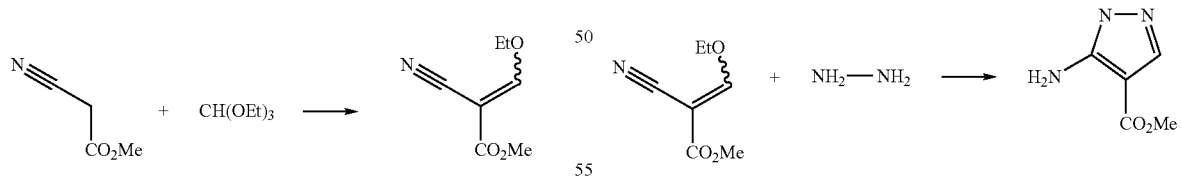

In an apparatus fitted with a Vigreux column, 198 g (1998 mmol) of methyl cyanoacetate, 296 g (1998 mmol) of triethyl orthoformate and 440 g (4310 mmol) of acetic anhydride were heated at reflux. Volatile components were distilled off, until a overhead temperature of 120° C. had been reached. After cooling, the mixture was fractionated under reduced pressure. This gave 5 g of methyl (2E/Z)-2-cyano-3-ethoxyacrylate (fraction 1: 65-100° C., 0.2 mbar, purity according to GCMS 88%) and a further 209 g of methyl (2E/Z)-2-cyano-3-ethoxyacrylate (fraction 2: 105-108° C., 0.2 mbar, purity according to GCMS>99%).

100 g (645 mol) of methyl (2E/Z)-2-cyano-3-ethoxyacrylate were initially charged in 481 ml of ethanol. With cooling (exothermic reaction!), 31 ml (645 mmol) of an 85% strength hydrazine hydrate solution were then added dropwise at room temperature over a period of 45 minutes. The mixture was stirred at 75° C. for another 12 hours. The hot mixture was filtered off, and the organic phase was concentrated under reduced pressure. This gave 64 g of methyl 5-amino-1H-pyrazole-4-carboxylate (logPs=−0.07; content according to HPLC: 86%).

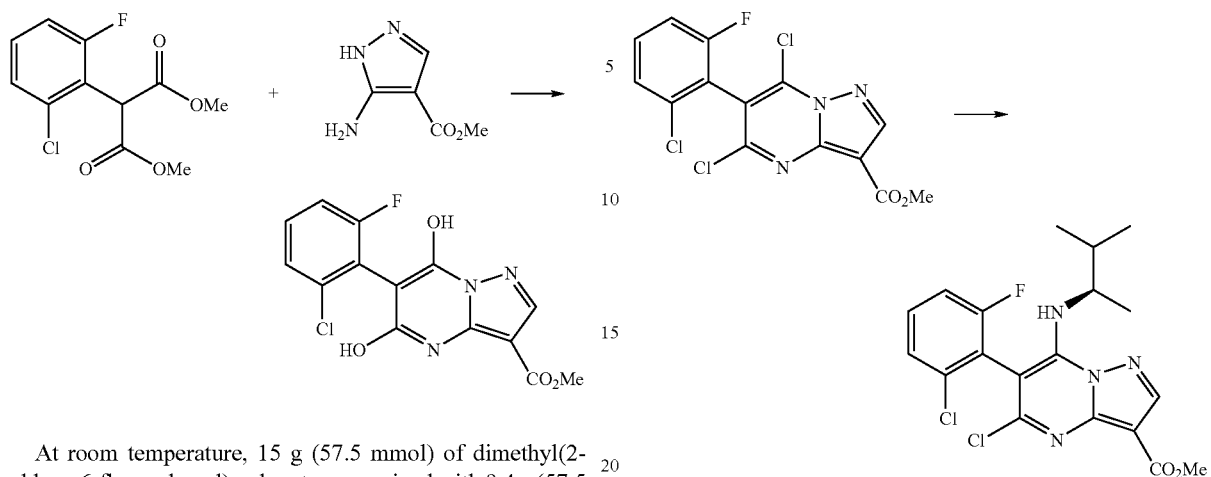

At room temperature, 15 g (57.5 mmol) of dimethyl(2-chloro-6-fluorophenyl)malonate were mixed with 9.4 g (57.5 mmol) of methyl 5-amino-1H-pyrazole-4-carboxylate and 15 ml (63.3 mmol) of tri-n-butylamine. The mixture was then stirred at 185° C. for 8 hours, during which time methanol was distilled off. After cooling, excess tri-n-butylamine was carefully decanted off. Concentration under reduced pressure gave 27 g of methyl 6-(2-chloro-6-fluorophenyl)-5,7-dihydroxypyrazolo[1,5-a]pyrimidine-3-carboxylate (logPs=0.55; content according to HPLC: 83%).

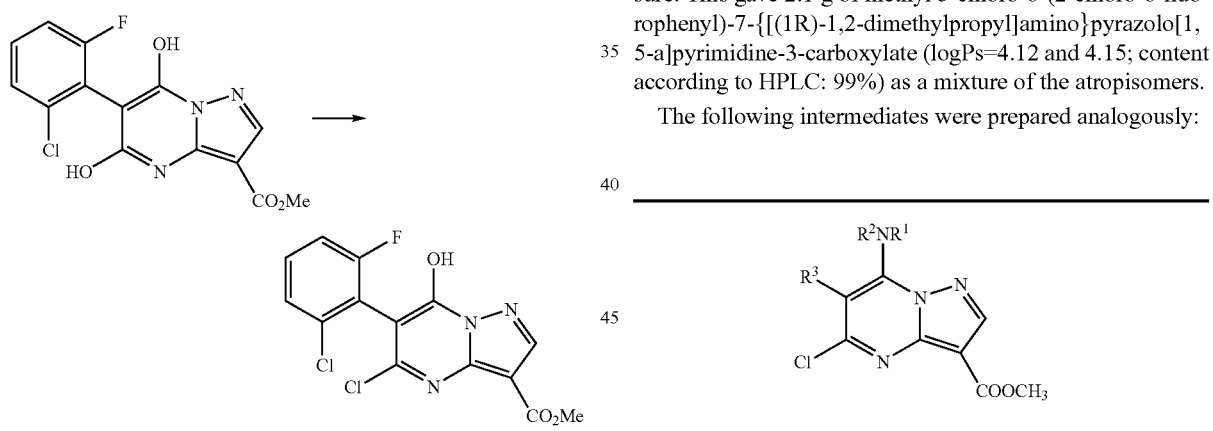

At room temperature, 27 g (80 mmol) of methyl 6-(2-chloro-6-fluorophenyl)-5,7-dihydroxypyrazolo[1,5-a]pyrimidine-3-carboxylate were mixed with 75 ml (800 mmol) of phosphorus oxychloride and 8.3 g (40 mmol) of phosphorus pentachloride. The mixture was then stirred at 115° C. for 4 hours. Excess phosphorus oxychloride was distilled off under reduced pressure. With cooling, 50 ml of dichloromethane and 20 ml of water were then added carefully to the residue. The organic phase was dried over sodium sulphate and then concentrated under reduced pressure. The residue was chromatographed on silica gel using a mixture of cyclohexane:ethyl acetate=gradient: 9:1, 5:1 and 3:1. This gave 10 g of methyl 5,7-dichloro-6-(2-chloro-6-fluorophenyl)pyrazolo[1,5-a]pyrimidine-3-carboxylate (logPs=3.17; content according to HPLC:>99%).

At room temperature, 2 g (5.33 mmol) of methyl 5,7-dichloro-6-(2-chloro-6-fluorophenyl)pyrazolo[1,5-a]pyrimidine-3-carboxylate in 20 ml of acetonitrile were mixed with 0.51 g (5.87 mmol) of 2-R-methyl-2-butylamine. 1.11 g (8.00 mmol) of potassium carbonate were added. The mixture was then stirred at 25° C. for 12 hours. 10 ml of dilute 1 N hydrochloric acid and 10 ml of dichloromethane were added to the reaction mixture. The organic phase was dried over sodium sulphate and then concentrated under reduced pressure. This gave 2.1 g of methyl 5-chloro-6-(2-chloro-6-fluorophenyl)-7-{[(1R)-1,2-dimethylpropyl]amino}pyrazolo[1,5-a]pyrimidine-3-carboxylate (logPs=4.12 and 4.15; content according to HPLC: 99%) as a mixture of the atropisomers.

The following intermediates were prepared analogously:

| $R^1$ | $R^2$ | $R^3$ | log P |
|---|---|---|---|
| CH(CH$_3$)—C(CH$_3$)$_3$ | H | 5-F-pyrimidin-4-yl | 3.15 |
| CH(CH$_3$)—CH(CH$_3$)$_2$ | H | 2-Cl-6-F-phenyl | 4.12 |
| (CH$_2$—CH$_2$—CHCH$_3$—CH$_2$—CH$_2$) | | 2-Cl-6-F-phenyl | 4.61 |
| CH(CH$_3$)—C(CH$_3$)$_3$ | H | 2-Cl-6-F-phenyl | 4.51 |
| CH(CH$_3$)—C(CH$_3$)$_3$ | H | 2,4,6-trifluorophenyl | 4.93 |
| CH(CH$_3$)—CH(CH$_3$)$_2$ | H | 2,4,6-trifluorophenyl | 4.05 |
| CH(CH$_3$)(CF$_3$) | H | 2,4,6-trifluorophenyl | 3.53 |
| CH(CH$_3$)(CF$_3$) | H | 2-Cl-4-F-phenyl | 3.75 |
| CH(CH$_3$)—CH(CH$_3$)$_2$ | H | 2-Cl-4-F-phenyl | 4.31 |
| CH(CH$_3$)—C(CH$_3$)$_3$ | H | 2-Cl-4-F-phenyl | 4.68 |
| CH(CH$_3$)—CH(CH$_3$)$_2$ | H | 2-Ci-phenyl | 4.21 |
| CH(CH$_3$)—C(CH$_3$)$_3$ | H | 2-Ci-phenyl | 4.61 |

Dimethyl 2-(3-methylthiophen-2-yl)malonate

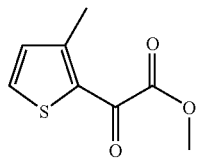

Aluminium trichloride (163 g, 1.222 mol) was initially charged in 540 ml of dichloromethane, the mixture was cooled to 0° C. and 112 ml (150 g, 1.222 mol) of methyl oxalyl chloride were added dropwise at this temperature. The mixture was then stirred at this temperature for another 10 min, 3-methylthiophene was added dropwise, again at 0° C., and, after warming to room temperature, the reaction mixture was stirred at this temperature overnight. Hydrolysis was carried out by pouring the mixture into 2 l of ice-water, and the organic phase was separated off, washed with sodium bicarbonate solution and dried over sodium sulphate, giving, after removal of the drying agent by filtration and concentration using a rotary evaporator, 119.5 g of methyl(3-methylthiophen-2-yl)-oxoacetate. Yield: 57%. $^1$H-NMR (DMSO): δ=8.09 (d, 1H), 7.19 (d, 1H), 7.67 (dd, 1H), 3.90 (s, 3H), 2.49 (s, 3H).

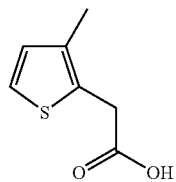

112.5 ml (116 g, 2.312 mol) of hydrazine hydrate were added slowly to a solution of 90 g (0.489 mol) of methyl(3-methylthiophen-2-yl)oxoacetate in 260 ml of diethylene glycol, and the mixture was heated under reflux for 30 min. After cooling to 3040° C., 82 g (1.246 mol) of potassium hydroxide were added a little at a time, which was accompanied by a temperature increase to 70-80° C. with simultaneous evolution of nitrogen. The mixture was then slowly heated to reflux and stirred at this temperature for a total of 5 h. After cooling to room temperature, the mixture was poured into 2 l of water, adjusted to pH=1 using 250 ml of semi-concentrated hydrochloric acid and extracted with ethyl acetate. The organic phase was dried over magnesium sulphate and filtered off and the solvent was removed, which gave 50 g of (3-methylthiophen-2-yl)acetic acid. Yield: 66%. $^1$H-NMR (DMSO): δ=7.25 (d, 1H), 6.84 (d, 2H), 3.67 (s, 2H), 2.11 (s, 3H).

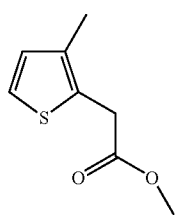

5 ml of concentrated sulphuric acid were added to a solution of 50 g (0.32 mol) of (3-methyl-thiophen-2-yl)acetic acid in 500 ml of methanol, and the mixture was heated under reflux for 8 h. The solvent was then removed using a rotary evaporator, and water and dichloromethane were added to the residue. Phase-separation and another extraction of the aqueous phase with dichloromethane gave, after drying of the organic phase over sodium sulphate, filtration and concentration using a rotary evaporator, 42.5 g of methyl(3-methylthiophen-2-yl)acetate. Yield: 70%. $^1$H-NMR (DMSO): δ=7.30 (d, 1H), 6.87 (d, 1H), 3.82 (s, 2H), 3.65 (s, 3H), 2.13 (s, 3H).

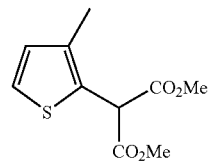

Under argon, 14.7 g of sodium hydride (60% in mineral oil) were added to 311 ml (332 g, 3.685 mol) of dimethyl carbonate, and the mixture was heated at 80° C. At this temperature, a solution of 41 g (0.217 mol) of methyl(3-methylthiophen-2-yl)acetate in 50 ml of toluene was slowly added dropwise, and the mixture was stirred under reflux overnight. For workup, the mixture was diluted with about 200 ml of methanol and poured into ice-water and acidified with dilute hydrochloric acid. Extraction with dichloromethane, drying of the organic phase over sodium sulphate, filtration and removal of the solvent gave 43.6 g of dimethyl 2-(3-methylthiophen-2-yl)malonate. Yield: 88%. $^1$H-NMR (DMSO): δ=7.42 (d, 1H), 6.89 (d, 1H), 5.27 (s, 1H), 3.69 (s, 6H), 2.15 (s, 3H).

Spectroscopic data of the intermediates, which were prepared in an analogous manner:

| Structure | $^1$H—NMR (DMSO) |
|---|---|
| ![](chloro-methyl oxoacetate) | δ = 8.30 (d, 1 H), 7.36 (d, 1 H), 3.92 (s, 3 H) |
| ![](chloro-acetic acid) | δ = 7.54 (d, 1 H), 7.02 (d, 1 H), 3.78 (s, 2 H) |
| ![](chloro-methyl acetate) | δ = 7.57 (d, 1 H), 7.04 (d, 1 H), 3.90 (s, 2 H), 3.66 (s, 3 H) |
| ![](chloro-dimethyl malonate) | δ = 7.71 (d, 1 H), 7.08 (d, 1 H), 5.25 (s, 1 H), 3.73 (s, 6 H) |

| Structure | ¹H—NMR (DMSO) |
|---|---|
| 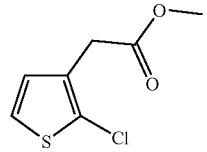 | δ = 7.42 (d, 1 H), 7.00 (d, 1 H), 3.66 (s, 2 H), 3.63 (s, 3 H) |
| 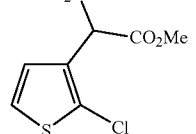 | δ = 7.49 (d, 1 H), 7.05 (d, 1 H), 4.98 (s, 1 H), 3.70 (s, 6 H) |

USE EXAMPLES

Example A

*Podosphaera* Test (Apple)/Protective

| Solvents: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound was mixed with the stated amounts of solvents and emulsifier, and the concentrate was diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation was carried out 10 days after the inoculation. 0% means an efficacy which corresponds to that of the control, whereas an efficacy of 100% means that no infection is observed.

In this test, the compounds according to the invention having the example numbers below exhibited, at an active compound concentration of 100 ppm, an efficacy of 70% or more.

8, 15, 25, 35, 65, 75, 105, 106, 108, 121, 125, 126, 127, 128, 135, 208, 211, 216, 217, 218, 219, 220, 221, 222, 223, 224, 226, 227, 233, 235, 238, 239, 240, 242, 244, 248, 249, 253, 255, 256, 257, 259, 261, 264, 267, 270, 272, 273, 275, 276, 280, 281, 286, 287, 289, 290, 291, 292, 293, 295, 296, 297, 298, 304, 307, 308, 311, 312, 313, 314, 323, 325, 330, 337, 345, 346, 351, 354, 356, 357, 363, 366, 373, 377, 378, 382, 384, 385, 391, 393, 394, 399, 409, 421, 424, 425, 428, 430, 435, 441, 442, 445, 447, 448, 450, 451, 454, 457, 459, 460, 462, 463, 472, 486, 494, 495, 496, 497, 498, 499, 501, 503, 504, 505, 506, 515, 516, 517, 519, 520, 522, 523, 529, 534, 536, 543, 550, 551, 559, 560, 561, 562, 563, 564, 570, 571, 574, 576, 587, 588, 589, 591, 597, 607, 608, 614, 619, 623, 629, 630, 631, 632, 636, 664, 665, 667, 668, 684, 687, 694, 695, 701, 705, 706, 707, 710, 711, 712, 713, 724, 732, 753, 757, 808, 810, 812, 814, 825, 826, 828, 836, 842, 844, 845, 846, 859, 866, 876

Example B

*Venturia* Test (Apple)/Protective

| Solvents: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound was mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabinet at about 20° C. and 100% relative atmospheric humidity for one day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds according to the invention having the example numbers below exhibited, at an active compound concentration of 100 ppm, an efficacy of 70% or more.

5, 8, 15, 25, 35, 65, 75, 105, 106, 108, 115, 121, 124, 125, 126, 128, 135, 179, 203, 208, 210, 211, 213, 216, 217, 218, 219, 220, 221, 222, 224, 225, 226, 227, 233, 234, 235, 238, 239, 240, 242, 244, 248, 249, 250, 251, 253, 255, 256, 257, 258, 259, 261, 262, 263, 264, 267, 270, 272, 273, 275, 276, 279, 280, 281, 284, 285, 286, 287, 289, 290, 291, 292, 293, 295, 296, 297, 298, 303, 304, 307, 308, 309, 311, 312, 313, 314, 323, 324, 325, 330, 337, 345, 347, 349, 351, 352, 354, 356, 357, 363, 366, 373, 377, 378, 382, 384, 385, 387, 391, 393, 394, 399, 400, 406, 408, 409, 410, 417, 421, 424, 425, 426, 428, 430, 435, 441, 442, 445, 447, 448, 450, 451, 454, 457, 459, 460, 462, 463, 472, 473, 486, 490, 491, 492, 493, 495, 496, 497, 498, 499, 501, 503, 504, 505, 506, 508, 511, 512, 515, 516, 517, 519, 520, 522, 523, 528, 529, 531, 534, 536, 543, 550, 551, 559, 560, 561, 562, 563, 564, 566, 570, 571, 574, 576, 578, 579, 580, 587, 588, 589, 591, 597, 605, 607, 608, 614, 619, 623, 629, 630, 631, 632, 635, 636, 643, 644, 645, 662, 663, 664, 665, 666, 667, 668, 670, 671, 672, 673, 678, 681, 682, 683, 684, 685, 687, 690, 691, 692, 693, 694, 695, 696, 701, 702, 705, 706, 707, 708, 710, 711, 712, 713, 714, 716, 720, 722, 724, 732, 737, 738, 739, 753, 757, 764, 765, 777, 804, 807, 808, 809, 810, 812, 815, 816, 817, 822, 825, 826, 828, 831, 832, 833, 834, 835, 836, 842, 844, 845, 846, 849, 850, 851, 852, 853, 854, 858, 859, 860, 861, 866, 868, 874, 876, 884

Example C

*Botrytis* Test (Bean)/Protective

| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound was mixed with the stated amounts of solvents and emulsifier, and the concentrate is diluted with water to the desired concentration.

To test for protective activity, young plants are sprayed with the preparation of active compound at the stated application rate. After the spray coating has dried on, two small pieces of agar colonized by *Botrytis cinerea* are placed onto each leaf. The inoculated plants are placed in a dark chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

In this test, the compounds according to the invention having the example numbers below exhibited, at an active compound concentration of 500 ppm, an efficacy of 70% or more.

5, 8, 15, 25, 35, 65, 75, 105, 106, 108, 115, 121, 122, 124, 125, 126, 128, 135, 179, 222, 223, 224, 226, 227, 233, 234, 235, 238, 239, 242, 244, 249, 255, 256, 264, 276, 281, 284, 285, 286, 287, 289, 290, 291, 292, 295, 296, 297, 298, 304, 307, 308, 312, 314, 325, 330, 337, 339, 345, 346, 349, 351, 354, 357, 363, 373, 377, 399, 400, 406, 409, 410, 417, 421, 424, 425, 426, 428, 435, 441, 442, 451, 463, 473, 486, 492, 493, 494, 495, 497, 498, 501, 503, 504, 505, 506, 511, 512, 515, 516, 519, 520, 523, 528, 531, 534, 536, 540, 543, 550, 551, 559, 561, 570, 580, 587, 588, 589, 605, 607, 608, 619, 623, 629, 630, 631, 632, 636, 651, 661, 662, 663, 664, 665, 667, 668, 670, 672, 673, 678, 683, 684, 685, 687, 688, 690, 692, 695, 696, 701, 708, 714, 716, 722, 737, 738, 739, 757, 777, 804, 807, 808, 809, 811, 812, 814, 816, 817, 822, 825, 826, 828, 829, 831, 833, 835, 836, 842, 850, 851, 853, 854, 858, 860, 861, 866, 874, 876, 884

Example D

*Pyricularia* Test (Rice)/Protective

| Solvent: | 50 parts by weight of N,N-dimethylformamide |
| Emulsifier: | 1 part by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound at the stated application rate. One day after the treatment, the plants are inoculated with an aqueous spore suspension of *Pyricularia oryzae*. The plants are then placed in a greenhouse at 100% relative atmospheric humidity and 25° C.

Evaluation is carried out 7 days after the inoculation. 0% means an efficacy which corresponds to that of the control, whereas an efficacy of 100% means that no infection is observed.

In this test, the compounds according to the invention having the example numbers below exhibited, at an active compound concentration of 1000 ppm, an efficacy of 70% or more:

5, 15, 65, 75, 105, 115, 124, 125, 208, 210, 216, 218, 226, 233, 235, 239, 244, 249, 261, 267, 272, 273, 276, 281, 287, 292, 293, 297, 304, 307, 308, 311, 312, 314, 346, 409, 424, 425, 428, 435, 441, 450, 451, 459, 460, 462, 483, 486, 490, 492, 498, 499, 505, 511, 519, 520, 523, 526, 527, 529, 559, 578, 588, 589, 608, 623, 629, 630, 636, 648, 664, 667, 668, 672, 673, 678, 682, 684, 687, 688, 690, 693, 694, 701, 737, 739, 751, 764, 811, 825, 828, 829, 831, 841, 848, 851, 852, 854, 858, 872, 882, 885

Example E

*Alternaria* Test (Tomato)/Protective

| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application-rate. One day after the treatment, the plants are inoculated with a spore suspension of *Alternaria solani* and then remain at 100% relative humidity and 20° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

In this test, the compounds according to the invention having the example numbers below exhibited, at an active compound concentration of 500 ppm, an efficacy of 70% or more.

5, 15, 25, 35, 65, 71, 75, 105, 106, 108, 115, 121, 122, 124, 125, 127, 128, 135, 201, 204, 206, 208, 210, 211, 215, 221, 224, 225, 230, 231, 234, 236, 237, 240, 243, 244, 254, 264, 266, 268, 269, 276, 279, 281, 285, 292, 293, 295, 303, 309, 311, 313, 316, 323, 324, 325, 330, 337, 339, 341, 343, 345, 347, 351, 352, 354, 357, 363, 373, 376, 377, 383, 389, 399, 400, 407, 408, 410, 421, 422, 423, 428, 430, 434, 437, 439, 440, 451, 453, 456, 463, 473, 479, 483, 486, 491, 494, 496, 497, 498, 499, 503, 505, 511, 517, 522, 525, 529, 531, 533, 534, 536, 539, 541, 544, 545, 546, 550, 551, 559, 561, 565, 569, 570, 573, 578, 579, 580, 582, 588, 589, 591, 595, 597, 598, 599, 600, 604, 606, 607, 610, 613, 614, 618, 619, 620, 624, 626, 629, 631, 634, 635, 644, 646, 647, 648, 661, 666, 674, 675, 676, 677, 678, 679, 681, 686, 690, 691, 692, 693, 697, 698, 699, 700, 701, 702, 703, 704, 709, 714, 715, 717, 720, 722, 725, 726, 727, 733, 734, 736, 737, 743, 745, 748, 749, 751, 753, 759, 764, 766, 767, 768, 770, 783, 784, 785, 789, 794, 795, 799, 800, 801, 804, 807, 810, 818, 819, 820, 821, 822, 823, 824, 827, 831, 833, 837, 838, 840, 841, 843, 847, 855, 856, 857, 862, 864, 865, 866, 867, 869, 871, 872, 873, 874, 877, 878, 880, 881, 882, 885, 886, 887, 888, 889

Example F

*Fusarium* nivale (var. *majus*) Test (Wheat)/Protective

| Solvent: | 50 parts of weight of N,N-dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium* nivale (var. *majus*).

The plants are placed in a greenhouse under translucent incubation hoods at a temperature of about 15° C. and a relative atmospheric humidity of about 100%.

Evaluation is carried out 6 days after the inoculation. 0% means an efficacy which corresponds to that of the control, whereas an efficacy of 100% means that no infection is observed.

In this test, the compounds according to the invention having the example numbers below exhibited, at an active compound concentration of 1000 ppm, an efficacy of 70% or more:

25, 35, 126, 128, 214, 228, 232, 238, 242, 248, 250, 251, 252, 253, 255, 256, 257, 259, 260, 263, 264, 270, 275, 283, 289, 291, 296, 328, 330, 337, 345, 347, 349, 351, 353, 354, 356, 357, 361, 362, 363, 364, 365, 378, 382, 387, 392, 393, 394, 400, 408, 421, 428, 430, 442, 445, 447, 448, 454, 457, 463, 473, 491, 495, 497, 501, 503, 504, 506, 512, 515, 516, 528, 531, 533, 534, 536, 543, 546, 548, 551, 560, 562, 563, 566, 571, 574, 580, 598, 635, 643, 644, 663, 670, 683, 685, 692, 695, 696, 705, 711, 724, 732, 739, 765, 808, 809, 812, 814, 816, 817, 822, 834, 835, 836, 845, 859, 860, 861, 866.

What is claimed is:

1. A compound of the formula (I)

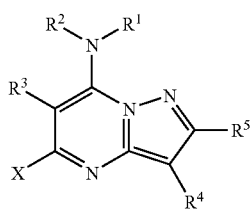

in which
R$^1$ is alkyl having 1 to 10 carbon atoms which is unsubstituted or mono- to pentasubstituted by identical or different substituents from the group consisting of halogen, cyano, hydroxyl, alkoxy having 1 to 4 carbon atoms, cycloalkyl having 3 to 6 carbon atoms, mercapto, alky-lthio having 1 to 4 carbon atoms, amino, mono- or dialkylamino having in each case 1 to 4 carbon atoms, or is alkenyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or is alkynyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or is cycloalkyl having 3 to 10 carbon atoms which is unsubstituted or mono- to trisubstituted by identical or different substituents from the group consisting of halogen and alkyl having 1 to 4 carbon atoms, or is saturated or unsaturated heterocyclyl having 3 to 10 ring members and 1 to 3 heteroatoms that are nitrogen, oxygen and/or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms and/or mercapto;

R$^2$ is hydrogen or alkyl having 1 to 6 carbon atoms;

R$^3$ is C$_1$-C$_{10}$-alkyl, C$_2$-C$_{10}$-alkenyl, C$_2$-C$_{10}$alkynyl, C$_3$-C$_8$-cycloalkyl, phenyl-C$_1$-C$_{10}$-alkyl, where R$^3$ is unsubstituted or partially or fully halogenated and/or optionally carries one to three radicals from the group R$^x$, or C$_1$-C$_{10}$-haloalkyl which optionally carries one to three radicals from the group R$^x$, and R$^x$ is cyano, nitro, hydroxyl, C$_1$-C$_6$-alkyl, C$_1$,-C$_6$-haloalkyl, C$_3$-C$_6$-cycloalkyl, C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulphinyl, C$_1$-C$_6$-haloalkylsulphinyl, C$_1$-C$_6$-alkylsulphonyl, C$_1$-C$_6$-haloalkylsulphonyl, C$_1$-C$_6$-alkylamino, di-C$_1$-C$_6$-alkylamino, C$_2$-C$_6$-alkenyl, C$_2$-C$_6$-alkenyloxy, C$_2$-C$_6$-alkynyl, C$_3$-C$_6$-alkynyloxy and optionally halogenated oxy-C$_1$-C$_4$-alkyl-C$_1$-C$_4$-alkenoxy, oxy-C$_1$-C$_4$-alkenyl-C$_1$-C$_4$-alkoxy, oxy-C$_1$-C$_4$-alkyl-C$_1$-C$_4$-alkyloxy, or is phenyl which may be mono- to tetrasubstituted by identical or different substituents from the group consisting of halogen, cyano, nitro, amino, hydroxyl, formyl, carboxyl, carboxyalkyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximnoalkyl or alkoximinoalkyl having in each case 1 to 6 carbon atoms in the individual alkyl moieties; cycloalkyl having 3 to 8 carbon atoms; 1,3-propanediyl which is attached in the 2,3-position, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents from the group consisting of halogen, alkyl having 1 to 4 carbon atoms and haloalkyl having 1 to 4 carbon atoms and 1 to 9 identical or different halogen atoms; or is saturated or fully or partially unsaturated or aromatic heterocyclyl having 3 to 8 ring members and 1 to 3 heteroatoms from the group consisting of nitrogen, oxygen and sulphur, where the heterocyclyl may be mono- or disubstituted by halogen, alkyl having 1 to 4 carbon atoms, alkoxy having 1 to 4 carbon atoms, alkylthio having 1 to 4 carbon atoms, haloalkoxy having 1 to 4 carbon atoms, haloalkylthio having 1 to 4 carbon atoms, hydroxyl, mercapto, cyano, nitro and/or cycloalkyl having 3 to 6 carbon atoms and/or carboxyalkyl; or is $C_1$-$C_8$-alkylamino, $C_2$-$C_8$-alkenylamino, $C_2$-$C_8$-alkynylamino, di-$C_2$-$C_8$-alkylamino, di-$C_2$-$C_8$-alkenylamino, di-$C_2$-$C_8$-alkynylamino, or $C_2$-$C_8$-alkenyl-($C_2$-$C_8$)-alkynylamino, $C_2$-$C_6$-alkynyl-($C_1$-$C_8$)-alkylamino, $C_2$-$C_8$-alkenyl-($C_1$-$C_8$)-alkylamino, $C_6$-$C_{10}$-arylamino, $C_6$-$C_{10}$-aryl-($C_1$-$C_8$)-alkylamino, $C_6$-$C_{10}$-aryl-($C_1$-$C_4$)-alkyl-($C_1$-$C_8$)-alkylamino, heterocyclyl-($C_1$-$C_8$)-alkylamino or heterocyclyl-($C_1$-$C_4$)-alkyl-($C_1$-$C_8$)-alkylamino;

$R^4$ is $CONR^6R^7$, $CONR^7$—$N(R^7)_2$, $CO$—$NR^7$—$OR^7$, $COOR^8$, $CSOR^7$, $COSR^7$, $SR^7$, $SOR^7$, $SO_2R^7$, $SO_3R^7$, $SON(R^7)_2$, $SO_2N(R^7)_2$, or $P(O)$-$(OR^7)_2$, $B(OR^7)_2$ or

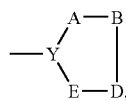 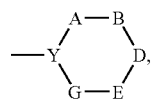

A, B, D, E, G are identical or different and are $CR^9$, $CR^9R^9$, N, $NR^9$, O or S, with the proviso that at least one group is N, O or S and that oxygen atoms are not adjacent to one another;

Y is C, $CR^9$ or N;

$R^9$ is $R^7$, halogen, $NR^7_2$, OH, $SR^7$ or $OR^7$;

$R^5$ is H, halogen, ($C_1$-$C_4$)-alkyl which is unsubstituted or substituted by one or more halogen atoms, cyclopropyl which is unsubstituted or substituted by one or more halogen atoms; $SCH_3$, $SOCH_3$, $SO_2CH_3$ or $OCH_3$;

X is H, fluorine, chlorine, bromine, CN, hydroxyl, alkoxy having 1 to 4 carbon atoms or alkylthio having 1 to 4 carbon atoms;

$R^6$ is $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, phenyl-$C_1$-$C_{10}$-alkyl, where $R^6$ is unsubstituted or partially or fully halogenated and/or optionally carries one to three radicals from the group $R^x$, or $C_1$-$C_{10}$-haloalkyl which optionally carries one to three radicals from the group $R^x$, and $R^x$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, $CONR^6R^7$, $CONR^7OR^7$, $COOR^8$, carboxy-($C_1$-$C_4$)-alkyl;

$R^7$ is H or $R^6$, or two radicals $R^7$ or one radical $R^7$ and one radical $R^8$ together form a cycle having 3 to 6 carbon atoms which is saturated or partially unsaturated and optionally contains 1 or 2 further nitrogen, sulphur or oxygen atoms, where the oxygen atoms may not be adjacent to one another; and $R^8$ is H, an alkali metal or alkaline earth metal, copper, $NH_4$, mono-($C_1$-$C_{10}$)-alkylammonium, di-($C_1$-$C_{10}$)-alkylammonium, tri-($C_1$-$C_{10}$)-alkylammonium tetra-($C_1$-$C_{10}$)-alkylammonium, where the alkyl substituents of the ammonium ions are optionally substituted by aryl or hydroxyl, cholinium, $C_2$-$C_{10}$-alkenyl, $C_2$-$C_{10}$-alkynyl, $C_3$-$C_8$-cycloalkyl, $C_3$-$C_8$-cycloalkenyl, where $R^8$ is unsubstituted or partially or fully halogenated and/or optionally carries one to three radicals from the group $R^x$, or $C_1$-$C_{10}$-haloalkyl which optionally carries one to three radicals from the group $R^x$, or $C_1$-$C_{10}$-alkyl which is partially or fully halogenated and/or carries one to three radicals from the group $R^x$, and $R^x$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, $CONR^6R^7$, $CONR^7OR^7$, $COOR^8$, carboxy-($C_1$-$C_4$)-alkyl or an agrochemically active salt thereof.

2. A compound of the formula (I) according to claim 1 in which $R^1$ is a radical of the formula

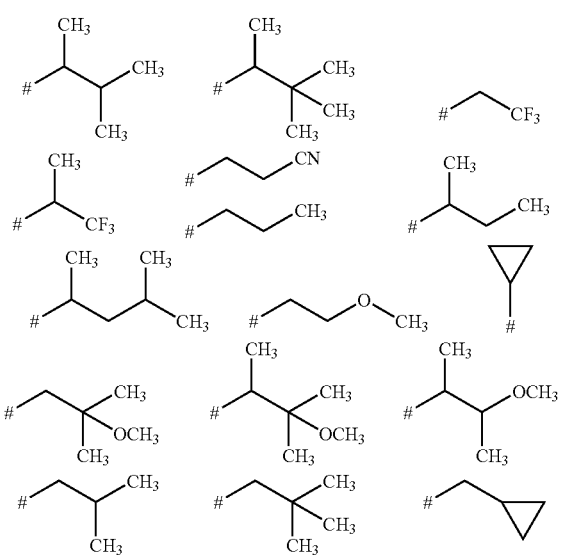

-continued

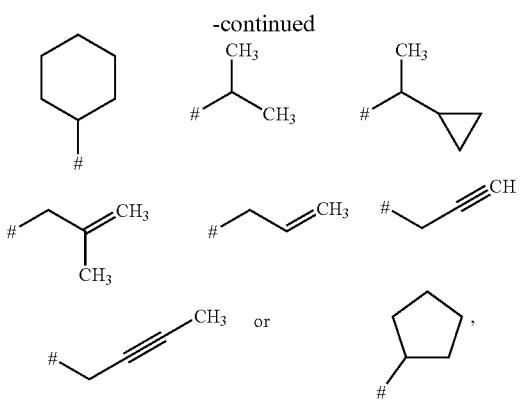

where # denotes the point of attachment, and wherein said radicals can be present both in optically pure form and as isomer mixtures;

$R^2$ is hydrogen, methyl, ethyl, propyl, or $R^3$ is $(C_1-C_8)$-alkyl, $(C_1-C_8)$-cycloalkyl, where $R^3$ is unsubstituted or substituted by one or more fluorine or chlorine atoms, or benzyl or is phenyl which may be mono- to trisubstituted by identical or different substituents from the group consisting of fluorine, chlorine, bromine, cyano, nitro, formyl, methyl, ethyl, n- or i- propyl, n-, i-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsuiphonyl, trichloroethynyloxy, trifluoroethynyloxy, chloroallyloxy, iodopropargyloxy, methylamino, ethylamino, n- or i- propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl and cyclohexyl, or by 1,3-propanediyl which is attached in the 2,3-position, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents from the group consisting of fluorine, chlorine, methyl, ethyl, n-propyl, i-propyl, trifluoromethyl, carboxyl and carboxymethyl; or is pyridyl which is attached in the 2- or 4-position and which may be mono- to tetrasubstituted by identical or different substituents from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl, or is pyrimidyl which is attached in the 2- or 4-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or is thienyl which is attached in the 2- or 3-position and which may be mono- to trisubstituted by identical or different substituents from the group consisting of fluorine, chlorine, bromine, cyano, nitro, hydroxyl, mercapto, methyl, ethyl, methoxy, methylthio, hyd roximinomethyl, hydroximinoethyl, methoximinomethyl, methoximinoethyl, trifluoromethyl, carboxyl and carboxymethyl, or is $C_1-C_8$-alkylamino or di-$C_1-C_8$-alkylamino, or is thiazolyl which is attached in the 2-, 4- or 5-position and which may be mono- to disubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or is N-piperidinyl, N-tetrazolyl, N-pyrazolyl, N-imidazolyl, N-1,2,4-triazolyl, N-pyrrolyl or N-morpholinyl, each of which is unsubstituted or mono- or polysubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl, $R^4$ is $CONR^6R^7$, $CONR^7—N(R^7)_2$, $CO—NR^7—OR^7$, $COOR^8$, $CSOR^7$, $COSR^7$, pyrrolyl, imidazolyl, pyrazolyl, 1,3,4-triazolyl, thiazolyl, 1,3,4-oxadiazolyl, 1,3,4-thiadiazolyl, oxazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1-C_4$-alkyl and halogen, $SR^7$, $SOR^7$, $SO_2R^7$, $SO_3R^7$, $SON(R^7)_2$, $SO_2N(R^7)_2$, $P(O)—(OR^7)_2$ or $B(OR^7)_2$;

$R^5$ is H, Cl, F, $CH_3$, —$CH(CH_3)_2$ or cyclopropyl; and

X is H, F, Cl, CN, $C_1-C_4$-alkyl which is unsubstituted or substituted by one or more fluorine or chlorine atoms;

$R^6$ is $(C_1-C_8)$-alkyl, $(C_3-C_6)$-alkenyl, $(C_1-C_8)$-cycloalkyl or benzyl, $CONR^6R^7$, $CONR^7OR^7$, $COOR^8$, carboxy-$(C_1-C_4)$-alkyl, or cyano;

$R^7$ is H or $R^6$; or two radicals $R^7$ or one radical $R^6$ and one radical $R^7$ together form a cycle having 3 to 6 carbon atoms, which is saturated or partially unsaturated and optionally contains 1 or 2 further nitrogen, sulphur or oxygen atoms, where oxygen atoms must not be adjacent to one another; and $R^8$ is H, Na, K, ½Ca, ½Mg, Cu, $NH_4$, $NH(CH_3)_3$, $N(CH_3)_4$, $HN(C_2H_5)_3$, $N(C_2H_5)_4$, $H_2N(iC_3H_7)_2$, $H_2N(Bn)_2$, $H_3N(Bn)$, $(C_1-C_4)$-alkyl which is fully or partially substituted by F and/or Cl, $CONR^6R^7$, $CONR^7OR^7$, $COOR^8$, carboxy-$(C_1-C_4)$-alkyl, $(C_1-C_4)$-alkoxy-$(C_1-C_4)$-alkyl, allyl, propargyl, cyclopropyl, benzyl, $(CHR^z—CHR^z—O)m(C_1-C_4)$alkyl where $R^z$ is H or $CH_3$ and m is 1 to 6.

3. A compound of the formula (I) according to claim 1 in which $R^3$ is $(C_1-C_6)$-alkyl, $(C_3-C_6)$-alkenyl, $(C_3-C_6)$-alkynyl, $(C_3-C_8)$-cycloalkyl, where $R^3$ is unsubstituted or substituted by one or more fluorine or chlorine atoms and/or alkyl, or is 2,4-, 2,5- or 2,6-disubstituted phenyl or 2-substituted phenyl or 2,4,6- or 2,4,5-trisubstituted phenyl having substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or is pyridyl which is attached in the 2- or 4-position and which may be mono- to tetrasubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl; or is pyrimidyl which is attached in the 4-position and which may be mono- to trisubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl; or is thienyl which is attached in the 2- or 3-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl;

$R^4$ is $CONR^6R^7$, $CONR^7$—$N(R^7)_2$, $CO$—$NR^7$—$OR^7$, $COOR^8$, 1H-pyrrolyl, 1H-imidazolyl, 1,3,4-oxadiazolyl, 1H-pyrazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1$-$C_4$-alkyl and halogen, $SR^7$, $SOR^7$, $SO_2R^7$, $SO_3R^7$, $SON(R^7)_2$, $SO_2N(R^7)_2$, or $P(O)$—$(OR^7)_2$;

$R^5$ is H, —$CH_3$, —$CH(CH_3)_2$, Cl or cyclopropyl; and

X is fluorine, chlorine, $(C_1$-$C_7)$-alkyl or $(C_1$-$C_3)$-haloalkyl;

$R^6$ is $(C_1$-$C_8)$-alkyl, $(C_3$-$C_6)$-alkenyl, $(C_1$-$C_8)$-cycloalkyl, benzyl, carboxy-$(C_1$-$C_4)$-alkyl, $CONR^6R^7$, $CONR^7OR^7$, $COOR^8$, or cyano;

$R^7$ is H or $R^6$, or two radicals $R^7$ or one radical $R^6$ and one radical $R^7$ together form a cycle having 3 to 6 carbon atoms, which is saturated or partially unsaturated and optionally contains 1 or 2 further nitrogen, sulphur or oxygen atoms, where the oxygen atoms must not be adjacent to one another; and $R^8$ is H, Na, K, $NH_4$, $H_2N(iPr)'_2$, $H_2N(Bn)_2$, $H_3N(Bn)$, $(C_1$-$C_4)$-alkyl which is fully or partially substituted by F and/or Cl and/or carboxy-$(C_1$-$C_4)$-alkyl, $CONR^6R^7$, $CONR^7OR^7$, $COOR^8$, $(C_1$-$C_4)$-alkoxy-$(C_1$-$C_4)$-alkyl, allyl, propargyl, cyclopropyl, benzyl, $(CHR^Z$—$CHR^Z$—$O)_m$-$(C_1C_4)$-alkyl where $R^Z$ is H, $CH_3$ and m is 1 to 6.

4. A composition for controlling unwanted microorganisms comprising one or more compounds of the formula (I) according to claim 1 and one or more extenders and/or surfactants.

5. A composition according to claim 4 comprising one or more further agrochemically active compounds.

6. A method for controlling unwanted microorganisms comprising applying an effective amount of one or more compounds of the formula (I) according to claim 1 to the unwanted microorganisms and/or their habitats.

7. A process for preparing compositions for controlling unwanted microorganisms comprising mixing one or more compounds of the formula (I) according to claim 1 with one or more extenders and/or surfactants.

8. A process for preparing compounds of the formula (I) in which X is halogen and $R^4$ represents $CONR^6R^7$, $CONR^7$—$N(R^7)_2$, $CONR^7OR^7$ or $COOR^8$, and $R^1$, $R^2$, $R^3$, and $R^5$ are as defined in formula (1) in claim 1 comprising a) reacting a substituted 3-aminopyrazole derivative of the formula II

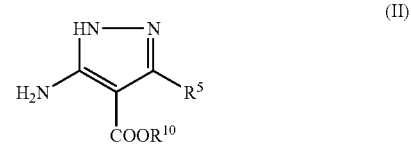

and a malonic ester IIa

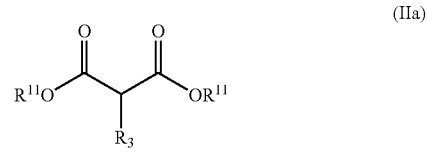

where $R^{10}$ represents $C_1$-$C_4$-alkyl and $R^{11}$ represents $C_1$-$C_8$-alkyl or aryl to give a dihydroxypyrazolopyrimidine III,

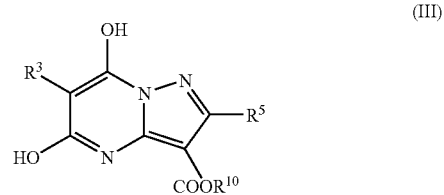

b) halogenating a dihydroxypyrazolopyrimidine III to give a halopyrazolopyrimidine IV,

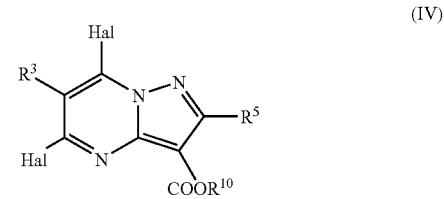

c) reacting a dihydroxypyrazolopyrimidine IV with an amine to give a 7-aminopyrazolopyrimidine V,

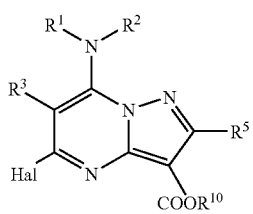

d) hydrolyzing a 7-aminopyrazolopyrimidine V, to give a pyrazolopyrimidinecarboxylic acid VI,

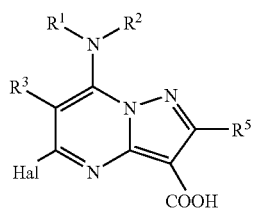

e) reacting a pyrazolopyrimidinecarboxylic acid VI with a chlorinating agent to give a pyrazolopyrimidine acid chloride VII,

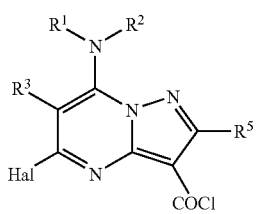

and f) (1) reacting a pyrazolopyrimidine acid chloride VII with an amine to give an amide of the formula (Ia)

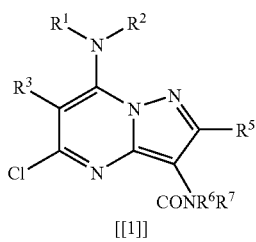

[[1]]

or (2) reacting a pyrazolopyrimidine acid chloride VII with a hydrazine to give a hydrazide of the formula (Ib)

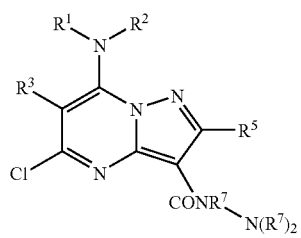

or (3) reacting a pyrazolopyrimidine acid chloride VII with a hydroxylamine to give a hydroxamide of the formula (Ic)

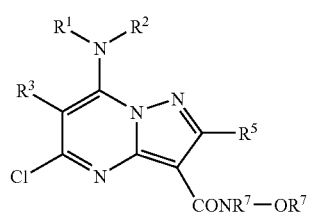

or (4) reacting a pyrazolopyrimidine acid chloride VII with an alcohol to give an ester of the formula (Id)

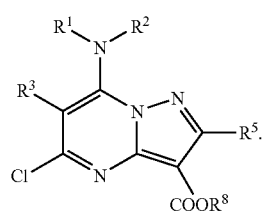

9. A compound selected from the group consisting of compounds of the formula III, IV, V and VII as follows:

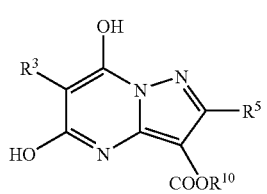

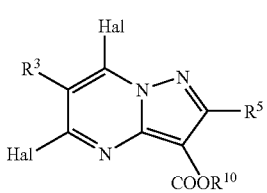

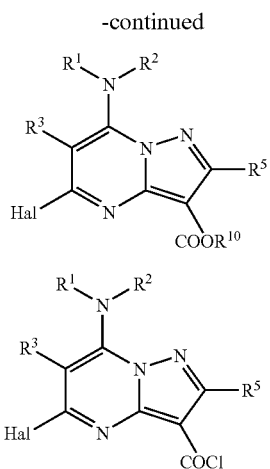

wherein
- R¹ is alkyl having 1 to 10 carbon atoms which is unsubstituted or mono- to pentasubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or
  - is alkenyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or
  - is alkynyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or
  - is cycloalkyl having 3 to 10 carbon atoms which is unsubstituted or mono- to trisubstituted by identical or different substituents from the group consisting of halogen and alkyl having 1 to 4 carbon atoms, or
  - is saturated or unsaturated heterocyclyl having 3 to 10 ring members and 1 to 3 heteroatoms that are nitrogen, oxygen and/or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms and/or mercapto;
- R² is hydrogen or alkyl having 1 to 6 carbon atoms;
- R³ is $(C_1$-$C_8)$-alkyl, $(C_1$-$C_8)$-cycloalkyl, where R³ is unsubstituted or substituted by one or more fluorine or chlorine atoms, or benzyl or
  - is phenyl which may be mono- to trisubstituted by identical or different substituents from the group consisting of
    - fluorine, chlorine, bromine, cyano, nitro, formyl, methyl, ethyl, n- or i-propyl, n-, i-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethynyloxy, trifluoroethynyloxy, chloroallyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl and cyclohexyl, or by
  - 1,3-propanediyl which is attached in the 2,3-position, 1,4-butanediyl, methylenedioxy ($-$O$-$CH$_2$$-$O$-$) or 1,2-ethylenedioxy ($-$O$-$CH$_2$$-$CH$_2$$-$O$-$), where these radicals may be mono- or polysubstituted by identical or different substituents from the group consisting of fluorine, chlorine, methyl, ethyl, n-propyl, -propyl, trifluoromethyl, carboxyl and carboxymethyl; or
  - is pyridyl which is attached in the 2- or 4-position and which may be mono- to tetrasubstituted by identical or different substituents from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl, or
  - is pyrimidyl which is attached in the 2- or 4-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or
  - is thienyl which is attached in the 2- or 3-position and which may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or
  - is $C_1$-$C_8$-alkylamino or di- $C_1$-$C_8$-alkylamino, or
  - is thiazolyl which is attached in the 2-, 4- or 5-position and which may be mono- to disubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl, or
  - is N-piperidinyl, N-tetrazolyl, N-pyrazolyl, N-imidazolyl, N-1,2,4-triazolyl, N-pyrrolyl or N-morpholinyl, each of which is unsubstituted or mono- or polysubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl;
- R⁵ is H, Cl, F, $CH_3$, $-$CH$(CH_3)_2$ or cyclopropyl; and
- R¹⁰ is $C_1$-$C_4$-alkyl.

* * * * *